US006559140B2

(12) United States Patent
Bennani et al.

(10) Patent No.: US 6,559,140 B2
(45) Date of Patent: May 6, 2003

(54) CYCLIC AND BICYCLIC DIAMINO HISTAMINE-3 RECEPTOR ANTAGONISTS

(75) Inventors: Youssef L. Bennani, Lake Bluff, IL (US); Lawrence A. Black, Libertyville, IL (US); Wesley J. Dwight, San Diego, CA (US); Ramin Faghih, Lake Forest, IL (US); Robert G. Gentles, Libertyville, IL (US); Huaqing Liu, Buffalo Grove, IL (US); Kathleen M. Phelan, Gurnee, IL (US); Anil Vasudevan, Gurnee, IL (US); Henry Q. Zhang, Grayslake, IL (US)

(73) Assignee: Abbott Laboratories, Abbott Park, IL (US)

(*) Notice: Subject to any disclaimer, the term of this patent is extended or adjusted under 35 U.S.C. 154(b) by 0 days.

(21) Appl. No.: 09/799,450

(22) Filed: Mar. 5, 2001

(65) Prior Publication Data

US 2001/0049367 A1 Dec. 6, 2001

Related U.S. Application Data

(60) Provisional application No. 60/187,933, filed on Mar. 9, 2000.

(51) Int. Cl.[7] ................. C07D 295/205; C07D 207/16; C07D 213/56; A61K 31/495; A61P 37/08
(52) U.S. Cl. ................. 514/210.02; 544/372; 544/360; 514/254.01; 514/253.12; 540/200
(58) Field of Search ................. 544/372, 360; 514/254.01, 210.02, 253.12; 540/200

(56) References Cited

U.S. PATENT DOCUMENTS 4,946,843 A * 8/1990 Janssens et al. ............. 514/253
5,324,728 A * 6/1994 Sekine et al. ................ 514/252

OTHER PUBLICATIONS

CAS printout for Mase et al.*
CAS printout for Sato et al.*
CAS printout for Janssen et al.*
CAS printout for Kimura et al.*
CAS printout for Mazaki et al.*
CAS printout for Protiva et al.*
Abstract 1991:514494 CAPLUS, Mase et al., "Preparation and formulation of thiazolidinecarboxamide derivatives as platelet-activating factor (PAF) antagonists".
Abstract 1991:207293 CAPLUS, Sato et al., "Preparation of homopiperazine and ethylenediamine derivatives as agents for protection of brain".
Abstract 1989:534153 CAPLUS, Janssen et al., "Preparation of (heterocyclylalkyl) imidazopyridines as anitallergy agents".
Abstract 1987:598361 CAPLUS, Kimura et al., "Pyroglutamide derivatives, procedure for their preparation, and their use as nootropics".

Abstract 1987:18610 CAPLUS, Mazaki et al., "Preparation of piperazine derivatives".
Abstract 1978:50922 CAPLUS, Protiva et al., "Tranquilizing 4-(4-acylpiperazino)-p-fluorobutyrophenones".
Arrang et al., "Auto-inhibition of brain histamine release mediated by a novel class ($H_3$) of histamine receptor", Nature, vol. 302, Apr. 28, 1983.
Arrang et al., "Highly potent and selective ligands for histamine H3-receptors", Nature, vol. 327, May 14, 1987.

* cited by examiner

Primary Examiner—Richard L. Raymond
Assistant Examiner—Hong Liu
(74) Attorney, Agent, or Firm—Portia Chen; Daniel W. Collins

(57) ABSTRACT

Compounds of formula (I)

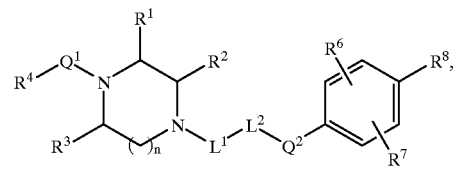

compounds of formula (II)

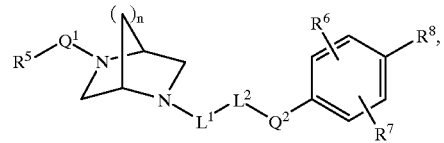

compounds of formula (III)

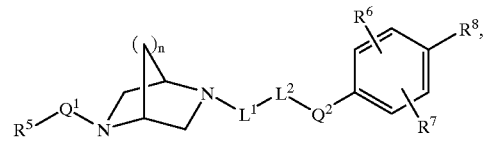

and
compounds of formula (IV)

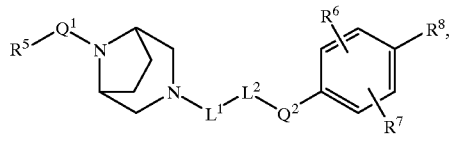

or pharmaceutically acceptable salts thereof are useful as $H_3$ receptor antagonists. Processes to make the compounds and methods of treatment using the compounds are also disclosed.

21 Claims, No Drawings

CYCLIC AND BICYCLIC DIAMINO HISTAMINE-3 RECEPTOR ANTAGONISTS

This application claims priority to the provisional application Serial No. 60/187,933 filed on Mar. 9, 2000.

TECHNICAL FIELD

This invention relates to compounds which may be useful for treating diseases caused or exacerbated by $H_3$ receptor activity, pharmaceutical compositions containing the compounds, preparation of the compounds, and methods of treatment using the compounds.

BACKGROUND OF THE INVENTION

Histamine is a well-known mediator in hypersensitive reactions (e.g. allergies, hay fever, and asthma) which are commonly treated with antagonists of histamine or "antihistamines." It has also been established that histamine receptors exist in at least two distinct types, referred to as $H_1$ and $H_2$ receptors.

A third histamine receptor (the $H_3$ receptor) is believed to play a role as a neurotransmitter in the central nervous system, where it is thought to be disposed presynaptically on histaminergic nerve endings (Nature, 302, 832–837 (1983)). The existence of the $H_3$ receptor has been confirmed by the development of selective $H_3$ agonists and antagonists (Nature, 327, 117–123 (1987)) and has subsequently been shown to regulate the release of other neurotransmitters in both the central nervous system and peripheral organs, particularly the lungs and gastrointestinal tract.

Thus, it is anticipated that $H_3$ receptor antagonists may have therapeutic utility for a number of indications such as asthma, ardiovasular disorders, gastrointestinal disorders, inflammation, sedatives, sleep regulators, anticonvulsants, and antidepressants.

SUMMARY OF THE INVENTION

In its principle embodiment, this invention discloses a compound selected from the group consisting of a compound of formula (I)

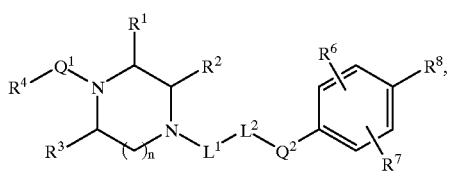

a compound of formula (II)

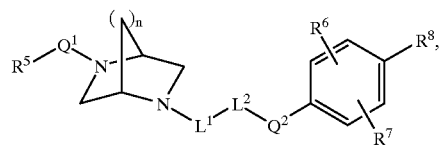

a compound of formula (III)

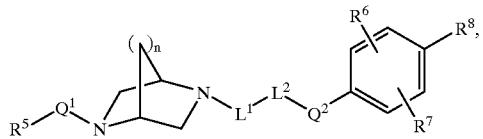

and
a compound of formula (IV)

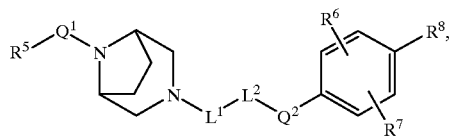

or pharmaceutically acceptable salts thereof wherein,
 $L^1$ is absent or optionally substituted cycloalkyl or optionally substituted cycloalkylalkylene;
 $L^2$ is absent or alkylene, optionally substituted with aryl;
 with the proviso that at least one of $L^1$ or $L^2$ is not absent;
 n is one or two;
 $Q^1$ is absent or selected from the group consisting of —C(=O)—, —C(=S)—, —SO$_2$—, and —C(=N—R$^9$)—;
 $Q^2$ is selected from the group consisting of —O—, —S—, —S(=O)—, —SO$_2$—, and acetylene;
 $R^1$, $R^2$, and $R^3$ are independently hydrogen or alkyl;
 $R^4$ is selected from the group consisting of alkoxy, amino, optionally substituted aryl, aryloxy, optionally substituted cycloalkyl, cycloalkoxy, optionally substituted heteroaryl, optionally substituted heterocycloalkyl, and —W$^1$—C(R$^{11}$)(R$^{11a}$)—NR$^{12}$R$^{12a}$;
 $R^5$ is hydrogen or $R^4$;
 with the proviso that $Q^1$ is not absent in compounds of formula (I) and when $Q^1$ is carbonyl in formula (I), then $R^4$ is not alkyl; and
 with the proviso that when $R^5$ is hydrogen, $Q^1$ is absent or —C(=O)—;
 $R^6$ and $R^7$ are independently selected from the group consisting of hydrogen, alkyl, alkenyl, alkynyl, alkoxy, amino, azido, carboxaldehyde, carboxyl, cyano, halo, hydroxyl, nitro, perfluoroalkyl, and perfluoroalkoxy; or
 $R^6$ and $R^7$ are on adjacent carbon atoms and taken together are —OCH$_2$C(O)—;
 $R^8$ is selected from the group consisting of alkyl, alkanoyl, alkoxy, alkoxycarbonyl, amino, optionally substituted aryl, arylalkyl, aryloyl, arylsulfonyl, carboxamido, cyano, cyanoalkyl, cycloalkyl, cycloalkylalkyl, cycloalkyloyl, halo, optionally substituted heteroaryl, heteroarylalkyl, heteroaryloyl, heteroarylsulfonyl, perfluoroalkyl, —C(H)(R$^3$)—OR, and —C(R$^{13}$)=N—OR$^{14}$;
 $R^9$ is selected from the group consisting of hydrogen, alkyl, alkoxy, aryl, arylalkyl, cycloalkyl, cycloalkylalkyl, and hydroxyl;
 $R^{10}$ is selected from the group consisting of hydrogen, alkyl, aryl, arylalkyl, cycloalkyl, cycloalkylalkyl, heteroaryl, heteroarylalkyl, and a nitrogen protecting group;
 $R^{11}$ and $R^{11a}$ are independently selected from the group consisting of hydrogen, alkyl, alkoxyalkyl, amino, aminoalkyl, arylalkyl, arylalkoxyalkyl, heteroarylalkyl, hydroxyalkyl, and ureidoalkyl;
 $W^1$ is absent or is optionally substituted alkylene;

$R^{12}$ and $R^{12a}$ are independently selected from the group consisting of hydrogen, alkyl, alkanoyl, alkylsulfonyl, a nitrogen protecting group, aminosulfonyl, optionally substituted aryl, arylalkyl, aryloyl, arylsulfonyl, cycloalkyl, cycloalkylalkyl, cycloalkyloyl, cycloalkylsulfonyl, optionally substituted heteroaryl, heteroarylalkyl, heteroaryloyl, heteroarylsulfonyl, optionally substituted heterocycloalkyl, heterocycloalkylalkyl, heterocycloalkylalkyloyl, heterocycloalkyloyl, and heterocycloalkylsulfonyl; or $R^{12}$ and $R^{12a}$, together with the nitrogen atom to which they are attached, form an optionally substituted heterocycloalkyl ring selected from the group consisting of azetidinyl, pyrrolidinyl, piperidinyl, azepanyl, morpholinyl, thiomorpholinyl, thiomorpholinyl sulfone, dihydropyrimidinyl, tetrahydropyrimidinyl, and hexahydropyrimidinyl; or $W^1$ is an optionally substituted alkylene, and $R^{11}$ and $R^{12}$ together with the carbon and nitrogen atom to which they are respectively attached, form an optionally substituted heterocycloalkyl ring selected from the group consisting of azetidinyl, pyrrolidinyl, piperidinyl, and azepanyl;

$R^{13}$ is selected from the group consisting of hydrogen, alkyl, cycloalkyl, cycloalkylalkyl, aryl, and arylalkyl; and $R^{14}$ is selected from the group consisting of hydrogen, alkyl, cycloalkyl, cycloalkylalkyl, aryl, arylalkyl, and an hydroxyl protecting group.

In another embodiment, this invention discloses a compound of formula (I)

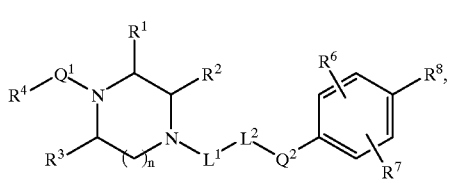

(I)

or a pharmaceutically acceptable salt thereof, wherein $L^1$, $L^2$, n, $Q^1$, $Q^2$, $R^1$, $R^2$, $R^3$, $R^4$, $R^6$, $R^7$, and $R^8$ are defined above.

In another embodiment, this invention discloses a compound of formula (I), wherein $L^1$ is absent and $L^2$ is alkylene optionally substituted with aryl.

In another embodiment, this invention discloses a compound of formula (I), wherein n is one.

In another embodiment, this invention discloses a compound of formula (I), wherein n is two.

In another embodiment, this invention discloses a compound of formula (I), wherein $Q^1$ is —C(=O)—.

In another embodiment, this invention discloses a compound of formula (I), wherein $Q^2$ is —O—.

In another embodiment, this invention discloses a compound of formula (I), wherein $R^1$, $R^2$, and $R^3$ are hydrogen.

In another embodiment, this invention discloses a compound of formula (I), wherein $R^4$ is

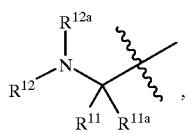

wherein one of $R^{11}$ and $R^{11a}$ is hydrogen or alkyl, and the other is selected from the group consisting of hydrogen, alkyl, alkoxyalkyl, amino, aminoalkyl, arylalkyl, heteroarylalkyl, hydroxyalkyl, and ureidoalkyl; and $R^{12}$ and $R^{12a}$ are independently selected from the group consisting of hydrogen, alkyl, alkanoyl, alkylsulfonyl, a nitrogen protecting group, aminosulfonyl, optionally substituted aryl, arylalkyl, aryloyl, arylsulfonyl, cycloalkyl, cycloalkylalkyl, cycloalkyloyl, cycloalkylsulfonyl, optionally substituted heteroaryl, heteroarylalkyl, heteroaryloyl, heteroarylsulfonyl, optionally substituted heterocycloalkyl, heterocycloalkylalkyl, heterocycloalkylalkyloyl, heterocycloalkyloyl, and heterocycloalkylsulfonyl.

In another embodiment, this invention discloses a compound of formula (I), wherein the relative stereochemistry of $R^4$ is depicted by the formula

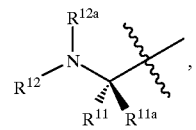

wherein $R^{11}$ is hydrogen; and $R^{11a}$, $R^{12}$ and $R^{12a}$ are defined in the embodiment immediately above.

In another embodiment, this invention discloses a compound of formula (I), wherein the relative stereochemistry of $R^4$ is depicted by the formula

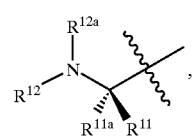

wherein $R^{11}$ is hydrogen; and $R^{11a}$, $R^{12}$ and $R^{12a}$ are defined in the embodiment proximally above.

In another embodiment, this invention discloses a compound of formula (I), wherein $R^4$ is

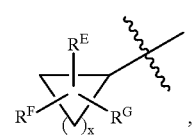

wherein $R^E$, and $R^F$, and $R^G$ are independently selected from the group consisting of hydrogen, alkyl, amino, alkoxy, alkoxycarbonyl, carboxaldehyde, carboxyl, halo, hydroxy, optionally substituted aryl, optionally substituted heteroaryl, optionally substituted heterocycloalkyl, and ureido; or $R^E$ and $R^F$ are taken together on the same carbon and are oxo or thioxo, and $R^G$ is selected from the group consisting of hydrogen, alkyl, amino, alkoxy, alkoxycarbonyl, carboxaldehyde, carboxyl, halo, hydroxy, optionally substituted aryl, optionally substituted heteroaryl, optionally substituted heterocycloalkyl, and ureido; and x is one, two, three, or four.

In another embodiment, this invention discloses a compound of formula (I), wherein the relative stereochemistry of $R^4$ is depicted by the formula

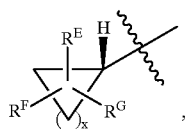

wherein $R^E$, $R^F$, $R^G$, and x are defined in the embodiment immediately above.

In another embodiment, this invention discloses a compound of formula (I), wherein the relative stereochemistry of $R^4$ is depicted by the formula

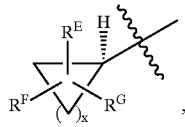

wherein $R^E$, $R^F$, $R^G$, and x are defined are defined in the embodiment proximally above.

In another embodiment, this invention discloses a compound of formula (I), wherein $R^4$ is

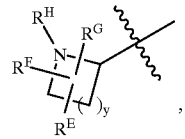

wherein $R^E$, $R^F$, $R^G$ and $R^H$ are independently selected from the group consisting of hydrogen; alkyl; alkenyl; alkynyl; alkoxy; alkanoyl; alkoxycarbonyl; alkylsulfonyl; amino; aminosulfonyl; azido; carboxamido; carboxy; cyano; halo; hydroxyl; oxo; thioxo; nitro; a nitrogen protecting group; perfluoroalkyl; perfluoroalkoxy; aryloyl; arylsulfonyl; heteroaryloyl; heteroarylsulfonyl; heterocycloalkyloyl; heterocycloalkylsulfonyl; phenyl; a heteroaryl selected from the group consisting of furanyl, thienyl, pyrrolyl, oxazolyl, thiazolyl, imidazolyl, isoxazolyl, isothiazolyl, oxadiazolyl, triazolyl, thiadiazolyl, pyridyl, pyridazinyl, pyrimidinyl, pyrazinyl, and triazinyl; and a heterocycloalkyl selected from the group consisting of tetrahydrofuranyl, piperidinyl, piperazinyl, and morpholinyl, wherein the phenyl, the heteroaryl, and the heterocycloalkyl groups can be optionally substituted with one, two, or three substituents independently selected from the group consisting of alkyl, alkoxy, carboxyl, azido, carboxaldehyde, halo, hydroxyl, perfluoroalkyl, and perfluoroalkoxy; or $R^E$ and $R^F$ are attached to the same carbon and are oxo or thioxo; and $R^G$ and $R^H$ are independently selected from the group consisting of hydrogen; alkyl; alkenyl; alkynyl; alkoxy; alkanoyl; alkoxycarbonyl; alkylsulfonyl; amino; aminosulfonyl; azido; carboxamido; carboxy; cyano; halo; hydroxyl; oxo; thioxo; nitro; a nitrogen protecting group; perfluoroalkyl; perfluoroalkoxy; aryloyl; arylsulfonyl; heteroaryloyl; heteroarylsulfonyl; heterocycloalkyloyl; heterocycloalkylsulfonyl; phenyl; a heteroaryl selected from the group consisting of furanyl, thienyl, pyrrolyl, oxazolyl, thiazolyl, imidazolyl, isoxazolyl, isothiazolyl, oxadiazolyl, triazolyl, thiadiazolyl, pyridyl, pyridazinyl, pyrimidinyl, pyrazinyl, and triazinyl; and a heterocycloalkyl selected from the group consisting of tetrahydrofuranyl, piperidinyl, piperazinyl, and morpholinyl, wherein the phenyl, the heteroaryl, and the heterocycloalkyl groups can be optionally substituted with one, two, or three substituents independently selected from the group consisting of alkyl, alkoxy, carboxyl, azido, carboxaldehyde, halo, hydroxyl, perfluoroalkyl, and perfluoroalkoxy; and y is one, two, or three.

In another embodiment, this invention discloses a compound of formula (I), wherein the relative stereochemistry of $R^4$ is depicted by the formula

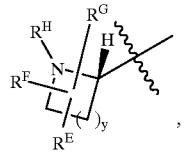

wherein $R^E$, $R^F$, $R^G$, $R^H$, and y are defined in the embodiment immediately above.

In another embodiment, this invention discloses a compound of formula (I), wherein the relative stereochemistry of $R^4$ is depicted by the formula

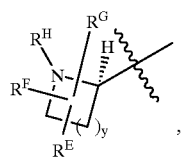

wherein $R^E$, $R^F$, $R^G$, $R^H$, and y are defined in the embodiment proximally above.

In another embodiment, this invention discloses a compound of formula (I), wherein $R^4$ is

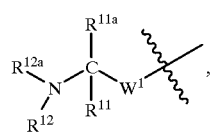

wherein one of $R^{11}$ and $R^{11a}$ is hydrogen or alkyl, and the other is selected from the group consisting of hydrogen, alkyl, alkoxyalkyl, amino, aminoalkyl, arylalkyl, heteroarylalkyl, hydroxyalkyl, and ureidoalkyl;

$R^{12}$ and $R^{12a}$ are independently selected from the group consisting of hydrogen, alkyl, alkanoyl, alkylsulfonyl, a nitrogen protecting group, aminosulfonyl, optionally substituted aryl, arylalkyl, aryloyl, arylsulfonyl, cycloalkyl, cycloalkylalkyl, cycloalkyloyl, cycloalkylsulfonyl, optionally substituted heteroaryl, heteroarylalkyl, heteroaryloyl, heteroarylsulfonyl, optionally substituted heterocycloalkyl, heterocycloalkylalkyl, heterocycloalkyloyl, and heterocycloalkylsulfonyl; and $W^1$ is alkylene.

In another embodiment, this invention discloses a compound of formula (I), wherein the relative stereochemistry of $R^4$ is depicted by the formula

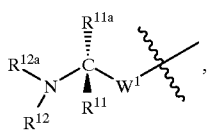

wherein
$R^{11}$, $R^{11a}$, $R^{12}$, $R^{12a}$, and $W^1$ are defined in the embodiment immediately above. In another embodiment, this invention discloses a compound of formula (I), wherein the relative stereochemistry of $R^4$ is depicted by the formula

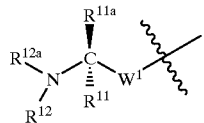

$R^{11}$, $R^{11a}$, $R^{12}$, $R^{12a}$, and $W^1$ are defined in the embodiment proximally above. In another embodiment, this invention discloses a compound of formula (I), wherein $R^4$ is

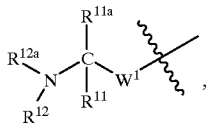

wherein
$W^1$ is alkylene;
$R^{11a}$ is hydrogen or alkyl;
$R^{12a}$ is selected from the group consisting of hydrogen, alkyl, alkanoyl, alkylsulfonyl, a nitrogen protecting group, aminosulfonyl, optionally substituted aryl, arylalkyl, aryloyl, arylsulfonyl, cycloalkyl, cycloalkylalkyl, cycloalkyloyl, cycloalkylsulfonyl, optionally substituted heteroaryl, heteroarylalkyl, heteroaryloyl, heteroarylsulfonyl, optionally substituted heterocycloalkyl, heterocycloalkylalkyl, heterocycloalkyloyl, and heterocycloalkylsulfonyl; and
$R^{11}$ and $R^{12}$, together with the carbon and nitrogen atom to which they are respectively attached, are a heterocycloalkyl ring selected from the group consisting of azetidinyl, pyrrolidinyl, piperidinyl, and azepanyl, wherein the heterocycloalkyl ring formed by $R^{11}$ and $R^{12}$ together can be optionally substituted with one, two, or three substituents independently selected from the group consisting of alkyl; alkenyl; alkynyl; alkoxy; alkanoyl; alkoxycarbonyl; alkylsulfonyl; amino; aminosulfonyl; azido; carboxamido; carboxy; cyano; halo; hydroxyl; oxo; thioxo; nitro; a nitrogen protecting group; perfluoroalkyl; perfluoroalkoxy; aryloyl; arylsulfonyl; heteroaryloyl; heteroarylsulfonyl; heterocycloalkyloyl; heterocycloalkylsulfonyl; phenyl; a heteroaryl selected from the group consisting of furanyl, thienyl, pyrrolyl, oxazolyl, thiazolyl, imidazolyl, isoxazolyl, isothiazolyl, oxadiazolyl, triazolyl, thiadiazolyl, pyridyl, pyridazinyl, pyrimidinyl, pyrazinyl, and triazinyl; and a heterocycloalkyl selected from the group consisting of tetrahydrofuranyl, piperidinyl, piperazinyl, and morpholinyl,
wherein the phenyl, the heteroaryl, and the heterocycloalkyl groups can be optionally substituted with one, two, or three substituents independently selected from the group consisting of alkyl, alkoxy, carboxyl, azido, carboxaldehyde, halo, hydroxyl, perfluoroalkyl, and perfluoroalkoxy.

In another embodiment, this invention discloses a compound of formula (I), wherein the relative stereochemistry of $R^4$ is depicted by the formula

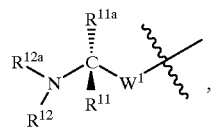

wherein
$R^{11}$, $R^{11a}$, $R^{12}$, $R^{12a}$, and $W^1$ are defined in the embodiment immediately above.

In another embodiment, this invention discloses a compound of formula (I), wherein the relative stereochemistry of $R^4$ is depicted by the formula

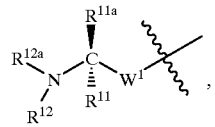

wherein
$R^{11}$, $R^{11a}$, $R^{12}$, $R^{12a}$, and $W^1$ are defined in the embodiment proximally above. In another embodiment, this invention discloses a compound of formula (I), wherein $R^6$ is hydrogen.

In another embodiment, this invention discloses a compound of formula (I), wherein $R^7$ is hydrogen or halo.

In another embodiment, this invention discloses a compound of formula (I), wherein $R^8$ is selected from the group consisting of alkanoyl, aryl, carboxamido, cycloalkyloyl, cyano, halo, heteroaryl, and perfluoroalkyl.

In another embodiment, this invention discloses a compound of formula (I), wherein $R^8$ is cyclopropanoyl.

In another embodiment, this invention discloses a compound of formula (I), wherein $R^8$ is 4-cyanophen-4'-yl.

In another embodiment, this invention discloses a compound of formula (I), wherein $R^8$ is optionally substituted heteroaryl of the formula

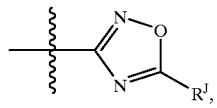

wherein
$R^J$ is selected from the group consisting of hydrogen, alkyl, alkoxyalkyl, alkoxyalkoxyalkyl, aminoalkyl, aryl, arylalkyl, cyanoalkyl, cycloalkyl, cycloalkylalkyl, heteroaryl, heterocycloalkyl, alkoxycarbonyl, and perfluoroalkyl.

In another embodiment, this invention discloses a compound of formula (II),

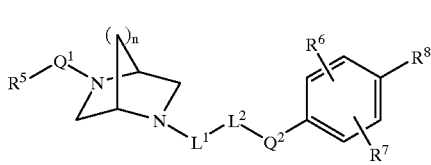

or a pharmaceutically acceptable salt thereof, wherein $L^1$, $L^2$, $Q^1$, $Q^2$, n, $R^5$, $R^6$, $R^7$, and $R^8$ are defined above.

In another embodiment, this invention discloses a compound of formula (II), wherein $L^1$ is absent and $L^2$ is alkylene, optionally substituted with aryl.

In another embodiment, this invention discloses a compound of formula (II), wherein $Q^1$ is absent or is —C(=O)— or —SO$_2$—.

In another embodiment, this invention discloses a compound of formula (II), wherein $Q^2$ is —O— or acetylene.

In another embodiment, this invention discloses a compound of formula (II), wherein n is one.

In another embodiment, this invention discloses a compound of formula (II), wherein $R^5$ is selected from the group consisting of hydrogen, alkyl, alkoxy, amino, aryl, heteroaryl, cycloalkyl, cycloalkoxy, aryloxy, and heterocycloalkyl.

In another embodiment, this invention discloses a compound of formula (II), wherein $R^5$ is

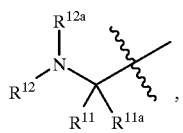

wherein one of $R^{11}$ and $R^{11a}$ is hydrogen or alkyl, and the other is selected from the group consisting of hydrogen, alkyl, alkoxyalkyl, amino, aminoalkyl, arylalkyl, heteroarylalkyl, hydroxyalkyl, and ureidoalkyl; and $R^{12}$ and $R^{12a}$ are independently selected from the group consisting of hydrogen, alkyl, alkanoyl, alkylsulfonyl, a nitrogen protecting group, aminosulfonyl, optionally substituted aryl, arylalkyl, aryloyl, arylsulfonyl, cycloalkyl, cycloalkylalkyl, cycloalkyloyl, cycloalkylsulfonyl, optionally substituted heteroaryl, heteroarylalkyl, heteroaryloyl, heteroarylsulfonyl, optionally substituted heterocycloalkyl, heterocycloalkylalkyl, heterocycloalkyloyl, and heterocycloalkylsulfonyl.

In another embodiment, this invention discloses a compound of formula (II), the relative stereochemistry of $R^5$ is depicted by the formula

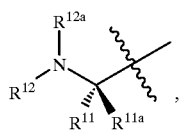

wherein $R^{11}$ is hydrogen; and $R^{11a}$, $R^{12}$ and $R^{12a}$ are defined in the embodiment immediately above.

In another embodiment, this invention discloses a compound of formula (II), wherein the relative stereochemistry of $R^5$ is depicted by the formula

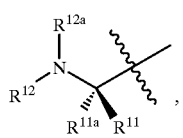

wherein $R^{11}$ is hydrogen; and $R^{11a}$, $R^{12}$ and $R^{12a}$ are defined in the embodiment proximally above.

In another embodiment, this invention discloses a compound of formula (II), wherein $R^5$ is

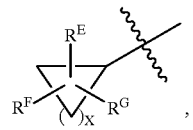

wherein $R^E$, and $R^F$, and $R^G$ are independently selected from the group consisting of hydrogen, alkyl, amino, alkoxy, alkoxycarbonyl, carboxaldehyde, carboxyl, halo, hydroxy, optionally substituted aryl, optionally substituted heteroaryl, optionally substituted heterocycloalkyl, and ureido; or $R^E$ and $R^F$ are taken together on the same carbon and are oxo or thioxo, and $R^G$ is selected from the group consisting of hydrogen, alkyl, amino, alkoxy, alkoxycarbonyl, carboxaldehyde, carboxyl, halo, hydroxy, optionally substituted aryl, optionally substituted heteroaryl, optionally substituted heterocycloalkyl, and ureido; and x is one, two, three, or four.

In another embodiment, this invention discloses a compound of formula (II), wherein the relative stereochemistry of $R^5$ is depicted by the formula

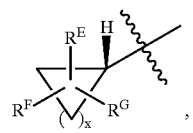

wherein $R^E$, $R^F$, $R^G$, and x are defined in the embodiment immediately above.

In another embodiment, this invention discloses a compound of formula (II), wherein the relative stereochemistry of $R^5$ is depicted by the formula

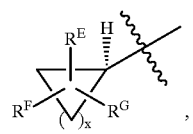

wherein $R^E$, $R^F$, $R^G$, and x are defined in the embodiment proximally above.

In another embodiment, this invention discloses a compound of formula (II), wherein $R^5$ is

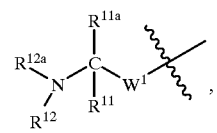

wherein one of $R^{11}$ and $R^{11a}$ is hydrogen or alkyl, and the other is selected from the group consisting of hydrogen, alkyl, alkoxyalkyl, amino, aminoalkyl, arylalkyl, heteroarylalkyl, hydroxyalkyl, and ureidoalkyl;

$R^{12}$ and $R^{12a}$ are independently selected from the group consisting of hydrogen, alkyl, alkanoyl, alkylsulfonyl, a nitrogen protecting group, aminosulfonyl, optionally substituted aryl, arylalkyl, aryloyl, arylsulfonyl, cycloalkyl, cycloalkylalkyl, cycloalkyloyl, cycloalkylsulfonyl, optionally substituted heteroaryl, heteroarylalkyl, heteroaryloyl, heteroarylsulfonyl, optionally substituted heterocycloalkyl, heterocycloalkylalkyl, heterocycloalkyloyl, and heterocycloalkylsulfonyl; and W$^1$ is alkylene.

In another embodiment, this invention discloses a compound of formula (II), wherein the relative stereochemistry of R$^5$ is depicted by the formula

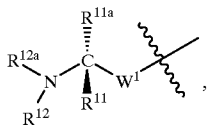

wherein

R$^{11}$, R$^{11a}$, R$^{12}$, R$^{12a}$, and W$^1$ are defined in the embodiment immediately above.

In another embodiment, this invention discloses a compound of formula (II), wherein the relative stereochemistry of R$^5$ is depicted by the formula

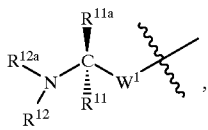

wherein

R$^{11}$, R$^{11a}$, R$^{12}$, R$^{12a}$, and W$^1$ are defined in the embodiment proximally above. In another embodiment, this invention discloses a compound of formula (II), wherein R$^6$ and R$^7$ are hydrogen.

In another embodiment, this invention discloses a compound of formula (II), wherein R$^8$ is alkanoyl or cycloalkyloyl.

In another embodiment, this invention discloses a compound of formula (II), wherein R$^8$ is cyclopropanoyl.

In another embodiment, this invention discloses a compound of formula (III)

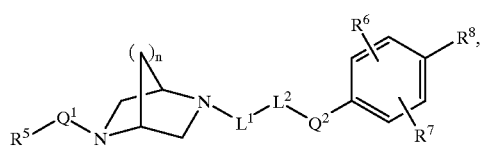

or a pharmaceutically acceptable salt thereof, wherein

L$^1$, L$^2$, Q$^1$, Q$^2$, n, R$^5$, R$^6$, R$^7$, and R$^8$ are defined above.

In another embodiment, this invention discloses a compound of formula (III), wherein L$^1$ is absent and L$^2$ is alkylene, optionally substituted with aryl.

In another embodiment, this invention discloses a compound of formula (III), wherein Q$^1$ is absent or is —C(=O)— or —SO$_2$—.

In another embodiment, this invention discloses a compound of formula (III), wherein Q$^2$ is —O— or acetylene.

In another embodiment, this invention discloses a compound of formula (III), wherein n is one.

In another embodiment, this invention discloses a compound of formula (III), wherein R$^5$ is selected from the group consisting of hydrogen, alkoxy, and aryl.

In another embodiment, this invention discloses a compound of formula (III), wherein R$^5$ is

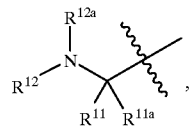

wherein one of R$^{11}$ and R$^{11a}$ is hydrogen or alkyl, and the other is selected from the group consisting of hydrogen, alkyl, alkoxyalkyl, amino, aminoalkyl, arylalkyl, heteroarylalkyl, hydroxyalkyl, and ureidoalkyl; and R$^{12}$ and R$^{12a}$ are independently selected from the group consisting of hydrogen, alkyl, alkanoyl, alkylsulfonyl, a nitrogen protecting group, aminosulfonyl, optionally substituted aryl, arylalkyl, aryloyl, arylsulfonyl, cycloalkyl, cycloalkylalkyl, cycloalkyloyl, cycloalkylsulfonyl, optionally substituted heteroaryl, heteroarylalkyl, heteroaryloyl, heteroarylsulfonyl, optionally substituted heterocycloalkyl, heterocycloalkylalkyl, heterocycloalkyloyl, and heterocycloalkylsulfonyl.

In another embodiment, this invention discloses a compound of formula (III), wherein the relative stereochemistry of R$^5$ is depicted by the formula

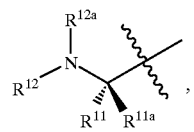

wherein

R$^{11}$, R$^{11a}$, R$^{12}$ and R$^{12a}$ are defined in the embodiment immediately above.

In another embodiment, this invention discloses a compound of formula (III), wherein the relative stereochemistry of R$^5$ is depicted by the formula

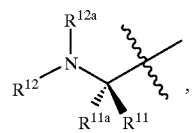

wherein

R$^{11}$, R$^{11a}$, R$^{12}$ and R$^{12a}$ defined in the embodiment proximally above.

In another embodiment, this invention discloses a compound of formula (III), wherein R$^6$ and R$^7$ are hydrogen.

In another embodiment, this invention discloses a compound of formula (III), wherein R$^8$ is cyclopropanoyl.

In another embodiment, this invention discloses a compound of formula (III), wherein R$^8$ is 4-cyanophen-4'-yl.

In another embodiment, this invention discloses a compound of formula (IV)

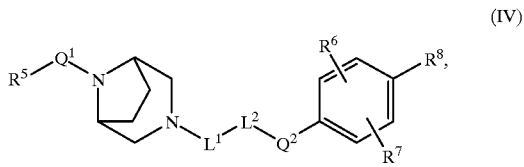

(IV)

or a pharmaceutically acceptable salt thereof, wherein $L^1$, $L^2$, $Q^1$, $Q^2$, n, $R^5$, $R^6$, $R^7$ and $R^8$ are defined above.

In another embodiment, this invention discloses a compound of formula (IV), wherein $L^1$ is absent.

In another embodiment, this invention discloses a compound of formula (IV), wherein $L^2$ is alkylene.

In another embodiment, this invention discloses a compound of formula (IV), wherein $Q^1$ is —C(=O)—.

In another embodiment, this invention discloses a compound of formula (IV), wherein $Q^2$ is —O— or acetylene.

In another embodiment, this invention discloses a compound of formula (IV), wherein $R^5$ is alkoxy.

In another embodiment, this invention discloses a compound of formula (IV), wherein $R^5$ is

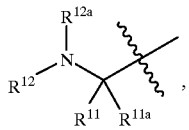

wherein one of $R^{11}$ and $R^{11a}$ is hydrogen or alkyl, and the other is selected from the group consisting of hydrogen, alkyl, alkoxyalkyl, amino, aminoalkyl, arylalkyl, heteroarylalkyl, hydroxyalkyl, and ureidoalkyl; and $R^{12}$ and $R^{12a}$ are independently selected from the group consisting of hydrogen, alkyl, alkanoyl, alkylsulfonyl, a nitrogen protecting group, aminosulfonyl, optionally substituted aryl, arylalkyl, aryloyl, arylsulfonyl, cycloalkyl, cycloalkylalkyl, cycloalkyloyl, cycloalkylsulfonyl, optionally substituted heteroaryl, heteroarylalkyl, heteroaryloyl, heteroarylsulfonyl, optionally substituted heterocycloalkyl, heterocycloalkylalkyl, heterocycloalkyloyl, and heterocycloalkylsulfonyl.

In another embodiment, this invention discloses a compound of formula (IV), wherein the relative stereochemistry of $R^5$ is depicted by the formula

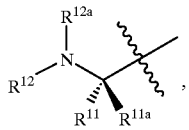

wherein $R^{11}$, $R^{11a}$, $R^{12}$ and $R^{12a}$ defined in the embodiment immediately above.

In another embodiment, this invention discloses a compound of formula (IV), wherein the relative stereochemistry of $R^5$ is depicted by the formula

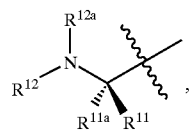

wherein $R^{11}$, $R^{11a}$, $R^{12}$ and $R^{12a}$ defined in the embodiment proximally above.

In another embodiment, this invention discloses a compound of formula (IV), wherein $R^6$ and $R^7$ are hydrogen.

In another embodiment, this invention discloses a compound of formula (IV), wherein $R^8$ is cyclopropanoyl.

In another embodiment, this invention discloses a method for antagonizing the $H_3$ receptor comprising administering a pharmaceutically acceptable amount of a compound of formula (I), or a pharmaceutically acceptable salt thereof, wherein $L^1$, $L^2$, n, $Q^1$, $Q^2$, $R^1$, $R^2$, $R^3$, $R^4$, $R^6$, $R^7$, and $R^8$ are defined above.

In another embodiment, this invention discloses a method for antagonizing the $H_3$ receptor comprising administering a pharmaceutically acceptable amount of a compound of formula (II), or a pharmaceutically acceptable salt thereof, wherein $L^1$, $L^2$, n, $Q^1$, $Q^2$, $R^5$, $R^6$, $R^7$, and $R^8$ are defined above.

In another embodiment, this invention discloses a method for antagonizing the $H_3$ receptor comprising administering a pharmaceutically acceptable amount of a compound of formula (III), or a pharmaceutically acceptable salt thereof, wherein $L^1$, $L^2$, n, $Q^1$, $Q^2$, $R^5$, $R^6$, $R^7$, and $R^8$ are defined above.

In another embodiment, this invention discloses a method for antagonizing the $H_3$ receptor comprising administering a pharmaceutically acceptable amount of a compound of formula (IV), or a pharmaceutically acceptable salt thereof, wherein $L^1$, $L^2$, $Q^1$, $Q^2$, $R^5$, $R^6$, $R^7$, and $R^8$ are defined above.

In another embodiment, this invention discloses a method for treating disorders or diseases which may be alleviated by $H_3$ receptor activity in a mammal comprising administering to the mammal in recognized need of such treatment a pharmaceutically acceptable amount of a compound of formula (I), or a pharmaceutically acceptable salt thereof, wherein $L^1$, $L^2$, n, $Q^1$, $Q^2$, $R^1$, $R^2$, $R^3$, $R^4$, $R^6$, $R^7$, and $R^8$ are defined above.

In another embodiment, this invention discloses a method for treating disorders or diseases which may be alleviated by $H_3$ receptor activity in a mammal comprising administering to the mammal in recognized need of such treatment a pharmaceutically acceptable amount of a compound of formula (II), or a pharmaceutically acceptable salt thereof, wherein $L^1$, $L^2$, n, $Q^1$, $Q^2$, $R^5$, $R^6$, $R^7$, and $R^8$ are defined above.

In another embodiment, this invention discloses a method for treating disorders or diseases which may be alleviated by $H_3$ receptor activity in a mammal comprising administering to the mammal in recognized need of such treatment a pharmaceutically acceptable amount of a compound of formula (III), or a pharmaceutically acceptable salt thereof, wherein $L^1$, $L^2$, n, $Q^1$, $Q^2$, $R^5$, $R^6$, $R^7$, and $R^8$ are defined above.

In another embodiment, this invention discloses a method for treating disorders or diseases which may be alleviated by $H_3$ receptor activity in a mammal comprising administering to the mammal in recognized need of such treatment a pharmaceutically acceptable amount of a compound of formula (IV), or a pharmaceutically acceptable salt thereof, wherein $L^1$, $L^2$, $Q^1$, $Q^2$, $R^5$, $R^6$, $R^7$, and $R^8$ are defined above.

In another embodiment, this invention discloses a composition comprising a compound of formula (I), or a pharmaceutically acceptable salt thereof, wherein $L^1$, $L^2$, n, $Q^1$, $Q^2$, $R^1$, $R^2$, $R^3$, $R^4$, $R^6$, $R^7$, and $R^8$ are defined above, and a pharmaceutically acceptable carrier.

In another embodiment, this invention discloses a composition comprising a compound of formula (II), or a pharmaceutically acceptable salt thereof, wherein $L^1$, $L^2$, n, $Q^1$, $Q^2$, $R^5$, $R^6$, $R^7$, and $R^8$ are defined above, and a pharmaceutically acceptable carrier.

In another embodiment, this invention discloses a composition comprising a compound of formula (III), or a pharmaceutically acceptable salt thereof, wherein $L^1$, $L^2$, n, $Q^1$, $Q^2$, $R^5$, $R^6$, $R^7$, and $R^8$ are defined above, and a pharmaceutically acceptable carrier.

In another embodiment, this invention discloses a composition comprising a compound of formula (IV), or a pharmaceutically acceptable salt thereof, wherein $L^1$, $L^2$, $Q^1$, $Q^2$, $R^5$, $R^6$, $R^7$, and $R^8$ are defined above, and a pharmaceutically acceptable carrier.

DETAILED DESCRIPTION OF THE INVENTION

This invention discloses series of asymmetrically N,N'-disubstituted 1,4-piperazines (compounds of formula (I), wherein n is one), 1,4-diazepanes (compounds of formula (I), wherein n is two), (1S, 4S)-2,5-diazabicyclo(3.2.1) heptanes (compounds of formula (II)), (1R,4R)-2,5-diazabicyclo(2.2.1)heptanes (compounds of formula (III)), and 3,8-diazabicyclo(3.2.1)octanes (compounds of formula (IV)) which may be useful for antagonizing the $H_3$ receptor and may be therefore useful for treating diseases caused or exacerbated by $H_3$ receptor activity.

Definition of Terms

All references cited herein are incorporated by reference. In the case of inconsistencies, the instant disclosure, including definitions, will prevail.

As used for this invention, the following terms have the meanings ascribed.

The term "acetylene" as used herein refers to ethyne.

The term "alkanoyl," as used herein, refers to an alkyl group, as defined herein, attached to the parent molecular moiety through a carbonyl group, as defined herein.

The term "alkenyl," as used herein, refers to a monovalent straight or branched chain hydrocarbon radical having from two to ten carbon atoms and at least one carbon-carbon double bond.

The term "alkoxy," as used herein, refers to an alkyl group, as defined herein, connected to the parent molecular moiety through an oxygen atom.

The term "alkoxyalkoxy," as used herein, refers to an alkoxy group, as defined herein, attached to the parent molecular moiety through another alkoxy group, as defined herein.

The term "alkoxyalkoxyalkyl," as used herein, refers to an alkoxyalkoxy group, as defined herein, attached to the parent molecular moiety through an alkyl group, as defined herein.

The term "alkoxyalkyl," as used herein, refers to an alkoxy group, as defined herein, attached to the parent molecular moiety through an alkyl group as defined herein.

The term "alkoxycarbonyl," as used herein, refers to an alkoxy group, as defined herein, attached to the parent molecular moiety through a carbonyl group, as defined herein.

The term "alkyl," as used herein, refers to a monovalent straight or branched chain saturated hydrocarbon radical having from one to ten carbon atoms.

The term "alkylene," as used herein, refers to a divalent straight or branched chain saturated hydrocarbon diradical having from one to ten carbon atoms.

The term "alkylsulfonyl," as used herein, refers to an alkyl group, as defined herein, attached to the parent molecular moiety through a sulfonyl group, as defined herein.

The term "alkynyl," as used herein, refers to a monovalent straight or branched chain hydrocarbon radical having from two to ten carbon atoms and at least one carbon-carbon triple bond. The alkynyl groups of this invention can be optionally substituted with a substituent selected from the group consisting of alkenyl, aryl, cycloalkyl, heteroaryl, and heterocycloalkyl.

The term "amino," as used herein, refers to $-NH_2$ or a derivative thereof formed by independent replacement of one or both hydrogen atoms thereon with a substituent or substituents independently selected from the group consisting of alkanoyl, alkenyl, alkyl, alkylsulfonyl, alkynyl, aminosulfonyl, aryl, arylalkenyl, arylalkyl, aryloyl, arylsulfonyl, cycloalkyl, cycloalkylalkyl, cycloalkyloyl, cycloalkylsulfonyl, heteroaryl, heteroarylalkyl, heteroaryloyl, heteroarylalkenyl, heteroarylsulfonyl, heterocycloalkylalkyl, heterocycloalkyloyl, heterocycloalkylsulfonyl, a nitrogen protecting group, optionally substituted aryl, optionally substituted heteroaryl, and optionally substituted heterocycloalkyl.

The term "aminoalkyl," as used herein, refers to an amino group, as defined herein, attached to the parent molecular moiety through an alkyl group, as defined herein.

The terms "amino protecting group," and "nitrogen protecting group," as used herein, refer to selectively introducible and removable groups which protect amino groups against undesirable side reactions during synthetic procedures. Examples of amino protecting groups include trichloroethoxycarbonyl, benzyloxycarbonyl (Cbz), chloroacetyl, trifluoroacetyl, phenylacetyl, formyl, acetyl, benzoyl, tert-butoxycarbonyl (Boc), para-methoxybenzyloxycarbonyl, diphenylmethoxycarbonyl, phthaloyl, succinyl, benzyl, diphenylmethyl, triphenylmethyl (trityl), methanesulfonyl, para-toluenesulfonyl, trimethylsilyl, triethylsilyl, triphenylsilyl, and the like. Preferred nitrogen protecting groups of this invention are benzyloxycarbonyl (Cbz), and tert-butoxycarbonyl (Boc).

The term "aminosulfonyl," as used herein, refers to an amino group, as defined herein, attached to the parent molecular moiety through a sulfonyl group.

The term "aryl," as used herein, refers to a six-membered aromatic carbocyclic ring. The aryl groups of this invention are exemplified by phenyl.

The term "arylalkenyl," as used herein, refers to an aryl group, as defined herein, attached to the parent molecular moiety through an alkenyl group, as defined herein.

The term "arylalkyl," as used herein, refers to an aryl group, as defined herein, attached to the parent molecular moiety through an alkyl group, as defined herein. The aryl part or parts of the arylalkyl can be optionally substituted with one, two, or three substituents independently selected from the group consisting of alkanoyl, alkoxy, alkoxycarbonyl, alkyl, amino, azido, carboxaldehyde, carboxamido, carboxyl, cyano, cycloalkyl, halo, hydroxyl, perfluoroalkoxy, and perfluoroalkyl.

The term "arylalkoxyalkyl," as used herein, refers to an aryl group, as defined herein, attached to the parent molecular moiety through an alkoxyalkyl group, as defined herein.

The term "aryloxy," as used herein, refers to an aryl group, as defined herein, attached to the parent molecular moiety through an oxygen atom. The aryl part or parts of the arylalkyl can be optionally substituted with one, two, or three substituents independently selected from the group consisting of alkanoyl, alkoxy, alkoxycarbonyl, alkyl, amino, azido, carboxaldehyde, carboxamido, carboxyl, cyano, cycloalkyl, halo, hydroxyl, perfluoroalkoxy, and perfluoroalkyl.

The term "aryloyl," as used herein, refers to an aryl group, as defined herein, attached to the parent molecular moiety through a carbonyl group. The aryl part of the aryloyl can be optionally substituted with one, two, or three substituents independently selected from the group consisting of alkanoyl, alkoxy, alkoxycarbonyl, alkyl, amino, aryloxy, azido, carboxaldehyde, carboxamido, carboxyl, cyano, cycloalkyl, halo, hydroxyl, methylenedioxy, perfluoroalkoxy, and perfluoroalkyl.

The term "arylsulfonyl," as used herein, refers to an aryl group, as defined herein, attached to the parent molecular moiety through a sulfonyl group. The aryl part or parts of the arylalkyl can be optionally substituted with one, two, or three substituents independently selected from the group consisting of alkanoyl, alkoxy, alkoxycarbonyl, alkyl, amino, azido, carboxaldehyde, carboxamido, carboxyl, cyano, cycloalkyl, halo, hydroxyl, perfluoroalkoxy, and perfluoroalkyl.

The term "azido," as used herein, refers to —$N_3$.

The term "carbonyl," as used herein, refers to —(C=O)—.

The term "carboxaldehyde," as used herein, refers to —CHO.

The term "carboxamido," as used herein, refers to an amino group, as defined herein, attached to the parent molecular moiety through a carbonyl group, as defined herein.

The terms "carboxyl" or "carboxy," as used herein, refers to —$CO_2H$ or a derivative thereof formed by replacement of the hydrogen atom thereon with a carboxyl protecting group. The terms carboxy protecting group, and carboxyl protecting group, as used herein refer to a carboxylic acid protecting ester group employed to block or protect the carboxylic acid functionality while the reactions involving other functional sites of the compound are carried out. In addition, a carboxy-protecting group can be used as a prodrug whereby the carboxy protecting group can be readily cleaved in vivo, for example by enzymatic hydrolysis, to release the biologically active parent. Representative carboxy-protecting groups are methyl, ethyl or tert-butyl; benzyl; 4-methoxybenzyl; nitrobenzyl; dimethylaminoethyl; pivaloyloxymethyl, propionyloxymethyl; benzoyloxyethyl; methoxycarbonylmethyl, cyclohexyloxycarbonylmethyl; tert-butyloxycarbonyloxymethyl; tert-butyloxycarbonylaminomethyl; methylaminocarbonylaminomethyl; acetylaminomethyl; 4-methylpiperazinylcarbonyloxymethyl; dimethylaminocarbonylmethyl; (5-tert-butyl-2-oxo-1,3-dioxolen-4-yl)methyl; and (5-phenyl-2-oxo-1,3-dioxolen-4-yl)methyl.

The term "cyano," as used herein, refers to —CN.

The term "cyanoalkyl," as used herein, refers to a cyano group, as defined herein, attached to the parent molecular moiety through an alkyl group, as defined herein.

The term "cycloalkoxy," as used herein, refers to cycloalkyl group, as defined herein, attached to the parent molecular moiety through an oxygen atom. The cycloalkyl part of the cycloalkoxy can be optionally substituted with one, two, or three groups independently selected from the group consisting of alkoxy, alkoxycarbonyl, alkyl, amino, hydroxyl, and oxo.

The term "cycloalkyl," as used herein, refers to a monovalent saturated cyclic hydrocarbon radical having three to seven carbon atoms.

The term "cycloalkylalkyl," as used herein, refers to a cycloalkyl group, as defined herein, attached to the parent molecular moiety through an alkyl group, as defined herein. The cycloalkyl part or parts of the cycloalkylalkyl can be optionally substituted with one, two, or three a groups independently selected from the group consisting of alkoxy, alkoxycarbonyl, alkyl, amino, aryl, azido, carboxaldehyde, carboxyl, halo, hydroxyl, optionally substituted heteroaryl, optionally substituted heterocycloalkyl, oxo, perfluoroalkoxy, perfluoroalkyl, thioxo, and uriedo.

The term "cycloalkylene," as used herein, refers to a divalent saturated cyclic hydrocarbon diradical having from three to seven carbon atoms.

The term "cycloalkyloyl," as used herein, refers to a cycloalkyl group, as defined herein, attached to the parent molecular moiety through a carbonyl group, as defined herein. The cycloalkyl part of the cycloalkyloyl can be optionally substituted with one, two, or three groups independently selected from the consisting of alkoxy, alkoxycarbonyl, alkyl, amino, aryl, azido, carboxaldehyde, carboxyl, halo, hydroxyl, optionally substituted heteroaryl, optionally substituted heterocycloalkyl, oxo, perfluoroalkoxy, perfluoroalkyl, thioxo, and uriedo.

The term "cycloalkylsulfonyl," as used herein, refers to a cycloalkyl group, as defined herein, attached to the parent molecular moiety through a sulfonyl group, as defined herein. The cycloalkyl part of the cycloalkylsulfonyl can be optionally substituted with one, two, or three groups independently selected from the consisting of alkoxy, alkoxycarbonyl, alkyl, amino, aryl, azido, carboxaldehyde, carboxyl, halo, hydroxyl, optionally substituted heteroaryl, optionally substituted heterocycloalkyl, oxo, perfluoroalkoxy, perfluoroalkyl, thioxo, and uriedo.

The terms "halo" or "halide," as used herein, refer to F, Cl, Br, or I.

The term "heteroaryl," as used herein, refers to a cyclic, aromatic five-or six-membered ring having at least one heteroatom selected from the group consisting of oxygen, nitrogen, and sulfur. The five-membered rings have two double bonds, and the six-membered rings have three double bonds. Heteroaryls of this invention are exemplified by furanyl, thienyl, pyrrolyl, oxazolyl, thiazolyl, imidazolyl, isoxazolyl, isothiazolyl, oxadiazolyl, triazolyl, thiadiazolyl, pyrazolyl, pyridyl, pyridazinyl, pyrimidinyl, pyrazinyl, and triazinyl. The heteroaryl groups of this invention are connected through a carbon atom in the ring.

The term "heteroarylalkenyl," as used herein, refers to a heteroaryl group, as defined herein, attached to the parent molecular moiety through an alkenyl group, as defined herein.

The term "heteroarylalkyl," as used herein, refers to a heteroaryl group, as defined herein, attached to the parent molecular moiety through an alkyl group, as defined herein. The heteroaryl part or of the heteroarylalkyl can be optionally substituted with one, two, or three substituents independently selected from the group consisting of alkanoyl, alkoxy, alkoxycarbonyl, alkyl, amino, azido, carboxaldehyde, cyano, cycloalkyl, halo, hydroxyl, perfluoroalkoxy, and perfluoroalkyl.

The term "heteroaryloyl," as used herein, refers to a heteroaryl group, as defined herein, attached to the parent molecular moiety through a carbonyl group, as defined herein. The heteroaryl part of the heteroaryloyl can be optionally substituted with one, two, or three substituents independently selected from the group consisting of alkanoyl, alkoxy, alkoxycarbonyl, alkyl, amino, azido, carboxaldehyde, cyano, cycloalkyl, halo, hydroxyl, perfluoroalkoxy, and perfluoroalkyl.

The term "heteroarylsulfonyl," as used herein, refers to a heteroaryl group, as defined herein, attached to the parent molecular moiety through a sulfonyl group, as defined herein. The heteroaryl part of the heteroarylsulfonyl can be optionally substituted with one, two, or three substituents independently selected from the group consisting of alkanoyl, alkoxy, alkoxycarbonyl, alkyl, amino, azido, carboxaldehyde, cyano, cycloalkyl, halo, hydroxyl, perfluoroalkoxy, and perfluoroalkyl.

The term "heterocycloalkyl," as used herein, refers to a non-aromatic four-, five-or six-membered ring having at least one heteroatom selected from the group consisting of oxygen, nitrogen, and sulfur. The four-membered rings have zero double bonds, the five-membered rings have zero or one double bond and the six-membered rings have zero, one or two double bonds. Heterocycloalkyls of this invention are exemplified by tetrahydrofuranyl, pyrrolinyl, dioxolanyl, imidazolinyl, pyrazolinyl, pyrazolidinyl, pyranyl, dihydropyridinyl, tetrahydropyridinyl, piperidinyl, azepanyl, dioxanyl, morpholinyl, dithianyl, dihydropyridazinyl, tetrahydropyridazinyl, dihydropyrazinyl, tetrahydrohydropyrazinyl, and piperazinyl. The heterocycloalkyl groups of this invention can be connected through either a carbon atom or a nitrogen atom in the ring.

The term "heterocycloalkylalkyl," as used herein, refers to a heterocycloalkyl group, as defined herein, attached to the parent molecular moiety through an alkyl group, as defined herein. The heterocycloalkyl part or parts of the heterocycloalkylalkyl can be optionally substituted with one, two, or three groups independently selected from the group consisting of alkanoyl, alkoxy, alkoxycarbonyl, alkyl, amino, azido, carboxaldehyde, carboxamido, carboxy, cyano, cycloalkyl, halo, hydroxyl, perfluoroalkoxy, and perfluoroalkyl.

The term "heterocycloalkylalkyloyl," as used herein, refers to a heterocycloalkylalkyl group attached to the parent molecular moiety through a carbonyl group. The heterocycloalkyl part of the heterocycloalkylalkyloyl can be optionally substituted with one, two, or three groups independently selected from the group consisting of alkanoyl, alkoxy, alkoxycarbonyl, alkyl, amino, azido, carboxaldehyde, carboxamido, carboxy, cyano, cycloalkyl, halo, hydroxyl, perfluoroalkoxy, and perfluoroalkyl.

The term "heterocycloalkyloyl," as used herein, refers to a heterocycloalkyl group attached to the parent molecular moiety through a carbonyl group. The heterocycloalkyl part of the heterocycloalkyloyl can be optionally substituted with one, two, or three groups independently selected from the group consisting of alkanoyl, alkoxy, alkoxycarbonyl, alkyl, amino, azido, carboxaldehyde, carboxamido, carboxy, cyano, cycloalkyl, halo, hydroxyl, perfluoroalkoxy, and perfluoroalkyl.

The term "heterocycloalkyloylalkyl," as used herein, refers to a heterocycloalkyloyl group attached to the parent molecular moiety through an alkyl group. The heterocycloalkyl part of the heterocycloalkyloylalkyl can be optionally substituted with one, two, or three groups independently selected from the group consisting of alkanoyl, alkoxy, alkoxycarbonyl, alkyl, amino, azido, carboxaldehyde, carboxamido, carboxy, cyano, cycloalkyl, halo, hydroxyl, perfluoroalkoxy, and perfluoroalkyl.

The term "heterocycloalkylsulfonyl," as used herein, refers to a heterocycloalkyl group attached to the parent molecular moiety through a sulfonyl group. The heterocycloalkyl part of the heterocycloalkylsulfonyl can be optionally substituted with one, two, or three groups independently selected from the group consisting of alkanoyl, alkoxy, alkoxycarbonyl, alkyl, amino, azido, carboxaldehyde, carboxamido, carboxy, cyano, cycloalkyl, halo, hydroxyl, perfluoroalkoxy, and perfluoroalkyl.

The terms "hydroxyl," or "hydroxy," as used herein, refers to —OH or a derivative thereof formed by replacement of the hydrogen atom thereon with a hydroxyl protecting group.

The term "hydroxyl protecting group," as used herein, refers to selectively introducible and removable groups which protect hydroxyl groups against undesirable side reactions during synthetic procedures. Examples of hydroxyl protecting groups include groups such as benzyloxycarbonyl, 4-nitrobenzyloxycarbonyl, 4-bromobenzyloxycarbonyl, 4-methoxybenzyloxycarbonyl, methoxycarbonyl, tert-butoxycarbonyl, isopropoxycarbonyl, diphenylmethoxycarbonyl, 2,2,2-trichloroethoxycarbonyl, 2-(trimethylsilyl)ethoxycarbonyl, 2-furfuryloxycarbonyl, allyloxycarbonyl, alkanoyl, formyl, chloroacetyl, trifluoroacetyl, methoxyacetyl, phenoxyacetyl, benzoyl, methyl, tert-butyl, 2,2,2-trichloroethyl, 2-trimethylsilylethyl, 1,1-dimethyl-2-propenyl, 3-methyl-3-butenyl, allyl, benzyl, para-methoxybenzyldiphenylmethyl, triphenylmethyl (trityl), tetrahydrofuryl, tetrahydropyranyl, methoxymethyl, methylthiomethyl, benzyloxymethyl, 2,2, 2-trichloroethoxymethyl, 2-(trimethylsilyl)ethoxymethyl, methanesulfonyl, para-toluenesulfonyl, trimethylsilyl, triethylsilyl, and triisopropylsilyl. Preferred hydroxyl protecting groups for this invention are alkanoyl, benzyl, methanesulfonyl, tert-butyldimethylsilyl, and tert-butyl.

The term "hydroxyalkyl," as used herein, refers to a hydroxyl group, as defined herein, attached to the parent molecular moiety through an alkyl group, as defined herein.

The term "methylenedioxy," as used herein, refers to a —$OCH_2O$— group wherein the oxygen atoms of the methylenedioxy are attached to the parent molecular moiety through two adjacent carbon atoms.

The term "nitro," as used herein, refers to a —$NO_2$ group.

The term "oxo," as used herein, refers to a group formed by the replacement of two hydrogen atoms on the same carbon atom with a single oxygen atom.

The term "perfluoroalkoxy," as used herein, refers to a perfluoroalkyl group, as defined herein, attached to the parent molecular moiety through an oxygen atom.

The term "perfluoroalkyl," as used herein, refers to an alkyl group, as defined herein, in which all of the hydrogen atoms have been replaced with fluoride atoms.

The term "pharmaceutically acceptable salt," as used herein, represents salts or zwitterionic forms of the compounds which are water or oil-soluble or dispersible and are suitable for ailments and or diseases without undue toxicity, irritation, and allergic response, which are commensurate with a reasonable benefit/risk ratio, and which are effective for their intended use. The salts may be prepared during the final isolation and purification of the compounds or separately by reacting a free base group with a suitable acid. Representative acid addition salts include acetate, adipate, alginate, citrate, aspartate, benzoate, benzenesulfonate, bisulfate, butyrate, camphorate, camphorsufonate, digluconate, glycerophosphate, hemisulfate, heptanoate, hexanoate, formate, fumarate, hydrochloride, hydrobromide, hydroiodide, 2-hydroxyethansulfonate (isethionate), lactate, maleate, mesitylenesulfonate, methanesulfonate, naphthylenesulfonate, nicotinate, 2-naphthalenesulfonate, oxalate, pamoate, pectinate, persulfate, 3-phenylpropionate, picrate, pivalate, propionate, succinate, tartrate, thiocyanate, trichloroacetic, trifluoroacetic, phosphate, glutamate, bicarbonate, para-toluenesulfonate, and undecanoate. Also, the basic nitrogen-containing groups can be quaternized with alkyl halides such as methyl, ethyl, propyl, and butyl chlorides, bromides and iodides; dialkyl sulfates such as dimethyl, diethyl, dibutyl, and diamyl sulfates; long chain halides such as decyl, lauryl, myristyl, and stearyl chlorides, bromides, and iodides; arylalkyl halides such as benzyl and phenethyl bromides. Examples of acids which may be employed to form pharmaceutically acceptable acid addition salts include inorganic acids such as hydrochloric, hydrobromic, sulphuric, and phosphoric and organic acids such as oxalic, maleic, succinic, and citric.

Basic addition salts can be prepared during the final isolation and purification of the compounds by reacting a carboxylic acid-containing group with a suitable base such as the hydroxide, carbonate, or bicarbonate of a metal cation or with ammonia or an organic primary, secondary or tertiary amine. Pharmaceutically acceptable salts include cations based on alkali metals or alkaline earth metals such as lithium, sodium, potassium, calcium, magnesium, and aluminum salts and nontoxic quaternary ammonia and amine cations such as ammonium, tetramethylammonium, tetraethylammonium, methylamine, dimethylamine, trimethylamine, triethylamine, diethylamine, ethylamine, tributlyamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

The term "substituted alkylene," as used herein, refers to an alkylene group, as defined herein, substituted with one or two amino or aryl substituents. The aryl groups substituting the alkylene groups of this invention can be further substituted with one, two, three, four, or five substituents independently selected from the group consisting of amino, alkoxy, alkoxycarbonyl, carboxaldehyde, carboxyl, halo, and hydroxy.

The term "substituted aryl," as used herein, refers to an aryl group, as defined herein, substituted with one, two, three, four, or five substituents independently selected from the group consisting of alkanoyl; alkoxy; alkoxycarbonyl; alkenyl; alkyl; alkynyl; alkylsulfonyl; amino; aminosulfonyl; azido; carboxamido; carboxy; cyano; halo; hydroxyl; nitro; perfluoroalkoxy; perfluoroalkyl; aryloyl; arylsulfonyl; heteroaryloyl; heteroarylsulfonyl; heterocycloalkyloyl; heterocycloalkylsulfonyl; phenyl; a heteroaryl selected from the group consisting of furanyl, thienyl, pyrrolyl, oxazolyl, thiazolyl, imidazolyl, isoxazolyl, isothiazolyl, oxadiazolyl, triazolyl, thiadiazolyl, pyridyl, pyridazinyl, pyrimidinyl, pyrazinyl, and triazinyl; and a heterocycloalkyl selected from the group consisting of tetrahydrofuranyl, piperidinyl, piperazinyl, and morpholinyl. The phenyl, the heteroaryl, and the heterocycloalkyl groups substituting the aryl groups of this invention can also be optionally further substituted with one, two, or three substituents independently selected from the group consisting of alkoxy, alkyl, azido, carboxaldehyde, carboxamido, carboxyl, halo, hydroxyl, perfluoroalkoxy, and perfluoroalkyl.

The term "substituted cycloalkyl," as used herein, refers to an cycloalkyl group substituted with one, two, or three substituents independently selected from the group consisting of alkyl, amino, alkoxy, alkoxycarbonyl, carboxaldehyde, carboxyl, halo, hydroxy, optionally substituted aryl, optionally substituted heteroaryl, optionally substituted heterocycloalkyl, oxo, thioxo, and ureido.

The term "substituted cycloalkylene," as used herein, refers to a cycloalkylene group independently substituted with one or two fluoride or chloride substituents.

The term "substituted heteroaryl," as used herein, refers to a heteroaryl group substituted with one, two, or three, substituents independently selected from the group consisting of alkanoyl, alkenyl, alkoxy, alkoxyalkyl, alkoxyalkoxyalkyl, alkoxycarbonyl, alkyl, alkylsulfonyl, alkynyl, amino, aminoalkyl, aminosulfonyl, aryl, arylalkyl, aryloyl, arylsulfonyl, azido, carboxamido, carboxy, cyano, cyanoalkyl, cycloalkyl, cycloalkylalkyl, halo, heteroaryl, heteroaryloyl, heteroarylsulfonyl, heterocycloalkyl, heterocycloalkyloyl, heterocycloalkyloylalkyl, heterocycloalkylsulfonyl, hydroxyl, nitro, perfluoroalkoxy, perfluoroalkyl, phenyl, or another heteroaryl selected from the group consisting of furanyl, thienyl, pyrrolyl, oxazolyl, thiazolyl, imidazolyl, isoxazolyl, isothiazolyl, oxadiazolyl, triazolyl, thiadiazolyl, pyridyl, pyridazinyl, pyrimidinyl, pyrazinyl, and triazinyl; and a heterocycloalkyl selected from the group consisting of tetrahydrofuranyl, piperidinyl, piperazinyl, and morpholinyl. The phenyl, the heteroaryl, and the heterocycloalkyl groups optionally substituting the heteroaryl groups of this invention can be optionally substituted with one, two, or three substituents independently selected from the group consisting of alkoxy, alkyl, azido, carboxaldehyde, carboxamido, carboxyl, cyano, halo, hydroxyl, perfluoroalkoxy, and perfluoroalkyl.

The term "substituted heterocycloalkyl," as used herein, refers to a heterocycloalkyl group substituted with one, two, or three substituents independently selected from the group consisting of alkanoyl; alkoxy; alkoxycarbonyl; alkenyl; alkyl; alkylsulfonyl; alkynyl; amino; aminosulfonyl; aryloyl; arylsulfonyl; azido; carboxamido; carboxy; cyano; halo; heteroaryloyl; heteroarylsulfonyl; heterocycloalkyloyl; heterocycloalkylsulfonyl; hydroxyl; nitro; a nitrogen protecting group; oxo; perfluoroalkyl; perfluoroalkoxy; thioxo; phenyl; a heteroaryl selected from the group consisting of furanyl, thienyl, pyrrolyl, oxazolyl, thiazolyl, imidazolyl, isoxazolyl, isothiazolyl, oxadiazolyl, triazolyl, thiadiazolyl, pyridyl, pyridazinyl, pyrimidinyl, pyrazinyl, and triazinyl; and another heterocycloalkyl selected from the group consisting of tetrahydrofuranyl, piperidinyl, piperazinyl, and morpholinyl. The phenyl, the heteroaryl, and the heterocycloalkyl groups substituting the heterocycloalkyl groups of this invention, can be optionally substituted with one, two, or three substituents independently selected from the group consisting of alkoxy, alkyl, azido, carboxaldehyde, carboxamido, carboxyl, halo, hydroxyl, perfluoroalkoxy, and perfluoroalkyl.

The term "sulfonyl," as used herein, refers to a —$SO_2$— group.

The term "thioxo," as used herein, refers to a group formed by the replacement of two hydrogen atoms on the same carbon atom with a single sulfur atom.

The term "thioalkoxy," as used herein, refers to an alkyl group, as defined herein, connected to the parent molecular moiety through a sulfur atom.

The term "ureido," as used herein, refers to —NHC(O)$NH_2$ or a derivative thereof formed by independent replacement of a hydrogen atom or hydrogen atoms thereon by a radical or radicals independently selected from the group consisting of alkyl, cycloalkyl, cycloalkylalkyl, aryl, and arylalkyl.

The term "ureidoalkyl," as used herein, refers to a ureido group attached to the parent molecular moiety through an alkyl group.

Asymmetric centers can exist in the compounds of this invention. This invention contemplates stereoisomers and mixtures thereof. Individual stereoisomers of compounds are prepared by synthesis from starting materials containing the chiral centers or by preparation of mixtures of enantiomeric products followed by separation such as conversion to a mixture of diastereomers followed by separation or recrystallization, chromatographic techniques, or direct separation of the enantiomers on chiral chromatographic columns. Starting compounds of particular stereochemistry are either commercially available or are made by the methods described herein and resolved by techniques well-known in the art.

The compounds of this invention can exist as pharmaceutically acceptable prodrugs. The term pharmaceutically acceptable prodrug, as used herein, represents those prodrugs of the compounds of this invention which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of this invention.

The term "prodrug," as used herein, represents compounds which are rapidly transformed in vivo to the parent compound of the above formula, for example, by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987.

In accordance to the methods of treatment of this invention, the compounds can be administered alone, in combination with, or in concurrent therapy with other $H_3$ antagonists. When using the compounds as $H_3$ antagonists, the specific therapeutically effective dose level for any particular patient will depend upon factors such as the disorder being treated and the severity of the disorder; the activity of the particular compound used; the specific composition employed; the age, body weight, general health, sex, and diet of the patient; the time of administration; the route of administration; the rate of excretion of the compound employed; the duration of treatment; and drugs used in combination with or coincidently with the compound used. The compounds can be administered orally, parenterally, osmotically (nasal sprays), rectally, vaginally, or topically in unit dosage formulations containing carriers, adjuvants, diluents, vehicles, or combinations thereof. The term "parenteral" includes infusion as well as subcutaneous, intravenous, intramuscular, and intrasternal injection.

Parenterally administered aqueous or oleaginous suspensions of the compounds can be formulated with dispersing, wetting, or suspending agents. The injectable preparation can also be an injectable solution or suspension in a diluent or solvent. Among the acceptable diluents or solvents employed are water, saline, Ringers solution, buffers, dilute acids or bases, dilute amino acid solutions, monoglycerides, diglycerides, fatty acids such as oleic acid, and fixed oils such as monoglycerides or diglycerides.

The $H_3$ antagonistic activity of parenterally administered compounds can be prolonged by slowing their absorption.

One way to slow the absorption of a particular compound is administering injectable depot forms comprising suspensions of crystalline, amorphous, or otherwise water-insoluble forms of the compound. The rate of absorption of the compound is dependent on its rate of dissolution which is, in turn, dependent on its physical state. Another way to slow absorption of a particular compound is administering injectable depot forms comprising the compound as an oleaginous solution or suspension. Yet another way to slow absorption of a particular compound is administering injectable depot forms comprising microcapsule matrices of the compound trapped within liposomes, microemulsions, or biodegradable polymers such as polylactide-polyglycolide, polyorthoesters or polyanhydrides. Depending on the ratio of drug to polymer and the composition of the polymer, the rate of drug release can be controlled.

Transdermal patches also provide controlled delivery of the compounds. The rate of absorption can be slowed by using rate controlling membranes or by trapping the compound within a polymer matrix or gel. Conversely, absorption enhancers can be used to increase absorption.

Solid dosage forms for oral administration include capsules, tablets, pills, powders, and granules. In these solid dosage forms, the active compound can optionally comprise diluents such as sucrose, lactose, starch, talc, silicic acid, aluminum hydroxide, calcium silicates, polyamide powder, tableting lubricants, and tableting aids such as magnesium stearate or microcrystalline cellulose. Capsules, tablets and pills can also comprise buffering agents; and tablets and pills can be prepared with enteric coatings or other release-controlling coatings. Powders and sprays can also contain excipients such as talc, silicic acid, aluminum hydroxide, calcium silicate, polyamide powder, or mixtures thereof. Sprays can additionally contain customary propellants such as chlorofluorohydrocarbons or substitutes therefor.

Liquid dosage forms for oral administration include emulsions, microemulsions, solutions, suspensions, syrups, and elixirs comprising inert diluents such as water. These compositions can also comprise adjuvants such as wetting, emulsifying, suspending, sweetening, flavoring, and perfuming agents.

Topical dosage forms include ointments, pastes, creams, lotions, gels, powders, solutions, sprays, inhalants, and transdermal patches. The compound is mixed under sterile conditions with a carrier and any needed preservatives or buffers. These dosage forms can also include excipients such as animal and vegetable fats, oils, waxes, paraffins, starch, tragacanth, cellulose derivatives, polyethylene glycols, silicones, bentonites, silicic acid, talc and zinc oxide, or mixtures thereof. Suppositories for rectal or vaginal administration can be prepared by mixing the compounds with a suitable nonirritating excipient such as cocoa butter or polyethylene glycol, each of which is solid at ordinary temperature but fluid in the rectum or vagina. Ophthalmic formulations comprising eye drops, eye ointments, powders, and solutions are also contemplated as being within the scope of this invention.

The total daily dose of the compounds administered to a host in single or divided doses can be in amounts from about 0.01 to about 500 mg/kg body weight or preferably from about 0.01 to about 100 mg/kg body weight. Single dose compositions can contain these amounts or submultiples thereof to make up the daily dose.

Representative compounds of the invention include:
(4-(3-(4-((2S)-2-aminopropanoyl)-1-piperazinyl)propoxy) phenyl)(cyclopropyl)methanone,
(2S)-1-(4-(3-(4-(5-methyl-1,2,4-oxadiazol-3-yl)phenoxy) propyl)-1-piperazinyl)-1-oxo-2-propanamine, tert-butyl 2-(4-(3-(4-bromophenoxy)propyl)-1-piperazinyl)-2-oxoethylcarbamate,
2-(4-(3-(4-bromophenoxy)propyl)-1-piperazinyl)-2-oxoethanamine,
tert-butyl 3-(4-(3-(4-bromophenoxy)propyl)-1-piperazinyl)-3-oxopropylcarbamate,
3-(4-(3-(4-bromophenoxy)propyl)-1-piperazinyl)-3-oxo-1-propanamine,
tert-butyl (1R)-2-(4-(3-(4-bromophenoxy)propyl)-1-piperazinyl)-1-methyl-2-oxoethylcarbamate,
(2R)-1-(4-(3-(4-bromophenoxy)propyl)-1-piperazinyl)-1-oxo-2-propanamine,
tert-butyl (1S)—2-(4-(3-(4-bromophenoxy)propyl)-1-piperazinyl)-1-methyl-2-oxoethylcarbamate,
(2S)-1-(4-(3-(4-bromophenoxy)propyl)-1-piperazinyl)-1-oxo-2-propanamine,
tert-butyl (2S)-2-((4-(3-(4-bromophenoxy)propyl)-1-piperazinyl)carbonyl)-1-pyrrolidinecarboxylate,
4-bromophenyl 3-(4-((2S)-pyrrolidinylcarbonyl)1-piperazinyl)propyl ether
tert-butyl (2R)-2-((4-(3-(4-bromophenoxy)propyl)-1-piperazinyl)carbonyl)-1-pyrrolidinecarboxylate,
4-bromophenyl 3-(4-((2R)-pyrrolidinylcarbonyl)-1-piperazinyl)propyl ether
tert-butyl (1R)-1-methyl-2-oxo-2-(4-(3-(4-(trifluoromethyl)phenoxy)propyl)-1-piperazinyl)ethylcarbamate,
tert-butyl (1R)-2-(4-(3-(4-cyanophenoxy)propyl)-1-piperazinyl)-1-methyl-2-oxoethylcarbamate,
tert-butyl 3-(4-(3-(4-cyano-3-fluorophenoxy)propyl)-1-piperazinyl)-3-oxopropylcarbamate,
tert-butyl (1R)-2-(4-(3-(4-(aminocarbonyl)-3-fluorophenoxy)propyl)-1-piperazinyl)-1-methyl-2-oxoethylcarbamate,
tert-butyl (1R)-2-(4-(3-(4-acetylphenoxy)propyl)-1-piperazinyl)-1-methyl-2-oxoethylcarbamate,
1-(4-(3-(4-((2R)-2-aminopropanoyl)-1-piperazinyl)propoxy)phenyl)ethanone,
N-((1R)-2-(4-(3-(4-acetylphenoxy)propyl)-1-piperazinyl)-1-methyl-2-oxoethyl)acetamide,
ethyl (1R)-2-(4-(3-(4-acetylphenoxy)propyl)-1-piperazinyl)-1-methyl-2-oxoethylcarbamate,
N-((1R)-2-(4-(3-(4-acetylphenoxy)propyl)-1-piperazinyl)-1-methyl-2-oxoethyl)cyclopropanecarboxamide,
tert-butyl (1R)-2-(4-((1R)-3-(4-acetylphenoxy)-1-methylpropyl)-1-piperazinyl)-1-methyl-2-oxoethylcarbamate,
tert-butyl (1S)-2-(4-(3-(4-acetylphenoxy)propyl)-1-piperazinyl)-1-methyl-2-oxoethylcarbamate,
tert-butyl (2R)-2-((4-(3-(4-acetylphenoxy)propyl)-1-piperazinyl)carbonyl)-1-pyrrolidinecarboxylate,
tert-butyl (2S)-2-((4-(3-(4-acetylphenoxy)propyl)-1-piperazinyl)carbonyl)-1-pyrrolidinecarboxylate,
N-((1R)-2-(4-(3-(4-acetylphenoxy)propyl)-1-piperazinyl)-1-methyl-2-oxoethyl)methanesulfonamide,
N'-((1R)-2-(4-(3-(4-acetylphenoxy)propyl)-1-piperazinyl)-1-methyl-2-oxoethyl)-N,N-dimethylsulfamide,
1-(4-(3-(4-((methylamino)acetyl)-1-piperazinyl)propoxy)phenyl)-1-hexanone,
tert-butyl 2-(4-(3-(4-hexanoylphenoxy)propyl)-1-piperazinyl)-2-oxoethylcarbamate,
1-(4-(3-(4-(3-aminopropanoyl)-1-piperazinyl)propoxy)phenyl)-1-hexanone,
1-(4-(3-(4-((2R)-2-aminopropanoyl)-1-piperazinyl)propoxy)phenyl)-1-hexanone,
tert-butyl (1S)-1-((4-(3-(4-hexanoylphenoxy)propyl)-1-piperazinyl)carbonyl)-2-methylpropylcarbamate,
1-(4-(3-(4-((2S)-2-amino-3-methylbutanoyl)-1-piperazinyl)propoxy)phenyl)-1-hexanone,
tert-butyl (1R)-1-((4-(3-(4-hexanoylphenoxy)propyl)-1-piperazinyl)carbonyl)-2-methylpropylcarbamate,
1-(4-(3-(4-((2R)-2-amino-3-methylbutanoyl)-1-piperazinyl)propoxy)phenyl)-1-hexanone,
tert-butyl (1S)-1-((4-(3-(4-hexanoylphenoxy)propyl)-1-piperazinyl)carbonyl)-3-methylbutylcarbamate,
1-(4-(3-(4-((2S)-2-amino-4-methylpentanoyl)-1-piperazinyl)propoxy)phenyl)-1-hexanone,
tert-butyl (1R)-1-((4-(3-(4-hexanoylphenoxy)propyl)-1-piperazinyl)carbonyl)-3-methylbutylcarbamate,
1-(4-(3-(4-((2R)-2-amino-4-methylpentanoyl)-1-piperazinyl)propoxy)phenyl)-1-hexanone,
tert-butyl (1S)-1-((benzyloxy)methyl)-2-(4-(3-(4-hexanoylphenoxy)propyl)-1-piperazinyl)-2-oxoethylcarbamate,
1-(4-(3-(4-((2R)-2-amino-3-hydroxypropanoyl)-1-piperazinyl)propoxy)phenyl)-1-hexanone,
1-(4-(3-(4-((2S)-2-amino-3-(benzyloxy)propanoyl)-1-piperazinyl)propoxy)phenyl)-1-hexanone,
tert-butyl (1S)-2-(4-(3-(4-hexanoylphenoxy)propyl)-1-piperazinyl)-2-oxo-1-(4-pyridinylmethyl)ethylcarbamate,
1-(4-(3-(4-((2S)-2-amino-3-(4-pyridinyl)propanoyl)-1-piperazinyl)propoxy)phenyl)-1-hexanone,
tert-butyl (1R)-2-(4-(3-(4-hexanoylphenoxy)propyl)-1-piperazinyl)-2-oxo-1-(4-pyridinylmethyl)ethylcarbamate,
1-(4-(3-(4-((2R)-2-amino-3-(4-pyridinyl)propanoyl)-1-piperazinyl)propoxy)phenyl)-1-hexanone,
tert-butyl (1S)-2-(4-(3-(4-hexanoylphenoxy)propyl)-1-piperazinyl)-1-(1H-imidazol-4-ylmethyl)-2-oxoethylcarbamate,
1-(4-(3-(4-((2S)-2-amino-3-(1H-imidazol-4-yl)propanoyl)-1-piperazinyl)propoxy)phenyl)-1-hexanone,
(4-(((3R)-3-(4-(3-aminopropanoyl)-1-piperazinyl)butyl)oxy)phenyl)(cyclopropyl)methanone,
tert-butyl (1R)-2-(4-((1R)-3-(4-(cyclopropylcarbonyl)phenoxy)-1-methylpropyl)-1-piperazinyl)-1-methyl-2-oxoethylcarbamate,
(4-(((3R)-3-(4-((2R)-2-aminopropanoyl)-1-piperazinyl)butyl)oxy)phenyl)(cyclopropyl)methanone,
tert-butyl (1R)-2-(4-((1S)-3-(4-(cyclopropylcarbonyl)phenoxy)-1-methylpropyl)-1-piperazinyl)-1-methyl-2-oxoethylcarbamate,
tert-butyl (1R)-2-(4-(3-(4-(cyclopropylcarbonyl)phenoxy)propyl)-1-piperazinyl)-1-methyl-2-oxoethylcarbamate,
cyclopropyl(4-(((3R)-3-(4-((methylamino)acetyl)-1-piperazinyl)butyl)oxy)phenyl)methanone,
(4-(3-(4-((2R)-2-amino-3,3-dimethylbutanoyl)-1-piperazinyl)propoxy)phenyl)(cyclopropyl)methanone,
tert-butyl (1R)-1-((4-(3-(4-(cyclopropylcarbonyl)phenoxy)propyl)-1-piperazinyl)carbonyl)-3,3-dimethylbutylcarbamate,
tert-butyl (1R)-1-((4-(3-(4-(cyclopropylcarbonyl)phenoxy)propyl)-1-piperazinyl)carbonyl)-3,3-dimethylbutylcarbamate,
(4-(3-(4-((2R)-2-aminobutanoyl)-1-piperazinyl)propoxy)phenyl)(cyclopropyl)methanone,
cyclopropyl(4-(3-(4-((2R)-2-(methylamino)-3-phenylpropanoyl)-1-piperazinyl)propoxy)phenyl)methanone,
(4-(3-(4-((2R, 3S)-2-amino-3-hydroxybutanoyl)-1-piperazinyl)propoxy)phenyl)(cyclopropyl)methanone,
benzyl (1R)-1-(tert-butoxymethyl)-2-(4-(3-(4-(cyclopropylcarbonyl)phenoxy)propyl)-1-piperazinyl)-2-oxoethylcarbamate,
(4-(3-(4-((2R)-2-amino-3-tert-butoxypropanoyl)-1-piperazinyl)propoxy)phenyl)(cyclopropyl)methanone,
tert-butyl (1R, 2S)-2-tert-butoxy-1-((4-(3-(4-(cyclopropylcarbonyl)phenoxy)propyl)-1-piperazinyl)carbonyl)propylcarbamate, (4-(3-(4-((2R)-2-amino-3-(benzyloxy)propanoyl)-1-piperazinyl)propoxy)phenyl)(cyclopropyl)methanone,
tert-butyl (1R,2S)-2-(benzyloxy)-1-((4-(3-(4-(cyclopropylcarbonyl)phenoxy)propyl-1-piperazinyl)carbonyl)propylcarbamate,
tert-butyl (1R)-5-((aminocarbonyl)amino)-1-((4-(3-(4-(cyclopropylcarbonyl)phenoxy)propyl)-1-piperazinyl)carbonyl)pentylcarbamate,
tert-butyl (1R)-4-((aminocarbonyl)amino)-1-((4-(3-(4-(cyclopropylcarbonyl)phenoxy)propyl)-1-piperazinyl)carbonyl)butylcarbamate,
tert-butyl (1R)-1-benzyl-2-(4-(3-(4-(cyclopropylcarbonyl)phenoxy)propyl)-1-piperazinyl)-2-oxoethylcarbamate,
tert-butyl (1R)-2-(4-(3-(4-(cyclopropylcarbonyl)phenoxy)propyl)-1-piperazinyl)-1-(4-fluorobenzyl)-2-oxoethylcarbamate,
(4-(3-(4-((2R)-2-amino-3-(4-fluorophenyl)propanoyl)-1-piperazinyl)propoxy)phenyl)(cyclopropyl)methanone,
(4R)-4-((4-(3-(4-(cyclopropylcarbonyl)phenoxy)propyl)-1-piperazinyl)carbonyl)-2-azetidinone,
(4S)-4-((4-(3-(4-(cyclopropylcarbonyl)phenoxy)propyl)-1-piperazinyl)carbonyl)-2-azetidinone,
tert-butyl (2S)-2-((4-(3-(4-(cyclopropylcarbonyl)phenoxy)propyl)-1-piperazinyl)carbonyl)-1-pyrrolidinecarboxylate,
cyclopropyl(4-(3-(4-((2S)-pyrrolidinylcarbonyl)-1-piperazinyl)propoxy)phenyl)methanone,
cyclopropyl(4-(3-(4-((2R)-pyrrolidinylacetyl)-1-piperazinyl)propoxy)phenyl)methanone,
(4-(3-(4-((2R)-2-amino-3-(2-thienyl)propanoyl)-1-piperazinyl)propoxy)phenyl)(cyclopropyl)methanone,
(4-(3-(4-((2R)-2-amino-3-(1-methyl-1H-imidazol-4-yl)propanoyl)-1-piperazinyl)propoxy)phenyl)(cyclopropyl)methanone,
tert-butyl (1R)-2-(4-(3-(4-(cyclopropylcarbonyl)phenoxy)propyl)-1-piperazinyl)-2-oxo-1-(1,3-thiazol-5-ylmethyl)ethylcarbamate,
1-((1S)-1-((4-(3-(4-(cyclopropylcarbonyl)phenoxy)propyl)-1-piperazinyl)carbonyl)-2-methylpropyl)tetrahydro-2(1H)-pyrimidinone,
tert-butyl (1S)-2-(4-(2-((4-cyano(1,1'-biphenyl)-4-yl)oxy)ethyl)-1-piperazinyl)-1-methyl-2-oxoethylcarbamate,
4'-(2-(4-((2S)-2-aminopropanoyl)-1-piperazinyl)ethoxy)(1,1'-biphenyl)-4-carbonitrile,
tert-butyl (1R)-2-(4-(2-((4-cyano(1,1'-biphenyl)-4-yl)oxy)ethyl)-1-piperazinyl)-1-methyl-2-oxoethylcarbamate,
4'-(2-(4-((2R)-2-aminopropanoyl)-1-piperazinyl)ethoxy)(1,1'-biphenyl)-4-carbonitrile,
4-(3-(4-(((tert-butoxycarbonyl)(methyl)amino)acetyl)-1-piperazinyl)propoxy)-4-cyano-1,1'-biphenyl
4'-(3-(4-((methylamino)acetyl)-1-piperazinyl)propoxy)(1,1'-biphenyl)-4-carbonitrile,
tert-butyl (1R)-2-(4-(2-((4-cyano(1,1'-biphenyl)-4-yl)oxy)ethyl)-1-piperazinyl)-1-methyl-2-oxoethyl(methyl)carbamate,
4'-(2-(4-((2R)-2-(methylamino)propanoyl)-1-piperazinyl)ethoxy)(1,1'-biphenyl)-4-carbonitrile,
tert-butyl (1R)-2-(4-(3-((4'-cyano( 1,1'-biphenyl)-4-yl)oxy)propyl)-1-piperazinyl)-1-methyl-2-oxoethylcarbamate,
4'-(3-(4-((2R)-2-aminopropanoyl)-1-piperazinyl)propoxy)(1,1'-biphenyl)-4-carbonitrile,
tert-butyl (1R)-2-(4-(3-((4-cyano(1,1'-biphenyl)-4-yl)oxy)propyl)-1-piperazinyl)-1-methyl-2-oxoethyl(methyl)carbamate,
4'-(3 -(4-((2R)-2-(methylamino)propanoyl)-1-piperazinyl)propoxy)(1,1'-biphenyl)-4-carbonitrile,
tert-butyl (1S)-2-(4-(3-((4'-cyano( 1,1'-biphenyl)-4-yl)oxy)propyl)-1-piperazinyl)-1-methyl-2-oxoethylcarbamate,
tert-butyl (2R)-2-((4-(2-((4-cyano(1,1'-biphenyl)-4-yl)oxy)ethyl)-1-piperazinyl)carbonyl)-1-pyrrolidinecarboxylate,
4'-(2-(4-((2R)-pyrrolidinylcarbonyl)-1-piperazinyl)ethoxy)(1,1'-biphenyl)-4-carbonitrile,
tert-butyl (2S)-2-((4-(2-((4'-cyano(1,1'-biphenyl)-4-yl)oxy)ethyl)-1-piperazinyl)carbonyl)-1-pyrrolidinecarboxylate,
tert-butyl (2R)-2-((4-(3-((4'-cyano(1,1'-biphenyl)-4-yl)oxy)propyl)-1-piperazinyl)carbonyl)-1-pyrrolidinecarboxylate,
4'-(3-(4-(aminoacetyl)-1-piperazinyl)propoxy)(1,1'-biphenyl)-4-carbonitrile,
4-(3-(4-(3-((tert-butoxycarbonyl)amino)propanoyl)-1-piperazinyl)propoxy)-4-cyano-1,1'-biphenyl
4'-(3-(4-(3-aminopropanoyl)-1-piperazinyl)propoxy)(1,1'-biphenyl)-4-carbonitrile,
N-(3 -(4-(3 -((4'-cyano(1,1'-biphenyl)-4-yl)oxy)propyl)-1-piperazinyl)-3-oxopropyl)-2,2-dimethylpropanamide,
N-(3 -(4-(3 -((4'-cyano(1,1'-biphenyl)-4-yl)oxy)propyl)-1-piperazinyl)-3-oxopropyl)-3,3-dimethylbutanamide,
N-(3-(4-(3-((4'-cyano(1,1'-biphenyl)-4-yl)oxy)propyl)-1-piperazinyl)-3-oxopropyl)cyclopropanecarboxamide,
N-(3-(4-(3-((4'-cyano( 1,1'-biphenyl)-4-yl)oxy)propyl)-1-piperazinyl)-3-oxopropyl)-4-morpholinecarboxamide,
tert-butyl 3-(4-(3 -(4-(cyclopropylcarbonyl)phenoxy)propyl)-1,4-diazepan-1-yl)-3-oxopropylcarbamate,
tert-butyl (1R)-2-(4-(3-(4-(cyclopropylcarbonyl)phenoxy)propyl)-1,4-diazepan-1-yl)-1-methyl-2-oxoethylcarbamate,
(4-(3-(4-((2S)-2-aminopropanoyl)-1,4-diazepan-1-yl)propoxy)phenyl)(cyclopropyl)methanone,
4'-(3-(4-((2R)-2-aminopropanoyl)-1,4-diazepan-1-yl)propoxy)(1,1'-biphenyl)-4-carbonitrile,
tert-butyl (1S)-2-(4-(3-((4'-cyano( 1,1'-biphenyl)-4-yl)oxy)propyl)-1,4-diazepan-1-yl)-1-methyl-2-oxoethylcarbamate,
tert-butyl (1R)-1-((4-(3-(4-(cyclopropylcarbonyl)phenoxy)propyl)-1,4-diazepan-1-yl)carbonyl)propylcarbamate,
(4-(3-(4-((2R)-2-aminobutanoyl)-1,4-diazepan-1-yl)propoxy)phenyl)(cyclopropyl)methanone,
4'-(3-(4-((2R)-2-aminobutanoyl)-1,4-diazepan-1-yl)propoxy)( 1,1'-biphenyl)-4-carbonitrile,
tert-butyl (2S)-2-(2-(4-(3 -(4-(cyclopropylcarbonyl)phenoxy)propyl)-1,4-diazepan-1-yl)-2-oxoethyl)-1-pyrrolidinecarboxylate,
cyclopropyl(4-(3-(4-((2S)-pyrrolidinylacetyl)-1,4-diazepan-1-yl)propoxy)phenyl)methanone,
tert-butyl (2S)-2-(2-(4-(3-((4-cyano( 1,1'-biphenyl)-4-yl)oxy)propyl)-1,4-diazepan-1-yl)-2-oxoethyl)-1-pyrrolidinecarboxylate,
N-((1R)-2-(4-(3-(4-(cyclopropylcarbonyl)phenoxy)propyl)-1-piperazinyl)-1-methyl-2-oxoethyl)-2-furamide,
N-((1R)-2-(4-(3-(4-(cyclopropylcarbonyl)phenoxy)propyl)-1-piperazinyl)-1-methyl-2-oxoethyl)-2-thiophenecarboxamide,
(4-(3-(4-(((1S, 2R)-2-aminocyclopropyl)carbonyl)-1-piperazinyl)propoxy)phenyl)(cyclopropyl)methanone,
(2R)-N-((1R)-2-(4-(3-(4-(cyclopropylcarbonyl)phenoxy)propyl)-1-piperazinyl)-1-methyl-2-oxoethyl)-2-pyrrolidinecarboxamide,
(4-(3-(4-((2-aminocyclopentyl)carbonyl)-1-piperazinyl)propoxy)phenyl)(cyclopropyl)methanone,
(4-(3-(4-((2R)-azetidinylcarbonyl)-1-piperazinyl)propoxy)phenyl)(cyclopropyl)methanone,
(4-(((3R)-3-(4-((2R)-2-aminobutanoyl)-1-piperazinyl)butyl)oxy)phenyl)(cyclopropyl)methanone,
(4-(((3R)-3-(4-((2R)-2-aminopentanoyl)-1-piperazinyl)butyl)oxy)phenyl)(cyclopropyl)methanone, tert-butyl 3-((4-(3-(4-(cyclopropylcarbonyl)phenoxy) propyl)-1-piperazinyl)carbonyl)-1-azetidinecarboxylate, tert-butyl 4-(4-(3-(4-(cyclopropylcarbonyl)phenoxy) propyl)-1-piperazinyl)-4-oxobutylcarbamate, tert-butyl (1R)-2-(4-((3S)-3-(4-(cyclopropylcarbonyl) phenoxy)-3-phenylpropyl)-1-piperazinyl)-1-methyl-2-oxoethylcarbamate, N-((1R)-2-(4-(3-((4-cyano(1,1'-biphenyl)-4-yl)oxy)propyl)-1,4-diazepan-1-yl)-2-oxo-1-(1,3-thiazol-4-ylmethyl) ethyl)-2-furamide, (4-(3-(4-((2R)-2-aminopropanoyl)-1-piperazinyl)propoxy) phenyl)(cyclopropyl)methanone, cyclopropyl(4-(3 -(4-((2R)-2-(isopropylamino)propanoyl)-1-piperazinyl)propoxy)phenyl)methanone, 4'-(2-(4-((2S)-pyrrolidinylcarbonyl)-1-piperazinyl)ethoxy) (1,1'-biphenyl)-4-carbonitrile, N-((1S)-2-(4-(3-(3-fluoro-4-( 1,2,4-oxadiazol-3-yl) phenoxy)propyl)-1,4-diazepan-1-yl)-1-methyl-2-oxoethyl)-2-furamide, N-((1S)-2-(4-(3-(3-fluoro-4-(5-methyl-1,2,4-oxadiazol-3-yl)phenoxy)propyl)-1,4-diazepan-1-yl)-1-methyl-2-oxoethyl)-2-furamide, N-((1S)-2-(4-(3-(4-(5-ethyl-1,2,4-oxadiazol-3-yl)-3-fluorophenoxy)propyl)-1,4-diazepan-1-yl)-1-methyl-2-oxoethyl)-2-furamide, N-((1S)-2-(4-(3-(3 -fluoro-4-(5-isopropyl-1,2,4-oxadiazol-3-yl)phenoxy)propyl)-1,4-diazepan-1-yl)-1-methyl-2-oxoethyl)-2-furamide, N-((1S)-2-(4-(3-(3-fluoro-4-(5-propyl-1,2,4-oxadiazol-3-yl) phenoxy)propyl)-1,4-diazepan-1-yl)-1-methyl-2-oxoethyl)-2-furamide, N-((1S)-2-(4-(3 -(3-fluoro-4-(5-isobutyl-1,2,4-oxadiazol-3-yl)phenoxy)propyl)-1,4-diazepan-1-yl)-1-methyl-2-oxoethyl)-2-furamide, N-((1S)-2-(4-(3-(4-(5-tert-butyl-1,2,4-oxadiazol-3-yl)-3-fluorophenoxy)propyl)-1,4-diazepan-1-yl)-1-methyl-2-oxoethyl)-2-furamide, N-((1S)-2-(4-(3 -(4-(5-butyl-1,2,4-oxadiazol-3-yl)-3-fluorophenoxy)propyl)-1,4-diazepan-1-yl)-1-methyl-2-oxoethyl)-2-furamide, N-((1S)-2-(4-(3-(3 -fluoro-4-(5-isopentyl-1,2,4-oxadiazol-3-yl)phenoxy)propyl)-1,4-diazepan-1-yl)-1-methyl-2-oxoethyl)-2-furamide, N-((1S)-2-(4-(3-(3 -fluoro-4-(5-neopentyl-1,2,4-oxadiazol-3 -yl)phenoxy)propyl)-1,4-diazepan-1-yl)-1-methyl-2-oxoethyl)-2-furamide, N-(( 1S)-2-(4-(3 -(4-(5-(1-ethylpropyl)-1,2,4-oxadiazol-3-yl)-3-fluorophenoxy)propyl)-1,4-diazepan-1-yl)-1-methyl-2-oxoethyl)-2-furamide, N-((1S)-2-(4-(3-(3-fluoro-4-(5-(methoxymethyl)-1,2,4-oxadiazol-3-yl)phenoxy)propyl)-1,4-diazepan-1-yl)-1-methyl-2-oxoethyl)-2-furamide, N-((1S)-2-(4-(3-(3-fluoro-4-(5-(isopropoxymethyl)-1,2,4-oxadiazol-3-yl)phenoxy)propyl)-1,4-diazepan-1-yl)-1-methyl-2-oxoethyl)-2-furamide, N-((1S)-2-(4-(3-(3-fluoro-4-(5-((2-methoxyethoxy) methyl)-1,2,4-oxadiazol-3-yl)phenoxy)propyl)-1,4-diazepan-1-yl)-1-methyl-2-oxoethyl)-2-furamide, N-((1S)-2-(4-(3-(3-fluoro-4-(5-tetrahydro-2-furanyl-1,2,4-oxadiazol-3-yl)phenoxy)propyl)-1,4-diazepan-1-yl)-1-methyl-2-oxoethyl)-2-furamide, N-((1S)-2-(4-(3-(3-fluoro-4-(5-tetrahydro-3-furanyl-1,2,4-oxadiazol-3-yl)phenoxy)propyl)-1,4-diazepan-1-yl)-1-methyl-2-oxoethyl)-2-furamide, N-((1S)-2-(4-(3-(3-fluoro-4-(5-(trifluoromethyl)-1,2,4-oxadiazol-3-yl)phenoxy)propyl)-1,4-diazepan-1-yl)-1-methyl-2-oxoethyl)-2-furamide, N-((1S)-2-(4-(3-(4-(5-cyano-1,2,4-oxadiazol-3-yl)-3-fluorophenoxy)propyl)-1,4-diazepan-1-yl)-1-methyl-2-oxoethyl)-2-furamide, N-((1S)-2-(4-(3-(4-(5-cyclopropyl-1,2,4-oxadiazol-3-yl)-3-fluorophenoxy)propyl)-1,4-diazepan-1-yl)-1-methyl-2-oxoethyl)-2-furamide, N-((1S)-2-(4-(3-(4-(5-(cyclopropylmethyl)-1,2,4-oxadiazol-3-yl)-3-fluorophenoxy)propyl)-1,4-diazepan-1-yl)-1-methyl-2-oxoethyl)-2-furamide, N-((1S)-2-(4-(3-(4-(5-cyclobutyl-1,2,4-oxadiazol-3-yl)-3-fluorophenoxy)propyl)-1,4-diazepan-1-yl)-1-methyl-2-oxoethyl)-2-furamide, N-((1S)-2-(4-(3-(4-(5 -cyclopentyl-1,2,4-oxadiazol-3-yl)-3-fluorophenoxy)propyl)-1,4-diazepan-1-yl)-1-methyl-2-oxoethyl)-2-furamide, N-((1S)-2-(4-(3-(4-(5-(cyclopentylmethyl)-1,2,4-oxadiazol-3-yl)-3-fluorophenoxy)propyl)-1,4-diazepan-1-yl)-1-methyl-2-oxoethyl)-2-furamide, N-((1S)-2-(4-(3-(4-(5-cyclohexyl-1,2,4-oxadiazol-3-yl)-3-fluorophenoxy)propyl)-1,4-diazepan-1-yl)-1-methyl-2-oxoethyl)-2-furamide, N-((1S)-2-(4-(3-(4-(5-(cyclohexylmethyl)-1,2,4-oxadiazol-3-yl)-3-fluorophenoxy)propyl)-1,4-diazepan-1-yl)-1-methyl-2-oxoethyl)-2-furamide, N-((1S)-2-(4-(3-(4-(5-((dimethylamino)methyl)-1,2,4-oxadiazol-3-yl)-3-fluorophenoxy)propyl)-1,4-diazepan-1-yl)-1-methyl-2-oxoethyl)-2-furamide, N-((1S)-2-(4-(3-(4-(5-(2-(dimethylamino)ethyl)-1,2,4-oxadiazol-3-yl)-3-fluorophenoxy)propyl)-1,4-diazepan-1-yl)-1-methyl-2-oxoethyl)-2-furamide, N-((1S)-2-(4-(3-(3-fluoro-4-(5-(1-pyrrolidinylmethyl)-1,2, 4-oxadiazol-3-yl)phenoxy)propyl)-1,4-diazepan-1-yl)-1-methyl-2-oxoethyl)-2-furamide, N-((1S)-2-(4-(3-(3-fluoro-4-(5-(2-(1-pyrrolidinyl)ethyl)-1, 2,4-oxadiazol-3-yl)phenoxy)propyl)-1,4-diazepan-1-yl)-1-methyl-2-oxoethyl)-2-furamide, N-((1S)-2-(4-(3-(3-fluoro-4-(5-(1-piperidinylmethyl)-1,2,4-oxadiazol-3-yl)phenoxy)propyl)-1,4-diazepan-1-yl)-1-methyl-2-oxoethyl)-2-furamide, N-((1S)-2-(4-(3-(3-fluoro-4-(5-(2-(1-piperidinyl)ethyl)-1,2, 4-oxadiazol-3-yl)phenoxy)propyl)-1,4-diazepan-1-yl)-1-methyl-2-oxoethyl)-2-furamide, N-((1S)-2-(4-(3-(3-fluoro-4-(5-(4-morpholinylmethyl)-1,2, 4-oxadiazol-3-yl)phenoxy)propyl)-1,4-diazepan-1-yl)-1-methyl-2-oxoethyl)-2-furamide, N-((1S)-2-(4-(3-(3-fluoro-4-(5-(2-(4-morpholinyl)ethyl)-1, 2,4-oxadiazol-3-yl)phenoxy)propyl)-1,4-diazepan-1-yl)-1-methyl-2-oxoethyl)-2-furamide, N-((1S)-2-(4-(3-(4-(5-(tert-butoxymethyl)-1,2,4-oxadiazol-3-yl)-3-fluorophenoxy)propyl)-1,4-diazepan-1-yl)-1-methyl-2-oxoethyl)-2-furamide, N-((1S)-2-(4-(3-(4-(5-(2-tert-butoxyethyl)-1,2,4-oxadiazol-3-yl)-3-fluorophenoxy)propyl)-1,4-diazepan-1-yl)-1-methyl-2-oxoethyl)-2-furamide, tert-butyl 3-(2-fluoro-4-(3-(4-((2S)-2-(2-furoylamino) propanoyl)-1,4-diazepan-1-yl)propoxy)phenyl)-1,2,4-oxadiazole-5-carboxylate, tert-butyl (3-(2-fluoro-4-(3-(4-((2S)-2-(2-furoylamino) propanoyl)-1,4-diazepan-1-yl)propoxy)phenyl)-1,2,4-oxadiazol-5-yl)acetate, N-((1S)-2-(4-(3-(4-(5 -((1S)-1-aminoethyl)-1,2,4-oxadiazol-3-yl)-3-fluorophenoxy)propyl)-1,4-diazepan-1-yl)-1-methyl-2-oxoethyl)-2-furamide, N-((1S)-2-(4-(3-(4-(5-((1S)-1-amino-2-methylpropyl)-1,2, 4-oxadiazol-3-yl)-3-fluorophenoxy)propyl)-1,4-diazepan-1-yl)-1-methyl-2-oxoethyl)-2-furamide, N-((1S)-2-(4-(3-(4-(5-((1S)-1-amino-3-methylbutyl)-1,2,4-oxadiazol-3-yl)-3-fluorophenoxy)propyl)-1,4-diazepan-1-yl)-1-methyl-2-oxoethyl)-2-furamide, N-((1S)-2-(4-(3-(3-fluoro-4-(5-((2S)-pyrrolidinyl)-1,2,4-oxadiazol-3-yl)phenoxy)propyl)-1,4-diazepan-1-yl)-1-methyl-2-oxoethyl)-2-furamide,
N-((1S)-2-(4-(3-(4-(5-((1S)-1-amino-2-phenylethyl)-1,2,4-oxadiazol-3-yl)-3-fluorophenoxy)propyl)-1,4-diazepan-1-yl)-1-methyl-2-oxoethyl)-2-furamide,
N-((1S)-2-(4-(3-(4-(5-((1S)-1-amino-2-(1H-indol-3-yl)ethyl)-1,2,4-oxadiazol-3-yl)-3-fluorophenoxy)propyl)-1,4-diazepan-1-yl)-1-methyl-2-oxoethyl)-2-furamide,
N-((1S)-2-(4-(3-(4-(5-((1S)-1-amino-2-hydroxyethyl)-1,2,4-oxadiazol-3-yl)-3-fluorophenoxy)propyl)-1,4-diazepan-1-yl)-1-methyl-2-oxoethyl)-2-furamide,
N-((1S)-2-(4-(3-(4-(5-((1S)-1-amino-2-(4-hydroxyphenyl)ethyl)-1,2,4-oxadiazol-3-yl)-3-fluorophenoxy)propyl)-1,4-diazepan-1-yl)-1-methyl-2-oxoethyl)-2-furamide,
N-((1S)-2-(4-(3-(4-(5-((1R)-1-aminoethyl)-1,2,4-oxadiazol-3-yl)-3-fluorophenoxy)propyl)-1,4-diazepan-1-yl)-1-methyl-2-oxoethyl)-2-furamide,
N-((1S)-2-(4-(3-(4-(5-((1R)-1-amino-2-phenylethyl)-1,2,4-oxadiazol-3-yl)-3-fluorophenoxy)propyl)-1,4-diazepan-1-yl)-1-methyl-2-oxoethyl)-2-furamide,
N-((1S)-2-(4-(3-(3-fluoro-4-(5-(2-furyl)-1,2,4-oxadiazol-3-yl)phenoxy)propyl)-1,4-diazepan-1-yl)-1-methyl-2-oxoethyl)-2-furamide,
N-((1S)-2-(4-(3-(3-fluoro-4-(5-(3-furyl)-1,2,4-oxadiazol-3-yl)phenoxy)propyl)-1,4-diazepan-1-yl)-1-methyl-2-oxoethyl)-2-furamide,
N-((1S)-2-(4-(3-(3-fluoro-4-(5-(2-thienyl)-1,2,4-oxadiazol-3-yl)phenoxy)propyl)-1,4-diazepan-1-yl)-1-methyl-2-oxoethyl)-2-furamide,
N-((1S)-2-(4-(3-(3-fluoro-4-(5-(3-thienyl)-1,2,4-oxadiazol-3-yl)phenoxy)propyl)-1,4-diazepan-1-yl)-1-methyl-2-oxoethyl)-2-furamide,
N-((1S)-2-(4-(3-(3-fluoro-4-(5-(1H-pyrrol-2-yl)-1,2,4-oxadiazol-3-yl)phenoxy)propyl)-1,4-diazepan-1-yl)-1-methyl-2-oxoethyl)-2-furamide,
N-((1S)-2-(4-(3-(3-fluoro-4-(5-(1H-pyrrol-3-yl)-1,2,4-oxadiazol-3-yl)phenoxy)propyl)-1,4-diazepan-1-yl)-1-methyl-2-oxoethyl)-2-furamide,
N-((1S)-2-(4-(3-(3-fluoro-4-(5-(1,3-oxazol-4-yl)-1,2,4-oxadiazol-3-yl)phenoxy)propyl)-1,4-diazepan-1-yl)-1-methyl-2-oxoethyl)-2-furamide,
N-((1S)-2-(4-(3-(3-fluoro-4-(5-(1,3-thiazol-2-yl)-1,2,4-oxadiazol-3-yl)phenoxy)propyl)-1,4-diazepan-1-yl)-1-methyl-2-oxoethyl)-2-furamide,
N-((1S)-2-(4-(3-(3-fluoro-4-(5-(1H-imidazol-4-yl)-1,2,4-oxadiazol-3-yl)phenoxy)propyl)-1,4-diazepan-1-yl)-1-methyl-2-oxoethyl)-2-furamide,
N-((1S)-2-(4-(3-(3-fluoro-4-(5-(1H-pyrazol-4-yl)-1,2,4-oxadiazol-3-yl)phenoxy)propyl)-1,4-diazepan-1-yl)-1-methyl-2-oxoethyl)-2-furamide,
N-((1S)-2-(4-(3-(3-fluoro-4-(5-(5-isoxazolyl)-1,2,4-oxadiazol-3-yl)phenoxy)propyl)-1,4-diazepan-1-yl)-1-methyl-2-oxoethyl)-2-furamide,
N-((1S)-2-(4-(3-(3-fluoro-4-(5-(2-pyridinyl)-1,2,4-oxadiazol-3-yl)phenoxy)propyl)-1,4-diazepan-1-yl)-1-methyl-2-oxoethyl)-2-furamide,
N-((1S)-2-(4-(3-(3-fluoro-4-(5-(2-pyridinylmethyl)-1,2,4-oxadiazol-3-yl)phenoxy)propyl)-1,4-diazepan-1-yl)-1-methyl-2-oxoethyl)-2-furamide,
N-((1S)-2-(4-(3-(3-fluoro-4-(5-(3-pyridinyl)-1,2,4-oxadiazol-3-yl)phenoxy)propyl)-1,4-diazepan-1-yl)-1-methyl-2-oxoethyl)-2-furamide,
N-((1S)-2-(4-(3-(3-fluoro-4-(5-(3-pyridinylmethyl)-1,2,4-oxadiazol-3-yl)phenoxy)propyl)-1,4-diazepan-1-yl)-1-methyl-2-oxoethyl)-2-furamide,
N-((1S)-2-(4-(3-(3-fluoro-4-(5-(4-pyridinyl)-1,2,4-oxadiazol-3-yl)phenoxy)propyl)-1,4-diazepan-1-yl)-1-methyl-2-oxoethyl)-2-furamide,
N-((1S)-2-(4-(3-(3-fluoro-4-(5-(4-pyridinylmethyl)-1,2,4-oxadiazol-3-yl)phenoxy)propyl)-1,4-diazepan-1-yl)-1-methyl-2-oxoethyl)-2-furamide,
N-((1S)-2-(4-(3-(3-fluoro-4-(5-(4-pyridazinyl)-1,2,4-oxadiazol-3-yl)phenoxy)propyl)-1,4-diazepan-1-yl)-1-methyl-2-oxoethyl)-2-furamide,
N-((1S)-2-(4-(3-(3-fluoro-4-(5-(4-pyrimidinyl)-1,2,4-oxadiazol-3-yl)phenoxy)propyl)-1,4-diazepan-1-yl)-1-methyl-2-oxoethyl)-2-furamide,
N-((1S)-2-(4-(3-(3-fluoro-4-(5-(2-pyrazinyl)-1,2,4-oxadiazol-3-yl)phenoxy)propyl)-1,4-diazepan-1-yl)-1-methyl-2-oxoethyl)-2-furamide,
N-((1S)-2-(4-(3-(4-(5-benzyl-1,2,4-oxadiazol-3-yl)-3-fluorophenoxy)propyl)-1,4-diazepan-1-yl)-1-methyl-2-oxoethyl)-2-furamide,
N-((1S)-2-(4-(3-(4-(5-benzyl-1,2,4-oxadiazol-3-yl)-3-fluorophenoxy)propyl)-1,4-diazepan-1-yl)-1-methyl-2-oxoethyl)-2-furamide,
N-((1S)-2-(4-(3-(3-fluoro-4-(5-(2-phenylethyl)-1,2,4-oxadiazol-3-yl)phenoxy)propyl)-1,4-diazepan-1-yl)-1-methyl-2-oxoethyl)-2-furamide,
N-((1S)-2-(4-(3-(3-fluoro-4-(5-(6-quinolinyl)-1,2,4-oxadiazol-3-yl)phenoxy)propyl)-1,4-diazepan-1-yl)-1-methyl-2-oxoethyl)-2-furamide,
N-((1S)-2-(4-(3-(4-(5-(1,3-benzothiazol-6-yl)-1,2,4-oxadiazol-3-yl)-3-fluorophenoxy)propyl)-1,4-diazepan-1-yl)-1-methyl-2-oxoethyl)-2-furamide,
N-((1S)-2-(4-(3-(4-(5-(1,3-benzoxazol-4-yl)-1,2,4-oxadiazol-3-yl)-3-fluorophenoxy)propyl)-1,4-diazepan-1-yl)-1-methyl-2-oxoethyl)-2-furamide,
N-((1S)-2-(4-(3-(4-(5 -(1H-benzimidazol-6-yl)-1,2,4-oxadiazol-3-yl)-3-fluorophenoxy)propyl)-1,4-diazepan-1-yl)-1-methyl-2-oxoethyl)-2-furamide,
N-((1S)-2-(4-(3-(3-fluoro-4-(5-(1H-indol-6-yl)-1,2,4-oxadiazol-3-yl)phenoxy)propyl)-1,4-diazepan-1-yl)-1-methyl-2-oxoethyl)-2-furamide,
tert-butyl 3-(3-(4-acetylphenoxy)propyl)-3,8-diazabicyclo(3.2.1)octane-8-carboxylate,
tert-butyl 3-(3-(4-(cyclopropylcarbonyl)phenoxy)propyl)-3,8-diazabicyclo(3.2.1)octane-8-carboxylate,
tert-butyl (1R)-2-(3-(3-(4-(cyclopropylcarbonyl)phenoxy)propyl)-3,8-diazabicyclo(3.2.1)oct-8-yl)-1-methyl-2-oxoethylcarbamate,
(4-(3-(8-((2R)-2-aminopropanoyl)-3,8-diazabicyclo(3.2.1)oct-3-yl)propoxy)phenyl)(cyclopropyl)methanone,
tert-butyl (1S, 4S)-5-(3-(4-acetylphenoxy)propyl)-2,5-diazabicyclo(2.2.1)heptane-2-carboxylate,
tert-butyl (1R, 4R)-5-(3-(4-(cyclopropylcarbonyl)phenoxy)propyl)-2,5-diazabicyclo(2.2.1)heptane-2-carboxylate,
tert-butyl (1S, 4S)-5-(3-(4-(cyclopropylcarbonyl)phenoxy)propyl)-2,5-diazabicyclo(2.2.1)heptane-2-carboxylate,
cyclopropyl(4-(3-((1R, 4R)-2,5-diazabicyclo(2.2.1)hept-2-yl)propoxy)phenyl)methanone,
cyclopropyl(4-(3-((1S, 4S)-2,5-diazabicyclo(2.2.1)hept-2-yl)propoxy)phenyl)methanone,
cyclopropyl(4-(3-((1S,4S)-5-(cyclopropylcarbonyl)-2,5-diazabicyclo(2.2.1)hept-2-yl)propoxy)phenyl)methanone,
4'-(2-((1R, 4R)-5-((4-methylphenyl)sulfonyl)-2,5-diazabicyclo(2.2.1)hept-2-yl)ethoxy)(1,1'-biphenyl)-4-carbonitrile,
4'-(3-((1R, 4R)-5 -((4-methylphenyl)sulfonyl)-2,5-diazabicyclo(2.2.1)hept-2-yl)propoxy)(1,1'-biphenyl)-4-carbonitrile,
tert-butyl (1R)-2-((1R, 4R)-5-(3-(4-(cyclopropylcarbonyl)phenoxy)propyl)-2,5-diazabicyclo(2.2.1)hept-2-yl)-1-methyl-2-oxoethylcarbamate, (4-(3-((1R, 4R)-5-((2R)-2-aminopropanoyl)-2,5-diazabicyclo(2.2.1)hept-2-yl)propoxy)phenyl)(cyclopropyl)methanone,
tert-butyl (1R)-2-((1S, 4S)-5-(3-(4-(cyclopropylcarbonyl)phenoxy)propyl)-2,5-diazabicyclo(2.2.1)hept-2-yl)-1-methyl-2-oxoethylcarbamate,
tert-butyl (1S)-2-((1S, 4S)-5-(3-(4-(cyclopropylcarbonyl)phenoxy)propyl)-2,5-diazabicyclo(2.2.1)hept-2-yl)-1-methyl-2-oxoethylcarbamate,
tert-butyl 3-((1S, 4S)-5-(3-(4-(cyclopropylcarbonyl)phenoxy)propyl)-2,5-diazabicyclo(2.2.1)hept-2-yl)-3-oxopropylcarbamate,
cyclopropyl(4-(3-((1S, 4S)-5-(ethylsulfonyl)-2,5-diazabicyclo(2.2.1)hept-2-yl)propoxy)phenyl)methanone,
cyclopropyl(4-(3-((1S, 4S)-5-(4-morpholinylcarbonyl)-2,5-diazabicyclo(2.2.1)hept-2-yl)propoxy)phenyl)methanone,
(1S, 4S)-5-(3-(4-(cyclopropylcarbonyl)phenoxy)propyl)-N,N-dimethyl-2,5-diazabicyclo(2.2.1)heptane-2-sulfonamide,
cyclopentyl (1S, 4S)-5-(3-(4-(cyclopropylcarbonyl)phenoxy)propyl)-2,5-diazabicyclo(2.2.1)heptane-2-carboxylate,
(1S, 4S)-5-(3-(4-(cyclopropylcarbonyl)phenoxy)propyl)-N,N-dimethyl-2,5-diazabicyclo(2.2.1)heptane-2-carboxamide,
ethyl (1S, 4S)-5-(3-(4-(cyclopropylcarbonyl)phenoxy)propyl)-2,5-diazabicyclo(2.2.1)heptane-2-carboxylate,
(4-(3-((1S, 4S)-5-(cyclobutylcarbonyl)-2,5-diazabicyclo(2.2.1)hept-2-yl)propoxy)phenyl)(cyclopropyl)methanone,
cyclopropyl(4-(3-((1S, 4S)-5-(3,3-dimethylbutanoyl)-2,5-diazabicyclo(2.2.1)hept-2-yl)propoxy)phenyl)methanone,
(4-(3-((1S, 4S)-5-(cyclohexylcarbonyl)-2,5-diazabicyclo(2.2.1)hept-2-yl)propoxy)phenyl)(cyclopropyl)methanone,
cyclopropyl(4-(3-((1S, 4S)-5-(4-fluorobenzoyl)-2,5-diazabicyclo(2.2.1)hept-2-yl)propoxy)phenyl)methanone,
cyclopropyl(4-(3-((1S, 4S)-5-(2-thienylcarbonyl)-2,5-diazabicyclo(2.2.1)hept-2-yl)propoxy)phenyl)methanone,
cyclopropyl(4-(3-((1S, 4S)-5-(2-furoyl)-2,5-diazabicyclo(2.2.1)hept-2-yl)propoxy)phenyl)methanone,
(4-(3-((1S, 4S)-5-benzoyl-2,5-diazabicyclo(2.2.1)hept-2-yl)propoxy)phenyl)(cyclopropyl)methanone,
(1S, 4S)-5-(3-(4-(cyclopropylcarbonyl)phenoxy)propyl)-N-methyl-N-phenyl-2,5-diazabicyclo(2.2.1)heptane-2-carboxamide,
cyclopropyl(4-(3-((1S, 4S)-5-(phenylsulfonyl)-2,5-diazabicyclo(2.2.1)hept-2-yl)propoxy)phenyl)methanone,
4-fluorophenyl (1S, 4S)-5-(3-(4-(cyclopropylcarbonyl)phenoxy)propyl)-2,5-diazabicyclo(2.2.1)heptane-2-carboxylate,
cyclopropyl(4-(3-((1S, 4S)-5-(2-pyridinylcarbonyl)-2,5-diazabicyclo(2.2.1)hept-2-yl)propoxy)phenyl)methanone,
(4-(3-((1S, 4S)-5-((2R)-2-aminopropanoyl)-2,5-diazabicyclo(2.2.1)hept-2-yl)propoxy)phenyl)(cyclopropyl)methanone, and
(4-(3-((1S,4S)-5-(3-aminopropanoyl)-2,5-diazabicyclo(2.2.1)hept-2-yl)propoxy)phenyl)(cyclopropyl)methanone.
4'-(4-(1,4-diazepan-1-yl)-1-butynyl)(1,1'-biphenyl)-4-carbonitrile,
N-((1R)-2-(4-(4-(4-(cyclopropylcarbonyl)phenyl)-3-butynyl)-1-piperazinyl)-1-methyl-2-oxoethyl)-2-furamide,
N-((1R)-2-(4-(4-(4-cyano(1,1'-biphenyl)-4-yl)-3-butynyl)-1,4-diazepan-1-yl)-1-methyl-2-oxoethyl)-2-furamide,
tert-butyl 4-(4-(4-cyano(1,1'-biphenyl)-4-yl)-3-butynyl)-1,4-diazepane-1-carboxylate,
tert-butyl 4-(4-(4-(cyclopropylcarbonyl)phenyl)-3-butynyl)-1-piperazinecarboxylate hydrochloride,
Preferred compounds of the instant invention include
(4-(3-(4-((2S)-2-aminopropanoyl)-1-piperazinyl)propoxy)phenyl)(cyclopropyl)methanone,
(2S)-1-(4-(3-(4-(5-methyl-1,2,4-oxadiazol-3-yl)phenoxy)propyl)-1-piperazinyl)-1-oxo-2-propanamine,
tert-butyl 2-(4-(3-(4-bromophenoxy)propyl)-1-piperazinyl)-2-oxoethylcarbamate,
2-(4-(3-(4-bromophenoxy)propyl)-1-piperazinyl)-2-oxoethanamine,
tert-butyl 3-(4-(3-(4-bromophenoxy)propyl)-1-piperazinyl)-3-oxopropylcarbamate,
3-(4-(3-(4-bromophenoxy)propyl)-1-piperazinyl)-3-oxo-1-propanamine,
tert-butyl (1R)-2-(4-(3-(4-bromophenoxy)propyl)-1-piperazinyl)-1-methyl-2-oxoethylcarbamate,
(2R)-1-(4-(3-(4-bromophenoxy)propyl)-1-piperazinyl)-1-oxo-2-propanamine,
tert-butyl (1S)-2-(4-(3-(4-bromophenoxy)propyl)-1-piperazinyl)-1-methyl-2-oxoethylcarbamate,
(2S)-1-(4-(3-(4-bromophenoxy)propyl)-1-piperazinyl)-1-oxo-2-propanamine,
tert-butyl (2S)-2-((4-(3-(4-bromophenoxy)propyl)-1-piperazinyl)carbonyl)-1-pyrrolidinecarboxylate,
4-bromophenyl 3-(4-((2S)-pyrrolidinylcarbonyl)-1-piperazinyl)propyl ether
tert-butyl (2R)-2-((4-(3-(4-bromophenoxy)propyl)-1-piperazinyl)carbonyl)-1-pyrrolidinecarboxylate,
4-bromophenyl 3-(4-((2R)-pyrrolidinylcarbonyl)-1-piperazinyl)propyl ether
tert-butyl (1R)-1-methyl-2-oxo-2-(4-(3-(4-(trifluoromethyl)phenoxy)propyl)-piperazinyl)ethylcarbamate,
tert-butyl (1R)-2-(4-(3-(4-cyanophenoxy)propyl)-1-piperazinyl)-1-methyl-2-oxoethylcarbamate,
tert-butyl 3-(4-(3-(4-cyano-3-fluorophenoxy)propyl)-1-piperazinyl)-3-oxopropylcarbamate,
tert-butyl (1R)-2-(4-(3-(4-(aminocarbonyl)-3-fluorophenoxy)propyl)-1-piperazinyl)-1-methyl-2-oxoethylcarbamate,
tert-butyl (1R)-2-(4-(3-(4-acetylphenoxy)propyl)-1-piperazinyl)-1-methyl-2-oxoethylcarbamate,
1-(4-(3-(4-((2R)-2-aminopropanoyl)-1-piperazinyl)propoxy)phenyl)ethanone,
N-((1R)-2-(4-(3-(4-acetylphenoxy)propyl)-1-piperazinyl)-1-methyl-2-oxoethyl)acetamide,
ethyl (1R)-2-(4-(3-(4-acetylphenoxy)propyl)-1-piperazinyl)-1-methyl-2-oxoethylcarbamate,
N-((1R)-2-(4-(3-(4-acetylphenoxy)propyl)-1-piperazinyl)-1-methyl-2-oxoethyl)cyclopropanecarboxamide,
tert-butyl (1R)-2-(4-((1R)-3-(4-acetylphenoxy)-1-methylpropyl)-1-piperazinyl)-1-methyl-2-oxoethylcarbamate,
tert-butyl (1S)-2-(4-(3-(4-acetylphenoxy)propyl)-1-piperazinyl)-1-methyl-2-oxoethylcarbamate,
tert-butyl (2R)-2-((4-(3-(4-acetylphenoxy)propyl)-1-piperazinyl)carbonyl)-1-pyrrolidinecarboxylate,
tert-butyl (2S)-2-((4-(3-(4-acetylphenoxy)propyl)-1-piperazinyl)carbonyl)-1-pyrrolidinecarboxylate,
N-((1R)-2-(4-(3-(4-acetylphenoxy)propyl)-1-piperazinyl)-1-methyl-2-oxoethyl)methanesulfonamide, N-((1R)-2-(4-(3-(4-acetylphenoxy)propyl)-1-piperazinyl)-1-methyl-2-oxoethyl)-N,N-dimethylsulfamide,
1-(4-(3-(4-((methylamino)acetyl)-1-piperazinyl)propoxy)phenyl)-1-hexanone,
tert-butyl 2-(4-(3-(4-hexanoylphenoxy)propyl)-1-piperazinyl)-2-oxoethylcarbamate,
1-(4-(3-(4-(3-aminopropanoyl)-1piperazinyl)propoxy)phenyl)-1-hexanone,
1-(4-(3-(4-((2R)-2-aminopropanoyl)-1-piperazinyl)propoxy)phenyl)-1-hexanone,
tert-butyl (1S)-1-((4-(3-(4-hexanoylphenoxy)propyl)-1-piperazinyl)carbonyl)-2-methylpropylcarbamate,
1-(4-(3-(4-((2S)-2-amino-3-methylbutanoyl)-1-piperazinyl)propoxy)phenyl)-1-hexanone,
tert-butyl (1R)-1-((4-(3-(4-hexanoylphenoxy)propyl)-1-piperazinyl)carbonyl)-2-methylpropylcarbamate,
1-(4-(3-(4-((2R)-2-amino-3-methylbutanoyl)-1-piperazinyl)propoxy)phenyl)-1-hexanone,
tert-butyl (1S)-1-((4-(3-(4-hexanoylphenoxy)propyl)-1-piperazinyl)carbonyl)-3-methylbutylcarbamate,
1-(4-(3-(4-((2S)-2-amino-4-methylpentanoyl)-1-piperazinyl)propoxy)phenyl)-1-hexanone,
tert-butyl (1R)-1-((4-(3-(4-hexanoylphenoxy)propyl)-1-piperazinyl)carbonyl)-3-methylbutylcarbamate,
1-(4-(3-(4-((2R)-2-amino-4-methylpentanoyl)-1-piperazinyl)propoxy)phenyl)-1-hexanone,
tert-butyl (1S)-1-((benzyloxy)methyl)-2-(4-(3-(4-hexanoylphenoxy)propyl)-1-piperazinyl)-2-oxoethylcarbamate,
1-(4-(3-(4-((2R)-2-amino-3-hydroxypropanoyl)-1-piperazinyl)propoxy)phenyl)-1-hexanone,
1-(4-(3-(4-((2S)-2-amino-3-(benzyloxy)propanoyl)-1-piperazinyl)propoxy)phenyl)-1-hexanone,
tert-butyl (1S)-2-(4-(3-(4-hexanoylphenoxy)propyl)-1-piperazinyl)-2-oxo-1-(4-pyridinylmethyl)ethylcarbamate,
1-(4-(3-(4-((2S)-2-amino-3-(4-pyridinyl)propanoyl)-1-piperazinyl)propoxy)phenyl)-1-hexanone,
tert-butyl (1R)-2-(4-(3-(4-hexanoylphenoxy)propyl)-1-piperazinyl)-2-oxo-1-(4-pyridinylmethyl)ethylcarbamate,
1-(4-(3-(4-((2R)-2-amino-3-(4-pyridinyl)propanoyl)-1-piperazinyl)propoxy)phenyl)-1-hexanone,
tert-butyl (1S)-2-(4-(3-(4-hexanoylphenoxy)propyl)-1-piperazinyl)-1-(1H-imidazol-4-ylmethyl)-2-oxoethylcarbamate,
1-(4-(3-(4-((2S)-2-amino-3-(1H-imidazol-4-yl)propanoyl)-1-piperazinyl)propoxy)phenyl)-1-hexanone,
(4-(((3R)-3-(4-(3-aminopropanoyl)-1-piperazinyl)butyl)oxy)phenyl)(cyclopropyl)methanone,
tert-butyl (1R)-2-(4-((1R)-3-(4-(cyclopropylcarbonyl)phenoxy)-1-methylpropyl)-1-piperazinyl)-1-methyl-2-oxoethylcarbamate,
(4-(((3R)-3-(4-((2R)-2-aminopropanoyl)-1-piperazinyl)butyl)oxy)phenyl)(cyclopropyl)methanone,
tert-butyl (1R)-2-(4-((1S)-3-(4-(cyclopropylcarbonyl)phenoxy)-1-methylpropyl)-1-piperazinyl)-1-methyl-2-oxoethylcarbamate,
tert-butyl (1R)-2-(4-(3-(4-(cyclopropylcarbonyl)propyl)-1-piperazinyl)-1-methyl-2-oxoethylcarbamate,
cyclopropyl(4-(((3R)-3-(4-((methylamino)acetyl)-1-piperazinyl)butyl)oxy)phenyl)methanone,
(4-(3-(4-((2R)-2-amino-3,3-dimethylbutanoyl)-1-piperazinyl)propoxy)phenyl)(cyclopropyl)methanone,
tert-butyl (1R)-1-((4-(3-(4-(cyclopropylcarbonyl)phenoxy)propyl)-1-piperazinyl)carbonyl)-3,3-dimethylbutylcarbamate,
tert-butyl (1R)-1-((4-(3-(4-(cyclopropylcarbonyl)phenoxy)propyl)-1-piperazinyl)carbonyl)-3,3-dimethylbutylcarbamate,
(4-(3-(4-((2R)-2-aminobutanoyl)-1-piperazinyl)propoxy)phenyl)(cyclopropyl)methanone,
cyclopropyl(4-(3-(4-((2R)-2-(methylamino)-3-phenylpropanoyl)-1-piperazinyl)propoxy)phenyl)methanone,
(4-(3-(4-((2R,3S)-2-amino-3-hydroxybutanoyl)-1-piperazinyl)propoxy)phenyl)(cyclopropyl)methanone,
benzyl (1R)-1-(tert-butoxymethyl)-2-(4-(3-(4-(cyclopropylcarbonyl)phenoxy)propyl)-1-piperazinyl)-2-oxoethylcarbamate,
(4-(3-(4-((2R)-2-amino-3-tert-butoxypropanoyl)-1-piperazinyl)propoxy)phenyl)(cyclopropyl)methanone,
tert-butyl (1R,2S)-2-tert-butoxy-1-((4-(3-(4-(cyclopropylcarbonyl)phenoxy)propyl)-1-piperazinyl)carbonyl)propylcarbamate,
(4-(3-(4-((2R)-2-amino-3-(benzyloxy)propanoyl)-1-piperazinyl)propoxy)phenyl)(cyclopropyl)methanone,
tert-butyl (1R,2S)-2-(benzyloxy)-1-((4-(3-(4-(cyclopropylcarbonyl)phenoxy)propyl)-1-piperazinyl)carbonyl)propylcarbamate,
tert-butyl (1R)-5-((aminocarbonyl)amino)-1-((4-(3-(4-(cyclopropylcarbonyl)phenoxy)propyl)-1-piperazinyl)carbonyl)pentylcarbamate,
tert-butyl (1R)-4-((aminocarbonyl)amino)-1-((4-(3-(4-(cyclopropylcarbonyl)phenoxy)propyl)-1-piperazinyl)carbonyl)butylcarbamate,
tert-butyl (1R)-1-benzyl-2-(4-(3-(4-(cyclopropylcarbonyl)phenoxy)propyl)-1-piperazinyl)-2-oxoethylcarbamate,
tert-butyl (1R)-2-(4-(3-(4-(cyclopropylcarbonyl)phenoxy)propyl)-1-piperazinyl)-1-(4-fluorobenzyl)-2-oxoethylcarbamate,
(4-(3-(4-((2R)-2-amino-3-(4-fluorophenyl)propanoyl)-1-piperazinyl)propoxy)phenyl)(cyclopropyl)methanone,
(4R)-4-((4-(3-(4-(cyclopropylcarbonyl)phenoxy)propyl)-1-piperazinyl)carbonyl)-2-azetidinone,
(4S)-4-((4-(3-(4-(cyclopropylcarbonyl)phenoxy)propyl)-1-piperazinyl)carbonyl)-2-azetidinone,
tert-butyl (2S)-2-((4-(3-(4-(cyclopropylcarbonyl)phenoxy)propyl)-1-piperazinyl)carbonyl)-1-pyrrolidinecarboxylate,
cyclopropyl(4-(3.-(4-((2)-pyrrolidinylcarbonyl)-1-piperazinyl)propoxy)phenyl)methanone,
cyclopropyl(4-(3-(4-((2R)-pyrrolidinylacetyl)-1-piperazinyl)propoxy)phenyl)methanone,
(4-(3-(4-((2R)-2-amino-3-(2-thienyl)propanoyl)-1-piperazinyl)propoxy)phenyl)(cyclopropyl)methanone,
(4-(3-(4-((2R)-2-amino-3-(1-methyl-1H-imidazol-4-yl)propanoyl)-1-piperazinyl)propoxy)phenyl)(cyclopropyl)methanone,
tert-butyl (1R)-2-(4-(3-(4-(cyclopropylcarbonyl)phenoxy)propyl)-1-piperazinyl)-2-oxo-1-(1,3-thiazol-5-ylmethyl)ethylcarbamate,
1-((1S)-1-((4-(3-(4-(cyclopropylcarbonyl)phenoxy)propyl)-1-piperazinyl)carbonyl)-2-methylpropyl)tetrahydro-2(1H)-pyrimidinone,
tert-butyl (1S)-2-(4-(2-((4-cyano(1,1'-biphenyl)-4-yl)oxy)ethyl)-1-piperazinyl)-1-methyl-2-oxoethylcarbamate,
4'-(2-(4-((2S)-2-aminopropanoyl)-1-piperazinyl)ethoxy)(1,1'-biphenyl)-4-carbonitrile,
tert-butyl (1R)-2-(4-(2-((4-cyano(1,1'-biphenyl)-4-yl)oxy)ethyl)-1-piperazinyl)-1-methyl-2-oxoethylcarbamate,
4'-(2-(4-((2R)-2-aminopropanoyl)-1-piperazinyl)ethoxy)(1,1'-biphenyl)-4-carbonitrile,
4-(3-(4-(((tert-butoxycarbonyl)(methyl)amino)acetyl)-1-piperazinyl)propoxy)-4-cyano-1,1'-biphenyl
4'-(3-(4-((methylamino)acetyl)-1-piperazinyl)propoxy)(1,1'-biphenyl)-4-carbonitrile, tert-butyl (1R)-2-(4-(2-((4'-cyano(1,1 -biphenyl)-4-yl)oxy) ethyl)-1-piperazinyl)-1-methyl-2-oxoethyl(methyl) carbamate,
4'-(2-(4-((2R)-2-(methylamino)propanoyl)-1-piperazinyl) ethoxy)(1,1'-biphenyl)-4-carbonitrile,
tert-butyl (1R)-2-(4-(3-((4'-cyano(1,1'-biphenyl)-4-yl)oxy) propyl)-1-piperazinyl)-1-methyl-2-oxoethylcarbamate,
4'-(3-(4-((2R)-2-aminopropanoyl)-1-piperazinyl)propoxy) (1,1'-biphenyl)-4-carbonitrile,
tert-butyl (1R)-2-(4-(3-((4'-cyano(1,1'-biphenyl)-4-yl)oxy) propyl)-1-piperazinyl)-1-methyl-2-oxoethyl(methyl) carbamate,
4'-(3-(4-((2R)-2-(methylamino)propanoyl)-1-piperazinyl) propoxy)(1,1'-biphenyl)-4-carbonitrile,
tert-butyl (1S)-2-(4-(3-((4'-cyano(1,1'-biphenyl)-4-yl)oxy) propyl)-1-piperazinyl)-1-methyl-2-oxoethylcarbamate,
tert-butyl (2R)-2-((4-(2-((4'-cyano(1,1'-biphenyl)-4-yl)oxy) ethyl)-1-piperazinyl)carbonyl)-1-pyrrolidinecarboxylate,
4'-(2-(4-((2R)-pyrrolidinylcarbonyl)-1-piperazinyl)ethoxy) (1,1'-biphenyl)-4-carbonitrile,
tert-butyl (2S)-2-((4-(2-((4'-cyano(1,1'-biphenyl)-4-yl)oxy) ethyl)-1-piperazinyl)carbonyl)-1-pyrrolidinecarboxylate,
tert-butyl (2R)-2-((4-(3-((4'-cyano(1,1'-biphenyl)-4-yl)oxy) propyl)-1-piperazinyl)carbonyl)-1-pyrrolidinecarboxylate,
4'-(3-(4-(aminoacetyl)-1-piperazinyl)propoxy)(1,1'-biphenyl)-4-carbonitrile,
4-(3-(4-(3-((tert-butoxycarbonyl)amino)propanoyl)-1-piperazinyl)propoxy)-4'-cyano-1,1'-biphenyl
4'-(3-(4-(3-aminopropanoyl)-1-piperazinyl)propoxy)(1,1'-biphenyl)-4-carbonitrile,
N-(3-(4-(3-((4'-cyano(1,1'-biphenyl)-4-yl)oxy)propyl)-1-piperazinyl)-3-oxopropyl)-2,2-dimethylpropanamide,
N-(3-(4-(3-((4'-cyano(1,1'-biphenyl)-4-yl)oxy)propyl)-1-piperazinyl)-3-oxopropyl)-3,3-dimethylbutanamide,
N-(3-(4-(3-((4'-cyano(1,1'-biphenyl)-4-yl)oxy)propyl)-1-piperazinyl)-3-oxopropyl)cyclopropanecarboxamide,
N-(3-(4-(3-((4'-cyano(1,1'-biphenyl)-4-yl)oxy)propyl)-1-piperazinyl)-3-oxopropyl)-4-morpholinecarboxamide,
tert-butyl 3-(4-(3-(4-(cyclopropylcarbonyl)phenoxy)propyl)-1,4-diazepan-1-yl)-3-oxopropylcarbamate,
tert-butyl (1R)-2-(4-(3-(4-(cyclopropylcarbonyl)phenoxy)propyl)-1,4-diazepan-1-yl)-1-methyl-2-oxoethylcarbamate,
(4-(3-(4-((2S)-2-aminopropanoyl)-1,4-diazepan-1-yl)propoxy)phenyl)(cyclopropyl)methanone,
4'-(3-(4-((2R)-2-aminopropanoyl)-1,4-diazepan-1-yl)propoxy)(1,1'-biphenyl)-4-carbonitrile,
tert-butyl (1S)-2-(4-(3-((4'-cyano(1,1'-biphenyl)-4-yl)oxy) propyl)-1,4-diazepan-1-yl)-1-methyl-2-oxoethylcarbamate,
tert-butyl (1R)-1-((4-(3-(4-(cyclopropylcarbonyl)phenoxy) propyl)-1,4-diazepan-1-yl)carbonyl)propylcarbamate,
(4-(3-(4-((2R)-2-aminobutanoyl)-1,4-diazepan-1-yl) propoxy)phenyl)(cyclopropyl)methanone,
4'-(3-(4-((2R)-2-aminobutanoyl)-1,4-diazepan-1-yl) propoxy)(1,1'-biphenyl)-4-carbonitrile,
tert-butyl (2S)-2-(2-(4-(3-(4-(cyclopropylcarbonyl) phenoxy)propyl)-1,4-diazepan-1-yl)-2-oxoethyl)-1-pyrrolidinecarboxylate,
cyclopropyl(4-(3-(4-((2S)-pyrrolidinylacetyl)-1,4-diazepan-1-yl)propoxy)phenyl)methanone,
tert-butyl (2S)-2-(2-(4-(3-((4'-cyano(1,1'-biphenyl)-4-yl) oxy)propyl)-1,4-diazepan-1-yl)-2-oxoethyl)-1-pyrrolidinecarboxylate,
N-((1R)-2-(4-(3-(4-(cyclopropylcarbonyl)phenoxy)propyl)-1-piperazinyl)-1-methyl-2-oxoethyl)-2-furamide,
N-((1R)-2-(4-(3-(4-(cyclopropylcarbonyl)phenoxy)propyl)-1-piperazinyl)-1-methyl-2-oxoethyl)-2-thiophenecarboxamide,
(4-(3-(4-(((1S,2R)-2-aminocyclopropyl)carbonyl)-1-piperazinyl)propoxy)phenyl)(cyclopropyl)methanone,
(2R)-N-((1R)-2-(4-(3-(4-(cyclopropylcarbonyl)phenoxy) propyl)-1-piperazinyl)-1-methyl-2-oxoethyl)-2-pyrrolidinecarboxamide,
(4-(3-(4-((2-aminocyclopentyl)carbonyl)-1-piperazinyl) propoxy)phenyl)(cyclopropyl)methanone,
(4-(3-(4-((2R)-azetidinylcarbonyl)-1-piperazinyl)propoxy) phenyl)(cyclopropyl)methanone,
(4-(((3R)-3-(4-((2R)-2-aminobutanoyl)-1-piperazinyl) butyl)oxy)phenyl)(cyclopropyl)methanone,
(4-(((3R)-3-(4-((2R)-2-aminopentanoyl)-1-piperazinyl) butyl)oxy)phenyl)(cyclopropyl)methanone,
tert-butyl 3-((4-(3-(4-(cyclopropylcarbonyl)phenoxy) propyl)-1-piperazinyl)carbonyl)-1-azetidinecarboxylate,
tert-butyl 4-(4-(3-(4-(cyclopropylcarbonyl)phenoxy) propyl)-1-piperazinyl)-4-oxobutylcarbamate,
tert-butyl (1R)-2-(4-((3S)-3-(4-(cyclopropylcarbonyl) phenoxy)-3-phenylpropyl)-1-piperazinyl)-1-methyl-2-oxoethylcarbamate,
N-((1R)-2-(4-(3-((4'-cyano(1,1'-biphenyl)-4-yl)oxy) propyl)-1,4-diazepan-1-yl)-2-oxo-1-(1,3-thiazol-4-ylmethyl)ethyl)-2-furamide,
(4-(3-(4-((2R)-2-aminopropanoyl)-1-piperazinyl)propoxy) phenyl)(cyclopropyl)methanone,
cyclopropyl(4-(3-(4-((2R)-2-(isopropylamino)propanoyl)-1-piperazinyl)propoxy)phenyl)methanone,
4'-(2-(4-((2S)-pyrrolidinylcarbonyl)-1-piperazinyl)ethoxy) (1,1'-biphenyl)-4-carbonitrile;
N-[(1R)-2-(4-{3-[3-fluoro-4-(5-propyl-1,2,4-oxadiazol-3-yl)phenoxy]propyl}-1,4-diazepan-1-yl)-1-methyl-2-oxoethyl]-2-furamide,
N-[(1R)-2-(4-{3-[3-fluoro-4-(5-isopentyl-1,2,4-oxadiazol-3-yl)phenoxy]propyl}-1,4-diazepan-1-yl)-1-methyl-2-oxoethyl]-2-furamide,
N-{(1R)-2-[4-(3-{3-fluoro-4-[5-(isopropoxymethyl)-1,2,4-oxadiazol-3-yl]phenoxy}propyl)-1,4-diazepan-1-yl]-1-methyl-2-oxoethyl}-2-furamide,
N-[(1R)-2-(4-{3-[4-(5-cyclopentyl-1,2,4-oxadiazol-3-yl)-3-fluorophenoxy]propyl}-1,4-diazepan-1-yl)-1-methyl-2-oxoethyl]-2-furamide,
N-{(1R)-2-[4-(3-{4-[5-(cyclopentylmethyl)-1,2,4-oxadiazol-3-yl]-3-fluorophenoxy}propyl)-1,4-diazepan-1-yl]-1-methyl-2-oxoethyl}-2-furamide,
tert-butyl (1S)-1-{3-[2-fluoro-4-(3-{4-[(2R)-2-(2-furoylamino)propanoyl]-1,4-diazepan-1-yl}propoxy) phenyl]-1,2,4-oxadiazol-5-yl}ethylcarbamate,
N-{(1R)-2-[4-(3-{3-fluoro-4-[5-(3-furyl)-1,2,4-oxadiazol-3-yl]phenoxy}propyl)-1,4-diazepan-1-yl]-1-methyl-2-oxoethyl}-2-furamide,
N-{(1R)-2-[4-(3-{3-fluoro-4-[5-(2-thienyl)-1,2,4-oxadiazol-3-yl]phenoxy}propyl)-1,4-diazepan-1-yl]-1-methyl-2-oxoethyl}-2-furamide,
N-{(1R)-2-[4-(3-{3-fluoro-4-[5-(1,3-thiazol-2-yl)-1,2,4-oxadiazol-3-yl]phenoxy}propyl)-1,4-diazepan-1-yl]-1-methyl-2-oxoethyl}-2-furamide,
N-{(1R)-2-[4-(3-{3-fluoro-4-[5-(4-pyridinyl)-1,2,4-oxadiazol-3-yl]phenoxy}propyl)-1,4-diazepan-1-yl]-1-methyl-2-oxoethyl}-2-furamide,
N-[(1R)-2-(4-{3-[3-fluoro-4-(5-phenyl-1,2,4-oxadiazol-3-yl)phenoxy]propyl}-1,4-diazepan-1-yl)-1-methyl-2-oxoethyl]-2-furamide,
N-{(1R)-2-[4-(3-{3-fluoro-4-[5-(2-phenylethyl)-1,2,4-oxadiazol-3-yl]phenoxy}propyl)-1,4-diazepan-1-yl]-1-methyl-2-oxoethyl}-2-furamide, 4'-cyano-N-[3-(4-{3-[3-fluoro-4-(5-phenyl-1,2,4-oxadiazol-3-yl)phenoxy]propyl}-1-piperazinyl)-3-oxopropyl]benzamide, N-[3-(4-{3-[3-fluoro-4-(5-phenyl-1,2,4-oxadiazol-3-yl)phenoxy]propyl}-1-piperazinyl)-3-oxopropyl]-3-thiophenecarboxamide, (2R)-N-[3-(4-{3-[3-fluoro-4-(5-phenyl-1,2,4-oxadiazol-3-yl)phenoxy]propyl}-1-piperazinyl)-3-oxopropyl]tetrahydro-2-furancarboxamide, N-[3-(4-{3-[3-fluoro-4-(5-phenyl-1,2,4-oxadiazol-3-yl)phenoxy]propyl}-1-piperazinyl)-3-oxopropyl]-3,5-dimethyl-2-thiophenecarboxamide, N-[3-(4-{3-[3-fluoro-4-(5-phenyl-1,2,4-oxadiazol-3-yl)phenoxy]propyl}-1-piperazinyl)-3-oxopropyl]-2,5-dimethyl-3-furamide, N-[3-(4-{3-[3-fluoro-4-(5-phenyl-1,2,4-oxadiazol-3-yl)phenoxy]propyl}-1-piperazinyl)-3-oxopropyl]cyclopropanecarboxamide, N-[(1R)-2-(4-{3-[3-fluoro-4-(5-phenyl-1,2,4-oxadiazol-3-yl)phenoxy]propyl}-1-piperazinyl)-1-methyl-2-oxoethyl]-2-thiophenecarboxamide, N-[(1R)-2-(4-{3-[3-fluoro-4-(5-phenyl-1,2,4-oxadiazol-3-yl)phenoxy]propyl}-1-piperazinyl)-1-methyl-2-oxoethyl]nicotinamide, N-[(1R)-2-(4-{3-[3-fluoro-4-(5-phenyl-1,2,4-oxadiazol-3-yl)phenoxy]propyl}-1-piperazinyl)-1-methyl-2-oxoethyl]-2-furamide, N-[(1R)-2-(4-{3-[3-fluoro-4-(5-phenyl-1,2,4-oxadiazol-3-yl)phenoxy]propyl}-1-piperazinyl)-1-methyl-2-oxoethyl]-5-isoxazolecarboxamide, (2S)-N-[(1R)-2-(4-{3-[3-fluoro-4-(5-phenyl-1,2,4-oxadiazol-3-yl)phenoxy]propyl}-1-piperazinyl)-1-methyl-2-oxoethyl]tetrahydro-2-furancarboxamide, N-[(1R)-2-(4-{3-[3-fluoro-4-(5-phenyl-1,2,4-oxadiazol-3-yl)phenoxy]propyl}-1-piperazinyl)-1-methyl-2-oxoethyl]-3-(4-morpholinyl)propanamide, N-[(1R)-2-(4-{3-[3-fluoro-4-(5-phenyl-1,2,4-oxadiazol-3-yl)phenoxy]propyl}-1-piperazinyl)-1-methyl-2-oxoethyl]-3-methylbutanamide, (2R)-1-[4-(3-{4-[5-(cyclopentylmethyl)-1,2,4-oxadiazol-3-yl]-3-fluorophenoxy}propyl)-1-piperazinyl]-1-oxo-2-propanamine, (2R)-1-[4-(3-{4-[5-(cyclopentylmethyl)-1,2,4-oxadiazol-3-yl]-3-fluorophenoxy}propyl)-1,4-diazepan-1-yl]-1-oxo-2-propanamine, N-{(1R)-2-[4-(3-{4-[5-(cyclopentylmethyl)-1,2,4-oxadiazol-3-yl]-3-fluorophenoxy}propyl)-1-piperazinyl]-1-methyl-2-oxoethyl}propanamide, N-{(1R)-2-[4-(3-{4-[5-(cyclopentylmethyl)-1,2,4-oxadiazol-3-yl]-3-fluorophenoxy}propyl)-1-piperazinyl]-1-methyl-2-oxoethyl}-3,3-dimethylbutanamide, N-{(1R)-2-[4-(3-{4-[5-(cyclopentylmethyl)-1,2,4-oxadiazol-3-yl]-3-fluorophenoxy}propyl)-1-piperazinyl]-1-methyl-2-oxoethyl}-3-(4-morpholinyl)propanamide, N-{(1R)-2-[4-(3-{4-[5-(cyclopentylmethyl)-1,2,4-oxadiazol-3-yl]-3-fluorophenoxy}propyl)-1-piperazinyl]-1-methyl-2-oxoethyl}-4-methylbenzamide, N-{(1R)-2-[4-(3-{4-[5-(cyclopentylmethyl)-1,2,4-oxadiazol-3-yl]-3-fluorophenoxy}propyl)-1-piperazinyl]-1-methyl-2-oxoethyl}-4-fluorobenzamide, N-{(1R)-2-[4-(3-{4-[5-(cyclopentylmethyl)-1,2,4-oxadiazol-3-yl]-3-fluorophenoxy}propyl)-1-piperazinyl]-1-methyl-2-oxoethyl}-4-methoxybenzamide, 3,4-dichloro-N-{(1R)-2-[4-(3-{4-[5-(cyclopentylmethyl)-1,2,4-oxadiazol-3-yl]-3-fluorophenoxy}propyl)-1-piperazinyl]-1-methyl-2-oxoethyl}benzamide, N-{(1R)-2-[4-(3-{4-[5-(cyclopentylmethyl)-1,2,4-oxadiazol-3-yl]-3-fluorophenoxy}propyl)-1,4-diazepan-1-yl]-1-methyl-2-oxoethyl}-2-methylpropanamide, 4-chloro-N-{(1R)-2-[4-(3-{4-[5-(cyclopentylmethyl)-1,2,4-oxadiazol-3-yl]-3-fluorophenoxy}propyl)-1,4-diazepan-1-yl]-1-methyl-2-oxoethyl}benzamide, 4'-cyano-N-{(1R)-2-[4-(3-{4-[5-(cyclopentylmethyl)-1,2,4-oxadiazol-3-yl]-3-fluorophenoxy}propyl)-1,4-diazepan-1-yl]-1-methyl-2-oxoethyl}benzamide, N-{(1R)-2-[4-(3-{4-[5-(cyclopentylmethyl)-1,2,4-oxadiazol-3-yl]-3-fluorophenoxy}propyl)-1-piperazinyl]-1-methyl-2-oxoethyl}-4-(dimethylamino)benzamide, N-{(1R)-2-[4-(3-{4-[5-(cyclopentylmethyl)-1,2,4-oxadiazol-3-yl]-3-fluorophenoxy}propyl)-piperazinyl]-1-methyl-2-oxoethyl}nicotinamide, 2-chloro-N-{(1R)-2-[4-(3-{4-[5-(cyclopentylmethyl)-1,2,4-oxadiazol-3-yl]-3-fluorophenoxy}propyl)-1-piperazinyl]-1-methyl-2-oxoethyl}benzamide, N-{(1R)-2-[4-(3-{4-[5 -(cyclopentylmethyl)-1,2,4-oxadiazol-3-yl]-3-fluorophenoxy}propyl)-1-piperazinyl]-1-methyl-2-oxoethyl}-1,3-benzodioxole-5-carboxamide, N-{(1R)-2-[4-(3-{4-[5-(cyclopentylmethyl)-1,2,4-oxadiazol-3-yl]-3-fluorophenoxy}propyl)-1-piperazinyl]-1-methyl-2-oxoethyl}-4-isopropoxybenzamide, N-{(1R)-2-[4-(3-{4-[5-(cyclopentylmethyl)-1,2,4-oxadiazol-3-yl]-3-fluorophenoxy}propyl)-1-piperazinyl]-1-methyl-2-oxoethyl}-3-fluoro-4-methoxybenzamide, 4-[({(1R)-2-[4-(3-{4-[5-(cyclopentylmethyl)-1,2,4-oxadiazol-3-yl]-3-fluorophenoxy}propyl)-1-piperazinyl]-1-methyl-2-oxoethyl}amino)carbonyl]benzoic acid, N-{(1R)-2-[4-(3-{3-fluoro-4-[5-(3-methylphenyl)-1,2,4-oxadiazol-3-yl]phenoxy}propyl)-1-piperazinyl]-1-methyl-2-oxoethyl}-2-thiophenecarboxamide, N-{(1R)-2-[4-(3-{4-[5-(3-cyanophenyl)-1,2,4-oxadiazol-3-yl]-3-fluorophenoxy}propyl)-1-piperazinyl]-1-methyl-2-oxoethyl}-2-thiophenecarboxamide, N-{(1R)-2-[4-(3-{4-[5-(3,5-dichlorophenyl)-1,2,4-oxadiazol-3-yl]-3-fluorophenoxy}propyl)-1-piperazinyl]-1-methyl-2-oxoethyl}-2-thiophenecarboxamide, N-((1R)-2-{4-[3-(3-fluoro-4-{5-[3-oxo-3-(1-pyrrolidinyl)propyl]-1,2,4-oxadiazol-3-yl}phenoxy)propyl]-1-piperazinyl}-1-methyl-2-oxoethyl)-2-thiophenecarboxamide, ethyl 3-{2-fluoro-4-[3-(4-{(2R)-2-[(2-thienylcarbonyl)amino]propanoyl}-1-piperazinyl)propoxy]phenyl}-1,2,4-oxadiazole-5-carboxylate, N-[(1R)-2-(4-{3-[4-(cyclopropylcarbonyl)phenoxy]propyl}-1-piperazinyl)-1-methyl-2-oxoethyl]-2-methylbenzamide, N-[(1R)-2-(4-{3-[4-(cyclopropylcarbonyl)phenoxy]propyl}-1-piperazinyl)-1-methyl-2-oxoethyl]-3-methoxybenzamide, 4-bromo-N-[(1R)-2-(4-{3-[4-(cyclopropylcarbonyl)phenoxy]propyl}-1-piperazinyl)-1-methyl-2-oxoethyl]benzamide, N-[(1R)-2-(4-{3-[4-(cyclopropylcarbonyl)phenoxy]propyl}-1-piperazinyl)-1-methyl-2-oxoethyl]-4-phenoxybenzamide, N-[(1R)-2-(4-{3-[4-(cyclopropylcarbonyl)phenoxy]propyl}-1-piperazinyl)-1-methyl-2-oxoethyl]-3,5-dimethylbenzamide, N-[(1R)-2-(4-{3-[4-(cyclopropylcarbonyl)phenoxy]propyl}-1-piperazinyl)-1-methyl-2-oxoethyl]-2,5-dimethoxybenzamide, and N-{(1R)-2-[4-(3-{3-fluoro-4-[5-(4-methoxyphenyl)-1,2,4-oxadiazol-3-yl]phenoxy}propyl)-1-piperazinyl]-1-methyl-2-oxoethyl}-2-thiophenecarboxamide.

Determination of Biological Activity
H₃ Receptor Binding

To determine the effectiveness of representative compounds of this invention as $H_3$ receptor ligands, the following tests were conducted according to methods previously described ((*European Journal of pharmacology*, 188:219–227 (1990); *Journal of Pharmacology and Experimental Therapeutics*, 275: 598–604 (1995); *Journal of Pharmacology and Experimental Therapeutics*, 276:1009–1015 (1996); *Biochemical Pharmacology*, 22: 3099–3108 (1973)).

Briefly, male Sprague-Dawley rat brain cortices were homogenized (1 g tissue/10 mL buffer) in 50 mM Tris-HCl/5 mM EDTA containing protease inhibitor cocktail (Calbiochem) using a polytron set at 20,500 rpm. Homogenates were centrifuged for 20 minutes at 40,000×g. The supernatant was decanted, and pellets were weighed. The pellet was resuspended by polytron homogenization in 40 mL 50 mM Tris-HCl/5 mM EDTA with protease inhibitors and centrifuged for 20 minutes at 40,000×g. The membrane pellet was resuspended in 6.25 volumes (per gram wet weight of pellet) of 50 mM Tris-HCl/5 mM EDTA with protease inhibitors and aliquots flash frozen in liquid $N_2$ and stored at –70° C. until used in assays. Rat cortical membranes (12 mg wet weight/tube) were incubated with (³H)-N-α-methylhistamine (–0.6 nM) with or without $H_3$—HR antagonists in a total incubation volume of 0.5 mL of 50 mM Tris-HCl/5 mM EDTA (pH 7.7). Test compounds were added to the incubation mixtures prior to initiating the incubation assay by addition of the membranes. Thioperamide (3 μM) was used to determine nonspecific binding. Binding incubations were conducted for 30 minutes at 25° C. and terminated by addition of 2 mL of ice cold 50 mM Tris-HCl (H 7.7) and filtration through 0.3% polyethylenimine-soaked Unifilter plates (Packard). These filters were washed 4 additional times with 2 mL of ice-cold 50 mM Tris-HCl and dried for 1 hour. Radioactivity was determined using liquid scintillation counting techniques. Results were analyzed by Hill transformation and Ki values were determined using the Cheng-Prusoff equation. The data in Table 1Data represent the geometric mean values of 2–10 separate experiments.

TABLE 1

| Example | Ki (nM) |
|---|---|
| 1 | 19.6 |
| 52 | 8.39 |
| 61 | 0.74 |
| 62 | 1.46 |
| 64 | 2.07 |
| 66 | 12.1 |
| 69 | 1.24 |
| 75 | 4.67 |
| 79 | 4.78 |
| 86 | 4.64 |
| 88 | 6.56 |
| 100 | 12.4 |
| 117 | 1.07 |
| 124 | 4.03 |
| 126 | 0.742 |
| 129 | 0.425 |
| 137 | 0.208 |
| 138 | 0.996 |
| 139 | 7.29 |
| 140 | 818 |
| 141 | 2.34 |
| 142 | 0.72 |
| 143 | 4.00 |
| 144 | 1.36 |

TABLE 1-continued

| Example | Ki (nM) |
|---|---|
| 145 | 1.39 |
| 146 | 9.03 |
| 147 | 1.68 |
| 148 | 3.94 |
| 149 | 6.24 |
| 150 | 12.6 |
| 151 | 4.29 |
| 152 | 1.01 |
| 153 | 26.1 |
| 154 | 25.0 |
| 155 | 17.1 |
| 156 | 13.7 |
| 157 | 46.1 |
| 158 | 11.7 |
| 159 | 4.98 |
| 160 | 2.29 |
| 161 | 2.41 |
| 162 | 13.0 |
| 163 | 8.35 |
| 164 | 6.37 |
| 165 | 11.0 |
| 168 | 6.79 |
| 169 | 5.63 |
| 170 | 8.74 |
| 171 | 5.42 |
| 172 | 1.22 |
| 173 | 1.56 |
| 174 | 0.81 |
| 175 | 1.88 |
| 176 | 1.22 |
| 177 | 1.78 |
| 178 | 8.20 |
| 179 | 1.50 |
| 180 | 2.37 |
| 181 | 1.67 |
| 182 | 2.78 |
| 183 | 2.72 |
| 184 | 10.5 |
| 185 | 3.28 |
| 186 | 8.82 |
| 187 | 26.2 |
| 188 | 4.23 |
| 189 | 51.3 |
| 190 | 7.69 |
| 191 | 15.0 |
| 192 | 1.0 |
| 193 | 1.11 |
| 194 | 1.18 |
| 195 | 1.37 |
| 196 | 2.08 |
| 197 | 3.10 |
| 198 | 25.9 |

Abbreviations

Abbreviations which have been used in the descriptions of the schemes and the examples that follow are DMA for dimethylacetamide; HPLC for high pressure liquid chromatography; HOBt for 1-hydroxybenzotriazole; THF for tetrahydrofuran; Ac for acetate; MeCN for acetonitrile; MeOH for methanol; TMSCl for trimethylsilyl chloride; TMSBr for trimethylsilylbromide; TEA for triethylamine; DBU for 1,8-diazabicyclo(5.4.0)undec-7-ene; DMF for N,N-dimethyl formamide; DCM for dichloromethane, DMSO for dimethyl sulfoxide; Me for methyl; Et for ethyl; i—Pr for isopropyl; Ph for phenyl; TBME for tertiary-butyl methyl ether; PhOPh for diphenyl ether; LDA for lithium diisopropylamide; rpm for rotations per minute; g for gravity; NMP for N-methylpyrrolidine; EtOH for ethanol; EtOAc for ethyl acetate; DMAP for N,N-dimethylaminopyridine; HMPA for hexamethylphosphoramide; NCS for N-chlorosuccinimide, NBS for N-bromosuccinimide; BOPCl for bis(2-oxo-3-oxazolidinyl)phosphinic chloride; TFA for trifluoroacetic acid; DCC for 1,3-dicyclohexylcarbodiimide; CDI for 1,1-

Carbonyldiimidazole; HATU for O-(7-azabenzotriazol-1-yl)-N,N,N',N'-tetramethyluronium hexafluorophosphate; EDCI for 1-(3-dimethylaminopropyl)-3-ethylcarbodiimide hydrochloride; PyBOP for benzotriazol-1-yl-oxy-tris-pyrrolidino-phosphoniumhexafluorophosphate; TsOH for para-toluenesulfonic acid; DEAD for diethyl azodicarboxylate; DAID for diisopropyl azodicarboxylate; TBDMSCI for tertiary-butyldimethylsilyl chloride; Boc for tertiary-butoxycarbonyl; AcOH for acetic acid; DPPE for bis(diphenylphosphino)ethane.

Synthetic Methods

The compounds and processes of this invention will be better understood in connection with the following synthetic schemes which illustrate methods by which the compounds of this invention can be prepared. The compounds of this invention can be prepared by a variety of procedures. Representative procedures are shown in Schemes 1–5. The groups $L^1$, $L^2$, $Q^1$, $Q^2$, n, $R^5$, $R^6$, $R^7$ and $R^8$ are as defined above.

It will be readily apparent that other compounds of this invention can by synthesized by the substitution of appropriate starting materials and reagents in the syntheses shown below. It will also be apparent that protection and deprotection steps, as well as the order of the steps themselves, can be carried out in varying order, to successfully complete the syntheses of compounds of this invention. Starting materials and reagents are available commercially or can be prepared synthetically by known methods well-known in the art. In particular, optionally substituted 1,4-piperazines; optionally substituted 1,4-diazepanes; and (1S,4S)-(+)-2,5-diazabicyclo(2.2.1)heptane are commercially available. (1R, 4R)-(−)-2,5-diazabicyclo(2.2.1)heptane was prepared according to the procedure described in *J. Med. Chem.* 1990, 33, 1344. The preparation of 3,8-diazabicyclo(3.2.1)octane is described below.

All of the reactions discussed in the schemes are run in solvents in which the starting materials and products are not reactive, unless otherwise specified, and in which the starting materials are at least partially soluble. The appropriate solvent for each reaction will be apparent to one skilled in the art.

Scheme 1

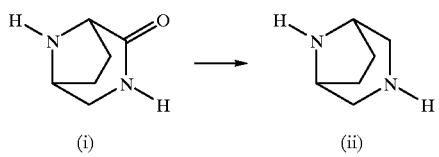

(i)           (ii)

As shown in Scheme 1, compound (i) can be converted to compound (ii) by treating the former with a reducing agent in a solvent. 3,8-diazabicyclo(3.2.1)octane, compound (i), was prepared according to the procedure described in *Tetrahedron* 1992, 48, 4985. Specific examples of reducing agents include LiAlH$_4$, BH$_3$-THF, and NaAlH$_2$(OCH$_2$CH$_2$OCH$_3$)$_2$. Specific examples of solvents include THF, diethyl ether, and glyme. Although the reaction generally proceeds at about 0° C., it can be run at lower or elevated temperatures, as needed. The reaction time is generally about 2 hours to about 24 hours and can be selected depending on the reaction temperature.

Scheme 2

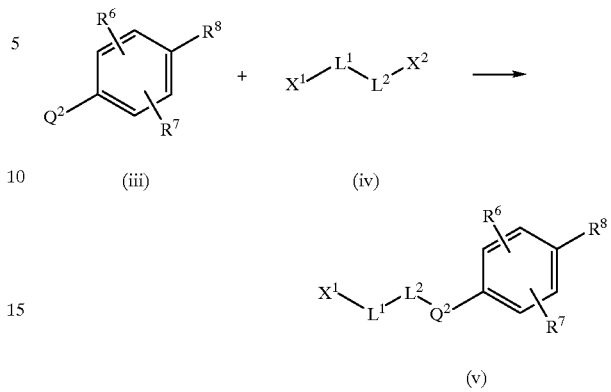

As shown in Scheme 2, the conversion of compounds of formula (iii) and (iv) to (v) can be accomplished by combining (iii) and (iv) with a base in a solvent. Specific examples of (iii) include cyclopropyl para-hydroxyphenyl ketone, 4-hydroxybenzonitrile, 4-bromophenol, 4'-cyano-4'-hydroxybiphenyl, 4-hydroxyacetophenone, 2-(4'-hydroxyphenyl)pyridine, 4'-cyano-3-fluorophenol, 4-trifluoromethylphenol, and 4-hydroxy-phenyl-1-hexanone. Specific examples of (iv), wherein $X^1$ and $X^2$ are the same or different halides, include 1-bromo-2-chloroethane; 1-bromo-3-chloropropane; 1-bromo-4-chlorobutane; 1,2-dibromoethane; 1,3-dibromopropane; 1,4-dibromobutane; 1-chloro-3-phenyl propanol; 1,3-butanediol. Specific examples of bases include K$_2$CO$_3$, Cs$_2$CO$_3$, NaHCO$_3$, LiOH, NaOH, KOH, pyridine, lutidine, TEA, DBU and diisopropylethylamine. Specific examples of solvents include 2-butanone, THF, DMF, NMP, acetone, benzene, toluene, DCM and chloroform. Although the reaction generally proceeds at about 70–80° C., it can be run at lower or elevated temperatures, as needed. The reaction time is generally about 6 hours to about 36 hours and can be selected depending on the reaction temperature. In a preferred embodiment, (iii) and (iv) in 2-butanone were treated with K$_2$CO$_3$ and refluxed for about 24 hours.

Alternatively, compounds of formula (iii) and (iv) can be combined to form compounds of formula (v) by treating the (iv) with a hydroxyl activating group precursor and a nucleophile. Specific examples of hydroxyl activating groups include trifluoroacetic anhydride, diazo compounds and phosphines, trifluoromethanesulfonic anhydride, methanesulfonyl chloride, and para-toluenesulfonyl chloride. Specific examples of diazo compounds include DEAD, and DIAD. Specific examples of phosphines include PPh$_3$, PEt$_3$, DPPE and PMe$_3$. Specific examples of nucleophiles include carboxylate anions, phenol anions, thiol anions and alkoxide anions. More preferred are the oxygen anions of cyclopropyl para-hydroxyphenyl ketone, cyclopropyl para-hydroxyphenyl ketone, 4-hydroxybenzonitrile, 4-bromophenol, 4'-cyano-4'-hydroxybiphenyl, 4-hydroxyacetophenone, 2-(4'-hydroxyphenyl)pyridine, 4'-cyano-3-fluorophenol, 4-trifluoromethylphenol, and 4-hydroxy-phenyl-1-hexanone. Specific examples of solvents include DCM; chloroform; CCl$_4$; THF; and 1,1,1-trichloroethane. Although the reaction generally proceeds at room temperature, it can be run at lower or elevated temperatures, as needed. The reaction time is generally about one hour to about 16 hours and can be selected depending on the reaction temperature. In a particularly preferred embodiment, (iv) and the oxygen anion of para-hydroxy-4-chlorobutyrophenone in about 0° C. DCM is treated with DEAD and PPh₃, warmed to room temperature and stirred for about 16 hours.

Scheme 3

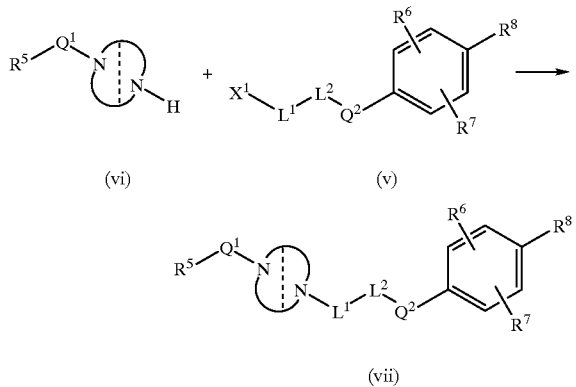

As shown in Scheme 3, the conversion of (vi) and (v) to (vii) can be achieved by combining (vi) and (v) in the presence of a base, and an optionally added additive, in a solvent. $R^1$, $R^2$, and $R^3$ are defined as in formula (I) and are substituents on the piperazine or diazepane ring. $R^4$ is synonymous with $R^5$ in this scheme and is defined in formula (I). Specific examples of (vi) include diamines such as piperazine, trans-1,4-diaminocyclohexane, 2-methylpiperazine, 2,6-dimethylpiperazine, trans-2,5-dimethylpiperazine, diazepane, and N,N'-dimethyl-1,3-propanediamine. Specific examples of bases include $K_2CO_3$, $Na_2CO_3$, $NaHCO_3$, $K_3PO_4$, LiOH, NaOH, and KOH. Specific examples of additives include KI, $I_2$, and HI. Specific examples of solvents include acetone, 2-butanone, THF, DCM, and chloroform. Although the reaction generally proceeds at reflux, the temperature of which can be determined by using a solvent of known boiling point at atmospheric pressure, it can be run at lower temperatures as needed. The reaction time is generally about 12 hours to about five days and can be selected depending on the reaction temperature.

If the diamine used above is protected, it can be deprotected by treating the coupled product with a deprotecting agent in a solvent. Specific examples of deprotecting agents include TBAF, HF, $H_2$ and Pd on carbon, $H_2$ and Pt on carbon, HCl in methanol, $Li/NH_3$, $BBr_3$, TsOH, AcOH and heat, $ZnBr_2$, $HgCl_2$, $K_2CO_3$, Zn, and TFA. Specific examples of solvents include diethyl ether, EtOAc, AcOH, isopropyl acetate, methanol, ethanol, DCM, chloroform, acetonitrile, water, THF and mixtures thereof. Although the reaction usually proceeds at room temperature, it may be run at higher or lower temperatures, as needed. The reaction time is generally about one hour to about 24 hours and can be selected depending on the reaction temperature. The deprotecting agent, solvent, temperature, and time are determined by the nature of the protecting group.

The free amine thus formed can then be treated with an acid or an acid derivative, a base and an additive in a solvent. Specific examples of acids or acid derivatives include amino acids, sulfonic acid chlorides, acid anhydrides, acid chlorides, and carboxylic acids. More preferred are the following acids: N—Boc—(L)—alanine; N—Boc—glycine; N—Boc-4-amino-butyric acid; N—Boc—beta—alanine; N—Boc—(D)—alanine; N—Boc—(L)—proline; N—Boc—(D)—proline; N—Boc—sarcosine; N—Boc—(L)—valine; N—Boc—(D)—valine; N—Boc—(L)—leucine; N—Boc—(D)—leucine; N—Boc—O—benzyl—(L)—serine; N—Boc—O—benzyl—(D)—serine; N—Boc—(S)—pyridyl-phenylalanine; N—Boc—(R)—pyridyl-phenylalanine; N—Boc—(L)—histidine; N—Boc-(2R)-2-amino-3,3-dimethylbutanoic acid; N—Boc-(2R)-2-amino-4,4-dimethylpentanoic acid; N—Boc-(2R)-2-aminobutanoic acid; N—Boc—(L)—N-methylphenyl alanine; N—Boc—(D)—threonine; N—CBz—(D)—O—tert-butyl-serine; N—Boc—(D)—O-tert-butyl-threonine; N—Boc—(D)—O-benzyl-threonine; N—Boc—(D)—2,6-diamino-carbonyl hexanoic acid; N—Boc—(D)—phenylalanine; N—Boc—(D)—4-fluoro-phenylalanine; N—Boc—(D)—4-fluoro-N-methyl-phenylalanine; (2R)-2-azetidinone-4-carboxylic acid; (2S)-2-azetidinone-4-carboxylic acid; N—Boc-(2R)-2-pyrrolidine acetic acid; N—Boc-(2R)-2-amino-3-(2)-thiophenyl propanoic acid; N—Boc—(D)—N-methyl histidine; N—Boc-(2R)-2-amino-3-(2)-thiazolpropanoic acid; (2S)-3-methyl-2-(2-oxotetrahydro-1(2H)-pyrimidinyl)butanoic acid; N—Boc—(D)—N-methylalanine; N—Boc-(2R)-2-aminobutanoic acid; N—Boc-(2S)-2-pyrrolidino-3-propionic acid; 2,3-methano-3-N—Boc-amino propionic acid; cis N—Boc-2-aminocyclopentane; N—Boc-2-azetidine carboxylic acid; N—Boc-(2R)-2-aminopropionic acid; N—Boc-(2R)-2-aminobutyric acid; N—Boc-3-azetidine carboxylic acid; and N—Boc-4-aminobutyric acid. Specific examples of bases include TEA; diisopropylethylamine; pyridine; lutidine; DBU, 2,6-di-tertiary-butylpyridine; and imidazole. Specific examples of additives include DMAP, EDCI, BOPCl, DCC, CDI, HATU, PyBOP and combinations thereof. Specific examples of solvents include DCM, chloroform, THF, dioxane, diethyl ether, DMF, NMP and acetonitrile. Although the reaction generally proceeds at room temperature, it can be run at lower or elevated temperatures, as needed. The reaction time is generally about four hours to about 24 hours and can be selected depending on the reaction temperature. In a preferred embodiment, the free amine, an N-protected amino acid, diisopropylethylamine, and DMAP in about 0° C. DCM were treated with EDCI, warmed to room temperature and stirred for about 16 hours.

The N-protected amine in the coupled product can be can be deprotected by treating it with a deprotecting agent in a solvent. Specific examples of deprotecting agents include $H_2$ and Pd on carbon, $H_2$ and Pt on carbon, HCl in methanol, and TFA. Specific examples of solvents include EtOAc, isopropyl acetate, methanol, ethanol, DCM, and THF. Although the reaction usually proceeds at room temperature, it may be run at higher or lower temperatures, as needed. The reaction time is generally about 1 hour to about 24 hours and can be selected depending on the reaction temperature.

The resulting free amine can be acylated by treating the former with an acid or acid derivative, a base and an additive in a solvent. Specific examples of acids or acid derivatives include amino acids, sulfonic acid chlorides, carboxylic acid chlorides, carboxylic acid anhydrides, and carboxylic acids. More preferred are the following acid derivatives: acetyl chloride; methyl chloroformate; cyclopropyl acetyl chloride; methanesulfonyl chloride; N,N-dimethyl sulfamoylchloride; 3,3-dimethylbutanoyl chloride; morpholine carbamoyl chloride; furanoyl chloride; and 2-thiophenyl chloride. Specific examples of bases include TEA, diisopropylethylamine, pyridine, lutidine, and imidazole. Specific examples of additives include no additive, DMAP, EDCI, BOPCl, DCC, CDI, HATU, PyBOP and mixtures thereof. Specific examples of solvents include DCM, chloroform, diethyl ether, THF, dioxane, DMF, NMP and acetonitrile. Although the reaction generally proceeds at room temperature, it can be run at lower or elevated temperatures, as needed. The reaction time is generally about four hours to about 24 hours and can be selected depending on the reaction temperature. In a preferred embodiment, the free amine and TEA in about 0° C. DCM were treated an acid chloride, warmed to room temperature and stirred for about 6 hours.

Or, the free amine can be reductively aminated by treating it with a carbonyl compound, a reducing agent, and an optionally added acid catalyst in a solvent. Specific examples of carbonyl compounds include aldehydes and ketones. More preferred is the following carbonyl compound, acetone. A specific example of an acid catalyst is AcOH. Specific examples of reducing agents include $NaBH_4$ and $NaCNBH_3$. Specific examples of solvents include THF, MeOH, EtOH and acetone. Although the reaction generally proceeds at room temperature, it can be run at lower or higher temperatures as needed. The reaction time is generally about two to about 24 hours and can be selected depending on the reaction temperature. In a preferred embodiment the free amine in room temperature acetone was treated with $NaCNBH_3$ and stirred for about 16 hours.

Scheme 4

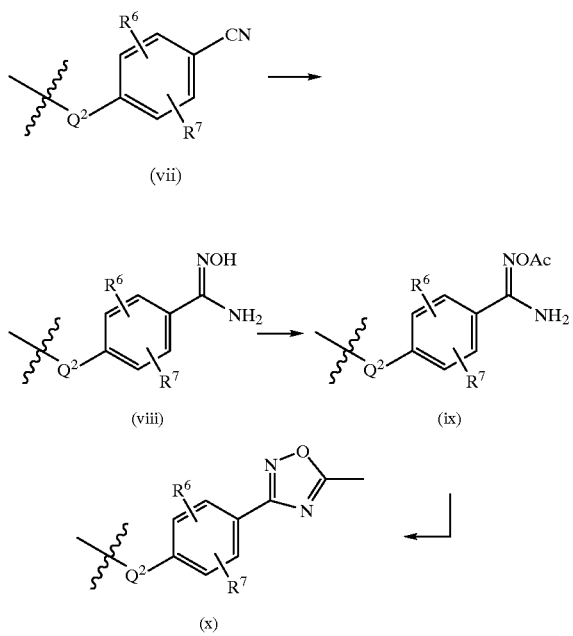

As shown in Scheme 4, the conversion of (vii) to (viii) can be accomplished by treating the former with a hydroxylamine source and a base in a solvent. Specific examples of hydroxylamine sources include hydroxylamine hydrochloride, hydroxylamine sulfate, hydroxylamine nitrate, hydroxylamine phosphate and aqueous hydroxylamine. Specific examples of bases include TEA, DBU, pyridine, LiOH, NaOH, KOH, $K_2CO_3$, $Na_2CO_3$, and $NaHCO_3$. Specific examples of solvents include ethanol, methanol, and isopropanol. Although the reaction generally proceeds at reflux, the temperature of which can be determined by using a solvent of known boiling point at atmospheric pressure, it can be run at lower temperatures as needed. The reaction time is generally about eight hours to about 24 hours and can be selected depending on the reaction temperature. In a preferred embodiment, (vii), hydroxylamine hydrochloride and $K_2CO_3$ were refluxed in ethanol for about 18 hours.

The conversion of (viii) to (ix) can be accomplished by treating the former with an acylating agent, and a base in a solvent. Specific examples of acylating agents include acid anhydrides and acid chlorides. More preferred is acetyl chloride. Specific examples of bases include TEA, diisopropylethylamine, pyridine, lutidine, and imidazole. Specific examples of solvents include acetone, THF, ethyl ether, DCM, chloroform and TBME. Although the reaction generally proceeds at room temperature, it can be run at lower or elevated temperatures as needed. The reaction time is generally about 30 minutes to about 16 hours. In a particularly preferred embodiment, (viii) and TEA in room temperature acetone were treated with acetyl chloride and stirred for about one hour.

The conversion of (ix) to (x) can be accomplished by thermally cyclizing the former in a solvent. Specific examples of solvents include toluene, benzene, xylene, glyme, 2-butanone and NMP. Although the reaction generally proceeds at reflux, the temperature of which can be determined by using a solvent of known boiling point at atmospheric pressure, it can be run at lower temperature as needed. The reaction time is generally about four hours to about 48 hours. In a preferred embodiment, (ix) in toluene was refluxed for about 24 hours.

Scheme 5

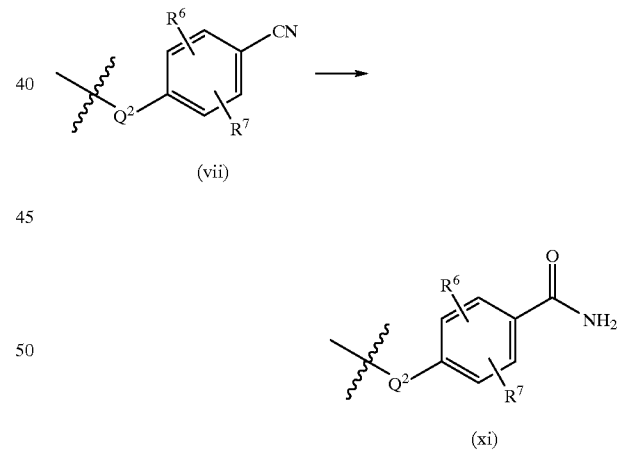

As shown in Scheme 5, the conversion of (vii) to (xi) can be accomplished by treating the former with a hydrolyzing agent in a solvent. Specific examples of hydrolyzing agents include LiOH, NaOH, KOH, $K_2CO_3$, and $Na_2CO_3$. Specific examples of solvents include THF, TBME, methanol, ethanol, water, and mixtures thereof. Although the reaction generally proceeds at room temperature, it can be run at lower or elevated temperatures as needed. The reaction time is generally about 30 minutes to about 24 hours. In a preferred embodiment, (vii), $NH_2OH.HCl$, and $K_2CO_3$ in ethanol were refluxed for about 18 hours.

Scheme 6

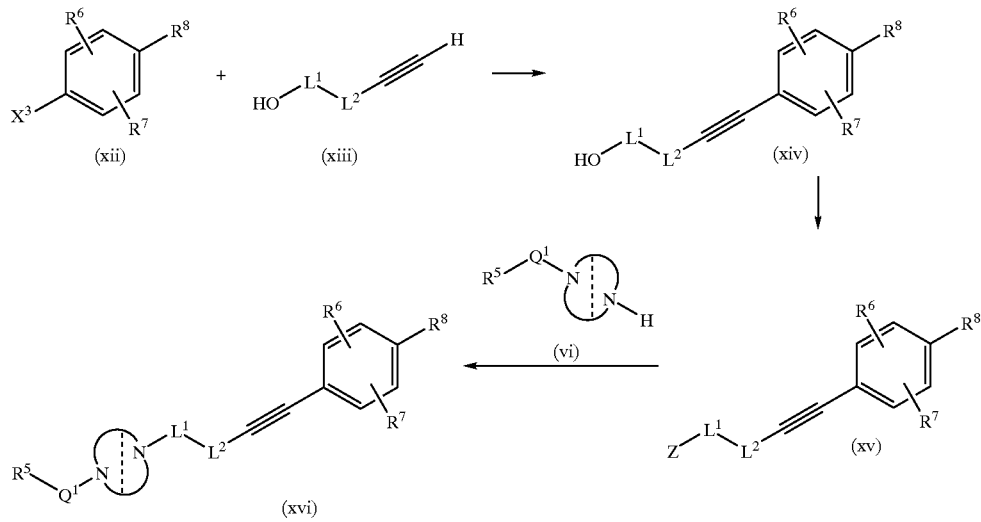

As shown in Scheme 6, the conversion of (xii) and (xiii) to (xiv) can be accomplished by a palladium-mediated coupling as in *Tetrahedron Letters*, 1987, 28(45), 5395–5398, wherein $X^3$ is a bromide, iodide or a triflate.

The conversion of (xiv) to (xv), wherein Z is a leaving group, can be accomplished by treating the former with a leaving group precursor and a base in a solvent. Specific examples of leaving group precursors include trifluoroacetic anhydride, trifluormethanesulfonyl chloride, methanesulfonyl chloride, and para-toluenesulfonyl chloride. Specific examples of bases include, TEA, pyridine, lutidine, collidine, diisopropylethylamine, and DBU. Specific examples of solvents include THF, DCM, toluene, pyridine and chloroform. Although the reaction generally proceeds at 0° C., it can be run at lower or elevated temperatures as needed. The reaction time is generally about 30 minutes to about 16 hours. In a preferred embodiment, (xiv) and TEA in 0° C. THF were treated with para-toluenesulfonyl chloride and stirred for about 16 hours.

The conversion of (xv) and (vi) to (xvi) can be accomplished by combining (xv) and (vi) in the presence of a base, and an optionally added additive, in a solvent. $R^1$, $R^2$, and $R^3$ are defined as in formula (I) and are substituents on the piperazine or diazepane ring. $R^4$ is synonymous with $R^5$ in this scheme and is defined in formula (I). Specific examples of (vi) include diamines such as piperazine, trans-1,4-diaminocyclohexane, 2-methylpiperazine, 2,6-dimethylpiperazine, trans-2,5-dimethylpiperazine, diazepane, and N,N-dimethyl-1,3-propanediamine. Specific examples of bases include $K_2CO_3$, $Na_2CO_3$, $NaHCO_3$, $K_3PO_4$, LiOH, NaOH, and KOH. Specific examples of additives include KI, $I_2$, and HI. Specific examples of solvents include acetone, 2-butanone, THF, DCM, and chloroform. Although the reaction generally proceeds at about 80° C. it can be run at lower temperatures as needed. The reaction time is generally about 12 hours to about five days and can be selected depending on the reaction temperature.

Scheme 7

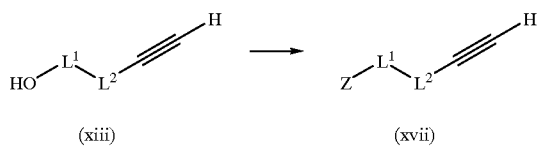

As shown in Scheme 7, the conversion of (xiii) to (xvii), wherein Z is a leaving group, can be accomplished by treating the former with a leaving group precursor and a base in a solvent. Specific examples of leaving group precursors include trifluoroacetic anhydride, trifluormethanesulfonyl chloride, methanesulfonyl chloride, and para-toluenesulfonyl chloride. Specific examples of bases include, TEA, pyridine, lutidine, collidine, diisopropylethylamine, and DBU. Specific examples of solvents include THF, DCM, toluene, pyridine and chloroform. Although the reaction generally proceeds at 0° C., it can be run at lower or elevated temperatures as needed. The reaction time is generally about 30 minutes to about 16 hours. In a preferred embodiment, (xiii) and TEA in 0° C. THF were treated with paratoluenesulfonyll chloride and stirred for about 16 hours.

Scheme 8

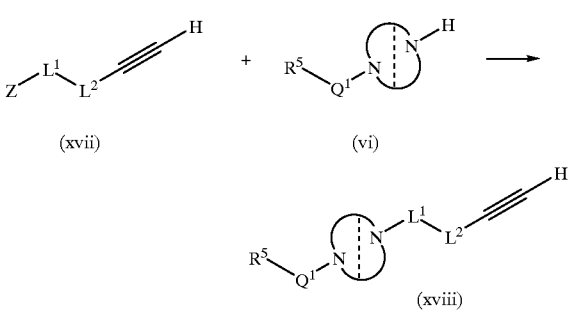

As shown in Scheme 8, the conversion of (xvii) and (vi) to (xviii) can be accomplished by combining (xvii) and (vi) in the presence of a base, and an optionally added additive, in a solvent. $R^1$, $R^2$, and $R^3$ are defined as in formula (I) and are substituents on the piperazine or diazepane ring. $R^4$ is synonymous with $R^5$ in this scheme and is defined in formula (I). Z is defined as a leaving group. Specific examples of (vi) include diamines such as piperazine, trans-1,4-diaminocyclohexane, 2-methylpiperazine, 2,6-dimethylpiperazine, trans-2,5-dimethylpiperazine, diazepane, and N,N'-dimethyl-1,3-propanediamine. Specific examples of bases include $K_2CO_3$, $Na_2CO_3$, $NaHCO_3$, $K_3PO_4$, LiOH, NaOH, and KOH. Specific examples of additives include KI, $I_2$, and HI. Specific examples of solvents include acetone, 2-butanone, THF, DCM, and chloroform. Although the reaction generally proceeds at 80° C. it can be run at lower temperatures as needed. The reaction time is generally about 12 hours to about five days and can be selected depending on the reaction temperature.

Scheme 9

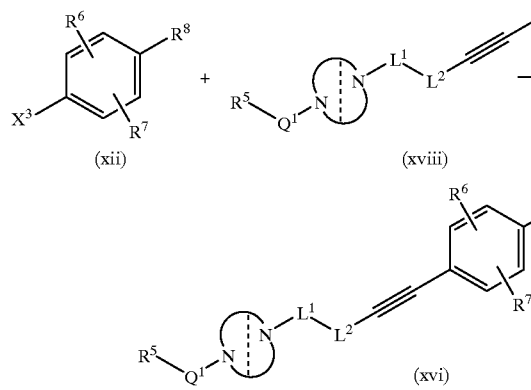

(xii)    (xviii)

(xvi)

shown in Scheme 9, the conversion of (xii) and (xviii) to (xvi) can be accomplished by a palladium-mediated coupling as in *Tetrahedron Letters*, 1987, 28(45), 5395–5398, wherein $X^3$ is a bromide, iodide or a triflate.

The following preparative chemical examples of compounds of this invention are provided to enable those skilled in the art to carry out this invention. However, these examples are not to be read as limiting the scope of this invention as it is defined by the appended claims.

EXAMPLE 1

(4-(3-(4-((2S)-2-aminopropanoyl)-1-piperazinyl) propoxy)phenyl)(cyclopropyl)methanone Example 1A Cyclopropyl(4-hydroxyphenyl)methanone A refluxing solution of sodium hydroxide in water (50% (w/w), 40.4 mL) was treated over a period of 15 minutes with para-hydroxy-4-chlorobutyrophenone (25.0 g, 137 mmol), followed by additional aqueous sodium hydroxide (25% (w/w), 177 mL). Additional para-hydroxy-4-chlorobutyrophenone (25.0 g, 137 mmol) was added portionwise to the reaction mixture, followed by solid sodium hydroxide (40.4 g). A yellow precipitate formed. After refluxing for 60 minutes, water (50 mL) was added and the resulting mixture was refluxed for another 60 minutes, cooled to room temperature, diluted with water (100 mL) and neutralized with acetic acid. The precipitate was collected by filtration, washed with water, air-dried, and triturated at 40° C. with chloroform (1.5 L). The chloroform solution was dried ($MgSO_4$), filtered, and concentrated. The concentrate was recrystallized from chloroform/hexanes to afford 26.65 g (95%) of the desired product.
MS (APCI(-)) m/z 161 (M—H)$^-$;
$^1$H NMR (300 MHz, $CDCl_3$) δ7.9 (d, 2H), 6.9 (d, 2H), 2.65 (m, 1H), 1.23 (m, 2H), 1.03 (m, 2H).

Example 1B (4-(3-chloropropoxy)phenyl)(cyclopropyl) methanone

A solution of Example 1A (10 g, 61.7 mmol), $K_2CO_3$ (12.7 g, 91.9 mmol), and 1-bromo-3-chloropropane (10.74 g, 68.2 mmol) in 2-butanone (100 mL) was refluxed for 24 hours, cooled to room temperature, filtered, and concentrated. The concentrate was heated to 40° C. under vacuum for three hours to afford 13.256 g (90%) of the desired product of sufficient purity for subsequent use without further purification.

Example 1C

Cyclopropyl(4-(3-(1-piperazinyl)propoxy)phenyl) methanone

A mixture of Example 1B (10 g, 42 mmol), KI (8.5 g, 51.2 mmol), $K_2CO_3$ (8.75 g, 63.3 mmol), and piperazine (10.75 g, 125 mmol) in 2-butanone (500 mL) was refluxed for 48 hours. The reaction mixture was then cooled to room temperature, treated with 1 M sodium thiosulfate (100 mL) and ethyl acetate (500 mL). The layers were separated, and the organic layer was washed with water and brine, dried ($MgSO_4$), filtered, and concentrated. The concentrate was purified by column chromatography on silica gel using 98:2:0.1 to 95:5:0.9 dichloromethane:methanol:concentrated ammonium hydroxide as the eluant to afford 9.931 g (82%) of the desired product.
MS (APCI(+)) m/z 289 (M+H)$^+$;
$^1$H NMR (300 MHz, $CDCl_3$) 68.0 (d, 2H), 6.9 (d, 2H), 4.0 (t, 2H), 2.9 (m, 4H), 2.6 (m, 1H), 2.5 (m, 8H), 2.0 (m, 2H), 1.2 (m, 2H), 1.0 (m, 2H).

Example 1D

Tert-butyl (1S)-2-(4-(3-(4-(cyclopropylcarbonyl) phenoxy)propyl)-1-piperazinyl)-1-methyl-2-oxoethylcarbamate A solution of Example 1C (4.5 g, 15.6 mmol), N,N-diisopropylethylamine (8.3 mL, 47.6 mmol), DMAP (380 mg, 3.1 mmol) and N—Boc—(L)—alanine (3.69 g, 19.5 mmol) in dichloromethane (120 mL) at 0° C. was treated with EDCI (3.6 g, 18.8 mmol). The reaction mixture was warmed to room temperature, stirred for 18 hours, treated with half-saturated $NaHCO_3$ (100 mL), and extracted with dichloromethane. The combined organic layers were washed sequentially with 0.5 M citric acid, water, and brine, dried ($MgSO_4$), filtered, and concentrated. The concentrate was purified by column chromatography on silica gel using 98:2 dichloromethane:methanol as the eluant to afford 4.66 g (65%) of the desired product.
MS (APCI(+)) m/z 460 (M+H)$^+$;
$^1$H NMR (300 MHz, $CDCl_3$) δ7.9 (d, 2H), 6.8 (d, 2H), 5.47 (d, 1H), 4.53 (m, 1H), 4.0 (m, 2H), 3.62-3.38 (m, 4H), 2.54 (m, 1H), 2.48 (m, 6H), 1.92 (m, 1H), 1.36 (s, 9H), 1.22 (d, 3H), 1.12 (m, 2H), 0.9 (m, 2H).

Example 1E (4-(3-(4-((2S)-2-aminopropanoyl)-1-piperazinyl)
propoxy)phenyl)(cyclopropyl)methanone A solution of Example 1D (3.0 g, 6.5 mmol) in dichloromethane (30 mL) at 0° C. was treated, over a period of 10 minutes, with trifluoroacetic acid (7.5 mL, 97 mmol). The reaction mixture was allowed to warm to room temperature, stirred for 24 hours, and concentrated. The concentrate was dissolved in dichloromethane (300 mL) and the solution was washed sequentially with saturated NaHCO$_3$, water, and brine, dried (MgSO$_4$), filtered, and concentrated. The concentrate was dissolved in methanol (120 mL), treated with L-tartaric acid (1.0 equivalent based on recovered material), stirred for 18 hours at room temperature, and concentrated. The concentrate was dissolved in water (25 mL) and lyophilized to afford the desired product in 83% yield.
MS (APCI(+)) m/z 360 (M+H)$^+$;
$^1$H NMR (300 MHz, D$_2$O) δ8.0 (d, 2H), 7.09 (d, 2H), 4.6 (m, 1H), 4.27 (m, 4H), 3.92 (br. s, 2H), 3.44 (m, 4H), 2.85 (m, 2H), 2.31 (m, 2H), 1.52 (d, 3H), 1.18 (m, 4H).

EXAMPLE 2

(2S)-1-(4-(3-(4-(5-methyl-1,2,4-oxadiazol-3-yl)
phenoxy)propyl)-1-piperazinyl)-1-oxo-2-
propanamine

Example 2A 4-(3-chloropropoxy)benzonitrile

The desired product was prepared according to the method described in Example 13, substituting 4-hydroxybenzonitrile for Example 1A.

Example 2B

Tert-butyl 4-(3-(4'-cyanophenoxy)propyl)-1-
piperazinecarboxylate

The desired product was prepared according to the method described in Example 1C, substituting Example 2A for Example 1B and tert-butyl 1-piperazinecarboxylate for piperazine.

Example 2C

Tert-butyl 4-(3-(4-(amino(hydroxyimino) methyl)
phenoxy)propyl)-1-piperazinecarboxylate A mixture of Example 2B (2.0 g, 5.8 mmol), finely divided K$_2$CO$_3$ (4.0 g, 29 mmol), and hydroxylamine hydrochloride (2.0 g, 29 mmol) in absolute ethanol (40 mL) was refluxed for 18 hours, cooled to room temperature, and filtered. The solids were washed with hot ethanol, and the combined filtrates were concentrated to afford 2.05 g, (93.5 %) of the desired product as a white powder.
MS (APCI(+)) m/z 379 (M+H)$^+$;
$^1$H NMR (300 MHz, CDCl$_3$) δ7.55 (d,, 2H), 6.85 (d,, 2H), 4.80 (m, 2H), 4.10 (m, 2H), 3.42 (m, 4H), 2.53 (m, 2H), 2.41 (m, 4H), 1.98 (m, 2H), 1.42 (s, 9H).

Example 2D

Tert-butyl 4-(3-(4-(((acetyloxy)amino)(amino)
methyl)phenoxy)propyl)-1-piperazinecarboxylate A solution of Example 2C (0.11 g, 0.29 mmol) and triethylamine (400 μL, 2.9 mmol) in acetone (10 mL) was treated with a solution of acetyl chloride (200 μL, 2.8 mmol) in acetone (1 mL) over 30 minutes, stirred for 1 hour, and concentrated. The concentrate was partitioned between water and dichloromethane. The layers were separated, and the aqueous layer was extracted with dichloromethane. The combined extracts were dried (Na$_2$SO$_4$), filtered and concentrated. The concentrate was purified by column chromatography on silica gel using 95:5 dichloromethane:methanol to afford 106 mg (87%) of the desired product.
MS (APCI(+)) m/z 421 (M+H)$^+$;
$^1$H NMR (300 MHz, CDCl$_3$) δ7.65 (d,, 2H), 6.95 (d,, 2H), 5.00 (s, 2H), 4.05 (m, 2H), 3.40 (m, 4H), 2.51 (m, 2H), 2.44 (m, 4H), 2.21 (s, 3H), 1.98 (m, 2H), 1.42 (s, 9H).

Example 2E

Tert-butyl 4-(3-(4-(5-methyl-1,2,4-oxadiazol-3-yl)
phenoxy)propyl)-1-pipierazinecarboxylate A solution of Example 2D (100 mg, 0.24 mmol) in toluene (10 mL) was refluxed for 24 hours and concentrated. The concentrate was triturated with a diethyl ether and dichloromethane mixture to afford 92 mg (95%) of the desired product of sufficient purity for subsequent use without further purification.
MS (APCI(+)) m/z 403 (M+H)$^+$;
$^1$H NMR (300 MHz, CDCl$_3$) δ7.95 (d, 2H), 6.97 (d,, 2H), 4.05 (m, 2H), 3.40 (m, 4H), 2.65 (s, 3H), 2.51 (m, 2H), 2.40 (m, 4H), 2.00 (m, 3H), 1.55 (m, 2H), 1.42 (s, 9H).

Example 2F 1-(3-(4-(5-methyl-1,2,4-oxadiazol-3-yl)phenoxy)
propyl)piperazine A solution of Example 2E in dichloromethane at room temperature is treated with trifluoroacetic acid, stirred for 12 hours, and concentrated. The concentrate is partitioned between dichloromethane and saturated aqueous Na$_2$CO$_3$. The layers are separated, and the dichloromethane layer is dried (MgSO$_4$), filtered and concentrated to afford the desired product.

Example 2G

Tert-butyl (1S)-1-methyl-2-(4-(3-(4-(5-methyl-1,2,4-
oxadiazol-3-yl) phenoxy)propyl)-1-piperazinyl)-2-
oxoethylcarbamate The desired product is prepared according to the method described in Example 1D, substituting Example 2F for Example 1C.

Example 2H (2S)-1-(4-(3-(4-(5-methyl-1,2,4-oxadiazol-3-yl)
phenoxy)propyl)-1-piperazinyl)-1-oxo-2-
propanamine The desired product is prepared according to the method described in Example 1E, substituting Example 2G for Example 1D.

EXAMPLE 3

1-(3-(4-bromophenoxy)propyl)piperazine

Example 3A 1-bromo-4-(3-chloropropoxy)benzene

The title compound was prepared according to the method described in Example 1B, substituting 4-bromophenol for Example 1A to afford the desired product.

Example 3B

1-(3-(4-bromophenoxy)propyl)piperazine

The title compound was prepared according to the method described in Example 1C, substituting Example 3A for Example 1B to afford the desired product.
MS (APCI(+)) m/z 299 (M+H)$^+$;
$^1$H NMR (300 MHz, CDCl$_3$) δ7.37 (m, 2H), 6.78 (m, 2H), 3.95 (t, 2H), 3.45 (br m, 4H), 2.58 (t, 2H), 2.42 (br m, 4H), 2.12 (br m, 1H), 1.97 (m, 2H).

EXAMPLE 4

(4-(2-chloroethoxy)phenyl)(cyclopropyl)methanone

The title compound was prepared according to the method described in Example 1B, substituting 1-bromo-2-chloroethane for 1-bromo-3-chloropropane to afford the desired product.
MS (APCI(+)) m/z 226 (M+H)$^+$;
$^1$H NMR (300 MHz, CDCl$_3$) δ1.41 (s, 3H), 1.45 (s, 6H), 1.86 (m, 2H), 1.90–2.27 (m, 4H), 2.61 (m, 4H), 2.88 (m, 2H), 3.40–3.80 (m, 7H), 4.19 (m, 2H), 4.60 (m, 1H), 7.00 (d, 2H), 7.53 (d, 2H), 7.67 (m, 4H).

EXAMPLE 5

4-(2-chloroethoxy)(1,1'-biphenyl)-4-carbonitrile

The title compound was prepared according to the method described in Example 1B, substituting 4'-cyano-4-hydroxybiphenyl for Example 1A and 1-bromo-2-chloroethane for 1-bromo-3-chloropropane to afford the desired product.
MS (APCI(+)) m/z 259 (+H)$^+$;
$^1$H NMR (300 MHz, CDCl$_3$) 2.57 (m, 4H), 2.82 (t, 2H), 2.92 (t, 4H), 4.17 (t, 2H), 7.00 (d, 2H), 7.52 (d, 2H), 7.66 (m, 4H).

EXAMPLE 6

1-(4-(3-(1-piperazinyl)propoxy)phenyl)ethanone

Example 6A

1-(4-(3-chloropropoxy)phenyl)ethanone

The title compound was prepared according to the method described in Example 1B, substituting 4-hydroxyacetophenone for Example 1A to afford the desired product.

Example 6B

1-(4-(3-(1-piperazinyl)propoxy)phenyl)ethanone

The title compound was prepared according to the method described in Example 1C, substituting Example 6A for Example 1B to afford the desired product.
MS (APCI(+)) m/z 263 (M+H)$^+$;
$^1$H NMR (300 MHz, CDCl$_3$) δ1.99 (quint., 2H), 2.47–2.55 (m, 6H), 2.55 (s, 3H), 2.62 (bs, 1H), 2.93 (t, 4H), 4.08 (t, 2H), 6.93 (d, 2H), 7.92 (d, 2H).

EXAMPLE 7

Cyclopropyl(4-(((3R)-3-(1-piperazinyl)butyl)oxyphenyl Methanone

Example 7A

(2S)-4-((tert-butyl(dimethyl)silyl)oxy)-2-butanol

A 0° C. solution of (S)—(+)-1,3-butanediol (2.1 g, 23.3 mmol), imidazole (1.74 g, 25.6 mmol), and N,N-dimethylformamide (1.0 mL) in dichloromethane (40 mL) was treated with tert-butyl-dimethylsilyl chloride (3.68 g, 23.3 mmol). The reaction mixture was warmed to room temperature, stirred overnight, quenched with saturated aqueous ammonium chloride and extracted with dichloromethane. The combined dichloromethane layers were dried (MgSO$_4$), filtered and concentrated to afford of the desired product of sufficient purity for subsequent use without further purification in near quantitative yield.
MS (DCI/NH$_3$) m/z 205 (M+H)$^+$;
$^1$H NMR (300 MHz, CDCl$_3$) δ3.95 (m, 1H), 3.79 (m, 2H), 3.27 (br s, 1H), 1.56 (m 2H), 1.11 (d, 3H), 0.82 (s, 9H), 0.016 (s, 6H).

Example 7B

(1S)-3-((tert-butyl(dimethyl)silyl)oxy)-1-methylpronyl Methanesulfonate

A 0° C. solution of Example 7A (4.75 g, 23.2 mmol) and TEA (3.3 mL, 23.7 mmol) in dichloromethane (40 mL) was treated with methanesulfonyl chloride (1.8 mL, 23.4 mmol). The reaction mixture was allowed to warm to room temperature, stirred for 2 hours, quenched with saturated aqueous ammonium chloride and extracted with dichloromethane. The combined dichloromethane layers were dried (MgSO$_4$), filtered and concentrated to afford of the desired product in quantitative yield and of sufficient purity for subsequent use without further purification.
MS (DCI/NH$_3$) m/z 300 (M+H)$^+$;
$^1$H NMR (300 MHz, CDCl$_3$) δ4.9 (m, 1H), 3.71 (m, 2H), 3.0 (s, 3H), 1.8 (m, 2H), 1.46 (d, Hz), 3H), 0.89 (s, 9H), 0.05 (s, 6H).

Example 7C

Tert-butyl 4-((1R)-3-hydroxy-1-methylpropyl)-1-piperazinecarboxylate

A mixture of N,N-diisopropylethylamine (5.0 mL, 28.7 mmol), N—Boc-piperazine (5.5 g, 29.5 mmol), and Example 7B (22.5 mmol) in acetonitrile (150 mL) was refluxed for 100 hrs and then cooled to room temperature. Water was added, followed by ethyl acetate extraction. The combined ethyl acetate layers were dried (MgSO$_4$), filtered and concentrated. The concentrate was purified by silica gel column chromatography using hexanes:ethyl acetate (1:1) as the eluant to afford 4.96 g of the coupled product.

A room temperature solution of the coupled product 4.95 g in THF (100 mL) was treated with a solution of tetrabutylammonium fluoride in THF (1 M, 25 mL). After stirring for 18 hours, the reaction mixture was quenched with water and extracted with dichloromethane. The combined dichloromethane layers were dried (Na$_2$SO$_4$), filtered and concentrated to afford 3.41 g (89%) of the desired product of sufficient purity for subsequent use without further purification.
MS (DCI/NH$_3$) m/z 259 (M+H)$^+$;
$^1$H NMR (300 MHz, CDCl$_3$) δ5.7 (s, 1H), 3.82 (m, 2H), 3.44 (m, 4H), 2.94 (m, 1H), 2.72 (m, 2H), 2.41 (m, 2H), 1.87 (m, 1H), 1.72 (s, 1H), 1.45 (s, 9H), 0.97 (d, 3H).

Example 7D

Tert-butyl 4-((1R)-3-(4-(cyclopropylcarbonyl)Phenoxy)-1-methylpropyl)-1-piperazinecarboxylate A 0° C. solution of triphenylphosphine (1.09 g, 4.14 mmol), Example 1A (0.67 g, 4.14 mmol), and Example 7°

C. (1.06 g, 4.1 mmol) in dry THF (25 mL) was treated with diethyl azodicarboxylate (0.65 mL, 4.14 mmol). The reaction mixture was allowed to warm and stirred at room temperature overnight. Additional diethyl azodicarboxylate (0.12 mL; 20%) and triphenylphosphine (0.2 g, 20%) were added and the reaction mixture was stirred for an additional two hours. The reaction mixture was concentrated and triturated with ether and hexanes, filtered and concentrated. The oily concentrate was purified by silica gel chromatography using hexanes:ethyl acetate (3:2) as the eluant to afford 1.35 g (81%) of the desired product.
MS (DCI/NH$_3$) m/z 403 (M+H)$^+$;
$^1$H NMR (300 MHz, CDCl$_3$) δ7.98 (d, 2H), 6.94 (d, 2H), 4.59 (m, 1H), 3.44 (br m, 4H), 2.64 (m, 1H), 2.48 (m, 6H), 2.05 (m, 2H), 1.45 (s, 9H), 1.35 (d, 3H), 1.19 (m, 2H), 1.00 (m, 2H).

Example 7E

Cyclopropyl(4-(((3R)-3-(1-piperazinyl)butyl)oxy) phenyl)methanone

A 0° C. solution of Example 7D (1.3 g, 3.5 mmol) in dichloromethane (30 mL) was treated with TFA (4.05 mL, 52 mmol). The reaction mixture was allowed to warm to room temperature and stirred overnight. The reaction mixture was concentrated and treated with NaOH (1 N), to a pH of approximately 12, followed by extraction with dichloromethane. The dichloromethane layers were combined, dried (Na$_2$SO$_4$), filtered, and concentrated to afford 954 mg, (90%) of the desired product of sufficient purity for subsequent use without further purification.
MS (DCI/NH$_3$) m/z 303 (M+H)$^+$;
$^1$H NMR (300 MHz, CDCl$_3$) δ8.00 (d, 2H), 6.96 (d, 2H), 4.23–4.04 (m, 2H), 2.96–2.75 (m, 5H), 2.69–2.50 (m, 4H), 2.50–2.40 (m, 2H), 2.09–1.96 (m, 1H), 1.83–1.69 (m, 1H), 1.31–1.17 (m, 2H), 1.07–0.96 (m, 2H), 1.04 (d, 3H).

EXAMPLE 8

Cyclopropyl(4-(((3S)-3-(1-piperazinyl)butyl)oxy) phenyl)methanone

Example 8A (2R)-4-((tert-butyl(dimethyl)silyl)oxy)-2-butanol

The title compound was prepared according to the method described in Example 7A, substituting (R)—(−)—1,3-butanediol for (S)-(+)-1,3-butanediol to afford the desired product.

Example 8B (1R)-3-((tert-butyl(dimethyl)silyl)oxy)-1-methylpropyl Methanesulfonate The title compound was prepared according to the method described in Example 7B, substituting Example 8A for Example 7A to afford the desired product.

Example 8C

Tert-butyl 4-((1S)-3-hydroxy-1-methylpropyl)-1-piperazinecarboxylate

The title compound was prepared according to the method described in Example 7C, substituting Example 8B for Example 7B to afford the desired product.

Example 8D

Tert-butyl 4-((1S)-3-(4-(cyclopropylcarbonyl) Phenoxy)-1-methylpropyl)-1-piperazinecarboxylate The title compound was prepared according to the method described in Example 7D, substituting Example 8C for Example 7C to afford the desired product.

Example 8E

Cyclopropyl(4-(((3S)-3-(1-piperazinyl)butyl)oxy) phenyl)methanone

The title compound was prepared according to the method described in Example 7E, substituting Example 8D for Example 7D to afford the desired product.
MS (DCI/NH$_3$) m/Z 303 (M+H)$^+$;
$^1$H NMR (300 MHz, CDCl$_3$) δ8.00 (d, 2H), 6.96 (d, 2H), 4.23–4.04 (m, 2H), 2.96–2.75 (m,5H), 2.69–2.54 (m, 3H), 2.50–2.40 (m, 2H), 2.18 (brs, 1H), 2.09–1.96 (m,1H), 1.83–1.69 (m, H), 1.31–1.17 (m,2H), 1.07–0.96 (m,2H), 1.04 (d, 3H).

EXAMPLE 9

4-(2-(1-piperazinyl)ethoxy)(1,1'-biphenyl)-4-carbonitrile

The title compound was prepared according to the method described in Example 1C, substituting Example 5A for Example 1B to afford the desired product.
MS (APCI(+)) m/z 308 (M+H)$^+$;
$^1$H NMR (300 MHz, CDCl$_3$) δ7.66 (m, 4H), 7.52 (d, 2H), 7.00 (d, 2H), 4.17 (t, 2H), 2.92 (t, 4H), 2.82 (t, 2H), 2.57 (m, 4H).

EXAMPLE 10

4-(3-(1-piperazinyl)propoxy)(1,1'-biphenyl)-4-carbonitrile

Example 10A 4-(3-chloropropoxy)(1,1'-biphenyl)-4-carbonitrile

The title compound was prepared according to the method described in Example 1B, substituting 4'-cyano-4-hydroxybiphenyl for Example 1A to afford the desired product.

Example 10B 4-(3-(1-piperazinyl)propoxy)(1,1'-biphenyl)-4-carbonitrile

The title compound was prepared according to the method described in Example 1C, substituting Example 10A for Example 1B.
MS (APCI(+)) m/z 322 (M+H)$^+$;
$^1$H NMR (300 MHz, CDCl$_3$) δ7.67 (m, 4H), 7.53 (d, 2H), 7.00 (d, 2H), 4.08 (t, 2H), 2.94 (m, 4H), 2.54 (m, 4H), 2.48 (br s, 1H), 2.00 (m, 4H).

EXAMPLE 12

Tert-butyl 2-(4-(3-(4-bromophenoxy)propyl)-1-piperazinyl)-2-oxoethylcarbamate

The desired product was prepared according to the method described in Example 1D, substituting Example 3B for Example 1C and N—Boc—glycine for N—Boc—(L)—alanine.
MS (APCI(+)) m/z 456 (M+H)$^+$;
$^1$H NMR (300 MHz, CDCl$_3$) δ7.37 (m, 2H), 6.78 (m, 2H), 4.33 (t, 1H), 3.95 (m, 4H), 3.65 (m, 2H), 3.51 (m, 1H), 3.45 (m, 2H), 2.58 (t, 1H), 2.42 (m, 3H), 2.12 (m, 1H), 1.97 (m, 2H), 1.46 (s, 9H).

EXAMPLE 13

2-(4-(3-(4-bromophenoxy)propyl)-1-piperazinyl)-2-oxoethanamine

The desired product was prepared according to the method described in Example 1E, substituting Example 12 for Example 1D.

MS (APCI(+)) m/z 356 (M+H)+;
1H NMR (300 MHz, DMSO-d6) δ7.43 (m, 2H), 6.90 (m, 2H), 4.18 (t, 1H), 4.05 (m, 2H), 3.35 (br m, 7H), 2.41 (t, 1H), 2.27 (br m, 4H), 2.12 (m, 1H), 1.97 (m, 2H).

EXAMPLE 14

Tert-butyl 3-(4-(3-(4-bromophenoxy)propyl)-1-piperazinyl)-3-oxopropylcarbamate

The desired product was prepared according to the method described in Example 1D, substituting Example 3B for Example 1C and N—Boc-4-amino-butyric acid for N—Boc—(L)—alanine.
MS (APCI(+)) m/z 470 (M+H)+;
1H NMR (300 MHz, CDCl3) δ7.37 (m, 2H), 6.78 (m, 2H), 4.29 (t, 1H), 3.95 (m, 4H), 3.64 (br m, 2H), 3.45 (br m, 3H), 2.58 (m, 3H), 2.42 (br m, 3H), 2.12 (m, 1H), 1.97 (m, 2H), 1.46 (s, 9H).

EXAMPLE 15

3-(4-(3-(4-bromophenoxy)propyl)-1-piperazinyl)-3-oxo-1-propanamine

The desired product was prepared according to the method described in Example 1E, substituting Example 14 for Example 1D.
MS (APCI(+)) m/z 370 (M+H)+.
1H NMR (300 MHz, CDCl3) δ7.37 (m, 2H), 6.78 (m, 2H), 4.29 (t, 1H), 3.95 (m, 4H), 3.64 (br m, 2H), 3.45 (br m, 3H), 2.58 (m, 3H), 2.42 (br m, 3H), 2.12 (m, 1H), 1.97 (m, 2H).

EXAMPLE 16

Tert-butyl (1R)-2-(4-(3-(4-bromophenoxy) propyl)-1-piperazinyl)-1-methyl-2-oxoethylcarbamate The desired product was prepared according to the method described in Example 1D, substituting Example 3B for Example 1C and N—Boc—(D)—alanine for N—Boc—(L)—alanine.
MS (APCI(+)) m/z 470 (M+H)+;
1H NMR (300 MHz, CDCl3) δ7.37 (m, 2H), 6.78 (m, 2H), 4.65 (q, 1H), 4.29 (t, 1H), 3.95 (m, 2H), 3.65 (br m, 2H), 3.45 (br m, 3H), 2.58 (t, 1H), 2.42 (br m, 3H), 2.12 (m, 1H), 1.97 (m, 2H), 1.46 (s, 9H), 1.24 (d, 3H).

EXAMPLE 17

(2R)-1-(4-(3-(4-bromophenoxy)propyl)-1-piperazinyl)-1-oxo-2-propanamine

The desired product was prepared according to the method described in Example 1E, substituting Example 16 for Example 1D.
MS (APCI(+)) m/z 370 (M+H)+;
1H NMR (300 MHz, CDCl3) δ7.37 (m, 2H), 6.78 (m, 2H), 4.29 (t, 1H), 3.95 (m, 2H), 3.85 (br m, 1H), 3.65 (br m, 2H), 3.45 (br m, 2H), 3.07 (br m, 2H), 2.58 (br m, 4H), 2.12 (m, 1H), 1.97 (m, 2H), 1.25 (d, 3H).

EXAMPLE 18

Tert-butyl (1S)-2-(4-(3-(4-bromophenoxy) propyl)-1-piperazinyl)-1-methyl-2-oxoethylcarbamate The desired product was prepared according to the method described in Example 1D, substituting Example 3B for Example 1C.

MS (APCI(+)) m/z 470 (M+H)+;
1H NMR (300 MHz, CDCl3) δ7.37 (m, 2H), 6.78 (m, 2H), 4.65 (q, 1H), 4.29 (t, 1H), 3.95 (m, 2H), 3.65 (br m, 2H), 3.45 (br m, 3H), 2.58 (t, 1H), 2.42 (br m, 3H), 2.12 (m, 1H), 1.97 (m, 2H), 1.46 (s, 9H), 1.24 (d, 3H).

EXAMPLE 19

(2S)-1-(4-(3-(4-bromophenoxy)propyl)-1-piperazinyl)-1-oxo-2-propanamine

The desired product was prepared according to the method described in Example 1E, substituting Example 18 for Example 1D.
MS (APCI(+)) m/z 370 (M+H)+;
1H NMR (300 MHz, CDCl3) δ7.37 (m, 2H), 6.78 (m, 2H), 4.29 (t, 1H), 3.95 (m, 2H), 3.85 (br m, 1H), 3.65 (br m, 2H), 3.45 (br m, 2H), 3.07 (br m, 2H), 2.58 (br m, 4H), 2.12 (m, 1H), 1.97 (m, 2H), 1.25 (d, 3H).

EXAMPLE 20

Tert-butyl (2S)-2-((4-(3-(4-bromophenoxy) propyl)-1piperazinyl)carbonyl)-1-pyrrolidinecarboxylate The desired product was prepared according to the method described in Example 1D, substituting Example 3B for Example 1C and N—Boc—(L)—proline for N—Boc—(L)—alanine.
MS (APCI(+)) m/z 496 (M+H)+;
1H NMR (300 MHz, CDCl3) δ7.37 (mn, 2H), 6.78 (m, 2H), 4.64 (br mn, 1H), 4.29 (t, 1H), 3.95 (m, 2H), 3.65 (br mn, 2H), 3.57 (br m, 2H), 3.45 (br m, 2H), 2.58 (t, 1H), 2.42 (br m, 3H), 2.12 (m, 1H), 2.06 (m, 2H), 1.97 (br m, 2H), 1.55 (m, 2H), 1.46 (s, 9H).

EXAMPLE 21

4-bromophenyl 3-(4-((2S)-pyrrolidinylcarbonyl)-1-piperazinyl)propyl Ether

The desired product was prepared according to the method described in Example 1E, substituting Example 20 for Example 1D.
MS (APCI(+)) m/z 396 (M+H)+;
1NMR (300 MHz, CDCl3) δ7.37 (mn, 2H), 6.78 (m, 2H), 4.75 (br t, 1H), 4.29 (t, 1H), 3.95 (m, 2H), 3.84 (br m, 1H), 3.65 (br m, 2H), 3.5 8 (br m, 2H), 3.45 (br m, 2H), 2.5 8 (br m, 4H), 2.12 (m, 1H), 1.97 (m, 3H), 1.25 (d, 3H).

EXAMPLE 22

Tert-butyl (2R)-2-((4-(3-(4-bromo-phenoxy) propyl)-1-piperazinyl)carbonyl)-1-pyrrolidinecarboxylate The desired product was prepared according to the method described in Example 1D, substituting Example 3B for Example 1C and N—Boc—(D)—proline for N—Boc—(L)—alanine.
MS (APCI(+)) m/z 496 (M+H)+;
1H NMR (300 MHz, CDCl3) δ7.37 (m, 2H), 6.78 (m, 2H), 4.64 (br m, 1H), 4.29 (t, 1H), 3.95 (m, 2H), 3.65 (br m, 2H), 3.57 (br m, 2H), 3.45 (br m, 2H), 2.58 (t, 1H), 2.42 (br m, 3H), 2.12 (m, 1H), 2.06 (m, 2H), 1.97 (br m, 2H), 1.55 (m, 2H), 1.46 (s, 9H).

EXAMPLE 23

4-bromophenyl 3-(4-((2R)-pyrrolidinylcarbonyl)-1-piperazinyl)propyl Ether

The desired product was prepared according to the method described in Example 1E, substituting Example 22 for Example 1D.

MS (APCI(+)) m/z 396 (M+H)+;
¹H NMR (300 MHz, CDCl₃) δ7.37 (m, 2H), 6.78 (m, 2H), 4.75 (br t, 1H), 4.29 (t, 1H), 3.95 (m, 2H), 3.84 (br m, 1H), 3.65 (br m, 2H), 3.58 (br m, 2H), 3.45 (br m, 2H), 2.58 (br m, 4H), 2.12 (m, 1H), 1.97 (m, 3H), 1.25 (d, 3H).

EXAMPLE 24

Tert-butyl (1R)-1-methyl-2-oxo-2-(4-(3-(4-(trifluoromethyl)phenoxy)propyl)-1-piperazinyl)ethylcarbamate

Example 24A 1-(3-chloropropoxy)-4-(trifluoromethyl)benzene

The desired product was prepared according to the method described in Example 1B, substituting 4-trifluoromethylphenol for Example 1A.

Example 24B 1-(3-(4-(trifluoromethyl)phenoxy)propyl)piperazine

The desired product was prepared according to the method described in Example 1C, substituting Example 24A for Example 1B.

Example 24C

Tert-butyl (1R)-1-methyl-2-oxo-2-(4-(3-(4-(trifluoromethyl)phenoxy)propyl)-1-piperazinyl)ethylcarbamate The desired product was prepared according to the method described in Example 1D, substituting Example 24B for Example 1C and N—Boc—(D)—alanine for N—Boc—(L)—alanine.
MS (DCI/NH₃) m/z 289 (M+H)+;
¹H NMR (300 MHz, CDCl₃) δ7.54 (d, 2H), 6.95 (d, 2H), 5.54 (br d, 1H), 4.61 (br quintet, 1H), 4.07 (t, 2H), 3.75–3.42 (m, 4H), 2.60–2.41 (m, 6H), 2.05–1.93 (m, 2H), 1.44 (s, 9H), 1.25 (d, 3H).

EXAMPLE 25

Tert-butyl (1R)-2-(4-(3-(4'-cyanophenoxy) propyl)-1-piperazinyl)-1-methyl-2-oxoethylcarbamate

Example 25A 4-(3-(1-piperazinyl)propoxy)benzonitrile

The desired product was prepared according to the method described in Example 1C, substituting Example 2A for Example 1B.

Example 25B

Tert-butyl (1R)-2-(4-(3-(4'-cyanophenoxy) propyl)-1-piperazinyl)-1-methyl-2-oxoethylcarbamate The desired product was prepared according to the method described in Example 1D, substituting Example 25A for Example 1C and N—Boc—(D)—alanine for N—Boc—(L)—alanine.
MS (APCI(+)) m/z 418 (M+H)+;
¹H NMR (300 MHz, CDCl₃) δ7.57 (d, 2H), 6.94 (d, 2H), 5.52 (m, 1H), 4.60 (quint., 1H), 3.75–3.4 (m, 4H), 4.07 (t, 2H), 2.54 (m, 2H), 2.46 (m, 4H), 1.99 (quint, 2H), 1.44 (s, 9H), 1.29 (d, 3H).

EXAMPLE 26

Tert-butyl 3-(4-(3-(4'-cyano-3-fluorophenoxy)propyl)-1-piperazinyl)-3-oxopropylcarbamate

Example 26A 4-(3-chloropropoxy)-2-fluorobenzonitrile

The desired product was prepared according to the method described in Example 1B, substituting 4'-cyano-3-fluorophenol for Example 1A.

Example 26B 2-fluoro-4-(3-(1-piperazinyl)propoxy)benzonitrile

The desired product was prepared according to the method described in Example 1C, substituting Example 26A for Example 1B.

Example 26C

Tert-butyl 3-(4-(3-(4'-cyano-3-fluorophenoxy)propyl)-1-piperazinyl)-3-oxopropylcarbamate The desired product was prepared according to the method described in Example 1D, substituting Example 26B for Example 1C and N—Boc—beta—alanine for N—Boc—(L)—alanine.
MS (APCI(+)) m/z 435 (M+H)+;
¹H NMR (300 MHz, CDCl₃) δ7.51 (m, 1H), 6.74 (m, 2H), 5.30 (m, 1H), 4.08 (t, 2H), 3.62 (m, 2H), 3.43 (m, 4H), 2.52 (m, 4H), 2.43 (m, 4H), 1.99 (quint., 2H), 1.43 (s, 9H).

EXAMPLE 27

Tert-butyl (1R)-2-(4-(3-(4-(aminocarbonyl)-3-fluorophenoxy) propyl)-1-piperazinyl)-1-methyl-2-oxoethylcarbamate

Example 27A

Tert-butyl (1R)-2-(4-(3-(4'-cyano-3-fluorophenoxy)propyl)-1-piperazinyl)-1-methyl-2-oxoethylcarbamate The desired product was prepared according to the method described in Example 1D, substituting Example 26B for Example 1C and N—Boc—(D)—alanine for N—Boc—(L)—alanine.

Example 27B

Tert-butyl (1R)-2-(4-(3-(4-(aminocarbonyl)-3-fluorophenoxy) propyl)-1-piperazinyl)-1-methyl-2-oxoethylcarbamate A mixture of Example 27A, finely divided K₂CO₃ and hydroxylamine hydrochloride in absolute ethanol was refluxed for 18 hours. The hot reaction mixture was filtered and the remaining solids were washed with hot ethanol. The combined filtrates were concentrated to the desired product in quantitative yield and of sufficient purity for subsequent use without further purification.
MS (APCI(+)) m/z 453 (M+H)+;
¹H NMR (300 MHz, CDCl₃) δ8.06 (t, 1H), 6.95 (m, 4H), 6.78 (dd, 1H), 6.53 (dd, 1H), 2.51–2.40 (m, 6H), 1.99 (m, 4H), 1.43 (s, 9H), 1.30 (d, 3H).

EXAMPLE 28

Tert-butyl (1R)-2-(4-(3-(4-acetylphenoxy)propyl)-1-piperazinyl)-1-methyl-2-oxoethylcarbamate The desired product was prepared according to the method described in Example 1D, substituting Example 6B for Example 1C and Boc—(D)—alanine for Boc—(L)—alanine.

MS (APCI(+)) m/z 434 (M+H)$^+$;
$^1$H NMR (300 MHz, CDCl$_3$) δ7.92 (d, 2H), 6.92 (d, 2H), 5.54 (m, 1H), 4.60 (quint., 1H), 4.09 (t, 2H), 3.68–3.46 (m, 4H), 2.56 (s, 3H), 2.56 (m, 2H), 2.48 (m, 4H), 2.00 (quint., 2H), 1.44 (s, 9H), 1.30 (d, 3H).

EXAMPLE 29

1-(4-(3-(4-((2R)-2-aminopropanoyl)-1-piperazinyl) propoxy)phenyl)ethanone

The desired product was prepared according to the method described in Example 1E, substituting Example 28 for Example 1D.
MS (APCI(+)) m/z 334 (M+H)$^+$;
$^1$H NMR (300 MHz, CDCl$_3$) δ7.93 (d, 2H), 6.93 (d, 2H), 4.10 (t, 2H), 3.80 (q, 1H), 3.65 (m, 2H), 3.49 (m, 2H), 2.56 (s, 3H), 2.56 (in, 4H); 2.47 (m, 4H), 2.00 (quint., 2H), 1.91 (br s, 2H), 1.26 (d, 3H).

EXAMPLE 30

N-((1R)-2-(4-(3-(4-acetylphenoxy)propyl)-1-piperazinyl)-1-methyl-2-oxoethyl)acetamide A 0° C. solution of Example 29 (1 mmol) and TEA (1.1 mmol) in dichloromethane (10 mL) was treated with acetyl chloride (1 mmol). After stirring for four hours at 0° C., the reaction mixture was quenched with water and extracted with dichloromethane. The combined dichloromethane layers were washed with brine, dried (Na$_2$SO$_4$), filtered and concentrated. The crude material was purified through silica gel chromatography to afford the desired product in 83% yield.
MS (APCI(+)) m/z 376 (M+H)$^+$;
$^1$H NMR (300 MHz, CDCl$_3$) δ7.92 (d, 2H), 6.92 (d, 2H), 6.68 (in, 1H), 4.88 (quint., 1H), 4.10 (t, 2H), 3.80–3.65 (m, 1H), 3.65–3.45 (m, 3H), 2.56 (s, 3H), 2.54–2.42 (m, 6H), 2.00 (s, 3H), 2.08–1.95(m, 2H), 1.31 (d, 3H).

EXAMPLE 31

Ethyl (1R)-2-(4-(3-(4-acetylphenoxy) propyl)-1-piperazinyl)-1-methyl-2-oxoethylcarbamate The desired product was prepared according to the method described in Example 30, substituting methyl chloroformate for acetyl chloride.
MS (APCI(+)) m/z 406 (M+H)$^+$;
$^1$H NMR (300 MHz, CDCl$_3$) δ7.93 (d, 2H), 6.92 (d, 2H), 5.72 (m, 1H), 4.65 (quint., 1H), 4.10 (m, 4H), 3.72–3.47 (m, 4H), 2.55 (s, 3H), 2.59–2.47 (m, 6H), 2.01 (m, 2H), 1.32 (d, 3H), 1.24 (t, 3H).

EXAMPLE 32

N-((1R)-2-(4-(3-(4-acetylphenoxy) propyl)-1-piperazinyl)-1-methyl-2-oxoethyl) cyclopropanecarboxamide The desired product was prepared according to the method described in Example 30, substituting cyclopropyl acetyl chloride for acetyl chloride.
MS (APCI(+)) m/z 402 (M+H)$^+$;
$^1$H NMR (300 MHz, CDCl$_3$) δ7.92 (d, 2H), 6.92 (d, 2H), 6.80 (m, 1H), 4.91 (quint., 1H), 4.10 (t, 2H), 3.80–3.49 (m, 4H), 2.56 (s, 3H), 2.65–2.42 (m, 6H), 2.01 (m, 2H), 1.46–1.38 (m, 1H), 1.32 (d, 3H), 0.94 (m, 2H), 0.74 (m, 2H).

EXAMPLE 33

Tert-butyl (1R)-2-(4-((1R)-3-(4-acetylphenoxy)-1-methylpropyl)-1-piperazinyl)-1-methyl-2-oxoethylcarbamate

Example 33A

Tert-butyl 4-((1R)-3-(4-acetylphenoxy)-1-methylpropyl)-1-piperazinecarboxylate

The desired product was prepared according to the method described in Example 7D, substituting 4-hydroxy acetophenone for Example 1A.

Example 33B 1-(4-(((3R)-3-(1-piperazinyl)butyl)oxy)phenyl) ethanone

The desired product was prepared according to the method described in Example 7E, substituting Example 33A for Example 7D.

Example 33C

Tert-butyl (1R)-2-(4-((1R)-3-(4-acetylphenoxy)-1-methylpropyl)-1-piperazinyl)-1-methyl-2-oxoethylcarbamate The desired product was prepared according to the method described in Example 1D, substituting Example 33B for Example 1C and Boc—(D)—alanine for Boc—(L)—alanine.
MS (APCI(+)) m/z 448 (M+H)$^+$;
$^1$H NMR (300 MHz, CDCl$_3$) δ7.92 (d, 2H), 6.92 (d, 2H), 5.56 (m, 1H), 4.60 (quint., 1H), 4.21–4.03 (m, 2H), 3.75–3.35 (m,4H), 2.92 (m, 1H), 2.56 (s, 3H), 2.56 (m, 1H), 2.46 (m, 2H), 2.00 (m, 1H), 1.78 (m, 2H), 1.43 (s, 9H), 1.29 (d, 3H), 1.02 (d, 3H).

EXAMPLE 34

Tert-butyl (1S)-2-(4-(3-(4-acetylphenoxy)propyl)-1-piperazinyl)-1-methyl-2-oxoethylcarbamate The desired product was prepared according to the method described in Example 1D, substituting Example 6B for Example 1C.
MS (APCI(+)) m/z 434 (M+H)$^+$;
$^1$H NMR (300 MHz, CDCl$_3$) δ7.92 (d, 2H), 6.92 (d, 2H), 5.54 (m, 1H), 4.60 (quint., 1H), 4.09 (t, 2H), 3.68–3.46 (m, 4H), 2.56 (s, 3H), 2.56 (m, 2H), 2.48 (m, 4H), 2.00 (quint., 2H), 1.44 (s, 9H), 1.30 (d, 3H).

EXAMPLE 35

Tert-butyl (2R)-2-((4-(3-(4-acetylphenoxy)propyl)-1-piperazinyl)carbonyl)-1-pyrrolidinecarboxylate The desired product was prepared according to the method described in Example 1D, substituting Example 6B for Example 1C and N—Boc—(D)—proline for N—Boc—(L)—alanine.
MS (APCI(+)) m/z 460 (M+H)$^+$;
$^1$H NMR (300 MHz, CDCl$_3$) δ7.92 (d, 2H), 6.92 (d, 2H), 4.60 (m, 1H), 4.22 (m, 1H), 4.09 (m, 2H), 3.95–3.79 (m, 2H), 3.70–3.30 (m, 6H), 2.86–2.61 (m, 4H), 2.56 (s, 3H), 2.22–1.85 (m, 5H), 1.43 (s, 9H).

EXAMPLE 36

Tert-butyl (2S)-2-((4-(3-(4-acetylphenoxy)propyl)-1-piperazinyl)carbonyl)-1-pyrrolidinecarboxylate The desired product was prepared according to the method described in Example 1D, substituting Example 6B for Example 1C and N—Boc—(L)—proline for N—Boc—(L)—alanine.
MS (APCI(+)) m/z 460 (M+H)$^+$;
$^1$H NMR (300 MHz, CDCl$_3$) δ7.93 (d, 2H), 6.92 (d, 2H), 4.60 (m, 1H), 4.10 (t, 2H), 3.70–3.41 (m, 6H), 2.56 (s, 3H), 2.54 (m, 2H), 2.47 (m, 3H), 2.22–1.78 (m, 7H), 1.44 (s, 9H).

EXAMPLE 37

N-((1R)-2-(4-(3-(4-acetylphenoxy)propyl)-1-piperazinyl)-1-methyl-2-oxoethyl) methanesulfonamide The desired product was prepared according to the method described in Example 7B, substituting Example 29 for Example 7A.

MS (APCI(+)) m/z 412 (M+H)+;
¹H NMR (300 MHz, CDCl₃) δ7.93 (d, 2H), 6.92 (d, 2H), 5.47 (m, 1H), 4.42 (quint., 1H), 4.10 (t, 2H), 3.80–3.40 (m, 4H), 2.90 (s, 3H), 2.56 (s, 3H), 2.60–2.40 (m, 6H), 2.00 (m, 2H), 1.38 (d, 3H).

EXAMPLE 38

N-((1R)-2-(4-(3-(4-acetylphenoxy)propyl)-1-piperazinyl)-1-methyl-2-oxoethyl)-N,N-dimethylsulfamide The desired product was prepared according to the method described in Example 7B, substituting Example 29 for Example 7A and N,N-dimethyl sulfamoylchloride for methanesulfonyl chloride.
MS (APCI(+)) m/z 441 (M+H)+;
¹H NMR (300 MHz, CDCl₃) δ7.92 (d, 2H), 6.92 (d, 2H), 5.44 (m, 1H), 4.30 (quint., 1H), 4.10 (t, 2H), 3.70–3.40 (m, 4H), 2.65–2.40 (m, 6H), 2.76 (s, 6H), 2.56 (s, 3H), 2.01 (m, 2H), 1.35 (d, 3H).

EXAMPLE 39

1-(4-(3-(4-((methylamino)acetyl)-1-piperazinyl)propoxy)phenyl)-1-hexanone

Example 39A 1-(4-(3-chloropropoxy)phenyl)-1-hexanone

The desired product was prepared according to the method described in Example 1B, substituting 4-hydroxyphenyl-1-hexanone for Example 1A.

Example 39B 1-(4-(3-(1-piperazinyl)propoxy)phenyl)-1-hexanone

The desired product was prepared according to the method described in Example 1C, substituting Example 39A for Example 1B.

Example 39C

Tert-butyl 2-(4-(3-(4-hexanoylphenoxy)propyl)-1-piperazinyl)-2-oxoethyl(methyl)carbamate The desired product was prepared according to the method described in Example 1D, substituting Example 39B for Example 1C and N—Boc-sarcosine for N—Boc—(L)—alanine.

Example 39D 1-(4-(3-(4-((methylamino)acetyl)-1-piperazinyl)propoxy)phenyl)-1-hexanone The desired product was prepared according to the method described in Example 1E, substituting Example 39C for Example 1D.
MS (ESI(+)) m/z 390 (M+H)+;
¹H NMR (300 MHz, DMSO-d₆) δ8.68 (br s, 1H), 7.90 (d, 2H), 6.94 (d, 2H), 4.10 (t, 2H), 4.05 (br m, 1H), 3.40 (m, 4H), 2.86 (t, 2H), 2.52 (m, 6H), 2.50 (d, 3H), 2.05 (m, 2H), 1.55 (quint., 2H), 1.25 (m, 4H), 0.82 (t, 3H).

EXAMPLE 40

Tert-butyl 2-(4-(3-(4-hexanoylphenoxy)propyl)-1-piperazinyl)-2-oxoethylcarbamate The desired product was prepared according to the method described in Example 1D, substituting Example 39B for Example 1C and N—Boc—glycine for N—Boc—(L)—alanine.
MS (ESI(+)) m/z 476 (M+H)+;
¹H NMR (300 MHz, DMSO-d₆) δ7.92 (d, 2H), 7.02 (d, 2H), 4.11 (t, 2H), 3.77 (m. 1H), 3.42 (m, 4H), 2.92 (t, 2H), 2.42 (m, 4H), 1.93 (m, 2H), 1.59 (m,2H), 1.37 (m, 9H), 1.29 (m, 4H), 0.86 (t, 3H).

EXAMPLE 41

1-(4-(3-(4-(3-aminopropanoyl)-1-piperazinyl)propoxy)phenyl)-1-hexanone

Example 41A

Tert-butyl 3-(4-(3-(4-hexanoylphenoxy)propyl)-1-piperazinyl)-3-oxopropylcarbamate The desired product was prepared according to the method described in Example 1D, substituting Example 39B for Example 1C and N—Boc-beta-alanine for N—Boc—(L)—alanine.

Example 41B 1-(4-(3-(4-(3-aminopropanoyl)-1-piperazinyl)propoxy)phenyl)-1-hexanone The desired product was prepared according to the method described in Example 1E, substituting Example 41A for Example 1D.
MS (ESI(+)) m/z 390 (M+H)+;
¹H NMR (300 MHz, DMSO-d₆) δ7.85 (d, 2H), 7.65 (br s, 2H), 6.95 (d, 2H), 4.08 (t, 2H), 3.32–3.30 (m, 4H), 2.94 (m, 4H), 2.85 (t, 2H), 2.62 (m, 4H), 2.08 (m, 2H), 1.50 (m, 2H), 1.20 (m, 4H), 0.80 (t, 3H).

EXAMPLE 42

1-(4-(3-(4-((2R)-2-aminopropanoyl)-1-piperazinyl)propoxy)phenyl)-1-hexanone

Example 42A

Tert-butyl (1R)-2-(4-(3-(4-hexanoylphenoxy)propyl)-1-piperazinyl)-1-methyl-2-oxoethylcarbamate The desired product was prepared according to the method described in Example 1D, substituting Example 39B for Example 1C and N—Boc—(D)—alanine for N—Boc—(L)—alanine.

Example 42B 1-(4-(3-(4-((2R)-2-aminopropanoyl)-1-piperazinyl)propoxy)phenyl)-1-hexanone The desired product was prepared according to the method described in Example 1E, substituting Example 42A for Example 1D.
MS (ESI(+)) m/z 390 (M+H)+;
¹H NMR (300 MHz, DMSO-d₆) δ8.00 (br s, 2H), 7.80 (d, 2H), 6.95 (d, 2H), 4.35 (br, 1H), 4.00 (t, 2H), 3.32–3.30 (m, 4H), 2.80 (t, 2H), 2.43–2.40 (m, 4H), 2.34 (m, 2H), 2.08 (br m, 2H), 1.55 (m, 2H), 1.25 (m, 7H), 0.82 (t, 3H).

EXAMPLE 43

Tert-butyl (1S)-1-((4-(3-(4-hexanoylphenoxy)propyl)-1-piperazinyl)carbonyl)-2-methylpropylcarbamate The desired product was prepared according to the method described in Example 1D, substituting Example 39B for Example 1C and N—Boc—(L)—valine for N—Boc—(L)—alanine.

MS (ESI(+)) m/z 518 (M+H)+;
$^1$H NMR (300 MHz, DMSO-$d_6$) δ7.94 (d, 2H), 7.07 (d, 2H), 6.72 (d, 1H), 4.20 (t, 1H), 4.15 (t, 2H), 3.45 (br m, 4H), 2.98 (t, 2H), 2.42 (m, 2H), 2.31 (br d, 4H), 1.95 (m, 4H), 1.60 (m, 2H), 1.40 (s, 9H), 1.25 (m, 3H), 0.90 (m, 9H).

EXAMPLE 44

1-(4-(3-(4-((2S)-2-amino-3-methylbutanoyl)-1-piperazinyl)propoxy)phenyl)-1-hexanone The desired product was prepared according to the method described in Example 1E, substituting Example 43 for Example 1D.
MS (ESI(+)) m/z 418 (M+H)+;
$^1$H NMR (300 MHz, DMSO-$d_6$) δ8.05 (br s, 2H), 7.89 (d, 2H), 6.95 (d, 2H), 4.20 (br s, 1H), 4.10 (t, 2H), 3.40–3.31 (m, 4H), 2.85 (t, 2H), 2.61–2.40 (m, 4H), 2.10–1.90 (m, 5H), 1.55 (m, 2H), 1.25 (m, 4H), 0.91 (d, 3H), 0.85 (d, 3H), 0.79 (t, 3H).

EXAMPLE 45

Tert-butyl (1R)-1-((4-(3-(4-hexanoylphenoxy)propyl)-1-piperazinyl)carbonyl)-2-methylpropylcarbamate The desired product was prepared according to the method described in Example 1D, substituting Example 39B for Example 1C and N—Boc—(D)—valine for N—Boc—(L)—alanine.
MS (ESI(+)) m/z 518 (M+H)+;
$^1$H NMR (300 MHz, DMSO-$d_6$) δ7.94 (d, 2H), 7.07 (d, 2H), 6.72 (d, 1H), 4.20 (t, 1H), 4.15 (t, 2H), 3.45 (br m, 4H), 2.98 (t, 2H), 2.42 (m, 2H), 2.31 (br d, 4H), 1.95 (m, 4H), 1.60 (m, 2H), 1.40 (s, 9H), 1.25 (m, 3H), 0.87 (m, 9H).

EXAMPLE 46

1-(4-(3-(4-((2R)-2-amino-3-methylbutanoyl)-1-piperazinyl)propoxy)phenyl)-1-hexanone The desired product was prepared according to the method described in Example 1E, substituting Example 45 for Example 1D.
MS (ESI(+)) m/z 418 (M+H)+;
$^1$H NMR (300 MHz, DMSO-$d_6$) δ8.05 (br s, 2H), 7.89 (d, 2H), 6.95 (d, 2H), 4.20 (br s, 1H), 4.10 (t, 2H), 3.40–3.31 (m, 4H), 2.85 (t, 2H), 2.61–2.40 (m, 4H), 2.10–1.90 (m, 5H), 1.55 (m, 2H), 1.25 (m, 4H), 0.91 (d, 3H), 0.85 (d, 3H), 0.79 (t, 3H).

EXAMPLE 47

Tert-butyl (1S)-1-((4-(3-(4-hexanoylphenoxy)propyl)-1-piperazinyl)carbonyl)-3-methylbutylcarbamate The desired product was prepared according to the method described in Example 1D, substituting Example 39B for Example 1C and N—Boc—(L)—leucine for N—Boc—(L)—alanine.
MS (ESI(+)) m/z 532 (M+H)+;
$^1$H NMR (300 MHz, DMSO-$d_6$) δ7.94 (d, 2H), 7.07 (d, 2H), 6.85 (d, 1H), 4.40 (t, 1H), 4.15 (t, 2H), 3.42 (br m, 4H), 2.98 (t, 2H), 2.42 (m, 2H), 2.31 (br d, 4H), 1.90 (m, 2H), 1.60 (m, 4H), 1.42 (m, 1H), 1.40 (s, 9H), 1.25 (m, 4H), 0.87 (m, 9H).

EXAMPLE 48

1-(4-(3-(4-((2S)-2-amino-4-methylpentanoyl)-1-piperazinyl)propoxy)phenyl)-1-hexanone The desired product was prepared according to the method described in Example 1E, substituting Example 47 for Example 1D.
MS (ESI(+)) m/z 432 (M+H)+;
$^1$H NMR (300 MHz, DMSO-$d_6$) δ8.10 (br s, 2H), 7.89 (d, 2H), 6.98 (d, 2H), 4.35 (br s, 1H), 4.10 (t, 2H), 3.35–3.32 (m, 4H), 2.87 (t, 2H), 2.60–2.41 (m, 4H), 2.10 (m, 2H), 1.55 (m, 1H), 1.51 (m, 2H), 1.47 (m, 1H), 1.42 (m, 5H), 0.90–0.80 (m, 9H).

EXAMPLE 49

Tert-butyl (1R)-1-((4-(3-(4-hexanoylphenoxy)propyl)-1-piperazinyl)carbonyl)-3-methylbutylcarbamate The desired product was prepared according to the method described in Example 1D, substituting Example 39B for Example 1C and N—Boc—(D)—leucine for N—Boc—(L)—alanine.
MS (ESI(+)) m/z 532 (M+H)+;
$^1$H NMR (300 MHz, DMSO-$d_6$) δ7.94 (d, 2H), 7.07 (d, 2H), 6.85 (d, 1H), 4.40 (t, 1H), 4.15 (t, 2H), 3.42 (br m, 4H), 2.98 (m, 2H), 2.42 (m, 2H), 2.31 (br d, 4H), 1.90 (m, 2H), 1.60 (m, 4H), 1.42 (m, 1H), 1.40 (s, 9H), 1.25 (m, 4H), 0.87 (m, 9H).

EXAMPLE 50

1-(4-(3-(4-((2R)-2-amino-4-methylpentanoyl)-1-piperazinyl)propoxy)phenyl)-1-hexanone The desired product was prepared according to the method described in Example 1E, substituting Example 49 for Example 1D.
MS (ESI(+)) m/z 432 (M+H)+;
$^1$H NMR (300 MHz, DMSO-$d_6$) δ8.00 (br s, 2H), 7.80 (d, 2H), 6.90 (d, 2H), 4.25 (br s, 1H), 4.00 (t, 3H), 3.35–3.32 (m, 4H), 2.80 (t, 2H), 2.60–2.41 (m, 4H), 2.10 (m, 2H), 1.55 (m, 1H), 1.51 (m, 2H), 1.47 (m, 1H), 1.42 (m, 5H), 0.90–0.80 (m, 9H).

EXAMPLE 51

Tert-butyl (1S)-1-((benzyloxy)methyl)-2-(4-(3-(4-hexanoylphenoxy)propyl)-1-piperazinyl)-2-oxoethylcarbamate The desired product was prepared according to the method described in Example 1D, substituting Example 39B for Example 1C and N—Boc—O—benzyl—(L)—serine for N—Boc—(L)—alanine.
MS (ESI(+)) m/z 596 (M+H)+;
$^1$H NMR (300 MHz, DMSO-$d_6$) δ7.91 (d, 2H), 7.37–7.25 (m, 5H), 7.12 (d, 2H), 6.95 (d, 1H), 4.60 (m, 1H), 4.58 (m, 8H), 4.10 (t, 2H), 3.59 (m, 2H), 3.50–3.43 (m, 4H), 2.92 (t, 2H), 2.40 (m, 2H), 2.31 (m, 4H), 1.89 (m, 2H), 1.61 (m, 2H), 1.48 (s, 9H), 1.30 (m, 4H), 0.89 (t, 3H).

EXAMPLE 52

1-(4-(3-(4-((2R)-2-amino-3-hydroxypropan-1-piperazinyl)propoxy)phenyl)-1-hexanone

Example 52A 1-(4-(3-(4-((2R)-2-amino-3-(benzyloxy)propanoyl)-1-piperazinyl)propoxy)phenyl)-1-hexanone The desired product was prepared according to the method described in Example 1E, substituting Example 51 for Example 1D.

Example 52B 1-(4-(3-(4-((2R)-2-amino-3-hydroxypropanoyl)-1-piperazinyl)propoxy)phenyl)-1-hexanone Example 52A (1 mmol) in methanol (10 mL) was treated with Pd/C (10%, 40 mg) and hydrogen gas for 16 hours. The reaction mixture was filtered and concentrated to afford the desired product of sufficient purity for subsequent use without further purification.
MS (ESI(+)) m/z 406 (M+H)$^+$,
$^1$H NMR (300 MHz, DMSO-d$_6$) δ8.05 (br s, 2H), 7.85 (d, 2H), 6.92 (d, 2H), 4.31 (br s, 1H), 4.05 (t, 2H), 3.60–3.50 (m, 2H), 3.34 (m, 4H), 2.82 (t, 2H), 2.42 (m, 6H), 2.05 (br s, 2H), 1.50 (m, 2H), 1.21 (m, 4H), 0.79 (t, 3H).

EXAMPLE 53

1-(4-(3-(4-((2S)-2-amino-3-(benzyloxy)propanoyl)-1-piperazinyl)propoxy)phenyl)-1-hexanone

Example 53A

Tert-butyl (1S)-1-((benzyloxy)methyl)-2-(4-(3-(4-hexanoylphenoxy)propyl)-1-piperazinyl)-2-oxoethylcarbamate The desired product was prepared according to the method described in Example 1D, substituting Example 39B for Example 1C and N—Boc—O—benzyl—(L)—serine for N—Boc—(L)—alanine.

Example 53B 1-(4-(3-(4-((2S)-2-amino-3-(benzyloxy)propanoyl)-1-piperazinyl)propoxy)phenyl)-1-hexanone The desired product was prepared according to the method described in Example 1E, substituting Example 53A for Example 1D.
MS (ESI(+)) m/z 496 (M+H)$^+$;
$^1$H NMR (300 MHz, DMSO-d$_6$) δ8.20 (br s, 2H), 7.89 (d, 2H), 7.34–7.25 (m, 5H), 6.95 (d, 2H), 4.6–4.4 (m, 3H), 4.1 (m, 2H), 3.64–3.52 (m, 2H), 3.5–3.4 (m, 4H), 2.92 (t, 2H), 2.41 (m, 4H), 2.31 (m, 2H), 1.91 (m, 2H), 1.60 (m, 2H), 1.29 (m, 4H), 0.81 (t, 3H).

EXAMPLE 54

Tert-butyl (1S)-2-(4-(3-(4-hexanoylphenoxy)propyl)-1-piperazinyl)-2-oxo-1-(4-pyridinylmethyl)ethylcarbamate The desired product was prepared according to the method described in Example 1D, substituting Example 39B for Example 1C and N—Boc—(S)-4-pyridyl-phenylalanine for N—Boc—(L)—alanine.
MS (ESI(+)) m/z 567 (M+H)$^+$;
$^1$H NMR (300 MHz, DMSO-d$_6$) δ8.42 (m, 2H), 7.94 (d, 2H), 7.26 (m, 2H), 7.18 (m, 1H), 7.07 (d, 2H), 4.61 (m, 1H), 4.15 (t, 2H), 3.45 (m, 2H), 3.38 (m, 2H), 2.98 (m, 5H), 2.78 (m, 1H), 2.40 (m, 2H), 2.20 (br s, 2H), 1.88 (m, 2H), 1.60 (m, 2H), 1.35 (s, 9H), 1.25 (m, 4H), 0.87 (m, 3H).

EXAMPLE 55

1-(4-(3-(4-((2S)-2-amino-3-(4-pyridinyl)propanoyl)-1-piperazinyl)propoxy)phenyl)-1-hexanone The desired product was prepared according to the method described in Example 1E, substituting Example 54 for Example 1D.
MS (ESI(+)) m/z 467 (M+H)$^+$;
$^1$H NMR (300 MHz, DMSO-d$_6$) δ8.50 (d, 2H), 8.20 (d, 2H), 7.89 (d, 2H), 7.24 (d, 2H), 6.95 (d, 2H), 4.70 (br s, 1H), 4.10 (t, 2H), 3.45 (m, 4H), 3.00 (m, 2H), 2.87 (t, 2H), 2.47–2.40 (m, 4H), 2.05 (m, 2H), 1.55 (m, 2H), 1.25 (m, 6H), 0.81 (t, 3H).

EXAMPLE 56

Tert-butyl (1R)-2-(4-(3-(4-hexanoylphenoxy)propyl)-1-piperazinyl)-2-oxo-1-(4-pyridinylmethyl)ethylcarbamate The desired product was prepared according to the method described in Example 1D, substituting Example 39B for Example 1C and N—Boc—(R)-4-pyridyl-phenylalanine for N—Boc—(L)—alanine.
MS (ESI(+)) m/z 567 (M+H)$^+$;
$^1$H NMR (300 MHz, DMSO-d$_6$) δ8.42 (m, 2H), 7.94 (d, 2H), 7.26 (m, 2H), 7.18 (m, 1H), 7.07 (d, 2H), 4.61 (m, 1H), 4.15 (t, 2H), 3.45 (m, 2H), 3.38 (m, 2H), 2.98 (m, 5H), 2.78 (m, 1H), 2.40 (m, 2H), 2.20 (br s, 2H), 1.88 (m, 2H), 1.60 (m, 2H), 1.35 (s, 9H), 1.25 (m, 4H), 0.87 (m, 3H).

EXAMPLE 57

1-(4-(3-(4-((2R)-2-amino-3-(4-pyridinyl)propanoyl)-1-piperazinyl)propoxy)phenyl)-1-hexanone The desired product was prepared according to the method described in Example 1E, substituting Example 56 for Example 1D.
MS (ESI(+)) m/z 467 (M+H)$^+$;
$^1$H NMR (300 MHz, DMSO-d$_6$) δ8.50 (d, 2H), 8.20 (d, 2H), 7.89 (d, 2H), 7.24 (d, 2H), 6.95 (d, 2H), 4.70 (br s, 1H), 4.10 (t, 2H), 3.45 (m, 4H), 3.00 (m, 2H), 2.87 (t, 2H), 2.47–2.40 (m, 4H), 2.05 (m, 2H), 1.55 (m, 2H), 1.25 (m, 6H), 0.81 (t, 3H).

EXAMPLE 58

Tert-butyl (1S)-2-(4-(3-(4-hexanoylphenoxy)propyl)-1-piperazinyl)-1-(1H-imidazol-4-ylmethyl)-2-oxoethylcarbamate The desired product was prepared according to the method described in Example 1D, substituting Example 39B for Example 1C and N—Boc—(L)—histidine for N—Boc—(L)—alanine.
MS (ESI(+)) m/z 556 (M+H)$^+$;
$^1$H NMR (300 MHz, DMSO-d$_6$) δ7.94 (d, 2H), 7.48 (s, 1H), 7.07 (d, 2H), 6.98 (m, 1H), 6.70 (m, 1H), 4.62 (m, 1H), 4.15 (t, 2H), 3.40 (m, 4H), 2.98 (t, 2H), 2.78 (m, 2H), 2.70 (m, 2H), 2.48 (m, 2H), 2.40 (m, 2H), 2.37 (m, 2H), 2.25 (m, 2H), 1.90 (m, 2H), 1.60 (m, 2H), 1.35 (s, 9H), 1.25 (m, 4H), 0.87 (m, 3H).

EXAMPLE 59

1-(4-(3-(4-((2S)-2-amino-3-(1H-imidazol-4-yl)propanoyl)-1-piperazinyl)propoxy)phenyl)-1-hexanone The desired product was prepared according to the method described in Example 1E, substituting Example 58 for Example 1D.
MS (ESI(+)) m/z 456 (M+H)$^+$;
$^1$H NMR (300 MHz, DMSO-d$_6$) δ8.70 (s, 2H), 7.91 (d, 2H), 7.35 (s, 1H), 7.05 (d, 2H), 4.65 (m, 1H), 4.18 (t, 2H), 3.42 (m, 4H), 2.95 (t, 2H), 2.49 (m, 4H), 2.12 (m, 2H), 1.60 (m, 2H), 1.30 (m, 4H), 0.87 (t, 3H).

EXAMPLE 60

(4-(((3R)-3-(4-(3-aminopropanoyl)-1-piperazinyl)butyl)oxy)phenyl)(cyclopropyl)methanone

Example 60A

Tert-butyl 3-(4-((1R)-3-(4-(cyclopropylcarbonyl)phenoxy)-1-methylpropyl)-1-piperazinyl)-3-oxopropylcarbamate The desired product was prepared according to the method described in Example 1D, substituting Example 7E for Example 1C and N—Boc—beta—alanine for N—Boc—(L)—alanine.

Example 60B (4-(((3R)-3-(4-(3-aminopropanoyl)-1-piperazinyl)
butyl)oxy)phenyl)(cyclopropyl)methanone The desired product was prepared according to the method described in Example 1E, substituting Example 60A for Example 1D.
MS (DCI/NH$_3$) m/z 374 (M+H)$^+$;
$^1$H NMR (300 MHz, CDCl$_3$) δ8.00 (d, 2H), 6.95 (d, 2H), 4.23–4.03 (m, 2H), 3.70–3.51 (m, 3H), 3.51–3.38 (m, 2H), 3.11–2.84 (m, 3H), 2.68–2.51 (m, 3H), 2.51–2.37 (m, 4H), 2.06–1.93 (m, 1H), 1.84–1.56 (m, 3H), 1.29–1.18 (m, 2H), 1.05–0.96 (m, 2H), 1.02 (d, 3H).

EXAMPLE 61

Tert-butyl (1R)-2-(4-((1R)-3-(4-
(cyclopropylcarbonyl)phenoxy)-1-methylpropyl)-1-
piperazinyl)-1-methyl-2-oxoethylcarbamate The desired product was prepared according to the method described in Example 1D, substituting Example 7E for Example 1C and N—Boc—(D)—alanine for N—Boc—(L)—alanine.
MS (DCI/NH$_3$) m/z 474 (M+H)$^+$;
$^1$H NMR (300 MHz, CDCl$_3$) δ8.00 (d, 2H), 6.94 (d, 2H), 5.54 (d, 1H), 4.60 (m, 1H), 4.22–4.03 (m, 2H), 3.68–3.37 (m, 4H), 2.96–2.87 (m, 1H), 2.68–2.54 (m, 3H), 2.54–2.38 (m, 2H), 2.06–1.92 (m, 1H), 1.85–1.71 (m, 1H), 1.43 (s, 9H), 1.30 (d, 3H), 1.20–1.18 (m, 2H), 1.04–0.96 (m, 2H), 1.02 (d, 3H).

EXAMPLE 62

(4-(((3R)-3-(4-((2R)-2-aminopropanoyl)-1-
piperazinyl)butyl)oxy)phenyl)(cyclopropyl)
methanone The desired product was prepared according to the method described in Example 1E, substituting Example 61 for Example 1D.
MS (DCI/MH$_3$) m/z 374 (M+H)$^+$;
$^1$H NMR (300 MHz, CDCl$_3$) δ8.01 (d, 2H), 6.95 (d, 2H), 4.23–4.03 (m, 2H), 3.73–3.54 (m, 2H), 3.54–3.37 (m, 2H), 3.00–2.86 (m, 1H), 2.71–2.38 (m, 8H), 2.08–1.94 (m, 1H), 1.85–1.72 (m, 1H), 1.29 (d, 3H), 1.26–1.18 (m, 2H), 1.09–0.96 (m, 2H), 1.03 (d, 3H).

EXAMPLE 63

Tert-butyl (1R)-2-(4-((1S)-3-(4-
(cyclopropylcarbonyl)phenoxy)-1-methylpropyl)-1-
piperazinyl)-1-methyl-2-oxoethylcarbamate The desired product was prepared according to the method described in Example 1D, substituting Example 8E for Example 1C and N—Boc—(D)—alanine for N—Boc—(L)—alanine.
MS (DCI/NH$_3$) m/z 474 (M+H)$^+$;
$^1$H NMR (300 MHz, CDCl$_3$) δ8.01 (d, 2H), 6.95 (d, 2H), 5.56 (br d, 1H), 4.61 (br m, 1H), 4.22–4.03 (m, 2H), 3.74–3.65 (m, 1H), 3.57–3.40 (m, 3H), 2.99–2.86 (m, 1H), 2.69–2.53 (m, 3H), 2.50–2.39 (m, 2H), 2.06–1.93 (m, 1H), 1.85–1.72 (m, 1H), 1.44 (s, 9H), 1.29 (d, 3H), 1.24–1.18 (m, 2H), 1.06–0.96 (m, 2H), 1.03 (d, 3H).

EXAMPLE 64

Tert-butyl (1R)-2-(4-(3-(4-(cyclopropylcarbonyl)
phenoxy)propyl)-1-piperazinyl)-1-methyl-2-
oxoethylcarbamate The desired product was prepared according to the method described in Example 1D, substituting N—Boc—(D)—alanine for Boc—(L)—alanine.
MS (DCI/NH$_3$) m/z 460 (M+H)$^+$;
$^1$H NMR (300 MHz, CDCl$_3$) δ7.9 (d, 2H), 6.8 (d, 2H), 5.47 (d, 1H), 4.53 (m, 1H), 4.0 (m, 2H), 3.62–3.38 (m, 4H), 2.54 (m, 1H), 2.48 (m, 6H), 1.92 (m, 1H), 1.36 (s, 9H), 1.22 (d, 5.8 Hz), 1.12 (m, 2H), 0.9 (m, 2H).

EXAMPLE 65

Cyclopropyl(4-(((3R)-3-(4-((methylamino)acetyl)-1-
piperazinyl)butyl)oxy)phenyl)methanone

Example 65A

Tert-butyl 2-(4-((1R)-3-(4-(cyclopropylcarbonyl)
phenoxy)-1-methylpropyl)-1-piperazinyl)-2-oxoethyl
(methyl)carbamate The desired product was prepared according to the method described in Example 1D, substituting Example 7E for Example 1C and N—Boc—sarcosine for N—Boc—(L)—alanine.

Example 65B

Cyclopropyl(4-(((3R)-3-(4-((methylamino)acetyl)-1-
piperazinyl)butyl)oxy)phenyl)methanone The desired product was prepared according to the method described in Example 1E, substituting Example 65A for Example 1D.
MS (DCI/NH$_3$) m/z 374 (M+H)$^+$;
$^1$H NMR (300 MHz, CD$_3$OD) δ8.02 (d, 2H), 7.02 (d, 2H), 4.43 (m, 2H), 4.28–4.19 (m, 1H), 4.18–4.08 (m, 1H), 4.04 (m, 2H), 3.66–3.58 (m, 2H), 3.45–3.38 (m, 2H), 3.07–2.94 (m, 1H), 2.83–2.63 (m, 2H), 2.73 (s, 3H), 2.63–2.47 (m, 2H), 2.12–1.97 (m, 1H), 1.88–1.74 (m, 1H), 1.33–1.24 (m, 1H), 1.14–1.00 (m, 4H), 1.08 (d, 3H).

EXAMPLE 66

(4-(3-(4-((2R)-2-amino-3,3-dimethylbutanoyl)-1-
piperazinyl)propoxy)phenyl)(cyclopropyl)
methanone

Example 66A

Tert-butyl (1R)-1-((4-(3-(4-(cyclopropylcarbonyl)
phenoxy)propyl)-1-piperazinyl)carbonyl)-3,3-
dimethylbutylcarbamate The desired product was prepared according to the method described in Example 1D, substituting N—Boc-(2R)-2-amino-3,3-dimethylbutanoic acid for N—Boc—(L)—alanine.

Example 66B (4-(3-(4-((2R)-2-amino-3,3-dimethylbutanoyl)-1-
piperazinyl)propoxy)phenyl)(cyclopropyl)
methanone The desired product was prepared according to the method described in Example 1E, substituting Example 66A for Example 1D.
MS (ESI(+)) m/z 402 (M+H)$^+$;
$^1$H NMR (300 MHz, CD$_3$OD) δ8.03 (d, 2H), 7.03 (d, 2H), 4.29 (s, 1H), 4.18 (t, 2H), 3.92–3.54 (m, 5H), 2.85–2.54 (m, 12H), 2.08 (quint., 2H), 1.11–1.02 (m, 13H).

EXAMPLE 67

(4-(3-(4-((2R)-2-amino-4,4-dimethylpentanoyl)-1-
piperazinyl)propoxyphenyl)(cyclopropyl)methanone The desired product was prepared according to the method described in Example 1D, substituting N—Boc-(2R)-2-amino-4,4-dimethylpentanoic acid for N—Boc—(L)—alanine.

MS (DCI/NH$_3$) m/z 516 (M+H)$^+$;
$^1$H NMR (300 MHz, CDCl$_3$) δ8.0 (d, 2H), 6.94 (d, 2H), 5.18 (d, 1H), 4.73 (td, 1H), 4.10 (t, 2H), 3.74–3.47 (m, 4H), 2.68–2.42 (m, 7H), 1.99 (quint., 2H), 1.50 (m, 2H), 1.21 (quint., 2H), 1.03–0.96 (m, 10H).

EXAMPLE 68

(4-(3-(4-((2R)-2-amino-4,4-dimethylpentanoyl)-1-piperazinyl)propoxy)phenyl)(cyclopropyl)methanone The desired product was prepared according to the method described in Example 1E, substituting Example 67 for Example 1D.
MS (ESI(+)) m/z 432 (M+H)$^+$;
$^1$H NMR (300 MHz, CD$_3$OD) δ8.03 (d, 2H), 7.03 (d, 2H), 4.48 (m, 1H), 4.15 (t, 2H), 3.75–3.57 (m, 7H), 2.86–2.72 (m, 5H), 2.68–2.54 (m, 7H), 2.05 (quint., 2H), 1.23 (s, 9H), 1.17 (s, 11H), 1.11–1.02 (m, 4H).

EXAMPLE 69

(4-(3-(4-((2R)-2-aminobutanoyl)-1-piperazinyl)propoxy)phenyl)(cyclopropyl)methanone

Example 69A

Tert-butyl (1R)-1-((4-(3-(4-(cyclopropylcarbonyl)phenoxy)propyl)-1-piperazinyl)carbonyl)propylcarbamate The desired product was prepared according to the method described in Example 1D, substituting N—Boc—(2R)-2-amino-butanoic acid for N—Boc—(L)—alanine.

Example 69B (4-(3-(4-((2R)-2-aminobutanoyl)-1-piperazinyl)propoxy)phenyl)(cyclopropyl)methanone The desired product was prepared according to the method described in Example 1E, substituting Example 69A for Example 1D.
MS (ESI(+)) m/z 374 (M+H)$^+$;
$^1$H NMR (300 MHz, CD$_3$OD) δ8.04 (d, 2H), 7.03 (d, 2H), 4.36 (dd, 1H), 4.17 (t, 2H), 3.75–3.55 (m, 4H), 2.90–2.7 (m, 5H), 2.68–2.54 (m, 7H), 2.05 (quint., 2H), 1.9–1.75 (m, 2H), 1.11–1.0 (m, 7H).

EXAMPLE 70

Cyclopropyl(4-(3-(4-((2R)-2-(methylamino)-3-phenylpropanoyl)-1-piperazinyl)propoxy)phenyl)methanone

Example 70A

Tert-butyl (1R)-1-benzyl-2-(4-(3-(4-(cyclopropylcarbonyl)phenoxy)propyl)-1-piperazinyl)-2-oxoethyl(methyl)carbamate The desired product was prepared according to the method described in Example 1D, substituting N—Boc—(L)—N-methylphenyl alanine for N—Boc—(L)—alanine.

Example 70B

Cyclopropyl(4-(3-(4-((2R)-2-(methylamino)-3-phenylpropanoyl)-1-piperazinyl)propoxy)phenyl)methanone The desired product was prepared according to the method described in Example 1E, substituting Example 70A for Example 1D.
MS (ESI(+)) m/z 450 (M+H)$^+$;
$^1$H NMR (300 MHz, CD$_3$OD) δ8.03 (d, 2H), 7.39–7.24 (m, 5H), 7.0 (d, 2H), 4.57 (q, 1H), 4.10 (t, 2H), 3.57–3.54 (m, 2H), 3.24 (t, 2H), 3.04–2.71 (m, 7H), 2.63 (s, 3H), 2.46 (t, 2H), 2.33–2.22 (m, 2H), 1.98–1.88 (m, 2H), 1.66–1.56 (m, 1H), 1.11–1.02 (m, 4H).

EXAMPLE 71

(4-(3-(4-((2R,3S)-2-amino-3-hydroxybutanoyl)-1-piperazinyl)propoxy)phenyl)(cyclopropyl)methanone

Example 71A

Tert-butyl (1R,2S)-1-((4-(3-(4-(cyclopropylcarbonyl)phenoxy)propyl)-1-piperazinyl)carbonyl)-2-hydroxypropylcarbamate The desired product was prepared according to the method described in Example 1D, substituting N—Boc—(D)—threonine for N—Boc—(L)—alanine.

Example 71B (4-(3-(4-((2R,3S)-2-amino-3-hydroxybutanoyl)-1-piperazinyl)propoxy)phenyl)(cyclopropyl)methanone The desired product was prepared according to the method described in Example 1E, substituting Example 71A for Example 1D.
MS (ESI(+)) m/z 390 (M+H)$^+$;
$^1$H NMR (300 MHz, CD$_3$OD) δ8.04 (d, 2H), 7.03 (d, 2H), 4.29 (d, 1H), 4.17 (t, 2H), 4.03 (t, 1H), 3.75–3.64 (m, 5H), 2.85–2.7 (m, 5H), 2.68–2.54 (m, 7H), 2.08–2.02 (m, 2H), 1.28 (d, 3H), 1.13–1.04 (m, 4H).

EXAMPLE 72

Benzyl (1R)-1-(tert-butoxymethyl)-2-(4-(3-(4-(cyclopropylcarbonyl)phenoxy)propyl)-1-piperazinyl)-2-oxoethylcarbamate The desired product was prepared according to the method described in Example 1D, substituting N—CBz—(D)—O—tert—butyl—serine for N—Boc—(L)—alanine.
MS (ESI(+)) m/z 564 (M+H)$^+$;
$^1$H NMR (300 MHz, CD$_3$OD) δ8.04 (d, 2H), 7.35–7.25 (m, 5H), 7.04 (d, 2H), 5.18 (s, 2H), 4.8–4.7 (m, 2H), 4.17 (t, 2H), 3.85–3.75 (m, 1H), 3.55–3.45 (m, 5H), 2.9–2.8 (m, 10H), 2.15–2.05 (m, 2H), 1.18 (s, 9H), 1.13–1.04 (m, 4H).

EXAMPLE 73

(4-(3-(4-((2R)-2-amino-3-tert-butoxypropanoyl)-1-piperazinyl)propoxy)phenyl)(cyclopropyl)methanone The desired product was prepared according to the method described in Example 52B, substituting Example 72 for Example 52A.
MS (ESI(+)) m/z 416 (M+H)$^+$;
$^1$H NMR (300 MHz, CD$_3$OD) δ8.03 (d, 2H), 7.03 (d, 2H), 4.44 (m, 1H), 4.17 (t, 2H), 3.80–3.4 (m, 6H), 2.86–2.72 (m, 5H), 2.68–2.5 (m, 7H), 2.05 (quint., 2H), 1.85 (dd, 1H), 1.69 (dd, 1H), 1.11–1.02 (m, 13H).

EXAMPLE 74

Tert-butyl (1R,2S)-2-tert-butoxy-1-((4-(3-(4-(cyclopropylcarbonyl)phenoxy)propyl)-1-piperazinyl)carbonyl)propylcarbamate The desired product was prepared according to the method described in Example 1D, substituting N—Boc—(D)—O—tert—butyl—threonine for N—Boc—(L)—alanine.

MS (DCI/NH₃) m/z 546 (M+H)⁺;
¹H NMR (300 MHz, CDCl₃) δ8.0 (d, 2H), 6.94 (d, 2H), 5.61 (d, 1H), 4.58 (dd, 1H), 4.11 (t, 2H), 3.86–3.52 (m, 5H), 2.67–2.38 (m, 8H), 2.01(quint., 2H), 1.45 (s, 9H), 1.20 (s, 9H), 1.09 (d, 3H), 1.03–0.96 (m, 2H).

EXAMPLE 75

(4-(3-(4-((2R)-2-amino-3-(benzyloxy)propanoyl)-1-piperazinyl)propoxy)phenyl)(cyclopropyl)methanone The desired product was prepared according to the method described in Example 1D, substituting O-benzyl—(D)—serine for N—Boc—(L)—alanine.
MS (ESI(+)) m/z 466 (M+H)⁺;
¹H NMR (300 MHz, CD₃OD) δ8.03 (d, 2H), 7.5–7.3 (m, 5H), 7.02 (d, 2H), 4.67–4.55 (m, 3H), 4.15 (t, 2H), 3.8–3.6 (m, 5H), 3.51–3.45 (m, 2H), 2.9–2.72 (m, 10H), 2.65–2.45 (m, 2H), 2.4–2.3 (m, 1H), 2.05–1.95 (m, 2H), 1.21–1.02 (m, 4H).

EXAMPLE 76

Tert-butyl (1R,2S)-2-(benzyloxy)-1-((4-(3-(4-(cyclopropylcarbonyl)phenoxy)propyl)-1-piperazinyl)carbonyl)propylcarbamate The desired product was prepared according to the method described in Example 1D, substituting N—Boc—(D)—O—benzyl—threonine for N—Boc—(L)—alanine.
MS (ESI(+)) m/z 580 (M+H)⁺;
¹H NMR (300 MHz, CDCl₃) δ8.0 (d, 2H), 7.32–7.28 (m, 5H), 6.94 (d, 2H), 5.64 (d, 1H), 4.62 (d, 1H), 4.5 (d, 1H), 4.07 (t, 2H), 3.78–3.64 (m, 2H), 3.593.48 (m, 3H), 2.64–2.57 (m, H1H), 2.49–2.42 (m, 2H), 2.36–2.25 (m, 2H), 2.24–2.16 (m, 1H), 1.93 (quint., 2H), 1.45 (s, 9H), 1.22–1.17 (m, 4H), 1.03–0.96 (m, 2H).

EXAMPLE 77

Tert-butyl (1R)-5-((aminocarbonyl)amino)-1-((4-(3-(4-(cyclopropylcarbonyl)phenoxy)propyl)-1-piperazinyl)carbonyl)pentylcarbamate The desired product was prepared according to the method described in Example 1D, substituting N—Boc—(D)—2,6-diamino-carbonyl hexanoic acid for N—Boc—(L)—alanine.
MS (ESI(+)) m/z 560 (M+H)⁺;
¹H NMR (300 MHz, CD₃OD) δ8.04 (d, 2H), 7.04 (d, 2H), 4.53–4.45 (m, 1H), 4.17 (t, 2H), 3.9–3.5 (m, 5H), 3.09 (t, 2H), 2.95–2.73 (m, 12H), 2.2–2.1 (m, 2H), 1.76–1.35 (m, 18H), 1.13–1.04 (m, 4H).

EXAMPLE 78

Tert-butyl (1R)-4-((aminocarbonyl)amino)-1-((4-(3-(4-(cyclopropylcarbonyl)phenoxy)propyl)-1-piperazinyl)carbonyl)butylcarbamate The desired product was prepared according to the method described in Example 1D, substituting N—Boc—(D)—2,5-diamino-carbonyl pentanoic acid for N—Boc—(L)—alanine.
MS (ESI(+)) m/z 460 (M+H)⁺;
¹H NMR (300 MHz, CD₃OD) δ8.04 (d, 2H), 7.03 (d, 2H), 4.4 (t, 1H), 4.17 (t, 2H), 3.75–3.5 (m, 5H), 3.12 (t, 2H), 2.9–2.6 (m, 14H), 2.12–2.02 (m, 2H), 1.85–1.75 (m, 2H), 1.6–1.3 (m, 6H), 1.13–1.04 (m, 4H).

EXAMPLE 79

Tert-butyl (1R)-1-benzyl-2-(4-(3-(4-(cyclopropylcarbonyl)phenoxy)propyl)-1-piperazinyl)-2-oxoethylcarbamate The desired product was prepared according to the method described in Example 1D, substituting N—Boc—(D)—phenylalanine for N—Boc—(L)—alanine.
MS (DCI/NH₃) m/z 550 (M+H)⁺;
¹H NMR (300 MHz, CDCl₃) δ8.0 (d, 2H), 7.32–7.2 (m, 5H), 6.94 (d, 2H), 5.48 (d, 1H), 4.65–4.5 (m, 1H), 4.1 (t, 2H), 3.6 (t, 2H), 3.4–3.2 (m, 2H), 2.7–2.3 (m, 9H), 2.02–1.8 (m, 4H), 1.48 (s, 9H), 1.20 (quint., 2H), 1.03–0.96 (m, 2H).

EXAMPLE 80

Tert-butyl (1R)-2-(4-(3-(4-(cyclopropylcarbonyl)phenoxy)propyl)-1-piperazinyl)-1-(4-fluorobenzyl)-2-oxoethylcarbamate The desired product was prepared according to the method described in Example 1D, substituting N—Boc—(D)—4-Fluoro-phenylalanine for N—Boc—(L)—alanine.
MS (ESI(+)) m/z 554 (M+H)⁺;
¹H NMR (300 MHz, CDCl₃, Free Base) δ8.0 (d, 2H), 7.15 (dd, 2H), 6.98 (d, 2H), 6.92 (d, 2H), 5.4 (d, 1H), 4.8 (q, 1H), 4.07 (t, 2H), 3.65–3.48 (m, 3H), 3.41–3.32 (m, 1H), 3.12–3.03 (m, 1H), 2.94 (d, 2H), 2.68–2.58 (m, 1H), 2.47 (t, 2H), 2.4–2.25 (m, 3H), 2.0–1.9 (m, 3H), 1.42 (s, 9H), 1.21 (quint., 2H), 1.05–0.95 (m, 2H).

EXAMPLE 81

(4-(3-(4-((2R)-2-amino-3-(4-fluorophenyl)propanoyl)-1-piperazinyl)propoxy)phenyl)(cyclopropyl)methanone.

The desired product was prepared according to the method described in Example 1E, substituting Example 80 for Example 1D.
MS (ESI(+)) m/z 454 (M+H)⁺;
¹H NMR (300 MHz, CD₃OD) δ8.03 (d, 2H), 7.39 (dd, 2H), 7.12 (t, 2H), 7.0 (d, 2H), 4.95 (t, 1H), 4.64 (t, 1H), 4.10 (t, 2H), 3.62–3.52 (m, 2H), 3.48 (m, 2H), 3.08 (mi, 2H), 2.88–2.72 (m, 10H), 2.58 (t, 2H), 2.52 (m, 1H), 2.43 (m, 2H), 2.0 (m, 2H), 1.21–1.02 (m, 4H).

EXAMPLE 82

(4R)-4-((4-(3-(4-(cyclopropylcarbonyl)phenoxy)propyl)-1-piperazinyl)carbonyl)-2-azetidinone The desired product was prepared according to the method described in Example 1D, substituting (2R)-2-azetidinone-4-carboxylic acid for N—Boc—(L)—alanine.
MS (APCI(+)) m/z 386 (M+H)⁺;
¹H NMR (300 MHz, CDCl₃) δ0.98 (m, 2H), 7.99 (d, 2H), 6.93 (d, 2H), 6.65 (br s, 1H), 4.29 (m, 1H), 4.11 (m,, 2H), 3.63 (m, 2H), 3.36 (m, 2H), 3.30 (m, 1H), 2.97 (m, 1H), 2.64 (m, 4H), 2.53 (m, 2H), 2.02 (m, 5H), 1.21 (m, 2H).

EXAMPLE 83

(4S)-4-((4-(3-(4-(cyclopropylcarbonyl)phenoxy)propyl)-1-piperazinyl)carbonyl-2-azetidinone The desired product was prepared according to the method described in Example 1D, substituting (2S)-2-azetidinone-4-carboxylic acid for N—Boc—(L)—alanine.

MS (APCI(+)) m/z 386 (M+H)⁺;
¹H NMR (300 MHz, CDCl₃) δ7.99 (d, 2H), 6.93 (d, 2H), 6.63 (br s, 11H), 4.30 (m, 11H), 4.09 (m,, 2H), 3.64 (m, 2H), 3.38 (m, 2H), 3.31 (m, 1H), 2.98 (m, 1H), 2.63 (m, 4H), 2.50 (m, 2H), 2.02 (m, 5H), 1.20 (m, 2H), 0.99 (m, 2H).

EXAMPLE 84

Tert-butyl (2S)-2-((4-(3-(4-(cyclopropylcarbonyl) phenoxy)propyl)-1-piperazinyl)carbonyl)-1-pyrrolidinecarboxylate The desired product was prepared according to the method described in Example 1D, substituting N—Boc—(L)—proline for N—Boc—(L)—alanine.
MS (APCI(+)) m/z 486 (M+H)⁺;
¹H NMR (300 MHz, CDCl₃) δ8.00 (d, 2H), 6.94 (d, 2H), 4.60 (m, 1H), 4.10 (t, 2H), 3.72–3.38 (m, 6H), 2.70–2.30 (m, 7H), 2.23–1.78 (m, 6H), 1.46 (s, 3H), 1.41 (s, 6H), 1.21 (m, 2H), 1.00 (m, 2H).

EXAMPLE 85

Cyclopropyl(4-(3-(4-((2S)-pyrrolidinylcarbonyl)-1-piperazinyl)propoxy)phenyl)methanone The desired product was prepared according to the method described in Example 1E, substituting Example 84 for Example 1D.
MS (DCI/NH₃) m/z 386 (M+H)⁺;
¹H NMR (300 MHz, CDCl₃) δ8.01 (d, 2H), 6.94 (d, 2H), 4.10 (t, 2H), 4.60 (dd, 1H), 3.76–3.41 (m, 4H), 3.27–3.15 (m, 1H), 3.03–2.93 (m, 1H), 2.68–2.41 (m, 4H), 2.24–1.64 (m, 8H), 1.25–1.18 (m, 2H), 1.04–0.96 (m, 2H).

EXAMPLE 86

Cyclopropyl(4-(3-(4-((2R)-pyrrolidinylacetyl)-1-piperazinyl)propoxy)phenyl)methanone

Example 86A

Tert-butyl (2R)-2-(2-(4-(3-(4-(cyclopropylcarbonyl) phenoxy)propyl)-1-piperazinyl)-2-oxoethyl)-1-pyrrolidinecarboxylate The desired product was prepared according to the method described in Example 1D, substituting N—Boc-(2R)-2-pyrrolidine acetic acid for N—Boc—(L)—alanine.

Example 86B

Cyclopropyl(4-(3-(4-((2R)-pyrrolidinylacetyl)-1-piperazinyl)propoxyphenyl)methanone The desired product was prepared according to the method described in Example 1E, substituting Example 86A for Example 1D.
MS (ESI(+)) m/z 400 (M+H)⁺;
¹H NMR (300 MHz, CD₃OD) δ8.04 (d, 2H), 7.03 (d, 2H), 4.36 (dd,H), 4.17 (t, 2H), 3.75–3.55 (m, 5H), 3.53–3.45 (m, 1H), 3.09–3.04 (m, 1H), 2.95–2.7 (m, 5H), 2.68–2.54 (m, 5H), 2.02 (m, 3H), 1.96–1.85 (m, 2H), 1.76–1.55 (m, 3H), 1.11–1.0 (m, 4H).

EXAMPLE 87

(4-(3-(4-((2R)-2-amino-3-(2-thienyl)propanoyl)-1-piperazinyl)propoxy)phenyl)(cyclopropyl) methanone

Example 87A

Tert-butyl (1R)-2-(4-(3-(4-(cyclopropylcarbonyl) phenoxy)propyl)-1-piperazinyl)-2-oxo-1-(2-thienylmethyl)ethylcarbamate The desired product was prepared according to the method described in Example 1D, substituting N—Boc-(2R)-2-amino-3-(2)-thiophenyl propanoic acid for N—Boc—(L)—alanine.

Example 87B (4-(3-(4-((2R)-2-amino-3-(2-thienyl)propanoyl)-1-piperazinyl)propoxy)phenyl)(cyclopropyl) methanone bis The desired product was prepared according to the method described in Example 1E, substituting Example 87A for Example 1D.
MS (ESI(+)) m/z 442 (M+H)⁺;
¹H NMR (300 MHz, CD₃OD) δ8.20 (d, 2H), 7.38 (dd, 1H), 7.05–6.97 (m, 4H), 4.63 (t, 1H), 4.13 (t, 2H), 3.7–3.4 (m, 3H), 2.88–2.75 (m, 10H), 2.65–2.45 (m, 4H), 2.15–1.95 (m, 3H), 1.11–1.02 (m, 4H).

EXAMPLE 88

(4-(3-(4-((2R)-2-amino-3-(1-methyl-1H-imidazol-4-yl)propanoyl)-1-piperazinyl)propoxy)phenyl) (cyclopropyl)methanone

Example 88A

Tert-butyl (1R)-2-(4-(3-(4-(cyclopropylcarbonyl) phenoxy)propyl)-1-piperazinyl)-1-((1-methyl-1H-imidazol-4-yl)methyl)-2-oxoethylcarbamate The desired product was prepared according to the method described in Example 1D, substituting N—Boc—(D)—N-methyl histidine for N—Boc—(L)—alanine.

Example 88B (4-(3-(4-((2R)-2-amino-3-(1-methyl-1H-imidazol-4-yl)propanoyl)-1-piperazinyl)propoxy)phenyl) (cyclopropyl)methanone The desired product was prepared according to the method described in Example 1E, substituting Example 88A for Example 1D.
MS (ESI(+)) m/z 440 (M+H)⁺;
¹H NMR (300 MHz, CD₃OD) δ8.03 (d, 2H), 7.72 (s, 1H), 7.03 (d, 2H), 6.95 (s, 1H), 4.55 (m, 1H), 4.17 (t, 2H), 3.7–3.4 (m, 7H), 3.13 (d, 2H), 2.86–2.7 (m, 6H), 2.62–2.46 (m, 5H), 2.15–2.05 (m, 1IH), 2.05 (quint., 2H), 1.11–1.02 (m, 4H).

EXAMPLE 89

Tert-butyl (1R)-2-(4-(3-(4-(cyclopropylcarbonyl) phenoxy)propyl)-1-piperazinyl)-2-oxo-1-(1,3-thiazol-5-ylmethyl)ethylcarbamate The desired product was prepared according to the method described in Example 1D, substituting N—Boc-(2R)-2-amino-3-(2)-thiazolpropanoic acid for N—Boc—(L)—alanine. N—Boc-(2R)-2-amino-3-(2)-thiazolpropanoic acid was prepared according to the method described in Synth. Comm. 1990, 20, 3507.
MS (ESI(+)) m/z 543 (M+H)⁺;
¹H NMR (300 MHz, CD₃OD) δ8.97 (d, 1H), 8.04 (d, 2H), 7.32 (d, 1H), 7.02 (d, 2H), 4.17 (t, 2H), 3.88–3.55 (m, 5H), 3.22–3.02 (m, 2H), 2.92–2.67 (m, 12H), 2.17–2.06 (m, 2H), 1.48 (s, 9H), 1.13–1.04 (m, 4H).

EXAMPLE 90

1-((1S)-1-((4-(3-(4-(cyclopropylcarbonyl)phenoxy) propyl)-1-piperazinyl)carbonyl)-2-methylpropyl) tetrahydro-2(1H)-pyrimidinone The desired product was prepared according to the method described in Example 1D, substituting (2S)-3- methyl-2-(2-oxotetrahydro-1(2H)-pyrimidinyl)butanoic acid for N—Boc—(L)—alanine. The (2S)-3-methyl-2-(2-oxotetrahydro-1(2H)-pyrimidinyl)butanoic acid was prepared according to the method described in Antimicrob. Agents Chemother. 1998, 42, 3218–3224.
MS (APCI(+)) m/z 471 (M+H)$^+$;
$^1$H NMR (300 MHz, CDCl$_3$) δ7.99 (d, 2H), 6.94 (d, 2H), 5.00 (bs, 1H), 4.93 (d,Hz, 1H), 4.09 (t, 2H), 3.82–3.53 (m, 4H), 3.38–3.16 (m, 4H), 2.64 (m, 1H), 2.55–2.41 (m, 4H), 2.41–2.31 (m, 3H), 1.98 (m, 2H), 1.87 (m, 2H), 1.19 (m, 2H), 1.00 (m, 2H), 0.90 (d, 6H).

EXAMPLE 91

Tert-butyl (1S)-2-(4-(2-((4'-cyano(1,1'-biphenyl)-4-yl)oxy)ethyl)-1-piperazinyl)-1-methyl-2-oxoethylcarbamate The desired product was prepared according to the method described in Example 1D, substituting Example 9 for Example 1C.
MS (APCI(+)) m/z 479 (M+H)$^+$;
$^1$H NMR (300 MHz, CDCl$_3$) δ7.67 (m, 4H), 7.53 (d, 2H), 7.01 (d, 2H), 5.42 (m, 1H), 4.60 (m, 1H), 4.23 (m, 2H), 3.65 (m, 4H), 2.95 (m, 2H), 2.67 (m, 4H), 1.44 (s, 9H), 1.30 (d, 3H).

EXAMPLE 92

4-(2-(4-((2S)-2-aminopropanoyl)-1-piperazinyl)ethoxy)(1,1-biphenyl)-4-carbonitrile The desired product was prepared according to the method described in Example 1E, substituting Example 91 for Example 1D.
MS (APCI(+)) m/z 379 (M+H)$^+$;
$^1$H NMR (300 MHz, CDCl$_3$) δ7.65 (m, 4H), 7.53 (d, 2H), 7.01 (d, 2H), 4.17 (t, 2H), 3.81 (m, 1H), 3.67 (m, 2H), 3.52 (m, 2H), 2.87 (t, 2H), 2.58 (m, 4H), 2.00 (m, 2H), 1.26 (d, 3H).

EXAMPLE 93

Tert-butyl (1R)-2-(4-(2-((4'-cyano(1,1'-biphenyl)-4-yl)oxy)ethyl)-1-piperazinyl)-1-methyl-2-oxoethylcarbamate The desired product was prepared according to the method described in Example 1D, substituting Example 9 for Example 1C and N—Boc—(D)—alanine for N—Boc—(L)—alanine.
MS (APCI(+)) m/z 479 (M+H)$^+$;
$^1$H NMR (300 MHz, CDCl$_3$) δ7.67 (m, 4H), 7.53 (d, 2H), 7.01 (d, 2H), 5.42 (m, 1H), 4.60 (m, 1H), 4.23 (m, 2H), 3.65 (m, 4H), 2.95 (m, 2H), 2.67 (m, 4H), 1.44 (s, 9H), 1.30 (d, 3H).

EXAMPLE 94

4-(2-(4-((2R)-2-aminopropanoyl)-1-piperazinyl)ethoxy)(1,1'-biphenyl)-4-carbonitrile The desired product was prepared according to the method described in Example 1E, substituting Example 93 for Example 1D.
MS (APCI(+)) m/z 379 (M+H)$^+$;
$^1$H NMR (300 MHz, CDCl$_3$) δ7.66 (m, 4H), 7.53 (d, 2H), 7.00 (d, 2H), 4.17 (t, 2H), 3.80 (m, 1H), 3.68 (m, 2H), 3.52 (m, 2H), 2.87 (t, 2H), 2.68 (m, 4H), 1.87 (m, 2H), 1.26 (d, 3H).

EXAMPLE 95

4-(3-(4-(((tert-butoxycarbonyl)(methyl)amino)acetyl)-1-piperazinyl)propoxy)-4'-cyano-1,1'-biphenyl The desired product was prepared according to the method described in Example 1D, substituting Example 10B for Example 1C and N—Boc-sarcosine for N—Boc—(L)—alanine.
MS (APCI(+)) m/z 493 (M+H)$^+$;
$^1$H NMR (300 MHz, CDCl$_3$) δ7.66 (m, 4H), 7.53 (d, 2H), 7.00 (d, 2H), 4.08 (t, 2H), 3.65 (m, 2H), 3.44 (m, 1H), 3.41 (s, 3H), 2.57 (m, 2H), 2.47 (m, 6H), 2.00 (quint., 2H), 1.44 (s, 9H).

EXAMPLE 96

4-(3-(4-((methylamino)acetyl)-1-piperazinyl)propoxy)(1,1'-biphenyl)-4-carbonitrile The desired product was prepared according to the method described in Example 1E, substituting Example 95 for Example 1D.
MS (APCI(+)) m/z 393 (M+H)$^+$;
$^1$H NMR (300 MHz, CDCl$_3$) δ7.66 (m, 4H), 7.53 (d, 2H), 6.99 (d, 2H), 4.08 (t, 2H), 3.65 (m, 2H), 3.41 (m, 4H), 2.57 (m, 2H), 2.47 (m, 5H), 2.37 (m, 5H), 2.00 (quint., 2H).

EXAMPLE 97

Tert-butyl (1R)-2-(4-(2-((4'-cyano(1,1'-biphenyl)-4-yl)oxy)ethyl)-1-piperazinyl)-1-methyl-2-oxoethyl(methyl)carbamate The desired product was prepared according to the method described in Example 1D, substituting Example 9 for Example 1C and N—Boc—(D)—N—methylalanine for N—Boc—(L)—alanine.
MS (APCI(+)) m/z 493 (M+H)$^+$;
$^1$H NMR (300 MHz, CDCl$_3$) δ7.67 (m, 4H), 7.53 (d, 2H), 6.99 (d, 2H), 5.11 (m, 1H), 4.16 (t, 2H), 3.93–3.40 (m, 4H), 2.72 (s, 3H), 2.65 (m, 2H), 2.47 (m, 2H), 1.47 (s, 9H), 1.26 (d, 3H).

EXAMPLE 98

4-(2-(4-((2R)-2-(methylamino)propanoyl)-1-piperazinyl)ethoxy)(1,1'-biphenyl)-4-carbonitrile The desired product was prepared according to the method described in Example 1E, substituting Example 95 for Example 1D.
MS (APCI(+)) m/z 393 (M+H)$^+$;
$^1$H NMR (300 MHz, CDCl$_3$) δ7.66 (m, 4H), 7.53 (d, 2H), 7.00 (d, 2H), 4.10 (t, 2H), 3.70 (m, 2H), 3.54 (m, 3H), 2.87 (m, 2H), 2.60 (m, 5H), 2.32 (s, 3H), 1.22 (d, 3H).

EXAMPLE 99

Tert-butyl (1R)-2-(4-(3-((4'-cyano(1,1'-biphenyl)-4-yl)oxy)propyl)-1-piperazinyl)-1-methyl-2-oxoethylcarbamate The desired product was prepared according to the method described in Example 1D, substituting Example 10B for Example 1C and N—Boc—(D)—alanine for N—Boc—(L)—alanine.
MS (APCI(+)) m/z 494 (M+H)$^+$;
$^1$H NMR (300 MHz, CDCl$_3$) δ7.65 (m, 4H), 7.53 (d, 2H), 6.99 (d, 2H), 5.58 (m, 1H), 4.62 (m, 1H), 4.08 (t, 2H), 3.70–3.45 (m, 4H), 2.57 (m, 2H), 2.47 (m, 4H), 2.00 (quint., 2H), 1.44 (s, 9H), 1.30 (d, 3H).

EXAMPLE 100

4-(3-(4-((2R)-2-aminopropanoyl)-1-piperazinyl) propoxy)(1,1'-biphenyl)-4-carbonitrile The desired product was prepared according to the method described in Example 1E, substituting Example 95 for Example 1D.
MS (APCI(+)) m/z 393 (M+H)$^+$;
$^1$H NMR (300 MHz, CDCl$_3$) δ7.66 (m, 4H), 7.53 (d, 2H), 7.00 (d, 2H), 4.09 (d, 2H), 3.78 (m, 1H), 3.66 (m, 2H), 3.50 (m, 2H), 2.57 (m, 2H), 2.46 (m, 4H), 2.00 (quint., 2H), 1.79 (m, 2H), 1.25 (d, 3H).

EXAMPLE 101

Tert-butyl (1R)-2-(4-(3-((4'-cyano(1,1'-biphenyl)-4-yl)oxy)propyl)-1-piperazinyl)-1-methyl-2-oxoethyl (methyl)carbamate The desired product was prepared according to the method described in Example 1D, substituting Example 10B for Example 1C and N—Boc—(D)—N—methylalanine for N—Boc—(L)—alanine.
MS (APCI(+)) m/z 507 (M+H)$^+$;
$^1$H NMR (300 MHz, CDCl$_3$) δ7.66 (m, 4H), 7.53 (d, 2H), 6.98 (d, 2H), 5.09 (m, 1H), 4.16 (m, 2H), 3.93–3.40 (m, 4H), 2.70 (bs, 3H), 2.70–2.25 (m, 6H), 2.23–1.85 (m, 2H), 1.46 (s, 9H), 1.27 (d, 3H).

EXAMPLE 102

4-(3-(4-((2R)-2-(methylamino)propanoyl)-1-piperazinyl)propoxy)(1,1'-biphenyl)-4-carbonitrile The desired product was prepared according to the method described in Example 1E, substituting Example 101 for Example 1D.
MS (APCI(+)) m/z 407 (M+H)$^+$;
$^1$H NMR (300 MHz, CDCl$_3$) δ7.66 (m, 4H), 7.53 (d, 2H), 7.00 (d, 2H), 4.09 (t, 2H), 3.68 (m, 2H), 3.50 (m, 3H), 2.57 (m, 2H), 2.48 (m, 4H), 2.32 (m, 3H), 2.00 (d, 2H), 1.22 (d, 3H).

EXAMPLE 103

Tert-butyl (1S)-2-(4-(3-((4'-cyano(1,1'-biphenyl)-4-yl)oxy)propyl)-1-piperazinyl)-1-methyl-2-oxoethylcarbamate The desired product was prepared according to the method described in Example 1D, substituting Example 10B for Example 1C.
MS (APCI(+)) m/z 493 (M+H)$^+$;
$^1$H NMR (300 MHz, CDCl$_3$) δ7.67 (m, 4H), 7.53 (d, 2H), 6.99 (d, 2H), 5.54 (m, 1H), 4.61 (quint., 1H), 4.08 (t, 2H), 3.60 (m, 2H), 2.57 (m, 2H), 2.47 (m, 4H), 2.00 (m, 2H), 1.44 (s, 9H), 1.30 (d, 3H).

EXAMPLE 104

Tert-butyl (2R)-2-((4-(2-((4'-cyano(1,1'-biphenyl)-4-yl)oxy)ethyl)-1-piperazinyl)carbonyl)-1-pyrrolidinecarboxylate The desired product was prepared according to the method described in Example 1D, substituting Example 9 for Example 1C and N—Boc—(D)—proline for N—Boc—(L)—alanine.
MS (APCI(+)) m/z 505 (M+H)$^+$;
$^1$H NMR (300 MHz, CDCl$_3$) δ7.66 (m, 4H), 7.53 (d, 2H), 7.01 (d, 2H), 4.65 (m, 1H), 4.55 (m, 1H), 4.20 (m, 2H), 3.60 (m, 4H), 3.45 (m, 2H), 2.95 (m, 2H), 2.65 (m, 2H), 2.15 (m, 2H), 1.88 (m, 2H), 1.45 (m, 6H), 1.41(m, 3H).

EXAMPLE 105

4-(2-(4-((2R)-pyrrolidinylcarbonyl)-1-piperazinyl) ethoxy)(1,1'-biphenyl)-4-carbonitrile The desired product was prepared according to the method described in Example 1E, substituting Example 104 for Example 1D.
MS (APCI(+)) m/z 405 (M+H)$^+$;
$^1$H NMR (300 MHz, CDCl$_3$) δ8.04 (br s, 1H), 7.66 (m, 4H), 7.54 (d, 2H), 7.01 (d, 2H), 4.46 (m, 1H), 4.16 (t, 2H), 3.80–3.40 (m, 4H), 3.40–3.15 (m, 2H), 2.87 (m, 2H), 2.60 (m, 4H), 2.32 (m, 1H), 2.02–1.77 (m, 3H).

EXAMPLE 106

Tert-butyl (2S)-2-((4-(2-((4'-cyano(1,1'-biphenyl)-4-yl)oxy)ethyl)-1-piperazinyl)carbonyl)-1-pyrrolidinecarboxylate The desired product was prepared according to the method described in Example 1D, substituting Example 9 for Example 1C and N—Boc—(L)—proline for N—Boc—(L)—alanine.
MS (APCI(+)) m/z 405 (M+H)$^+$;
$^1$H NMR (300 MHz, CDCl$_3$) δ8.04 (br s, 1H), 7.66 (m, 4H), 7.54 (d, 2H), 7.01 (d, 2H), 4.46 (m, 1H), 4.16 (t, 2H), 3.80–3.40 (m, 4H), 3.40–3.15 (m, 2H), 2.87 (m, 2H), 2.60 (m, 4H), 2.32 (m, 1H), 2.02–1.77 (m, 3H).

EXAMPLE 107

Tert-butyl (2R)-2-((4-(3-((4'-cyano(1,1'-biphenyl)-4-yl)oxy)propyl)-1-piperazinyl)carbonyl)-1-pyrrolidinecarboxylate The desired product was prepared according to the method described in Example 1D, substituting Example 10B for Example 1C and N—Boc—(D)—proline for N—Boc—(L)—alanine.
MS (APCI(+)) m/z 519 (M+H)$^+$;
$^1$H NMR (300 MHz, CDCl$_3$) δ7.67 (m, 4H), 7.53 (d, 2H), 6.99 (d, 2H), 4.60 (m, 1H), 4.08 (t, 2H), 3.67–3.41 (m, 6H), 2.57 (m, 2H), 2.48 (m, 4H), 2.02 (m, 4H), 1.84 (m, 2H), 1.44 (s, 9H).

EXAMPLE 108

4-(3-(4-(aminoacetyl)-1-piperazinyl)propoxy)(1,1'-biphenyl)-4-carbonitrile

Example 108A 4-(3-(4-(((tert-butoxycarbonyl)amino)acetyl)-1-piperazinyl)propoxy)-4'-cyano-1,1'-biphenyl The desired product was prepared according to the method described in Example 1D, substituting Example 10B for Example 1C and N—Boc—glycine for N—Boc—(L)—alanine.

Example 108B 4-(3-(4-(aminoacetyl)-1-piperazinyl)propoxy)(1,1'-biphenyl)-4-carbonitrile The desired product was prepared according to the method described in Example 1E, substituting Example 108A for Example 1D.

MS (APCI(+)) m/z 379 (M+H)+;
1H NMR (300 MHz, CDCl3) δ7.65 (m, 4H), 7.53 (d, 2H), 6.99 (d, 2H), 4.08 (t, 2H), 3.65 (m, 2H), 3.46 (m, 2H), 3.39 (m, 2H), 2.56 (m, 2H), 2.46 (m, 4H), 1.97 (m, 4H).

EXAMPLE 109

4-(3-(4-(3-((tert-butoxycarbonyl)amino)propanoyl)-1-piperazinyl)propoxy)-4'-cyano-1,1'-biphenyl The desired product was prepared according to the method described in Example 1D, substituting Example 10B for Example 1C and N—Boc-beta-alanine for N—Boc—(L)—alanine.
MS (APCI(+)) m/z 493 (M+H)+;
1H NMR (300 MHz, CDCl3) δ7.66 (m, 4H), 7.53 (d, 2H), 6.97 (d, 2H), 5.25 (m, 1H), 4.15 (m, 2H), 3.91 (m, 2H), 3.60 (m, 1H), 3.42 (m, 2H), 3.17 (m, 1H), 2.82 (m, 1H), 2.56 (m, 2H), 2.45 (m, 2H), 1.60 (m, 1H), 1.44 (s, 9H).

EXAMPLE 110

4-(3-(4-(3-aminopropanoyl)-1-piperazinyl)propoxy)(1,1'-biphenyl)-4-carbonitrile

The desired product was prepared according to the method described in Example 1E, substituting Example 109 for Example 1D.
MS (APCI(+)) m/z 393 (M+H)+;
1H NMR (300 MHz, CDCl3) δ7.66 (m, 4H), 7.53 (d, 2H), 7.00 (d, 2H), 4.08 (d, 2H), 3.63 (m, 2H), 3.47 (m, 2H), 3.03 (m, 2H), 2.60–2.35 (m, 9H), 2.00 (quint., 2H).

EXAMPLE 111

N-(3-(4-(3-((4'-cyano(1,1'-biphenyl)-4-yl)oxy)propyl)-1-piperazinyl)-3-oxopropyl)-2,2-dimethylpropanamide The desired product was prepared according to the method described in Example 7B, substituting Example 110 for Example 7A and pivaloyl chloride for methanesulfonyl chloride.
MS (APCI(+)) m/z 477 (M+H)+;
1H NMR (300 MHz, CDCl3) δ7.66 (m, 4H), 7.53 (d, 2H), 6.99 (d, 2H), 6.60 (m, 1H), 4.08 (t, 2H), 3.63 (m, 2H), 3.52 (m, 4H), 2.60 (m, 2H), 2.02 (quint., 2H), 2.52 (m, 6H), 1.16 (s, 9H).

EXAMPLE 112

N-(3-(4-(3-((4'-cyano(1,1'-biphenyl)-4-yl)oxy)propyl)-1-piperazinyl)-3-oxopropyl)-3,3-dimethylbutanamide The desired product was prepared according to the method described in Example 7B, substituting Example 110 for Example 7A and 3,3-dimethyl butanoyl chloride for methanesulfonyl chloride.
MS (APCI(+)) m/z 491 (M+H)+;
1H NMR (300 MHz, CDCl3) δ7.66 (m, 4H), 7.53 (d, 2H), 6.99 (d, 2H), 6.26 (m, 1H), 4.08 (t, 2H), 3.63 (m, 2H), 3.54 (m, 2H), 3.44 (m, 2H), 2.53 (m, 4H), 2.45 (m, 4H), 2.02 (br s, 2H), 1.98 (m, 2H), 1.01 (s, 9H).

EXAMPLE 113

N-(3-(4-(3-((4'-cyano(1,1'-biphenyl)-4-yl)oxy)propyl)-1-piperazinyl)-3-oxopropyl)cyclopropanecarboxamide The desired product was prepared according to the method described in Example 7B, substituting Example 110 for Example 7A and cyclopropyl acetyl chloride for methanesulfonyl chloride.
MS (APCI(+)) m/z 461 (M+H)+
1H NMR (300 MHz, CDCl3) δ7.66 (m, 4H), 7.53 (d, 2H), 6.99 (d, 2H), 4.11 (m, 3H), 3.65 (m, 2H), 3.54 (m, 2H), 2.70–2.49 (m, 8H), 2.30 (m, 1H), 2.02 (m, 1H), 1.59 (m, 1H), 1.14 (m, 2H), 0.95 (m, 2H), 0.90 (m, 2H).

EXAMPLE 114

N-(3-(4-(3-((4'-cyano(1,1-biphenyl)-4-yl)oxy)propyl)-1-piperazinyl)-3-oxopropyl)-4-morpholinecarboxamide The desired product was prepared according to the method described in Example 7B, substituting Example 110 for Example 7A and morpholine carbamoyl chloride for methanesulfonyl chloride.
MS (APCI(+)) m/z 506 (M+H)+;
1H NMR (300 MHz, CDCl3) δ7.66 (m, 4H), 7.53 (d, 2H), 6.99 (d, 2H), 5.58 (m, 1H), 4.08 (t, 2H), 3.66 (m, 6H), 3.54 (m, 2H), 3.47 (m, 2H), 3.32 (m, 4H), 2.55 (m, 4H), 2.47 (m, 4H), 2.01 (m, 2H).

EXAMPLE 115

Tert-butyl 3-(4-(3-(4-(cyclopropylcarbonyl)phenoxy)propyl-1,4-diazepan-1-yl)-3-oxopropylcarbamate

Example 115A

Cyclopropyl(4-(3-(1,4-diazepan-1-yl)propoxy)phenyl)methanone

The desired product was prepared according to the method described in Example 1C, substituting homopiperazine for piperazine.
MS (ESI(+)) m/z 303 (M+H)+;
1H NMR (300 MHz, CDCl3) δ7.98 (d, Hz, 2H), 6.88 (d, 2H), 4.05 (t, 2H), 2.64 (m, 6H), 1.93 (m, 4H), 1.63 (m, 1H), 1.21 (m, 2H), 1.00 (m, 2H).

Example 115B

Tert-butyl 3-(4-(3-(4-(cyclopropylcarbonyl)phenoxy)propyl)-1,4-diazepan-1-yl)-3-oxopropylcarbamate The desired product was prepared according to the method described in Example 1D, substituting Example 115A for Example 1C and N—Boc—beta—alanine for N—Boc—(L)—alanine.
MS (APCI(+)) m/z 474 (M+H)+;
1H NMR (300 MHz, CDCl3) δ7.99 (d, 2H), 6.92 (d, 2H), 5.24 (m, 2H), 4.09 (m, 2H), 3.81 (m, 1H), 3.65 (m, 1H), 3.54 (m, 1H), 3.42 (m, 4H), 3.18 (bs, 1H), 3.11 (m, 1H), 3.01 (m, 4H), 2.85 (m, 1H), 2.62 (m, 1H), 2.48 (m, 4H), 2.16 (m, 2H1), 1.43 (s, 9H), 1.20 (m, 2H), 1.01 (m, 2H).

EXAMPLE 116

Tert-butyl (1R)-2-(4-(3-(4-(cyclopropylcarbonyl)phenoxy)propyl)-1,4-diazepan-1-yl)-1-methyl-2-oxoethylcarbamate The desired product was prepared according to the method described in Example 1D, substituting Example 115A for Example 1C and N—Boc—(D)—alanine for N—Boc—(L)—alanine.

MS (APCI(+)) m/z 474 (M+H)⁺;
¹H NMR (300 MHz, CDCl₃) δ7.99 (d, 2H), 6.91 (d, 2H), 5.41 (m, 2H), 4.10 (m, 2H), 3.81 (m, 1H), 3.57 (m, 1H), 3.31 (m, 1H), 3.10 (m, 2H), 2.63 (m, 1H), 2.21 (m, 2H1), 1.43 (s, 9H), 1.34 (m, 2H), 1.21 (m, 2H), 1.01 (m, 2H).

EXAMPLE 117

(4-(3-(4-((2S)-2-aminopropanoyl)-1,4-diazepan-1-yl)propoxy)phenyl)(cyclopropyl)methanone The desired product was prepared according to the method described in Example 1E, substituting Example 116 for Example 1D.
MS (APCI(+)) m/z 374 (M+H)⁺;
¹H NMR (300 MHz, CDCl₃) δ0.99 (m, 2H), 7.99 (d, 2H), 6.93 (d, 2H), 4.08 (t, 2H), 3.80 (m, 1H), 3.53 (m, 2H), 2.87 (m, 2H), 2.67 (m, 6H), 1.96 (m, 4H), 1.27 (m, 4H), 1.20 (m, 2H).

EXAMPLE 118

4'-(3-(4-((2R)-2-aminopropanoyl)-1,4-diazepan-1-yl)propoxy)(1,1'-biphenyl)-4-carbonitrile

Example 118A

4'-(3-(1,4-diazepan-1-yl)propoxy)(1,1'-biphenyl)-4-carbonitrile

The desired product was prepared according to the method described in Example 1C, substituting Example 10A for Example 1B and homopiperazine for piperazine.
MS (ESI(+)) m/z 336 (M+H)⁺;
¹H NMR (300 MHz, CDCl₃) δ7.65 (m, 4H), 7.55 (d, 2H), 6.97 (d, Hz, 2H), 4.03 (m, 2H), 2.93 (m, 2H), 2.63 (m, 8H), 1.95 (m, 2H), 1.73 (m, 2H).

Example 118B

Tert-butyl (1R)-2-(4-(3-((4'-cyano(1,1'-biphenyl)-4-yl)oxypropyl)-1,4-diazepan 1-)yl-1-methyl-2-oxoethylcarbamate The desired product was prepared according to the method described in Example 1D, substituting Example 118A for Example 1C and N—Boc—(D)—alanine for N—Boc—(L)—alanine.

Example 118C

4'-(3-(4-((2R)-2-aminopropanoyl)-1,4-diazepan-1-yl)propoxy)(1,1'-biphenyl)-4-carbonitrile The desired product was prepared according to the method described in Example 1E, substituting Example 11 8B for Example 1D.
MS (APCI(+)) m/z 407 (M+H)⁺;
¹H NMR (300 MHz, CDCl₃) δ7.66 (q, 4H), 7.53 (d, 2H), 6.98 (d, 2H), 6.04 (br s, 2H), 4.05 (t, 2H), 3.95 (m, 1H), 3.80 (m, 1H), 3.68–3.42 (m, 4H), 2.75 (m, 6H), 2.00 (m, 7H), 1.31 (d, 3H).

EXAMPLE 119

Tert-butyl (1S)-2-(4-(3-((4'-cyano(1,1'-biphenyl)-4-yl)oxy)propyl)-1,4-diazepan-1-yl)-1-methyl-2-oxoethylcarbamate The desired product was prepared according to the method described in Example 1D, substituting Example 118A for Example 1C.
MS (APCI(+)) m/z 507 (M+H)⁺;
¹H NMR (300 MHz, CDCl₃) δ7.67 (q, 4H), 7.53 (d, 2H), 6.99 (d, 2H), 5.43 (m, 1H), 4.61 (m, 1H), 4.06 (t, 2H), 3.60 (m, 4H), 2.68 (m, 6H), 1.96 (m, 7H), 1.43 (s, 9H), 1.30 (dd, 3H).

EXAMPLE 120

Tert-butyl (1R)-1-((4-(3-(4-(cyclopropylcarbonyl)phenoxy)propyl-1,4-diazepan-1-yl)carbonyl)propylcarbamate The desired product was prepared according to the method described in Example 1D, substituting Example 115A for Example 1C and N—Boc-(2R)-2-amino-butanoic acid for N—Boc—(L)—alanine.
MS (APCI(+)) m/z 488 (M+H)⁺;
¹H NMR (300 MHz, CDCl₃) δ7.99 (d, 2H), 6.93 (d, 2H), 5.37 (m, 1H), 4.53 (m, 1H), 4.08 (t, 2H), 3.59 (m, 4H), 2.72 (m, 7H), 1.99 (m, 2H), 1.91 (m, 1H), 1.75 (m, 1H), 1.60 (m, 1H), 1.43 (s, 9H), 1.21 (m, 2H), 0.96 (m, 5H).

EXAMPLE 121

(4-(3-(4-((2R)-2-aminobutanoyl)-1,4-diazepan-1-yl)propoxy)phenyl)(cyclopropyl)methanone The desired product was prepared according to the method described in Example 1E, substituting Example 120 for Example 1D.
MS (APCI(+)) m/z 388 (M+H)⁺;
¹H NMR (300 MHz, CDCl₃) δ7.99 (d, 2H), 6.93 (d, 2H), 4.08 (t, 2H), 3.75 (m, 1H), 3.60 (m, 4H), 2.68 (m, 9H), 1.96 (m, 4H), 1.70 (m, 1H), 1.52 (m, 1H), 1.26 (m, 4H), 1.20 (m, 2H), 0.99 (m, 2H).

EXAMPLE 122

4'-(3-(4-((2R)-2-aminobutanoyl)-1,4-diazepan-1-yl)propoxy)(1,1'-biphenyl)-4-carbonitrile

Example 122A

Tert-butyl (1R)-1-((4-(3-((4'-cyano(1,1'-biphenyl)-4-yl)oxy)propyl)-1,4-diazepan-1-yl)carbonyl)propylcarbamate The desired product was prepared according to the method described in Example 1D, substituting Example 115A for Example 1C and N—Boc-(2R)-2-aminobutanoic acid for N—Boc—(L)—alanine.

Example 122B

4'-(3-(4-((2R)-2-aminobutanoyl)-1,4-diazepan-1-yl)propoxy)(1,1'-biphenyl)-4-carbonitrile The desired product was prepared according to the method described in Example 1E, substituting Example 122A for Example 1D.
MS (APCI(+)) m/z 421 (M+H)⁺;
¹H NMR (300 MHz, CDCl₃) δ7.66 (q, 4H), 7.53 (d, 2H), 6.99 (d, 2H), 4.06 (t, 2H), 3.75 (m, 1H), 3.58 (m, 4H), 2.69 (m, 6H), 2.46 (br s, 2H), 1.97 (m, 4H), 1.67 (m, 1H), 1.50 (m, 1H), 0.97 (t, 3H).

EXAMPLE 123

Tert-butyl (2S)-2-(2-(4-(3-(4-(cyclopropylcarbonyl)phenoxy)propyl)-1,4-diazepan-1-yl)-2-oxoethyl)-1-pyrrolidinecarboxylate The desired product was prepared according to the method described in Example 1D, substituting Example 115A for Example 1C and N—Boc-(2S)-2-pyrrolidino-3-propionic acid for N—Boc—(L)—alanine.
MS (APCI(+)) m/z 514 (M+H)$^+$;
$^1$H NMR (300 MHz, CDCl$_3$) δ7.99 (d, 2H), 6.92 (d, 2H), 4.90 (m, 1H), 4.72 (m, 1H), 4.10 (m, 2H), 3.80 (m, 2H), 3.72 (m, 1H), 3.04 (m, 6H), 2.64 (m, 1H), 2.25 (m, 4H), 1.65 (m, 4H), 1.44 (s, 9H), 1.20 (m, 2H), 1.01 (m, 2H).

EXAMPLE 124

Cyclopropyl(4-(3-(4-((2S)-pyrrolidinylacetyl)-1,4-diazepan-1-yl)propoxy)phenyl)methanone The desired product was prepared according to the method described in Example 1E, substituting Example 123 for Example 1D.
MS (APCI(+)) m/z 414 (M+H)$^+$;
$^1$H NMR (300 MHz, CDCl$_3$) δ0.99 (m, 2H), 7.99 (d, 2H), 6.93 (d, 2H), 4.07 (m, 2H), 3.79–3.49 (m, 6H), 3.22 (m, 1H), 2.65 (m, 8H), 1.94 (m, 4H), 1.74 (m, 2H), 1.49 (m, 2H), 1.20 (m, 2H).

EXAMPLE 125

Tert-butyl (2S)-2-(2-(4-(3-((4'-cyano(1,1'-biphenyl)-4-yl)oxy)propyl)-1,4-diazepan-1-yl)-2-oxoethyl)-1-pyrrolidinecarboxylate The desired product was prepared according to the method described in Example 1D, substituting Example 118A for Example 1C and N—Boc-(2S)-2-pyrrolidino-3-propionic acid for N—Boc—(L)—alanine.
MS (APCI(+)) m/z 547 (M+H)$^+$;
$^1$H NMR (300 MHz, CDCl$_3$) δ7.66 (q, 4H), 7.53 (d, 2H), 6.99 (d, 2H), 5.02 (m, 1H), 4.06 (m, 2H), 3.95–3.15 (m, 4H), 2.72 (m, 4H), 2.20–1.75 (m, 8H), 1.62 (m, 4H), 1.44 (s, 9H).

EXAMPLE 126

N-((1R)-2-(4-(3-(4-(cyclopropylcarbonyl)phenoxy)propyl)-1-piperazinyl)-1-methyl-2-oxoethyl)-2-furamide The desired product was prepared according to the method described in Example 7B, substituting Example 1C for Example 7A and furanoyl chloride for methanesulfonyl chloride.
MS (ESI(+)) m/z 453 (M+H)$^+$;
$^1$H NMR (300 MHz, CD$_3$OD) δ8.03 (d, 2H), 7.68 (m, 1H), 7.16 (d, 1H), 7.0 (d, 2H), 6.59 (q, 1H), 5.01 (q, 1H), 4.48 (m, 2H), 4.18 (t, 2H), 3.95–3.58 (m, 4H), 2.96–2.86 (m, 4H), 2.85–2.75 (m, 3H), 2.2–2.1 (m, 2H), 1.42 (d, 3H), 1.11–1.02 (m, 4H).

EXAMPLE 127

N-((1R)-2-(4-(3-(4-(cyclopropylcarbonyl)phenoxy)propyl)-1-piperazinyl)-1-methyl-2-oxoethyl)-2-thiophenecarboxamide The desired product was prepared according to the method described in Example 7B, substituting Example 1C for Example 7A and 2-thiophenyl chloride for methanesulfonyl chloride.
MS (DCI/NH$_3$) m/z 470 (M+H)$^+$;
$^1$H NMR (300 MHz, CDCl$_3$) δ8.01 (d, 2H), 7.55 (d, 1H), 7.49 (d, 1H), 7.18(m, 1H), 7.08 (dd, 1H), 6.95 (d, 2H), 5.04 (quint., 1H), 4.11 (t, 2H), 3.8–3.55 (m, 4H), 2.66–2.44 (m, 6H), 2.08–1.96 (m, 1H), 1.43 (d, 3H), 1.25–1.18 (m, 2H), 1.05–0.95 (m, 2H).

EXAMPLE 128

(4-(3-(4-(((1S,2R)-2-aminocyclopropyl)carbonyl)-1-piperazinyl)propoxy)phenyl)(cyclopropyl)methanone

Example 128A

Tert-butyl (1R,2S)-2-((4-(3-(4-(cyclopropylcarbonyl)phenoxy)propyl)-1-piperazinyl)carbonyl)cyclopropylcarbamate The desired product was prepared according to the method described in Example 1D, substituting 2,3-methano-3-N—Boc—amino propionic acid for N—Boc—(L)—alanine. 2,3-methano-3-N—Boc—amino propionic acid was prepared according to the method described in Helv. Chimica Acta 1995, 78, 403.

Example 128B (4-(3-(4-(((1S ,2R)-2-aminocyclopropyl)carbonyl)-1-piperazinyl)propoxy)phenyl)(cyclopropyl)methanone The desired product was prepared according to the method described in Example 1E, substituting Example 128A for Example 1D.
MS (DCI/NH$_3$) m/z 373 (M+H)$^+$;
$^1$H NMR (300 MHz, CDCl$_3$) δ8.01 (d, 2H), 6.95 (d, 2H), 4.12 (t, 2H), 3.7–3.5 (m, 4H), 2.9–2.82 (m, 2H), 2.68–2.42 (m, 6H), 2.15–2.0 (m, 2H), 1.25–1.20 (m, 2H), 1.05–0.98 (m, 2H).

EXAMPLE 129

(2R)-N-((1R)-2-(4-(3-(4-(cyclopropylcarbonyl)phenoxy)propyl)-1-piperazinyl)-1-methyl-2-oxoethyl)-2-pyrrolidinecarboxamide

Example 129A

Tert-butyl (2R)-2-((((1R)-2-(4-(3-(4-(cyclopropylcarbonyl)phenoxy)propyl)-1-piperazinyl)-1-methyl-2-oxoethyl)amino)carbonyl)-1-pyrrolidinecarboxylate The desired product was prepared according to the method described in Example 1D, substituting N—Boc—(D)—proline for N—Boc—(L)—alanine and Example 1E for Example 1C.

Example 129B (2R)-N-((1R)-2-(4-(3-(4-(cyclopropylcarbonyl)phenoxy)propyl)-1-piperazinyl)-1-methyl-2-oxoethyl)-2-pyrrolidinecarboxamide The desired product was prepared according to the method described in Example 1E, substituting Example 129A for Example 1D.
MS (DCI/NH$_3$) n/z 457 (M+H)$^+$;
$^1$H NMR (300 MHz, CDCl$_3$) δ8.18 (m, 1H), 8.01 (d, 2H), 6.95 (d, 2H), 4.85 (quint., 1H), 4.1 (t, 2H), 3.85 (dd, 1H), 3.75–3.65 (m, 1H), 3.6–3.48 (m, 4H), 3.15–2.98 (m, 1H), 2.68–2.45 (m, 8H), 2.23–2.15 (m, 1H), 2.04–1.86 (m, 3H), 1.78 (quint., 2H), 1.32 (d, 3H), 1.25–1.15 (m, 2H), 1.05–0.95 (m, 2H).

EXAMPLE 130

(4-(3-(4-((2-aminocyclopentyl)carbonyl)-1-piperazinyl)propoxy)phenyl)(cyclopropyl)methanone

Example 130A

Tert-butyl 2-((4-(3-(4-(cyclopropylcarbonyl)phenoxy)propyl)-1-piperazinyl)carbonyl)cyclopentylcarbamate The desired product was prepared according to the method described in Example 1D, substituting cis N—Boc-2-aminocyclopentane for N—Boc—(L)—alanine.

Example 130B (4-(3-(4-((2-aminocyclopentyl)carbonyl)-1-piperazinyl)propoxy)phenyl)(cyclopropyl)methanone The desired product was prepared according to the method described in Example 1E, substituting Example 130A for Example 1D.
MS (DCI/NH₃) m/z 400 (M+H)⁺;
¹H NMR (300 MHz, CDCl₃) δ8.01 (d, 2H), 6.95 (d, 2H), 4.11 (t, 2H), 3.7–3.5 (m, 6H), 3.15–2.9 (m, 4H), 2.66–2.44 (m, 7H), 2.05–1.88 (m, 6H), 1.78 (quint., 1H), 1.68–1.55 (m, 1H), 1.25–1.18 (m, 2H), 1.05–0.95 (m, 2H).

EXAMPLE 131

(4-(3-(4-((2R)-azetidinylcarbonyl)-1-piperazinyl)propoxy)phenyl)(cyclopropyl)methanone

Example 131A

Tert-butyl (2R)-2-((4-(3-(4-(cyclopropylcarbonyl)phenoxy)propyl)-1-piperazinyl)carbonyl)-1-azetidinecarboxylate The desired product was prepared according to the method described in Example 1D, substituting N—Boc-2-azetidine carboxylic acid for N—Boc—(L)—alanine.

Example 131B (4-(3-(4-((2R)-azetidinylcarbonyl)-1-piperazinyl)propoxy)phenyl)(cyclopropyl)methanone The desired product was prepared according to the method described in Example 1E, substituting Example 131A for Example 1D.
MS (DCI/NH₃) m/z 372 (M+H)⁺;
¹H NMR (300 MHz, CDCl₃) δ8.0 (d, 2H), 6.95 (d, 2H), 4.4 (dd, 4.11 (t, 2H), 3.72–3.65 (m, 3H), 3.5 (td, 1H), 3.25 (q, 2H), 2.92–2.78 (m, 1H), 2.55–2.4 (m, 7H), 2.3–2.2 (m, 2H), 2.0 (quint., 2H), 1.25–1.18 (m, 2H), 1.05–0.95 (m, 2H).

EXAMPLE 132

(4-(((3R)-3-(4-((2R)-2-aminobutanoyl)-1-piperazinyl)butyl)oxy)phenyl)(cyclopropyl)methanone

Example 132A

Tert-butyl (1R)-1-((4-((1R)-3-(4-(cyclopropylcarbonyl)phenoxy)-1-methylpropyl)-1-piperazinyl)carbonyl)propylcarbamate The desired product was prepared according to the method described in Example 1D, substituting N—Boc-(2R)-2-aminobutyric acid for N—Boc—(L)—alanine and Example 7E for Example 1C.

Example 132B (4-(((3R)-3-(4-((2R)-2-aminobutanoyl)-1-piperazinyl)butyl)oxy)phenyl)(cyclopropyl)methanone The desired product was prepared according to the method described in Example 1E, substituting Example 131A for Example 1D.
MS (DCI/NH₃) m/z 388 (M+H)⁺;
¹H NMR (300 MHz, CDCl₃) δ8.01 (d, 2H), 6.94 (d, 2H), 4.23–4.0 (m, 3H), 3.73–3.43 (m, 4H), 3.02–2.89 (m, 1H), 2.72–2.40 (m, 7H), 2.12–1.95 (m, 1H), 1.90–1.44 (m, 3H), 1.26–1.18 (m, 2H), 1.12–0.96 (m, 7H), 0.94–0.86 (m, 1H).

EXAMPLE 133

(4-(((3R)-3-(4-((2R)-2-aminobutanoyl)-1-piperazinyl)butyl)oxy)phenyl)(cyclopropyl)methanone

Example 133A

Tert-butyl (1R)-1-((4-((1R)-3-(4-(cyclopropylcarbonyl)phenoxy)-1-methylpropyl)-1-piperazinyl)carbonyl)butylcarbamate The desired product was prepared according to the method described in Example 1D, substituting N—Boc-(2R)-2-aminobutyric acid for N—Boc—(L)—alanine and Example 7E for Example 1C.

Example 133B (4-(((3R)-3-(4-((2R)-2-aminobutanoyl)-1-piperazinyl)butyl)oxy)phenyl)(cyclopropyl)methanone The desired product was prepared according to the method described in Example 1E, substituting Example 133A for Example 1D.
MS (DCI/NH₃) mn/z 402 (M+H)⁺;
¹H NMR (300 MHz, CD₃OD) δ7.93 (d, 2H), 6.93 (d, 2H), 4.35–4.24 (m, 1H), 4.30 (s, 2H), 4.20–4.10 (m, 1H), 4.10–3.99 (m, 1H), 3.70–3.58 (m, 1H), 3.58–3.37 (m, 3H), 3.04–2.90 (m, 1H), 2.75–2.45 (m, 5H), 2.08–1.95 (m, 1H), 1.80–1.60 (m, 3H), 1.42–1.27 (m, 2H), 1.06–0.86 (m, 10H).

EXAMPLE 134

Tert-butyl 3-((4-(3-(4-(cyclopropylcarbonyl)phenoxy)propyl)-1-piperazinyl)carbonyl)-1-azetidinecarboxylate The desired product was prepared according to the method described in Example 1D, substituting N—Boc-3-azetidine carboxylic acid for N—Boc—(L)—alanine.
MS (DCI/NH₃) m/z 472 (M+H)⁺;
¹H NMR (300 MHz, CDCl₃) δ8.01 (d, 2H), 6.94 (d, 2H), 4.24–4.04 (m, 7H), 3.64–3.58 (m, 2H), 3.52–3.23 (m, 3H), 2.68–2.40 (m, 6H), 2.14–1.95 (m, 2H), 1.43 (s, 9H), 1.24–1.18 (m, 2H), 1.04–0.97 (m, 2H).

EXAMPLE 135

Tert-butyl 4-(4-(3-(4-(cyclopropylcarbonyl)phenoxy)propyl)-1-piperazinyl)-4-oxobutylcarbamate The desired product was prepared according to the method described in Example 1D, substituting N—Boc-4-aminobutyric acid for N—Boc—(L)—alanine.
MS (DCI/NH₃) m/z 474 (M+H)⁺;
¹H NMR (300 MHz, CDCl₃) δ8.01 (d, 2H), 6.94 (d, 2H), 4.86–4.75 (m, 1H), 4.11 (t, 2H), 3.75–3.62 (m, 1H), 3.58–3.47 (m, 1H), 3.22–3.13 (m, 2H), 2.70–2.46 (m, 7H), 2.37 (t, 2H), 2.12–2.00 (m, 2H), 1.83 (quint., 2H), 1.44 (s, 9H), 1.24–1.18 (m, 2H), 1.04–0.97 (m, 2H).

EXAMPLE 136

Tert-butyl (1R)-2-(4-((3S)-3-(4-(cyclopropylcarbonyl)phenoxy)-3-phenylpropyl)-1-piperazinyl)-1-methyl-2-oxoethylcarbamate

Example 136A (4-(((1R)-3-chloro-1-phenylpropyl)oxy)phenyl)(cyclopropyl)methanone The desired product was prepared according to the method described in Example 7D, substituting 1-chloro-(3R)-3-phenyl propanol for Example 7C.

Example 136B

Tert-butyl 4-((3R)-3-(4-(cyclopropylcarbonyl)phenoxy)-3-phenylpropyl)-1-piperazinecarboxylate The desired product was prepared according to the method described in Example 1C, substituting Example 136A for Example 1B.

Example 136C

Cyclopropyl(4-(((1R)-1-phenyl-3-(1-piperazinyl)propyl)oxy)phenyl)methanone

The desired product was prepared according to the method described in Example 1E, substituting Example 136B for Example 1D.

Example 136D

Tert-butyl (1R)-2-(4-((3S)-3-(4-(cyclopropylcarbonyl)phenoxy)-3-pheny propyl)-1-piperazinyl)-1-methyl-2-oxoethylcarbamate The desired product was prepared according to the method described in Example 1D, substituting Example 136C for Example 1C and N—Boc—(D)—alanine for N—Boc—(L)—alanine.
MS (DCI/NH$_3$) Mn/z 536 (M+H)$^+$;
$^1$H NMR (300 MHz, CDCl$_3$) δ7.89 (d, 2H), 6.88 (d, 2H), 5.55–5.30 (m, 2H), 4.64–4.53 (m, 5H), 3.75–3.42 (m, 5H), 2.64–2.18 (m, 7H), 1.68–1.55 (m, 1H), 1.29 (d, 3H), 1.19–1.13 (m, 2H), 0.99–0.92 (m, 2H).

EXAMPLE 137

N-((1R)-2-(4-(3-((4'-cyano(1,1'-biphenyl)-4-yl)oxy)propyl)-1,4-diazepan-1-yl)-2-oxo-1-(1,3-thiazol-4-ylmethyl)ethyl)-2-furamide

Example 137A

Tert-butyl (1R)-2-(4-(3-((4'-cyano(1,1'-biphenyl)-4-yl)oxy)propyl)-1,4-diazepan-1-yl)-2-oxo-1-(1,3-thiazol-4-ylmethyl)ethylcarbamate The desired product was prepared according to the method described in Example 1D, substituting Example 118A for Example 1C and substituting N—Boc-(2R)-2-amino-3-(2)-thiazolpropanoic acid for N—Boc—(L)—alanine. N—Boc-(2R)-2-amino-3-(2)-thiazolpropanoic acid was prepared according to the method described in Synth. Comm. 1990, 20, 3507.

Example 137B 4-(3-(4-((2R)-2-amino-3-(1,3-thiazol-4-yl)propanoyl)-1,4-diazepan-1-yl)propoxy)(1,1'-biphenyl)-4-carbonitrile The desired product was prepared according to the method described in Example 1D, substituting Example 137A for Example 1E.

Example 137C

N-((1R)-2-(4-(3-((4'-cyano(1,1'-biphenyl)-4-yl)oxy)propyl)-1,4-diazepan-1-yl)-2-oxo-1-(1,3-thiazol-4-ylmethyl)ethyl)-2-furamide The desired product was prepared according to the method described in Example 7B, substituting Example 137B for Example 7A and furanoyl chloride for methanesulfonyl chloride.
MS (APCI+Q1MS) m/z 584 (M+H)$^+$;
MS (APCI-Q1MS) m/z 618 (M–H)$^-$;
$^1$H NMR (300 MHz, CDCl$_3$) δ8.75 (dd, 1H), 7.85 (d, 2H), 7.63 (d, 2H), 7.52 (d, 2H), 7.44 (s, 1H), 7.11 (dd, 1H), 7.06 (m, 1H), 6.97 (dd, 2H), 6.47 (In, 1H), 5.48 (m, 1H), 4.04 (t, 2H), 3.67 (m, 2H), 3.55 (m, 2H), 3.37 (m, 1H), 3.25 (m, 1H), 2.90–2.40 (m, 6H), 2.10–1.70 (m, 5H).

EXAMPLE 138

(4-(3-(4-((2R)-2-aminopropanoyl)-1-piperazinyl)propoxy)phenyl)(cyclopropyl)methanone The desired product was prepared according to the method described in Example 1E, substituting Example 64 for Example 1D.
MS (APCI(+)) m/z 360 (M+H)$^+$;
$^1$H NMR (300 MHz, D$_2$O) δ8.0 (d, 2H), 7.09 (d, 2H), 4.6 (m, 1H), 4.27 (m, 4H), 3.92 (br. s, 2H), 3.44 (m, 4H), 2.85 (m, 2H), 2.31 (m, 2H), 1.52 (d, 3H), 1.18 (m, 4H).

EXAMPLE 139

Cyclopropyl(4-(3-(4-((2R)-2-(isopropylamino)propanoyl)-1-piperazinyl)propoxy)phenyl)methanone Sodium cyanoborohydride (75 mg, 1.2 mmol) was added to a room temperature solution of Example 138 (401 mg, 1 mmol) in acetone (10 mL). After stirring overnight, the reaction mixture was concentrated, and the concentrate was taken up in dichloromethane and washed with water, and brine, dried (Na$_2$SO$_4$), filtered, concentrated and purified by silica gel column chromatography using dichloromethane:methanol (9:1) as the eluant. The product was obtained in 25% yield.
MS (ESI(+)) m/z 402 (M+H)$^+$;
$^1$H NMR (300 MHz, CD$_3$OD) δ8.03 (d, 2H), 7.03 (d, 2H), 4.49 (q, 1H), 4.17 (t, 2H), 3.75–3.62 (m, 5H), 2.90–2.7 (m, 9H), 2.70–2.61 (m, 7H), 2.07 (quint., 2H), 1.48 (d, 3H), 1.32 (dd, 6H), 1.11 –1.02 (m, 4H).

EXAMPLE 140

4'-(2-(4-((2S)-pyrrolidinylcarbonyl)-1-piperazinyl)ethoxy)(1,1'-biphenyl)-4-carbonitrile The desired product was prepared according to the method described in Example 1E, substituting Example 106 for Example 1D.
MS (APCI(+)) m/z 405 (M+H)$^+$;
$^1$H NMR (300 MHz, CDCl$_3$) δ7.66 (m, 4H), 7.53 (d, 2H), 7.01 (d, 2H), 6.51 (br s, 1H), 4.26 (m, 1H), 4.16 (t, 2H), 3.80–3.40 (m, 4H), 3.12 (m, 2H), 2.87 (m, 2H), 2.60 (m, 4H), 2.32 (m, 1H), 2.0–1.70 (m, 3H).

EXAMPLE 141

N-[(1R)-2-(4-{3-[3-fluoro-4-(5-propyl-1,2,4-oxadiazol-3-yl)phenoxy]propyl}-1,4-diazepan-1-yl)-1-methyl-2-oxoethyl]-2-furamide

Example 141A

Tert-butyl 4-[3-(4'-cyano-3-fluorophenoxy)propyl]-1,4-diazepane-1-carboxylate

The desired product was prepared according to the method described in Example 1C, substituting Example 26A for Example 1B and substituting tert-butyl 1,4-diazepane-1-carboxylate for piperazine.

Example 141B

4-[3-(1,4-diazepan-1-yl)propoxy]-2-fluorobenzonitrile

Example 141 A (11.3 g, 30 mmol) in dichloromethane (100 mL) was treated with TFA (25 mL) slowly at 0° C. The mixture was warmed to room temperature, stirred overnight and the solvent was removed under reduced pressure. The residue was diluted with dichloromethane, and washed with saturated aqueous sodium bicarbonate. The dichloromethane layer was dried ($MgSO_4$), filtered and concentrated to afford 8.18 g of the desired product.

Example 141C

Tert-butyl (1R)-2-{4-[3-(4'-cyano-3-fluorophenoxy)propyl]-1,4-diazepan-1-yl}-1-methyl-2-oxoethylcarbamate A solution of Example 141B (8.18 g, 29.5 mmol), N,N-diisopropylethylamine (17 mL), 4-dimethylaminopyridine (0.76 g, 6 mmol), and N-(tert-butoxycarbonyl)-D-alanine (7.4 g, 39 mmol) in dichloromethane (30 mL) was treated with 1-ethyl 3-(3-dimethylaminopropyl)carbodiimide (EDCI) hydrochloride (1.3 g, 7.14 mmol) at 0° C. The mixture was warmed to room temperature, stirred overnight and the solvent was removed. The residue was purified by silica gel column chromatography ($CH_2Cl_2$/MeOH, 6:1) to provide 11.8 g (84%) of the desired product.

Example 141D 4-(3-{4-[(2R)-2-aminopropanoyl]-1,4-diazepan-1-yl}propoxy)-2-fluorobenzonitrile Example 141C (24 mmol) and TFA were processed as described in Example 141B, substituting Example 141C for Example 141A to provide the desired compound.

Example 141E

N-((1R)-2-{4-[3-(4'-cyano-3-fluorophenoxy)propyl]-1,4-diazepan-1-yl}-1-methyl-2-oxoethyl)-2-furamide Example 141D (6.0 g) and triethylamine (5.5 mL) in dichloromethane (100 mL) were treated with 2-furoyl chloride (2.4 mL, 25 mmol) at 0° C. The mixture was warmed to room temperature, stirred overnight and the solvent was removed under reduced pressure. The residue was diluted with dichloromethane (300 mL), washed with saturated aqueous sodium bicarbonate, dried ($MgSO_4$), filtered and concentrated under reduced pressure. The residue was purified by silica gel column chromatography ($CH_2Cl_2$/MeOH, 12:1) to provide 6.4 g (85%) of the desire product.

Example 141F

N-{(1R)-2-[4-(3-{4-[amino(hydroxyimino)methyl]-3-fluorophenoxy}propyl)-1,4-diazepan-1-yl]-1-methyl-2-oxoethyl}-2-furamide A mixture of Example 141E (3.8 g, 8.6 mmol), finely divided $K_2CO_3$ (10.0 g) and hydroxylamine hydrochloride (5.0 g) in absolute ethanol, was refluxed for 18 hours. The hot reaction mixture was filtered and the remaining solids were washed with hot ethanol. The combined filtrates were concentrated to provide 3.8 g (94%) of the desired product as the white powder.

Example 141G

N-[(1R)-2-(4-{3-[3-fluoro-4-(5-propyl-1,2,4-oxadiazol-3-yl)phenoxy]propyl}-1,4-diazepan-1-yl)-1-methyl-2-oxoethyl]-2-furamide Butyric acid (0.2 mmol) was treated with 0.5 mL of a 0.46 M solution (0.23 mmol) of 1,1'-carbonyldiimidazole (CDI) in DMF in a 4 mL vial. After mixing for 30 minutes, 0.75 mL of a 0.17 M solution of Example 141F (0.13 mmol) in DMF was added to the vial. The resulting solution was mixed for 4 hours at room temperature. A further 0.5 mL of 0.35 M solution of CDI (0.175 mmol) in DMF was added to the vial. The resulting mixture was heated at 115° C. for 6 hours. After cooling to room temperature, the reaction mixture was concentrated under reduced pressure. The residue was purified by preparative HPLC to provide the desired products. $^1$H NMR ($CDCl_3$) δ1.05 (t, 3H), 1.50 (m, 5H), 1.90 (m, 2H), 2.41 (m, 2H), 2.92 (t, 2H), 3.30–3.70 (m, 4H), 4.10–4.50 (m, 8H), 4.95 (m, 1H), 6.50 (m, 1H), 6.75 (m, 2H), 7.10 (m, 2H), 7.50 (m, 1H), 7.98 (m, 1H); MS (APCI+) m/z 528 (M+H)$^+$.

EXAMPLE 142

N-[(1R)-2-(4-{3-[3-fluoro-4-(5-isopentyl-1,2,4-oxadiazol-3-yl)phenoxy]propyl}-1,4-diazepan-1-yl)-1-methyl-2-oxoethyl]-2-furamide The desired product was prepared according to the method described in Example 141G, substituting 4-methylpentanoic acid for butyric acid. $^1$H NMR ($CDCl_3$) δ0.98 (d, 6H), 1.50 (m, 5H), 1.70 (m, 1H), 1.80 (m, 2H), 2.41 (m, 2H), 2.94 (t, 2H), 3.30–3.70 (m, 4H), 4.10–4.50 (m, 8H), 4.95 (m, 1H), 6.50 (m, 1H), 6.75 (m, 2H), 7.00–7.10 (m, 2H), 7.48 (m, 1H), 7.98 (m, 1H); MS (APCI+) m/z 556 (M+H)$^+$.

EXAMPLE 143

N-{(1R)-2-[4-(3-{3-fluoro-4-[5-(isopropoxymethyl)-1,2,4-oxadiazol-3-yl]phenoxy}propyl)-1,4-diazepan-1-yl]-1-methyl-2-oxoethyl}-2-furamide The desired product was prepared according to the method described in Example 141G, substituting isopropoxyacetic acid acid for butyric acid. $^1$H NMR ($CDCl_3$) δ1.24 (d, 6H), 1.50 (m, 5H), 2.40–3.10 (m, 6H), 3.30–4.10 (m, 9H), 4.80 (s, 2H), 4.95 (m, 1H), 6.50 (m, 1H), 6.75 (m, 2H), 7.00–7.10 (m, 2H), 7.48 (m, 1H), 8.00 (m, 1H); MS (APCI+) m/z 558 (M+H)$^+$.

EXAMPLE 144

N-[(1R)-2-(4-{3-[4-(5-cyclopentyl-1,2,4-oxadiazol-3-yl)-3-fluorophenoxy]propyl}-1,4-diazepan-1-yl)-1-methyl-2-oxoethyl]-2-furamide The desired product was prepared according to the method described in Example 141G, substituting cyclopentanecarboxylic acid for butyric acid. $^1$H NMR ($CDCl_3$) δ1.44 (m, 4H), 1.70–2.40 (m, 1H), 3.20–4.20 (m, 13H), 4.96 (m, 1H), 6.50 (m, 1H), 6.75 (m, 2H), 7.00–7.10 (m, 2H), 7.48 (m, 1H), 8.00 (m, 1H); MS (APCI+) m/z 554 (M+H)$^+$.

EXAMPLE 145

N-{(1R)-2-[4-(3-{4-[5-(cyclopentylmethyl)-1,2,4-oxadiazol-3-yl]-3-fluorophenoxy}propyl)-1,4-diazepan-1-yl]-1-methyl-2-oxoethyl}-2-furamide The desired product was prepared according to the method described in Example 141G, substituting cyclopentylacetic acid for butyric acid. $^1$H NMR (CDCl$_3$) δ1.30 (2H), 1.46 (d, 3H), 1.60–1.90 (m, 6H), 2.50 (m, 5H), 2.95 (d, 2H), 3.00–3.60 (m, 8H), 4.05 (m, 4H), 4.96 (m, 1H), 6.50 (m, 1H), 6.75 (m, 2H), 7.00–7.10 (m, 2H), 7.48 (m, 1H), 8.00 (m, 1H); MS (APCI+) m/z 559 (M+H)$^+$.

EXAMPLE 146

Tert-butyl (1S)-1-{3-[2-fluoro-4-(3-{4-[(2R)-2-(2-furoylamino)propanoyl]-1,4-diazepan-1-yl}propoxy)phenyl]-1,2,4-oxadiazol-5-yl}ethylcarbamate The desired product was prepared according to the method described in Example 141G, substituting (2S)-2-[(tert-butoxycarbonyl)amino]propanoic acid for butyric acid. A-342607: $^1$H NMR (CDCl$_3$) δ1.50 (m, 12H), 1.60 (d, 3H), 2.30–2.70 (m, 4H), 3.30–4.20 (m, 12H), 4.95 (m, 1H), 5.20 (m, 1H), 6.50 (m, 1H), 6.75 (m, 2H), 7.00–7.10 (m, 2H), 7.46 (m, 1H), 7.98 (m, 1H); MS (APCI+) m/z 629 (M+H)$^+$.

EXAMPLE 147

N-{(1R)-2-[4-(3-{3-fluoro-4-[5-(3-furyl)-1,2,4-oxadiazol-3-yl]phenoxy}propyl)-1,4-diazepan-1-yl]-1-methyl-2-oxoethyl}-2-furamide The desired product was prepared according to the method described in Example 141G, substituting 3-furoic acid for butyric acid. $^1$H NMR (CDCl$_3$) δ1.45–1.80 (m, 5H), 2.41 (m, 2H), 3.30–3.70 (m, 8H), 4.10 (m, 4H), 4.95 (m, 1H), 6.50 (m, 1H), 6.75 (m, 2H), 7.00–7.10 (m, 2H), 7.25 (m, 1H), 7.46 (m, 1H), 7.60 (m, 1H), 7.98 (m, 1H), 8.26 (m, 1H); MS (APCI+) m/z 552 (M+H)$^+$.

EXAMPLE 148

N-{(1R)-2-[4-(3-{3-fluoro-4-[5-(2-thienyl)-1,2,4-oxadiazol-3-yl]phenoxy}propyl)-1,4-diazepan-1-yl]-1-methyl-2-oxoethyl}-2-furamide The desired product was prepared according to the method described in Example 141G, substituting 2-thiophenecarboxylic acid for butyric acid. $^1$H NMR (CDCl$_3$) δ1.45–1.80 (m, 5H), 2.41 (m, 2H), 3.10–3.70 (m, 8H), 4.10 (mn,4H), 4.95 (m, 1H), 6.50 (m, 1H), 6.78 (m, 2H), 7.05–7.15 (m, 2H), 7.22 (m, 1H), 7.44 (m, 1H), 7.62 (m, 1H), 7.98 (m, 1H), 8.26 (m, 1H),; MS (APCI+) m/z 568 (M+H)$^+$.

EXAMPLE 149

N-{(1R)-2-[4-(3-{3-fluoro-4-[5-(1,3-thiazol-2-yl)-1,2,4-oxadiazol-3-yl]phenoxy}propyl)-1,4-diazepan-1-yl]-1-methyl-2-oxoethyl}-2-furamide The desired product was prepared according to the method described in Example 141G, substituting 1,3-thiazole-2-carboxylic acid for butyric acid. $^1$H NMR (CDCl$_3$) δ1.45–1.60 (m, 5H), 2.41 (m, 2H), 3.20–4.20 (m, 12H), 4.95 (m, 11H), 6.50 (m, 1H), 6.80 (m, 2H), 7.00–7.15 (m, 2H), 7.48 (m, 1H), 7.62 (m, 1H), 7.98–8.20 (m, 2H); MS (APCI+) m/z 568 (M+H)$^+$.

EXAMPLE 150

N-{(1R)-2-[4-(3-{3-fluoro-4-[5-(4-pyridinyl)-1,2,4-oxadiazol-3-yl]phenoxy}propyl)-1,4-diazepan-1-yl]-1-methyl-2-oxoethyl}-2-furamide The desired product was prepared according to the method described in Example 141G, substituting isonico- tinic acid for butyric acid. $^1$H NMR (CDCl$_3$) δ1.45–1.60 (m, 5H), 2.41 (m, 2H), 3.20–4.20 (m, 12H), 4.95 (m, 1H), 6.50 (m, 1H), 6.80 (m, 2H), 7.00–7.15 (m, 2H), 7.48 (m, 3H), 8.02 (m, 1H), 8.28 (m, 1H), 8.98 (m, 1H); MS (APCI+) m/z 563 (M+H)$^+$.

EXAMPLE 151

N-[(1R)-2-(4-{3-[3-fluoro-4-(5-phenyl-1,2,4-oxadiazol-3-yl)phenoxy]propyl}-1,4-diazepan-1-yl)-1-methyl-2-oxoethyl]-2-furamide The desired product was prepared according to the method described in Example 141 G, substituting benzoic acid for butyric acid. $^1$H NMR (CDCl$_3$) δ1.45–1.60 (m, 5H), 2.41 (m, 2H), 3.20–4.20 (m, 12H), 4.95 (m, 1H), 6.50 (m, 1H), 6.80 (m, 2H), 7.00–7.15 (m, 2H), 7.48–7.80 (m, 4H), 8.06 (m, 1H), 8.20 (m, 2H);
MS (APCI+) m/z 562 (M+H)$^+$.

EXAMPLE 152

N-{(1R)-2-[4-(3-{3-fluoro-4-[5-(2-phenylethyl)-1,2,4-oxadiazol-3-yl]phenoxy}propyl)-1,4-diazepan-1-yl]-1-methyl-2-oxoethyl}-2-furamide The desired product was prepared according to the method described in Example 141G, substituting 3-phenylpropanoic acid for butyric acid. $^1$H NMR (CDCl$_3$) δ1.45–1.60 (m, 5H), 2.41–3.00 (m, 4H), 3.20–3.80 (m, 10H), 4.20 (m, 4H), 4.95 (m, 1H), 6.50 (m, 1H), 6.80 (m, 2H), 7.00–7.35 (m, 7H), 7.48 (m, 1H), 7.98 (m, 1H); MS (APCI+) m/z 590 (M+H)$^+$.

EXAMPLE 153

4'-cyano-N-[3-(4-{3-[3-fluoro-4-(5-phenyl-1,2,4-oxadiazol-3-yl)phenoxy]propyl}-1-piperazinyl)-3-oxopropyl]benzamide

Example 153A

Tert-butyl 4-[3-(4'-cyano-3-fluorophenoxy)propyl]-1-piperazinecarboxylate

The desired product was prepared according to the method described in Example 1C, substituting Example 26A for Example 1B and substituting tert-butyl 1-piperazinecarboxylate for piperazine.

Example 153B

Tert-butyl 4-(3-{4-[amino(hydroxyimino)methyl]-3-fluorophenoxy}propyl)-1-piperazinecarboxylate The desired product was prepared according to the method described in Example 141F, substituting Example 153A for Example 141E.

Example 153C

Tert-butyl 4-{3-[3-fluoro-4-(5-phenyl-1,2,4-oxadiazol-3-yl)phenoxy]propyl}-1-piperazinecarboxylate The desired product was prepared according to the method described in Example 141G, substituting benzoic acid for butyric acid and substituting Example 153B for Example 141F.

Example 153D

1-{3-[3-fluoro-4-(5-phenyl-1,2,4-oxadiazol-3-yl)phenoxy]propyl}piperazine

The desired product was prepared according to the method described in Example 141B, substituting Example 153C for Example 141A.

Example 153E

Tert-butyl 3-(4-{3-[3-fluoro-4-(5-phenyl-1,2,4-oxadiazol-3-yl)phenoxy]propyl}-1-piperazinyl)-3-oxopropylcarbamate The desired product was prepared according to the method described in Example 141C, substituting N-(tert-butoxycarbonyl)-β-alanine for N-(tert-butoxycarbonyl)-D-alanine and substituting Example 153D for Example 141B.

Example 153F 3-(4-{3-[3-fluoro-4-(5-phenyl-1,2,4-oxadiazol-3-yl)phenoxy]propyl}-1-piperazinyl)-3-oxopropylamine The desired product was prepared according to the method described in Example 141B, substituting Example 153E for Example 141A.

Example 153G

4'-cyano-N-[3-(4-{3-[3-fluoro-4-(5-phenyl-1,2,4-oxadiazol-3-yl)phenoxy]propyl}-1-piperazinyl)-3-oxopropyl]benzamide 4-Cyanobenzoic acid (0.1 mmol), N-cyclohexylcarbodimide and N-methyl polystyrene (140 mg, 0.2 mmol) were treated with HOBt (16 mg, 0.12 mmol) in 1 mL of DMA. After mixing for 15 minutes, Example 153F (25 mg, 0.055 mmol) in 2 mL of DMA/DCM(1:3) was added to the reaction mixture. The mixture was agitated at room temperature overnight and then trisamine resin (80 mg, 0.32 mmol) was added to the reaction mixture. The mixture was agitated for an additional 2 hours, filtered and the solid resin was washed with DCM (2×1 mL). The filtrate was concentrated under reduced pressure and the residue was purified by preparative HPLC to provide the desired product. $^1$H NMR (CDCl$_3$) δ2.35 (m, 2H), 2.70 (m, 6H), 3.30 (m, 4H), 3.80 (m, 2H), 3.90 (m, 2H), 4.10 (m, 2H), 6.80 (m, 2H), 7.20 (m, 1H), 7.60 (m, 3H), 7.72 (d, 2H), 7.82 (d, 2H), 8.10 (m, 1H), 8.22 (m, 2H); MS (APCI+) m/z 583 (M+H)$^+$.

EXAMPLE 154

N-[3-(4-{3-[3-fluoro-4-(5-phenyl-1,2,4-oxadiazol-3-yl)phenoxy]propyl}-1-piperazinyl)-3-oxopropyl]-3-thiophenecarboxamide The desired product was prepared according to the method described in Example 153G, substituting 3-thiophenecarboxylic acid for 4'-cyanobenzoic acid. $^1$H NMR (CDCl$_3$) Δ2.30 (m, 2H), 2.70 (m, 6H), 3.30 (m, 4H), 3.70 (m, 4H), 4.10 (m, 2H), 6.80 (m, 2H), 7.35 (m, 3H), 7.58 (m, 3H), 7.96 (d, 1H), 8.10 (m, 1H), 8.20 (m, 2H); MS (APCI+) m/z 564 (M+H)$^+$.

EXAMPLE 155

(2R)-N-[3-(4-{3-[3-fluoro-4-(5-phenyl-1,2,4-oxadiazol-3-yl)phenoxy]propyl}-1-piperazinyl)-3-oxopropyl]tetrahydro-2-furancarboxamide The desired product was prepared according to the method described in Example 153G, substituting (2R)-tetrahydro-2-furancarboxylic acid for 4'-cyanobenzoic acid. $^1$H NMR (CDCl$_3$) δ1.90 (m, 3H), 2.35 (m, 3H), 2.80–3.95 (m, 16H), 4.10 (m, 2H), 4.38 (m, 1H), 6.80 (m, 2H), 7.58 (m, 4H), 8.10 (m, 1H), 8.22 (m, 2H); MS (APCI+) m/z 552 (M+H)$^+$.

EXAMPLE 156

N-[3-(4-{3-[3-fluoro-4-(5-phenyl-1,2,4-oxadiazol-3-yl)phenoxy]propyl}-1-piperazinyl)-3-oxopropyl]-3,5-dimethyl-2-thiophenecarboxamide The desired product was prepared according to the method described in Example 153G, substituting 3,5-dimethyl-2-thiophenecarboxylic acid for 4'-cyanobenzoic acid. $^1$H NMR (CDCl$_3$) δ2.35 (m, 2H), 2.62 (s, 3H), 2.70 (m, 6H), 2.80 (s, 3H), 3.20–4.20 (m, 10H), 6.80 (m, 2H), 7.25 (m, 1H), 7.58 (m, 3H), 8.08 (m, 1H), 8.20 (m, 2H); MS (APCI+) m/z 592 (M+H)$^+$.

EXAMPLE 157

N-[3-(4-{3-[3-fluoro-4-(5-phenyl-1,2,4-oxadiazol-3-yl)phenoxy]propyl}-1-piperazinyl)-3-oxopropyl]-2,5-dimethyl-3-furamide The desired product was prepared according to the method described in Example 153G, substituting 2,5-dimethyl-3-furoic acid for 4'-cyanobenzoic acid. $^1$H NMR (CDCl$_3$) δ2.20 (s, 3H), 2.35 (m, 2H), 2.50 (s, 3H), 2.70 (m, 6H), 3.30 (m, 2H), 3.70 (m, 4H), 4.10 (m, 4H), 6.00 (s, 1H), 6.80 (m, 3H), 7.58 (m, 3H), 8.08 (m, 1H), 8.20 (m, 2H); MS (APCI+) m/z 576 (M+H)$^+$.

EXAMPLE 158

N-[3-(4-{3-[3-fluoro-4-(5-phenyl-1,2,4-oxadiazol-3-yl)phenoxy]propyl}-1-piperazinyl)-3-oxopropyl]cyclopentanecarboxamide The desired product was prepared according to the method described in Example 153G, substituting cyclopentanecarboxylic acid for 4'-cyanobenzoic acid. $^1$NMR (CDCl$_3$) δ1.60 (m, 2H), 1.70 (m, 4H), 1.80 (m, 2H), 2.35 (m, 2H), 2.50 (m, 1H), 2.70 (m, 2H), 3.30 (m, 6H), 3.60 (m, 2H), 3.90 (m, 2H), 4.10 (m, 4H), 6.45 (m, 1H), 6.80 (m, 2H), 7.58 (m, 3H), 8.08 (m, 1H), 8.20 (m, 2H); MS (APCI+) m/z 550 (M+H)$^+$.

EXAMPLE 159

N-[(1R)-2-(4-{3-[3-fluoro-4-(5-phenyl-1,2,4-oxadiazol-3-yl)phenoxy]propyl}-1-piperazinyl)-1-methyl-2-oxoethyl]-2-thiophenecarboxamide

Example 159A

Tert-butyl (1R)-2-(4-{3-[3-fluoro-4-(5-phenyl-1,2,4-oxadiazol-3-yl)phenoxy]propyl}-1-piperazinyl)-1-methyl-2-oxoethylcarbamate The desired product was prepared according to the method described in Example 141B, substituting Example 153D for Example 141A.

Example 159B (1R)-2-(4-{3-[3-fluoro-4-(5-phenyl-1,2,4-oxadiazol-3-yl)phenoxy]propyl}-1-piperazinyl)-1-methyl-2-oxoethylamine The desired product was prepared according to the method described in Example 141B, substituting Example 159A for Example 141A.

Example 159C

N-[(1R)-2-(4-{3-[3-fluoro-4-(5-phenyl-1,2,4-oxadiazol-3-yl)phenoxy]propyl}-1-piperazinyl)-1-methyl-2-oxoethyl]-2-thiophenecarboxamide The desired product was prepared according to the method described in Example 153G, substituting Example 159B for Example 153F and substituting 2-thiophenecarboxylic acid for 4'-cyanobenzoic acid. ¹H NMR (CDCl₃) δ1.50 (d, 3H), 2.35 (m, 2H), 3.30–3.80 (m, 8H), 3.98–4.25 (m, 4H), 5.05 (m, 1H), 6.80 (m, 3H), 7.10 (m, 1H), 7.58 (m, 5H), 8.10 (m, 1H), 8.22 (m, 2H); MS (APCI+) m/z 564 (M+H)⁺.

EXAMPLE 160

N-[(1R)-2-(4-{3-[3-fluoro-4-(5-phenyl-1,2,4-oxadiazol-3-yl)phenoxy]propyl}-1-piperazinyl)-1-methyl-2-oxoethyl]nicotinamide The desired product was prepared according to the method described in Example 153G, substituting Example 159B for Example 153F and substituting nicotinic acid for 4'-cyanobenzoic acid. ¹H NMR (CDCl₃) δ1.50 (d, 3H), 2.35 (m, 2H), 3.00–3.60 (m, 4H), 3.60–3.90 (m, 4H), 4.05–4.25 (m, 4H), 5.05 (m, 1H), 6.80 (m, 2H), 7.60 (m, 3H), 7.88 (m, 1H), 8.10 (m, 1H), 8.22 (m, 3H), 8.78 (m, 1H), 8.82 (m, 1H), 9.38 (m, 1H); MS (APCI+) m/z 559 (M+H)⁺.

EXAMPLE 161

N-[(1R)-2-(4-{3-[3-fluoro-4-(5-phenyl-1,2,4-oxadiazol-3-yl)phenoxy]propyl}-1-piperazinyl)-1-methyl-2-oxoethyl]-2-furamide The desired product was prepared according to the method described in Example 153G, substituting Example 159B for Example 153F and substituting 2-furoic acid for 4'-cyanobenzoic acid. ¹H NMR (CDCl₃) δ1.50 (d, 3H), 2.35 (m, 2H), 3.00–3.45 (m, 5H), 3.65–3.90 (m, 3H), 4.05–4.85 (m, 4H), 5.05 (m, 1H), 6.53 (m, 1H), 6.80 (m, 2H), 7.18 (m, 1H), 7.40 (m, 1H), 7.60 (m, 4H), 8.10 (m, 1H), 8.20 (m, 2H); MS (APCI+) m/z 548 (M+H)⁺.

EXAMPLE 162

N-[(1R)-2-(4-{3-[3-fluoro-4-(5-phenyl-1,2,4-oxadiazol-3-yl)phenoxy]propyl}-1-piperazinyl)-1-methyl-2-oxoethyl]-5-isoxazolecarboxamide The desired product was prepared according to the method described in Example 153G, substituting Example 159B for Example 153F and substituting 5-isoxazolecarboxylic acid for 4'-cyanobenzoic acid. ¹H NMR (CDCl₃) δ1.50 (d, 3H), 2.35 (m, 2H), 3.00–3.45 (m, 5H), 3.65–4.00 (m, 3H), 4.05–4.85 (m, 4H), 5.05 (m, 1H), 6.80 (m, 3H), 7.60 (m, 4H), 8.10 (m, 1H), 8.20 (m, 2H), 8.25 (m, 1H); MS (APCI+) m/z 549 (M+H)⁺.

EXAMPLE 163

(2S)-N-[(1R)-2-(4-{3-[3-fluoro-4-(5-phenyl-1,2,4-oxadiazol-3-yl)phenoxy]propyl}-1-piperazinyl)-1-methyl-2-oxoethyl]tetrahydro-2-furancarboxamide The desired product was prepared according to the method described in Example 153G, substituting Example 159B for Example 153F and substituting (2S)-tetrahydro-2-furancarboxylic acid for 4'-cyanobenzoic acid. ¹H NMR (CDCl₃) δ1.50 (d, 3H), 1.95 (m, 3H), 2.35 (m, 3H), 3.00–3.85 (m, 8H), 3.95 (m, 2H), 4.05–4.25 (m, 4H), 4.35 (m, 1H), 4.85 (m, 1H), 6.80 (m, 2H), 7.30 (m, 1H), 7.60 (m, 3H), 8.10 (m, 1H), 8.22 (m, 2H); MS (APCI+) m/z 552 (M+H)⁺.

EXAMPLE 164

N-[(1R)-2-(4-{3-[3-fluoro-4-(5-phenyl-1,2,4-oxadiazol-3-yl)-phenoxy]propyl}-1-piperazinyl)-1-methyl-2-oxoethyl]-3-(4-morpholinyl)propanamide The desired product was prepared according to the method described in Example 153G, substituting Example 159B for Example 153F and substituting 3-(4-morpholinyl)propanoic acid for 4'-cyanobenzoic acid. ¹H NMR (CDCl₃) δ1.50 (d, 3H), 2.35 (m, 2H), 2.80 (m, 2H), 3.00–4.75 (m, 22H), 4.85 (m, 1H), 6.80 (m, 2H), 7.60 (m, 4H), 8.10 (m, 1H), 8.22 (m, 2H); MS (APCI+) m/z 595 (M+H)⁺.

EXAMPLE 165

N-[(1R)-2-(4-{3-[3-fluoro-4-(5-phenyl-1,2,4-oxadiazol-3-yl)phenoxy]propyl}-1-piperazinyl)-1-methyl-2-oxoethyl]-3-methylbutanamide The desired product was prepared according to the method described in Example 153G, substituting Example 159B for Example 153F and substituting 3-methylbutanoic acid for 4'-cyanobenzoic acid. ¹H NMR (CDCl₃) δ0.98 (d, 6H), 1.50 (d, 3H), 2.05 (m, 3H), 2.35 (m, 2H), 3.00–4.75 (m, 12H), 4.85 (m, 1H), 6.80 (m, 3H), 7.60 (m, 3H), 8.10 (m, 1H), 8.20 (m, 2H); MS (APCI+) m/z 538 (M+H)⁺.

EXAMPLE 168

(2R)-1-[4-(3-{4-[5-(cyclopentylmethyl)-1,2,4-oxadiazol-3-yl]-3-fluorophenoxy}propyl)-1-piperazinyl]-1-oxo-2-propanamine

Example 168A 1-(3-{4-[5-(cyclopentylmethyl)-1 2,4-oxadiazol-3-yl]-3-fluorophenoxy}propyl)piperazine The desired product was prepared according to the method described in Example 141G, substituting cyclopentylacetic acid for butyric acid and substituting Example 153B for Example 141F.

Example 168B 1-(3-{4-[5-(cyclopentylmethyl)-1,2,4-oxadiazol-3-yl]-3-fluorophenoxy}propyl)piperazine The desired product was prepared according to the method described in Example 141B, substituting Example 168A for Example 141A. ¹H NMR (CDCl₃) δ1.30 (m, 2H), 1.60 (m, 4H), 1.90 (m, 2H), 2.20 (m, 2H), 2.40 (m, 1H), 2.98 (d, 2H), 3.15 (t, 2H), 3.40 (m, 4H), 3.50 (m, 4H), 4.10 (t, 2H), 6.80 (m, 2H), 7.16 (br s, 1H), 8.00 (m, 1H); MS (APCI+) m/z 389 (M+H)⁺.

Example 168C

Tert-butyl (1R)-2-[4-(3-{4-[5-(cyclopentylmethyl)-1,2,4-oxadiazol-3-yl]-3-fluorophenoxy}propyl)-1-piperazinyl]-1-methyl-2-oxoethylcarbamate The desired product was prepared according to the method described in Example 141C, substituting Example 168B for Example 141B.

Example 168D (2R)-1-[4-(3-{4-[5-(cyclopentylmethyl)-1,2,4-oxadiazol-3-yl]-3-fluorophenoxy}propyl)-1-piperazinyl]-1-oxo-2-propanamine The desired product was prepared according to the method described in Example 141B, substituting Example 168C for Example 141A. ¹H NMR (CDCl₃) δ1.30 (m, 2H), 1.45 (d, 3H), 1.60 (m, 4H), 1.90 (m, 2H), 2.20 (m, 2H), 2.40 (m, 1H), 2.98 (d, 2H), 2.90–3.15 (m, 6H), 3.50–3.80 (m, 3H), 4.10 (m, 3H), 4.45 (m, 1H), 6.80 (m, 2H), 7.16 (br s, 2H), 8.00 (m, 1H); MS (APCI+) m/z 460 (M+H)⁺.

EXAMPLE 169

(2R)-1-[4-(3-{4-[5-(cyclopentylmethyl)-1,2,4-oxadiazol-3-yl]-3-fluorophenoxy}propyl)-1,4-diazepan-1-yl]-1-oxo-2-propanamine

Example 169A

Tert-butyl 4-(3-{4-[amino(hydroxyimino)methyl]-3-fluorophenoxy}propyl)-1,4-diazepane-1-carboxylate The desired product was prepared according to the method described in Example 141F, substituting Example 141A for Example 141E.

Example 169B

Tert-butyl 4-(3-{4-[5-(cyclopentylmethyl)-1,2,4-oxadiazol-3-yl]-3-fluorophenoxy}propyl)-1,4-diazepane-1-carboxylate The desired product was prepared according to the method described in Example 141G, substituting Example 169A for Example 141F and substituting cyclopentylacetic acid for butyric acid.

Example 169C 1-(3-{4-[5-(cyclopentylmethyl)-1,2,4-oxadiazol-3-yl]-3-fluorophenoxy}propyl)-1,4-diazepane The desired product was prepared according to the method described in Example 141B, substituting Example 169B for Example 141A. $^1$H NMR (CDCl$_3$) δ1.30 (m, 2H), 1.60 (m, 4H), 1.90 (m, 2H), 2.05 (m, 4H), 2.40 (m, 11H), 2.90–3.15 (m, 8H), 3.30 (m, 4H), 4.10 (t, 2H), 6.80 (m, 2H), 7.16 (br s, 1H), 8.00 (m, 1H); MS (APCI+) m/z 403 (M+H)$^+$.

Example 169D

Tert-butyl (1R)-2-[4-(3-{4-[5-(cyclopentylmethyl)-1,2,4-oxadiazol-3-yl]-3-fluorophenoxy}propyl)-1,4-diazepan-1-yl]-1-methyl-2-oxoethylcarbamate The desired product was prepared according to the method described in Example 141C, substituting Example 169C for Example 141B.

Example 169E (2R)-1-[4-(3-{4-[5-(cyclopentylmethyl)-1,2,4-oxadiazol-3-yl]-3-fluorophenoxy}propyl)-1,4-diazepan-1-yl]-1-oxo-2-propanamine The desired product was prepared according to the method described in Example 141B, substituting Example 169D for Example 141A. $^1$H NMR (CDCl$_3$) δ1.30 (m, 2H), 1.45 (d, 3H), 1.60 (m, 4H), 1.90 (m, 2H), 2.10–2.30 (m, 4H), 2.40 (m, 1H), 2.98 (d, 2H), 3.10–3.60 (m, 8H), 3.70–4.20 (m, 4H), 4.45 (m, 1H), 6.80 (m, 2H), 7.16 (br s, 2H), 8.00 (m, 1H); MS (APCI+) m/z 474 (M+H)$^+$.

EXAMPLE 170

N-{(1R)-2-[4-(3-{4-[5-(cyclopentylmethyl)-1,2,4-oxadiazol-3-yl]-3-fluorophenoxy}propyl)-1-piperazinyl]-1-methyl-2-oxoethyl}propanamide Propionic acid (0.15 mmol), N-cyclohexylcarbodimide, N'-methyl polystyrene (120 mg, 0.2 mmol) was treated with HOBt (20 mg, 0.15 mmol) in 1 mL of DMA. After mixing for 15 minutes, Example 168D (20 mg, 0.043 mmol) in 2 mL of DMA/DCM (1:3) was added to the reaction mixture. The mixture was agitated at room temperature overnight and then trisamine resin (100 mg, 0.40 mmol) was added to the reaction mixture. The mixture was agitated for 2 hours, filtered, the solid resin was washed with DCM (2×1 mL) and the filtrate was concentrated under reduced pressure. The residue was purified by preparative HPLC to provide the desired product. $^1$H NMR (CDCl$_3$) δ1.15 (t, 3H), 1.30 (m, 5H), 1.60 (m, 4H), 1.90 (m, 2H), 2.20 (m, 4H), 2.40 (m, 1H), 2.80–4.20 (m, 14H), 4.90 (m, 1H), 6.45 (m, 1H), 6.80 (m, 2H), 8.00 (m, 1H); MS (APCI+) m/z 516 (M+H)$^+$.

EXAMPLE 171

N-{(1R)-2-[4-(3-{4-[5-(cyclopentylmethyl)-1,2,4-oxadiazol-3-yl]-3-fluorophenoxy}propyl)-1-piperazinyl]-1–1-methyl-2-oxoethyl}-3,3-dimethylbutanamide The desired product was prepared according to the method described in Example 170, substituting 3,3-dimethylbutanoic acid for propionic acid. $^1$H NMR (CDCl$_3$) δ1.02 (s, 9H), 1.30 (m, 5H), 1.60 (m, 4H), 1.90 (m, 2H), 2.08 (s, 2H), 2.20 (m, 2H), 2.40 (m, 1H), 2.80–3.20 (m, 8H), 3.60–3.90 (m, 3H), 4.10 (m, 3H), 4.90 (m, 1H), 6.40 (m, 1H), 6.80 (m, 2H), 8.00 (m, 1H); MS (APCI+) m/z 558 (M+H)$^+$.

EXAMPLE 172

N-{(1R)-2-[4-(3-{4-[5-(cyclopentylmethyl)-1,2,4-oxadiazol-3-yl]-3-fluorophenoxy}propyl)-1-piperazinyl]-1-methyl-2-oxoethyl}-3-(4-morpholinyl)propanamide The desired product was prepared according to the method described in Example 170, substituting 3-(4-morpholinyl)propanoic acid for propionic acid. $^1$H NMR (CDCl$_3$) δ1.30 (m, 5H), 1.60 (m, 4H), 1.90 (m, 2H), 2.24 (m, 2H), 2.40 (m, 1H), 2.80 (m, 2H), 2.95 (d, 2H), 3.00–3.40 (m, 12H), 3.60–4.10 (m, 10H), 4.80 (m, 1H), 6.80 (m, 2H), 7.82 (m, 1H), 8.00 (m, 1H); MS (APCI+) m/z 601 (M+H)$^+$.

EXAMPLE 173

N-{(1R)-2-[4-(3-{4-[5-(cyclopentylmethyl)-1,2,4-oxadiazol-3-yl]-3-fluorophenoxy}propyl)-1-piperazinyl]-1-methyl-2-oxoethyl}-4-methylbenzamide The desired product was prepared according to the method described in Example 170, substituting 4-methylbenzoic acid for propionic acid. $^1$H NMR (CDCl$_3$) δ1.30 (m, 2H), 1.42 (d, 3H), 1.60 (m, 4H), 1.90 (m, 2H), 2.30 (m, 2H), 2.40 (m, 1H), 2.41 (s, 3H), 2.95 (d, 2H), 3.10–3.40 (m, 6H), 3.80–4.20 (m, 6H), 5.05 (m, 1H), 6.80 (m, 2H), 6.98 (m, 1H), 7.12 (d, 2H), 7.64 (d, 2H), 8.00 (m, 1H); MS (APCI+) m/z 578 (M+H)$^+$.

EXAMPLE 174

N-{(1R)-2-[4-(3-{4-[5-(cyclopentylmethyl)-1,2,4-oxadiazol-3-yl]-3-fluorophenoxy}propyl)-1-piperazinyl]-1-methyl-2-oxoethyl}-4-fluorobenzamide The desired product was prepared according to the method described in Example 170, substituting 4-fluorobenzoic acid for propionic acid. $^1$H NMR (CDCl$_3$)

δ1.30 (m, 2H), 1.42 (d, 3H), 1.60 (m, 4H), 1.90 (m, 2H), 2.10 (m, 2H), 2.40 (m, 1H), 2.75 (m, 4H), 2.98 (d, 2H), 3.60–3.80 (m, 4H), 3.85–4.20 (m, 4H), 5.05 (m, 1H), 6.80 (m, 2H), 7.12 (m, 2H), 7.22 (m, 1H), 7.80 (m, 2H), 8.00 (m, 1H); MS (APCI+) m/z 582 (M+H)+.

EXAMPLE 175

N-{(1R)-2-[4-(3-{4-[5-(cyclopentylmethyl)-1,2,4-oxadiazol-3-yl]-3-fluorophenoxy}propyl)-1-piperazinyl]-1-methyl-2-oxoethyl}-4-methoxybenzamide The desired product was prepared according to the method described in Example 170, substituting 4-methoxybenzoic acid for propionic acid. $^1$H NMR (CDCl$_3$) δ1.30 (m, 2H), 1.42 (d, 3H), 1.60 (mn, 2H), 1.66 (m, 2H), 1.90 (m, 2H), 2.10 (m, 2H), 2.42 (m, 1H), 2.80 (mn, 4H), 2.98 (d, 2H), 3.60–3.80 (m, 4H), 3.83 (s, 3H), 3.90–4.20 (m, 4H), 5.05 (m, 1H), 6.80 (m, 2H), 6.95 (d, 2H), 7.12 (m, 1H), 7.80 (d, 2H), 8.00 (mn, 1H); MS (APCI+) m/z 594 (M+H)+.

EXAMPLE 176

3,4-dichloro-N-{(1R)-2-[4-(3-{4-[5-(cyclopentylmethyl)-1,2,4-oxadiazol-3-yl]-3-fluorophenoxy}propyl)-1-piperazinyl]-1-methyl-2-oxoethyl}benzamide The desired product was prepared according to the method described in Example 170, substituting 3,4-dichlorobenzoic acid for propionic acid. $^1$H NMR (CDCl$_3$) δ1.30 (m, 2H), 1.42 (d, 3H), 1.60 (m, 4H), 1.90 (m, 2H), 2.22 (m, 2H), 2.40 (m, 1H), 2.80–3.30 (m, 6H), 2.98 (d, 2H), 3.60–4.20 (m, 6H), 5.05 (m, 1H), 6.80 (m, 2H), 7.00 (m, 1H), 7.22 (m, 1H), 7.42 (d, 1H), 7.55 (d, 1H), 8.00 (m, 1H); MS (APCI+) m/z 632 (M+H)+.

EXAMPLE 177

N-{(1R)-2-[4-(3-{4-[5-(cyclopentylmethyl)-1,2,4-oxadiazol-3-yl]-3-fluorophenoxy}propyl)-1,4-diazepan-1-yl]-1-methyl-2-oxoethyl}-2-methylpropanamide The desired product was prepared according to the method described in Example 170, substituting 2-methylpropanoic acid for propionic acid and substituting Example 169E for Example 168D. $^1$H NMR (CDCl$_3$) δ1.15 (m, 6H), 1.30 (m, 5H), 1.60 (m, 4H), 1.90 (m, 2H), 2.25–2.45 (m, 6H), 2.98 (d, 2H), 3.10–3.75 (m, 8H), 3.90–4.30 (m, 4H), 4.90 (m, 1H), 6.30 (m, 1H), 6.80 (m, 2H), 8.00 (m, 1H); MS (APCI+) m/z 544 (M+H)+.

EXAMPLE 178

4-chloro-N-{(1R)-2-[4-(3-{4-[5-(cyclopentylmethyl)-1,2,4-oxadiazol-3-yl]-3-fluorophenoxy}propyl)-1,4-diazepan-1-yl]-1-methyl-2-oxoethyl}benzamide The desired product was prepared according to the method described in Example 170, substituting 4-chlorobenzoic acid for propionic acid and substituting Example 169E for Example 168D.
A-347224: $^1$H NMR (CDCl$_3$) δ1.30 (m, 2H), 1.42 (d, 3H), 1.60 (m, 4H), 1.90 (m, 2H), 2.20–2.50 (m, 5H), 2.98 (d, 2H), 3.10–3.80 (m, 8H), 3.90–4.20 (m, 4H), 5.00 (m, 1H), 6.78 (m, 2H), 7.20 (m, 1H), 7.40 (m, 2H), 7.76 (m, 2H), 8.00 (m, 1H); MS (APCI+) m/z 612 (M+H)+.

EXAMPLE 179

4'-cyano-N-{(1R)-2-[4-(3-{4-[5-(cyclopentylmethyl)-1,2,4-oxadiazol-3-yl]-3-fluorophenoxy}propyl)-1,4-diazepan-1-yl]-1-methyl-2-oxoethyl}benzamide The desired product was prepared according to the method described in Example 170, substituting 4'-cyanobenzoic acid for propionic acid and substituting Example 169E for Example 168D. $^1$H NMR (CDCl$_3$) δ1.30 (m, 2H), 1.42 (d, 3H), 1.60 (m, 4H), 1.90 (m, 2H), 2.10–2.50 (m, 5H), 2.98 (d, 2H), 3.00–3.70 (m, 6H), 3.70–4.20 (m, 6H), 5.02 (m, 1H), 6.78 (m, 2H), 7.40 (m, 1H), 7.75 (m, 2H), 7.98 (m, 3H); MS (APCI+) m/z 603 (M+H)+.

EXAMPLE 180

N-{(1R)-2-[4-(3-{4-[5-(cyclopentylmethyl)-1,2,4-oxadiazol-3-yl]-3-fluorophenoxy}propyl)-1-piperazinyl]-1-methyl-2-oxoethyl}-4-(dimethylamino)benzamide The desired product was prepared according to the method described in Example 170, substituting 4-(dimethylamino)benzoic acid for propionic acid. A-349413: $^1$H NMR (CDCl$_3$) δ1.30 (m, 2H), 1.42 (d, 3H), 1.60 (m, 4H), 1.90 (m, 2H), 2.30 (m, 2H), 2.40 (m, 1H), 2.98 (d, 2H), 3.00 (s, 6H), 3.10–3.60 (m, 6H), 3.70–4.20 (m, 6H), 5.02 (m, 1H), 6.65–6.80 (m, 5H), 7.68 (d, 2H), 7.98 (m, 1H); MS (APCI+) m/z 607 (M+H)+.

EXAMPLE 181

N-{(1R)-2-[4-(3-{4-[5-(cyclopentylmethyl)-1,2,4-oxadiazol-3-yl]-3-fluorophenoxy}propyl)-1-piperazinyl]-1-methyl-2-oxoethyl}nicotinamide The desired product was prepared according to the method described in Example 170, substituting nicotinic acid for propionic acid. $^1$H NMR (CDCl$_3$) δ1.30 (m, 2H), 1.45 (d, 3H), 1.60 (m, 4H), 1.90 (m, 2H), 2.35 (m, 2H), 2.40 (m, 1H), 2.98 (d, 2H), 3.00–3.60 (m, 6H), 3.70–4.20 (m, 6H), 5.02 (m, 1H), 6.80 (m, 2H), 7.22 (m, 1H), 7.60 (m, 1H), 7.98 (m, 1H), 8.12 (m, 1H), 8.78 (m, 1H), 9.05 (m, 1H); MS (APCI+) m/z 565 (M+H)+.

EXAMPLE 182

2-chloro-N-{(1R)-2-[4-(3-{4-[5-(cyclopentylmethyl)-1,2,4-oxadiazol-3-yl]-3-fluorophenoxy}propyl)-1-piperazinyl]-1-methyl-2-oxoethyl}benzamide The desired product was prepared according to the method described in Example 170, substituting 2-chlorobenzoic acid for propionic acid. $^1$H NMR (CDCl$_3$) δ1.30 (m, 2H), 1.45 (d, 3H), 1.60 (m, 4H), 1.90 (m, 2H), 2.35 (m, 2H), 2.40 (m, 1H), 2.98 (d, 2H), 3.00–3.70 (m, 6H), 3.80–4.20 (m, 6H), 5.02 (m, 1H), 6.80 (m, 2H), 7.00 (m, 1H), 7.40 (m, 3H), 7.62 (m, 1H), 8.00 (m, 1H); MS (APCI+) m/z 598 (M+H)+.

EXAMPLE 183

N-{(1R)-2-[4-(3-{4-[5-(cyclopentylmethyl)-1,2,4-oxadiazol-3-yl]-3-fluorophenoxy}propyl-1-piperazinyl]-1-methyl-2-oxoethyl}-1,3-benzodioxole-5-carboxamide The desired product was prepared according to the method described in Example 170, substituting 1,3- benzodioxole-5-carboxylic acid for propionic acid. $^{1}$H NMR (CDCl$_3$) δ1.30 (m, 2H), 1.45 (d, 3H), 1.60 (m, 4H), 1.90 (m, 2H), 2.35 (m, 2H), 2.40 (m, 1H), 2.98 (d, 2H), 3.10–3.70 (m, 6H), 3.80–4.20 (m, 6H), 5.02 (m, 1H), 6.00 (s, 2H), 6.78 (m, 2H), 6.82 (d, 1H), 6.90 (m, 1H), 7.25 (m, 1H), 7.35 (d, 1H), 8.00 (m, 1H); MS (APCI+) m/z 608 (M+H)$^+$.

EXAMPLE 184

N-{(1R)-2-[4-(3-{4-[5-(cyclopentylmethyl)-1,2,4-oxadiazol-3-yl]-3-fluorophenoxy}propyl)-1-piperazinyl]-1-methyl-2-oxoethyl}-4-isopropoxybenzamide The desired product was prepared according to the method described in Example 170, substituting 4-isopropoxybenzoic acid for propionic acid. $^1$H NMR (CDCl$_3$) δ1.30 (m, 2H), 1.38 (d, 6H), 1.45 (d, 3H), 1.60 (m, 4H), 1.90 (m, 2H), 2.35 (m, 2H), 2.40 (m, 1H), 2.98 (d, 2H), 3.20–3.70 (m, 6H), 3.80–4.20 (m, 6H), 4.60 (m, 1H), 5.02 (m, 1H), 6.78 (m, 2H), 6.90 (m, 3H), 7.75 (d, 2H), 8.00 (m, 1H); MS (APCI+) m/z 622 (M+H)$^+$.

EXAMPLE 185

N-{(1R)-2-[4-(3-{4-[5-(cyclopentylmethyl)-1,2,4-oxadiazol-3-yl]-3-fluorophenoxy}propyl)-1-piperazinyl]-1-methyl-2-oxoethyl}-3-fluoro-4-methoxybenzamide The desired product was prepared according to the method described in Example 170, substituting 3-fluoro-4-methoxybenzoic acid for propionic acid. $^1$H NMR (CDCl$_3$) δ1.30 (m, 2H), 1.45 (d, 3H), 1.60 (m, 4H), 1.90 (m, 2H), 2.35 (m, 2H), 2.40 (m, 1H), 2.98 (d, 2H), 3.00–3.70 (m, 6H), 3.95 (s, 3H), 3.80–4.20 (m, 6H), 5.02 (m, 1H), 6.78 (m, 2H), 6.95 (m, 1H), 7.10 (m, 1H), 7.55 (m, 2H), 8.00 (m, 1H); MS (APCI+) m/z 612 (M+H)$^+$.

EXAMPLE 186

4-[({(1R)-2-[4-(3-{4-[5-(cyclopentylmethyl)-1,2,4-oxadiazol-3-yl]-3-fluorophenoxy}propyl)-1-piperazinyl]-1-methyl-2-oxoethyl}amino)carbonyl]benzoic acid The desired product was prepared according to the method described in Example 170, substituting terephthalic acid for propionic acid. $^1$H NMR (CDCl$_3$) δ1.30 (m, 2H), 1.45–1.60 (m, 7H), 1.90 (m, 2H), 2.35 (m, 2H), 2.40 (m, 1H), 2.98 (d, 2H), 3.00–3.70 (m, 6H), 3.80–4.20 (m, 6H), 5.02 (m, 1H), 6.78 (m, 2H), 7.50–8.00 (m, 6H); MS (APCI+) m/z 608 (M+H)$^+$.

EXAMPLE 187

N-{(1R)-2-[4-(3-{3-fluoro-4-[5-(3-methylphenyl)-1,2,4-oxadiazol-3-yl]phenoxy}propyl)-1-piperazinyl]-1-methyl-2-oxoethyl}-2-thiophenecarboxamide

Example 187A

Tert-butyl (1R)-2-{4-[3-(4'-cyano-3-fluorophenoxy)propyl]-1-piperazinyl-1-methyl-2-oxoethylcarbamate The desired product was prepared according to the method described in Example 141 C, substituting Example 26B for Example 141B.

Example 187B 4-(3-{4-[(2R)-2-aminopropanoyl]-1-piperazinyl}propoxy)-2-fluorobenzonitrile The desired product was prepared according to the method described in Example 141B, substituting Example 187A for Example 141A.

Example 187B

N-((1R)-2-{4-[3-(4'-cyano-3-fluorophenoxy)propyl-1-piperazinyl}-1-methyl-2-oxoethyl)-2-thiophenecarboxamide The desired product was prepared according to the method described in Example 141C, substituting 2-thiophenecarboxylic acid for N-(tert-butoxycarbonyl)-D-alanine and substituting Example 187A for Example 141B.

Example 187C

N-{(1R)-2-[4-(3-{4-[amino(hydroxyimino)methyl]-3-fluorophenoxy}propyl)-1-piperazinyl]-1-methyl-2-oxoethyl}-2-thiophenecarboxamide The desired product was prepared according to the method described in Example 141F, substituting Example 187B for Example 141E.

Example 187D

N-{(1R)-2-[4-(3-{3-fluoro-4-[5-(3-methylphenyl)-1,2,4-oxadiazol-3-yl]phenoxy}propyl)-1-piperazinyl]-1-methyl-2-oxoethyl}-2-thiophenecarboxamide 3-Methylbenzoic acid (0.3 mmol) was treated with a 0.4 M solution of 1,1'-carbonyldiimidazole (CDI) (0.75 mL, 0.3 mmol) in DMF in a 4 mL vial. After mixing for 30 minutes, a 0.22 M solution of Example 187C (0.75 mL, 0.16 mol) in DMF was added to the vial. The mixture was stirred for 4 hours at room temperature and a 0.4 M solution of CDI (0.5 mL, 0.2 mmol) in DMF was added to the vial. After heating the mixture at 115° C. for 7 hours, the mixture was allowed to cool to room temperature and then was concentrated under reduced pressure. The residue was purified by preparative HPLC to provide the desired product. $^1$H NMR (CDCl$_3$) δ1.50 (d, 3H), 2.35 (m, 2H), 2.45 (s, 3H), 3.05–3.60 (m, 6H), 3.80–4.25 (m, 6H), 5.05 (m, 1H), 6.80 (m, 2H), 7.00 (m, 1H), 7.08 (m, 1H), 7.40 (m, 2H), 7.50 (m, 1H), 7.60 (m, 1H), 8.00 (m, 2H), 8.05 (m, 1H); MS (APCI+) m/z 564 (M+H)$^+$.

EXAMPLE 188

N-{(1R)-2-[4-(3-{4-[5-(3-cyanophenyl)-1,2,4-oxadiazol-3-yl]-3-fluorophenoxy}propyl)-1-piperazinyl]-1-methyl-2-oxoethyl}-2-thiophenecarboxamide The desired product was prepared according to the method described in Example 187D, substituting 3-cyanobenzoic acid for 3-methylbenzoic acid. $^1$H NMR (CDCl$_3$) δ1.44 (d, 3H), 2.35 (m, 2H), 3.00–3.70 (m, 8H), 3.90–4.25 (m, 4H), 5.05 (m, 1H), 6.80 (m, 3H), 7.08 (m, 1H), 7.54 (m, 1H), 7.58 (m, 1H), 7.70 (m, 1H), 7.90 (m, 1H), 8.05 (m, 1H), 8.42 (m, 1H), 8.50 (br s, 1H); MS (APCI+) m/z 589 (M+H)$^+$.

EXAMPLE 189

N-{(1R)-2-[4-(3-{4-[5-(3,5-dichlorophenyl)-1,2,4-oxadiazol-3-yl]-3-fluorophenoxy}propyl)-1-piperazinyl]-1-methyl-2-oxoethyl}-2-thiophenecarboxamide The desired product was prepared according to the method described in Example 187D, substituting 3,5-dichlorobenzoic acid for 3-methylbenzoic acid. $^1$H NMR (CDCl₃) δ1.42 (d, 3H), 2.35 (m, 2H), 3.00–3.70 (m, 8H), 3.90–4.25 (m, 4H), 5.05 (m, 1H), 6.80 (m, 3H), 7.08 (m, 1H), 7.60 (m, 3H), 8.08 (m, 3H); MS (APCI+) m/z 632 (M+H)⁺.

EXAMPLE 190

N-((1R)-2-{4-[3-(3-fluoro-4-{5-[3-oxo-3-(1-pyrrolidinyl)propyl]-1,2,4-oxadiazol-3-yl}phenoxy)propyl]-1-piperazinyl}-1-methyl-2-oxoethyl)-2-thiophenecarboxamide The desired product was prepared according to the method described in Example 187D, substituting 4-oxo-4-(1-pyrrolidinyl)butanoic acid for 3-methylbenzoic acid. ¹H NMR (CDCl₃) δ1.42 (d, 3H), 1.85 (m, 2H), 2.00 (m, 2H), 2.30 (m, 2H), 2.85 (t, 3H), 3.00–3.30 (m, 8H), 3.40–3.70 (m, 6H), 3.90–4.25 (m, 4H), 5.05 (m, 1H), 6.70 (m, 2H), 7.05 (m, 1H), 7.18 (m, 1H), 7.50 (m, 1H), 7.60 (m, 1H), 7.95 (m, 1H); MS (APCI+) m/z 613 (M+H)⁺.

EXAMPLE 191

Ethyl 3-{2-fluoro-4-[3-(4-{(2R)-2-[(2-thienylcarbonyl)amino]propanoyl}-1-piperazinyl)propoxy]phenyl}-1,2,4-oxadiazole-5-carboxylate Example 187C (0.1 mmol) in anhydrous pyridine (0.3 mL) was treated with ethyl oxalyl chloride (30 mg, 0.22 mmol) and heated at 90° C. for 30 minutes. The mixture was allowed to cool to room temperature and was concentrated under reduced pressure. The residue was diluted with DCM (2 mL), washed with water (1 mL) and concentrated under reduced pressure. The residue was purified by silica gel column chromatography (hexane/EtOAc 1:1, then EtOH) to provide the desired product. ¹H NMR (CDCl₃) δ1.40 (d, 3H), 1.42 (t, 3H), 2.30 (m, 2H), 3.00–3.60 (m, 8H), 3.90–4.25 (m, 4H), 4.58 (q, 2H), 5.05 (m, 1H), 6.78 (m, 2H), 6.90 (m, 1H), 7.08 (m, 1H), 7.50 (m, 1H), 7.58 (m, 1H), 8.05 (m, 1H); MS (APCI+) m/z 560 (M+H)⁺.

EXAMPLE 192

N-[(1R)-2-(4-{3-[4-(cyclopropylcarbonyl)phenoxy]propyl}-1-piperazinyl)-1-methyl-2-oxoethyl]-2-methylbenzamide 2-Methylbenzoic acid (0.05 mmol), N-cyclohexylcarbodimide and N-methyl polystyrene (50 mg, 0.075 mmol) was treated with HOBt (5 mg, 0.04 mmol) in 1 mL of DMA. After mixing for 15 minutes, Example 138 (10 mg, 0.03 mmol) in 1 mL of DMA/DCM (1:1) was added to the reaction mixture. The mixture was agitated at room temperature overnight and then trisamine resin (50 mg, 0.2 mmol) was added to the reaction mixture. The mixture was agitated for 3 hours, filtered, the solid resin was washed with DCM (2×1 mL) and the filtrate was concentrated under reduced pressure. The residue was purified by preparative HPLC to provide the desired product. ¹H NMR (CDCl₃) δ1.00 (m, 2H), 1.20 (m, 2H), 1.42 (d, 3H), 2.30 (m, 2H), 2.42 (s, 3H), 2.60 (m, 1H), 3.02–3.70 (m, 6H), 3.80–4.25 (m, 6H), 5.02 (m, 1H), 6.60 (m, 1H), 6.90 (d, 2H), 7.12 (m, 3H), 7.40 (m, 2H), 8.00 (d, 2H); MS (APCI+) m/z 478 (M+H)⁺.

EXAMPLE 193

N-[(1R)-2-(4-{3-[4-(cyclopropylcarbonyl)phenoxy]propyl}-1-piperazinyl)-1-methyl-2-oxoethyl]-3-methoxybenzamide The desired product was prepared according to the method described in Example 192, substituting 3-methoxybenzoic acid for 2-methylbenzoic acid. ¹H NMR (CDCl₃) δ1.00 (m, 2H), 1.20 (m, 2H), 1.42 (d, 3H), 2.30 (m, 2H), 2.60 (m, 1H), 3.02–3.70 (m, 6H), 3.80 (s, 3H), 3.85–4.25 (m, 6H), 5.02 (m, 1H), 6.90 (d, 2H), 7.05 (m, 2H), 7.35 (m, 3H), 8.00 (d, 2H); MS (APCI+) m/z 494 (M+H)⁺.

EXAMPLE 194

4-bromo-N-[(1R)-2-(4-{3-[4-(cyclopropylcarbonyl)phenoxy]propyl}-1-piperazinyl)-1-methyl-2-oxoethyl]benzamide The desired product was prepared according to the method described in Example 192, substituting 4-bromobenzoic acid for 2-methylbenzoic acid. ¹H NMR (CDCl₃) δ1.00 (m, 2H), 1.20 (m, 2H), 1.42 (d, 3H), 2.30 (m, 2H), 2.60 (m, 1H), 3.02–3.70 (m, 6H), 3.85–4.25 (m, 6H), 5.02 (m, 1H), 6.90 (d, 2H), 7.10 (m, 1H), 7.60 (d, 2H), 7.64 (d, 2H), 7.90–8.05 (m, 2H); MS (APCI+) m/z 543 (M+H)⁺.

EXAMPLE 195

N-[1R)-2-(4-{3-[4-(cyclopropylcarbonyl)phenoxy]propyl}-1-piperazinyl)-1-methyl-2-oxoethyl]-4-phenoxybenzamide The desired product was prepared according to the method described in Example 192, substituting 4-phenoxybenzoic acid for 2-methylbenzoic acid. ¹H NMR (CDCl₃) δ1.00 (m, 2H), 1.20 (m, 2H), 1.42 (d, 3H), 2.30 (m, 2H), 2.60 (m, 1H), 3.02–3.70 (m, 6H), 3.85–4.25 (m, 6H), 5.02 (m, 1H), 6.90 (m, 3H), 7.02 (m, 4H), 7.20 (m, 1H), 7.40 (m, 2H), 7.80 (d, 2H), 8.00 (d, 2H); MS (APCI+) m/z 556 (M+H)⁺.

EXAMPLE 196

N-[(1R)-2-(4-{3-[4-(cyclopropylcarbonyl)phenoxy]propyl}-1-piperazinyl)-1-methyl-2-oxoethyl]-3,5-dimethylbenzamide The desired product was prepared according to the method described in Example 192, substituting 3,5-dimethylbenzoic acid for 2-methylbenzoic acid. ¹H NMR (CDCl₃) δ1.00 (m, 2H), 1.20 (m, 2H), 1.42 (d, 3H), 2.30 (m, 2H), 2.32 (s, 3H), 2.40 (s, 3H), 2.60 (m, 1H), 3.02–3.70 (m, 6H), 3.85–4.25 (m, 6H), 5.02 (m, 1H), 6.60 (m, 1H), 6.90 (d, 2H), 7.00 (m, 2H), 7.30 (m, 1H), 8.05 (m, 2H); MS (APCI+) m/z 492 (M+H)⁺.

EXAMPLE 197

N-[(1R)-2-(4-{3-[4-(cyclopropylcarbonyl)phenoxy]propyl}-1-piperazinyl)-1-methyl-2-oxoethyl]-2,5-dimethoxybenzamide The desired product was prepared according to the method described in Example 192, substituting 2,5-dimethoxybenzoic acid for 2-methylbenzoic acid. ¹H NMR (CDCl₃) δ1.00 (m, 2H), 1.20 (m, 2H), 1.42 (d, 3H), 2.30 (m, 2H), 2.60 (m, 1H), 3.02–3.70 (m, 6H), 3.80 (s, 3H), 3.96 (s, 3H), 3.85–4.25 (m, 6H), 5.02 (m, 1H), 6.92 (m, 3H), 7.00 (m, 1H), 7.62 (br s, 1H), 8.05 (m, 2H), 8.78 (m, 1H); MS (APCI+) m/z 524 (M+H)⁺.

EXAMPLE 198

N-{(1R)-2-[4-(3-{3-fluoro-4-[5-(4-methoxyphenyl)-1,2,4-oxadiazol-3-yl]phenoxy}propyl)-1-piperazinyl]-1-methyl-2-oxoethyl}-2-thiophenecarboxamide The desired product was prepared according to the method described in Example 187D, substituting 4-methoxybenzoic acid for 3-methylbenzoic acid.

A-352563: $^1$H NMR (CDCl$_3$) δ1.50 (d, 3H), 2.35 (m, 2H), 3.00–3.70 (m, 6H), 3.90 (s, 3H), 3.92–4.25 (m, 6H), 5.05 (m, 1H), 6.80 (m, 2H), 6.95 (m, 1H), 7.08 (d, 2H), 7.08 (m, 1H), 7.50 (m, 1H), 7.60 (m, 1H), 8.08 (m, 1H), 8.15 (d, 2H); MS (APCI+) m/z 594 (M+H)$^+$.

What is claimed is:

1. A compound selected from the group consisting of: a compound of formula (I)

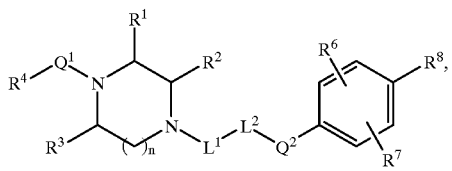

or pharmaceutically acceptable salts thereof wherein,

L$^1$ is absent or L$^1$ is selected from unsubstituted cycloalkyl, substituted cycloalkyl, unsubstituted cycloalkylylene, or substituted cycloalkylalkylene;

L$^2$ is absent or L$^2$ is unsubstituted alkylene or alkylene substituted with aryl; with the proviso that at least one of L$^1$ or L$^2$ is not absent;

n is one;

Q$^1$ is —C(=O);

Q$^2$ is selected from the group consisting of —O—, —S—, —S(=O)—, —SO$_2$—, and acetylene;

R$^1$, R$^2$, and R$^3$ are independently selected from the group consisting of hydrogen and alkyl;

R$^4$ is —W$^1$—C(R$^{11}$)(R$^{11a}$)—NR$^{12}$R$^{12a}$;

R$^6$ and R$^7$ are independently selected from the group consisting of hydrogen, alkyl, alkenyl, alkynyl, alkoxy, amino, azido, carboxaldehyde, carboxyl, cyano, halo, hydroxyl, nitro, perfluoroalkyl, and perfluoroalkoxy; or R$^6$ and R$^7$ are on adjacent carbon atoms and taken together are —OCH$_2$C(O)—;

R$^8$ is selected from the group consisting of alkyl, alkanoyl, alkoxy, alkoxycarbonyl, amino, unsubstituted or substituted aryl, arylalkyl, aryloyl, arylsulfonyl, carboxamido, cyano, cyanoalkyl, cycloalkyl, cycloalkylalkyl, cycloalkyloyl, halo, unsubstituted or substituted heteroaryl, heteroarylalkyl, heteroaryloyl, heteroarylsulfonyl, perfluoroalkyl, —C(H)(R$^{13}$)—OR$^{14}$, and —C(R$^{13}$)=N—OR$^{14}$;

W$^1$ is absent or W$^1$ is an unsubstituted or substituted alkylene;

R$^{11}$ and R$^{11a}$ are independently selected from the group consisting of hydrogen, alkyl, alkoxyalkyl, amino, aminoalkyl, arylalkyl, arylalkoxyalkyl, heteroarylalkyl, hydroxyalkyl, and ureidoalkyl;

R$^{12}$ and R$^{12a}$ are independently selected from the group consisting of hydrogen, alkyl, alkanoyl, alkylsulfonyl, a nitrogen protecting group, aminosulfonyl, unsubstituted or substituted aryl, arylalkyl, aryloyl, arylsulfonyl, cycloalkyl, cycloalkylalkyl, cycloalkyloyl, cycloalkylsulfonyl, unsubstituted or substituted heteroaryl, heteroarylalkyl, heteroaryloyl, heteroarylsulfonyl, unsubstituted or substituted heterocycloalkyl, heterocycloalkylalkyl, heterocycloalkyloyl, and heterocycloalkylsulfonyl;

R$^{13}$ is selected from the group consisting of hydrogen, alkyl, cycloalkyl, cycloalkylalkyl, aryl, and arylalkyl; and R$^{14}$ is selected from the group consisting of hydrogen, alkyl, cycloalkyl, cycloalkylalkyl, aryl, arylalkyl, and a hydroxyl protecting group.

2. A compound according to claim 1 wherein L$^1$ is absent.

3. A compound according to claim 1 wherein L$^2$ is unsubstituted alkylene or alkylene substituted with aryl.

4. A compound according to claim 1 wherein n is one.

5. A compound according to claim 1 wherein Q$^2$ is selected from —O— and acetylene.

6. A compound according to claim 1 wherein R$^1$, R$^2$, and R$^3$ are hydrogen.

7. A compound according to claim 1 wherein R$^4$ is

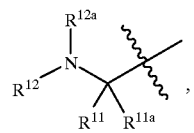

wherein one of R$^{11}$ and R$^{11a}$ is hydrogen or alkyl, and the other is selected from the group consisting of hydrogen, alkyl, alkoxyalkyl, amino, aminoalkyl, arylalkyl, heteroarylalkyl, hydroxyalkyl, and ureidoalkyl; and R$^{12}$ and R$^{12a}$ are independently selected from the group consisting of hydrogen, alkyl, alkanoyl, alkylsulfonyl, a nitrogen protecting group, aminosulfonyl, unsubstituted aryl or substituted aryl, arylalkyl, aryloyl, arylsulfonyl, cycloalkyl, cycloalkylalkyl, cycloalkyloyl, cycloalkylsulfonyl, unsubstituted heteroaryl or substituted heteroaryl, heteroarylalkyl, heteroaryloyl, heteroarylsulfonyl, unsubstituted heterocycloalkyl or substituted heterocycloalkyl, heterocycloalkylalkyl, heterocycloalkyloyl, and heterocycloalkylsulfonyl.

8. A compound according to claim 7 wherein the relative stereochemistry of R$^4$ is depicted by the formula

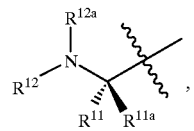

wherein

R$^{11}$ is hydrogen; and

R$^{11a}$, R$^{12}$ and R$^{12a}$ are defined therein.

9. A compound according to claim 7 wherein the relative stereochemistry of R$^4$ is depicted by the formula

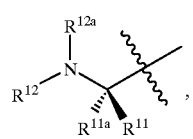

wherein

R$^{11}$ is hydrogen; and

R$^{11a}$, R$^{12}$ and R$^{12a}$ are defined therein.

10. A compound according to claim 1 wherein $R^4$ is

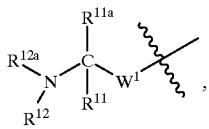

wherein one of $R^{11}$ and $R^{11a}$ is hydrogen or alkyl, and the other is selected from the group consisting of hydrogen, alkyl, alkoxyalkyl, amino, aminoalkyl, arylalkyl, heteroarylalkyl, hydroxyalkyl, and ureidoalkyl;

$R^{12}$ and $R^{12a}$ are independently selected from the group consisting of hydrogen, alkyl, alkanoyl, alkylsulfonyl, a nitrogen protecting group, aminosulfonyl, unsubstituted aryl or substituted aryl, arylalkyl, aryloyl, arylsulfonyl, cycloalkyl, cycloalkylalkyl, cycloalkyloyl, cycloalkylsulfonyl, unsubstituted heteroaryl or substituted heteroaryl, heteroarylalkyl, heteroaryloyl, heteroarylsulfonyl, unsubstituted heterocycloalkyl or substituted heterocycloalkyl, heterocycloalkylalkyl, heterocycloalkyloyl, and heterocycloalkylsulfonyl: and $W^1$ is alkylene.

11. A compound according to claim 10 wherein the relative stereochemistry of $R^4$ is depicted by the formula

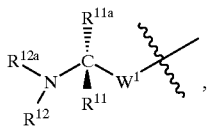

wherein $R^{11}$, $R^{11a}$, $R^{12}$, $R^{12a}$, and $W^1$ are defined therein.

12. A compound according to claim 10 wherein the relative stereochemistry of $R^4$ is depicted by the formula

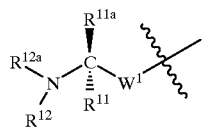

$R^{11}$, $R^{11a}$, $R^{12}$, $R^{12a}$, and $W^1$ are defined therein.

13. A compound according to claim 1 wherein $R^6$ is hydrogen.

14. A compound according to claim 1 wherein $R^7$ is hydrogen or halo.

15. A compound according to claim 1 wherein $R^8$ is selected from the group consisting of alkanoyl, aryl, carboxamido, cycloalkyloyl, cyano, halo, heteroaryl, and perfluoroalkyl.

16. A compound according to claim 1 wherein $R^8$ is cyclopropanoyl.

17. A compound according to claim 15 wherein $R^8$ is 4'-cyanophen-4-yl.

18. A compound according to claim 15 wherein $R^8$ is

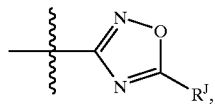

wherein $R^1$ is selected from the group consisting of hydrogen, alkyl, alkoxyalkyl, alkoxyalkoxyalkyl, aminoalkyl, aryl, arylalkyl, cyanoalkyl, cycloalkyl, cycloalkylalkyl, heteroaryl, heterocycloalkyl, alkoxycarbonyl, and perfluoroalkyl.

19. A compound of claim 1 selected from the group consisting of (4-(3-(4-((2S)-2-aminopropanoyl)-1-piperazinyl) propoxy)phenyl)(cyclopropyl)methanone, (2S)-1-(4-(3-(4-(5-methyl-1,2,4-oxadiazol-3-yl)phenoxy) propyl)-1-piperazinyl)-1-oxo-2-propanamine, tert-butyl 2-(4-(3-(4-bromophenoxy)propyl)-1-piperazinyl)-2-oxoethylcarbamate, 2-(4-(3-(4-bromophenoxy)propyl)-1-piperazinyl)-2-oxoethanamine, tert-butyl 3-(4-(3-(4-bromophenoxy)propyl)-1-piperazinyl)-3-oxopropylcarbamate, 3-(4-(3-(4-bromophenoxy)propyl)-1-piperazinyl)-3-oxo-1-propanamine, tert-butyl (1R)-2-(4-(3-(4-bromophenoxy)propyl)-1-piperazinyl)-1-methyl-2-oxoethylcarbamate, (2R)-1-(4-(3-(4-bromophenoxy)propyl)-1-piperazinyl)-1-oxo-2-propanamine, tert-butyl (1S)-2-(4-(3-(4-bromophenoxy)propyl)-1-piperazinyl)-1-methyl-2-oxoethylcarbamate, (2S)-1-(4-(3-(4-bromophenoxy)propyl)-1-piperazinyl)-1-oxo-2-propanamine, tert-butyl (1R)-1-methyl-2-oxo-2-(4-(3-(4-(trifluoromethyl)phenoxy)propyl)-piperazinyl) ethylcarbamate, tert-butyl (1R)-2-(4-(3-(4-cyanophenoxy)propyl)-1-piperazinyl)-1-methyl-2-oxoethylcarbamate, tert-butyl 3-(4-(3-(4-cyano-3-fluorophenoxy)propyl)-1-piperazinyl )-3-oxopropylcarbamate, tert-butyl (1R)-2-(4-(3-(4-(aminocarbonyl)-3-fluorophenoxy)propyl)-1-piperazinyl)-1-methyl-2-oxoethylcarbamate, tert-butyl (1R)-2-(4-(3-(4-acetylphenoxy)propyl)-1-piperazinyl)-1-methyl-2-oxoethylcarbamate, 1-(4-(3-(4-((2R)-2-aminopropanoyl)-1-piperazinyl) propoxy)phenyl)ethanone, N-((1R)-2-(4-(3-(4-acetylphenoxy)propyl)-1-piperazinyl)-1-methyl-2-oxoethyl)acetamide, ethyl (1R)-2-(4-(3-(4-acetylphenoxy)propyl)-1-piperazinyl)-1-methyl-2-oxoethylcarbamate, N-((1R)-2-(4-(3-(4-acetylphenoxy)propyl)-1-piperazinyl)-1-methyl-2-oxoethyl) cyclopropanecarboxamide, tert-butyl (1R)-2-(4-((1R)-3-(4-acetylphenoxy)-1-methylpropyl)-1-piperazinyl)-1-methyl-2-oxoethylcarbamate, tert-butyl (1S)-2-(4-(3-(4-acetylphenoxy)propyl)-1-piperazinyl)-1-methyl-2-oxoethylcarbamate, N-((1R)-2-(4-(3-(4-acetylphenoxy)propyl)-1-piperazinyl)-1-methyl-2oxoethyl) methanesulfonamide, N'-((1R)-2-(4-(3-(4-acetylphenoxy)propyl)-1-piperazinyl)-1-methyl-2-oxoethyl)-N,N-dimethylsulfamide, 1-(4-(3-(4-((methylamino)acetyl)-1-piperazinyl)propoxy)phenyl)-1-hexanone, tert-butyl 2-(4-(3-(4-hexanoylphenoxy)propyl)-1-piperazinyl)-2-oxoethylcarbamate, 1-(4-(3-(4-(3-aminopropanoyl)-1-piperazinyl)propoxy)phenyl)-1-hexanone, 1-(4-(3-(4-((2R)-2-aminopropanoyl)-1-piperazinyl)propoxy)phenyl)-1-hexanone, tert-butyl (1S)-1-((4-(3-(4-hexanoylphenoxy)propyl)-1-piperazinyl)carbonyl )-2-methylpropylcarbamate, 1-(4-(3-(4-((2S)-2-amino-3-methylbutanoyl)-1-piperazinyl)propoxy)phenyl)-1-hexanone, tert-butyl (1R)-1-((4-(3-(4-hexanoylphenoxy)propyl)-1-piperazinyl)carbonyl)-2-methylpropylcarbamate, 1-(4-(3-(4-((2R)-2-amino-3-methylbutanoyl)-1-piperazinyl)propoxy)phenyl)-1-hexanone, tert-butyl (1S)-1-((4-(3-(4-hexanoylphenoxy)propyl)-1-piperazinyl)carbonyl)-3-methylbutylcarbamate, 1-(4-(3-(4-((2S)-2-amino-4-methylpentanoyl)-1-piperazinyl)propoxy)phenyl)-1-hexanone, tert-butyl (1R)-1-((4-(3-(4-hexanoylphenoxy)propyl)-1-piperazinyl)carbonyl)-3-methylbutylcarbamate, 1-(4-(3-(4-((2R)-2-amino-4-methylpentanoyl)-1-piperazinyl)propoxy)pheny 1)-1-hexanone, tert-butyl (1S)-1-((benzyloxy)methyl)-2-(4-(3-(4-hexanoylphenoxy)propyl)-1-piperazinyl)-2-oxoethylcarbamate, 1-(4-(3-(4-((2R)-2-amino-3-hydroxypropanoyl)-1-piperazinyl)propoxy)phenyl)-1 -hexanone, 1-(4-(3-(4-((2S)-2-amino-3-(benzyloxy)propanoyl)-1-piperazinyl)propoxy)phenyl)-1-hexanone, tert-butyl (1S)-2-(4-(3-(4-hexanoylphenoxy)propyl)-1-piperazinyl)-2-oxo-1-(4-pyridinylmethyl)ethylcarbamate, 1-(4-(3-(4-((2S)-2-amino-3-(4-pyridinyl)propanoyl)-1-piperazinyl)propoxy)phenyl)-1-hexanone, tert-butyl (1R)-2-(4-(3-(4-hexanoylphenoxy)propyl)-1-piperazinyl)-2-oxo-1-(4-pyridinylmethyl)ethylcarbamate, 1-(4-(3-(4-((2R)-2-amino-3-(4-pyridinyl)propanoyl)-1-piperazinyl)propoxy)phenyl)-1-hexanone, tert-butyl (1S)-2-(4-(3-(4-hexanoylphenoxy)propyl)-1-piperazinyl)-1-(1H-imidazol-4-ylmethyl)-2-oxoethylcarbamate, 1-(4-(3-(4-((2S)-2-amino-3-(1H-imidazol-4-yl)propanoyl)-1-piperazinyl)propoxy)phenyl)-1-hexanone, (4-(((3R)-3-(4-(3-aminopropanoyl)-1-piperazinyl)butyl)oxy)phenyl)(cyclopropyl)methanone, tert-butyl (1R)-2-(4-((1 R)-3-(4-(cyclopropylcarbonyl)phenoxy)-1-methylpropyl)-1-piperazinyl)-1-methyl-2-oxoethylcarbamate, (4-(((3R)-3-(4-((2R)-2-aminopropanoyl)-1-piperazinyl)butyl)oxy)phenyl)(cyclopropyl)methanone, tert-butyl (1R)-2-(4-((1S)-3-(4-(cyclopropylcarbonyl)phenoxy)-1-methylpropyl)-1-piperazinyl)-1-methyl-2-oxoethylcarbamate, tert-butyl (1R)-2-(4-(3-(4-(cyclopropylcarbonyl)phenoxy)propyl)-1-piperazinyl)-1-methyl-2-oxoethylcarbamate, cyclopropyl(4-(((3R)-3-(4-((methylamino)acetyl)-1-piperazinyl)butyl)oxy)phenyl)methanone, (4-(3-(4-((2R)-2-amino-3,3-dimethylbutanoyl)-1-piperazinyl)propoxy)phenyl)(cyclopropyl)methanone, tert-butyl (1R)-1-((4-(3-(4-(cyclopropylcarbonyl)phenoxy)propyl)-1-piperazinyl)carbonyl)-3,3-dimethylbutylcarbamate, (4-(3-(4-((2R)-2-aminobutanoyl)-1-piperazinyl)propoxy)phenyl)(cyclopropyl)methanone, cyclopropyl(4-(3-(4-((2R)-2-(methylamino)-3-phenylpropanoyl)-1-piperazinyl)propoxy)phenyl)methanone, (4-(3-(4-((2R,3S)-2-amino-3-hydroxybutanoyl)-1-piperazinyl)propoxy)phenyl)(cyclopropyl)methanone, benzyl (1R)-1-(tert-butoxymethyl)-2-(4-(3-(4-(cyclopropylcarbonyl)phenoxy)propyl)-1-piperazinyl)-2-oxoethylcarbamate, (4-(3-(4-((2R)-2-amino-3-tert-butoxypropanoyl)-1-piperazinyl)propoxy)phenyl)(cyclopropyl)methanone, tert-butyl (1 R,2S)-2-tert-butoxy-1-((4-(3-(4-(cyclopropylcarbonyl)phenoxy)propyl)-1-piperazinyl)carbonyl)propylcarbamate, (4-(3-(4-((2R)-2-amino-3 -(benzyloxy)propanoyl)-1-piperazinyl)propoxy)phenyl)(cyclopropyl)methanone, tert-butyl (1 R,2S)-2-(benzyloxy)-1-((4-(3-(4-(cyclopropylcarbonyl)phenoxy)propyl)-1-piperazinyl)carbonyl)propylcarbamate, tert-butyl (1 R)-5-((aminocarbonyl)amino)-1-((4-(3-(4-(cyclopropylcarbonyl)phenoxy)propyl)-1-piperazinyl)carbonyl)pentylcarbamate, tert-butyl (1 R)-4-((aminocarbonyl)amino)-1-((4-(3-(4-(cyclopropylcarbonyl)phenoxy)propyl)-1-piperazinyl)carbonyl)butylcarbamate, tert-butyl (1 R)-1-benzyl-2-(4-(3-(4-(cyclopropylcarbonyl)phenoxy)propyl )-1-piperazinyl)-2-oxoethylcarbamate, tert-butyl (1R)-2-(4-(3 -(4-(cyclopropylcarbonyl)phenoxy)propyl)-1-piperazinyl)-1-(4-fluorobenzyl)-2-oxoethylcarbamate, (4-(3-(4-((2R)-2-amino-3-(4-fluorophenyl)propanoyl)-1-piperazinyl)propoxy)phenyl)(cyclopropyl)methanone, (4-(3-(4-((2R)-2-amino-3-(2-thienyl)propanoyl)-1-piperazinyl)propoxy)phenyl)(cyclopropyl)methanone, (4-(3-(4-((2R)-2-amino-3-(1-methyl-1H-imidazol-4-yl)propanoyl)-1-piperazinyl)propoxy)phenyl)(cyclopropyl)methanone, tert-butyl (1 R)-2-(4-(3-(4-(cyclopropylcarbonyl)phenoxy)propyl)-1-piperazinyl)-2-oxo-1-(1,3-thiazol-5-ylmethyl)ethylcarbamate, 1-((1S)-1-((4-(3-(4-(cyclopropylcarbonyl)phenoxy)propyl)-1-piperazinyl)carbonyl)-2-methylpropyl)tetrahydro-2(1H)-pyrimidinone, tert-butyl (1 S)-2-(4-(2-((4-cyano(1,1'-biphenyl)-4-yl)oxy)ethyl)-1-piperazinyl)-1-methyl-2-oxoethylcarbamate, 4-(2-(4-((2S)-2-aminopropanoyl)-1-piperazinyl)ethoxy)(1,1'-biphenyl)-4-carbonitrile, tert-butyl (1R)-2-(4-(2-((4'-cyano(1,1'-biphenyl)-4-yl)oxy)ethyl)-1-piperazinyl)-1-methyl-2-oxoethylearbamate, 4'-(3-(4-(aminoacetyl)-1-piperazinyl)propoxy)(1,1'-biphenyl)-4-carbonitrile, 4'-(2-(4-((2R)-2-aminopropanoyl)-1-piperazinyl)ethoxy)(1,1'-biphenyl)-4-carbonitrile, 4-(3-(4-(((tert-butoxycarbonyl)(methyl)amino)acetyl)-1-piperazinyl)propoxy)-4'-cyano-1,1'-biphenyl 4'-(3-(4-((methylamino)acetyl)-1-piperazinyl)propoxy)(1,1'-biphenyl)-4-carbonitrile, tert-butyl (1R)-2-(4-(2-((4-cyano(1,1'-biphenyl)-4-yl)oxy)ethyl)-1-piperazinyl)-1-methyl-2-oxoethyl(methyl)carbamate, 4'-(2-(4-((2R)-2-(methylamino)propanoyl)-1-piperazinyl)ethoxy)(1,1'-biphenyl)-4-carbonitrile, tert-butyl (1R)-2-(4-(3-((4'-cyano(1,1'-biphenyl)-4-yl)oxy)propyl)-1-piperazinyl )-1-methyl-2-oxoethylcarbamate, 4'-(3-(4-((2R)-2-aminopropanoyl)-1-piperazinyl)propoxy)(1,1 -biphenyl)-4-carbonitrile, tert-butyl (1 R)-2-(4-(3-((4'-cyano(1,1'-biphenyl)-4-yl)oxy)propyl)-1-piperazinyl)-1-methyl-2-oxoethyl(methyl)carbamate, 4-(3-(4-((2R)-2-(methylamino)propanoyl)-1-piperazinyl)propoxy)(1,1'-biphenyl)-4-carbonitrile, tert-butyl (1S)-2-(4-(3-((4-cyano(1,1'-biphenyl)-4-yl)oxy)propyl)-1-piperazinyl)-1-methyl-2-oxoethylcarbamate, 4'-(3-(4-(aminoacetyl)-1-piperazinyl)propoxy)(1,1'-biphenyl)-4-carbonitrile, 4-(3-(4-(3-((tert-butoxycarbonyl)amino)propanoyl)-1-piperazinyl)propoxy)-4-cyano-1,1'-biphenyl, 4'-(3-(4-(3-aminopropanoyl)-1-piperazinyl)propoxy)(1,1'-biphenyl)-4-carbonitrile, N-(3-(4-(3-(4'-cyano(1,1'-biphenyl-4-yl)oxy)propyl)-1-piperazinyl)-3-oxopropyl )-2,2-dimethylpropanamide, N-(3-(4-(3-(4'-cyano(1,1'-biphenyl-4-yl)oxy)propyl)-1-piperazinyl)-3-oxopropyl )-3,3 -dimethylbutanamide, N-(3-(4-(3-(4'-cyano(1,1'-biphenyl-4-yl)oxy)propyl)-1-piperazinyl)-3-oxopropyl)cyclopropanecarboxamide, N-(3-(4-(3-(4'-cyano(1,1'-biphenyl-4-yl)oxy)propyl)-1-piperazinyl)-3-oxopropyl)-4-morpholinecarboxamide, N-((1 R)-2-(4-(3-(4-(cyclopropylcarbonyl)phenoxy)propyl)-1-piperazinyl)-1-methyl-2-oxoethyl)-2-furamide, N-((1 R)-2-(4-(3-(4-(cyclopropylcarbonyl)phenoxy)propyl)-1-piperazinyl)-1-methyl-2-oxoethyl)-2-thiophenecarboxamide, (4-(3-(4-(((1S,2R)-2-aminocyclopropyl)carbonyl)-1-piperazinyl)propoxy)phenyl)(cyclopropyl)methanone, (4-(((3R)-3-(4-((2R)-2-aminobutanoyl)-1-piperazinyl)butyl)oxy)phenyl)(cyclopropyl)methanone, (4-(((3R)-3-(4-((2R)-2-aminopentanoyl)-1-piperazinyl)butyl)oxy)phenyl)(cyclopropyl)methanone, tert-butyl 4-(4-(3-(4-(cyclopropylcarbonyl)phenoxy)propyl)-1-piperazinyl)-4-oxobutylcarbamate, tert-butyl (1R)-2-(4-((3 S)-3-(4-(cyclopropylcarbonyl)phenoxy)-3-phenylpropyl )-1-piperazinyl)-1-methyl-2-oxoethylcarbamate, (4-(3-(4-((2R)-2-aminopropanoyl)-1-piperazinyl)propoxy)phenyl)(cyclopropyl)methanone, cyclopropyl(4-(3-(4-((2R)-2-(isopropylamino)propanoyl)-1-piperazinyl)propoxy)phenyl)methanone, N-((1 R)-2-(4-(4-(4-(cyclopropylcarbonyl)phenyl)-3-butynyl)-1-piperazinyl)-1-methyl-2-oxoethyl)-2-furamide, 4-cyano-N-{3-(4-[3-[3-fluoro-4-(5-phenyl-1,2,4-oxadiazol-3-yl)phenoxy]propyl}-1-piperazinyl)-3-oxopropyl]benzamide, N-[3-(4-{3-[3-fluoro-4-(5-phenyl-1,2,4-oxadiazol-3-yl)phenoxy]propyl}-1-piperazinyl)-3-oxopropyl}-3-thiophenecarboxamide, (2R)-N-[3-(4-{3-[3-fluoro-4-(5-phenyl-1,2,4-oxadiazol-3-yl)phenoxy]propyl)-1-piperazinyl)-3-oxopropyl]tetrahydro-2-furancarboxamide, N-[3-(4-{3-[3-fluoro-4-(5-phenyl-1,2,4-oxadiazol-3-yl)phenoxy]propyl}-1-piperazinyl)-3-oxopropyl]-3,5-dimethyl-2-thiophenecarboxamide, N-[3-(4-{3-[3-fluoro-4-(5-phenyl-1,2,4-oxadiazol-3-yl)phenoxy]propyl}-1-piperazinyl)-3-oxopropyl]-2,5-dimethyl-3-furamide, N-[3-(4-{3-[3-fluoro-4-(5-phenyl-1,2,4-oxadiazol-3-yl)phenoxy]propyl-1-piperazinyl)-3-oxopropyl]cyclopentanecarboxamide, N-[(1R)-2-(4-{3-[3-fluoro-4-(5-phenyl-1,2,4-oxadiazol-3-yl)phenoxy]propyl}-1-piperazinyl)-1-methyl-2-oxoethyl]-2-thiophenecarboxamide, N-[(1R)-2-(4-{3-[3-fluoro-4-(5-phenyl-1,2,4-oxadiazol-3-yl)phenoxy]propyl}-1-piperazinyl)-1-methyl-2-oxoethyl]nicotinamide, N-[1R)-2-(4-{3-[3-fluoro-4-(5-phenyl-1,2,4-oxadiazol-3-yl)phenoxy]propyl}-1-piperazinyl)-1-methyl-2-oxoethyl]-2-furamide, N-[(1R)-2-(4-{3-[3-fluoro-4-(5-phenyl-1,2,4-oxadiazol-3-yl)phenoxy]propyl}-1-piperazinyl)-1-methyl-2-oxoethyl]-5-isoxazolecarboxamide, (2S)-N-[(1R)-2-(4-{3-[3-fluoro-4-(5-phenyl-1,2,4-oxadiazol-3-yl)phenoxy]propyl}-piperazinyl)-1-methyl-2-oxoethyl]tetrahydro-2-furancarboxamide, N-[(1R)-2-(4-=3-[3-fluoro-4-(5-phenyl-1,2,4-oxadiazol-3-yl)phenoxy]propyl}-1-piperazinyl)-1-methyl-2-oxoethyl]-3-(4-morpholinyl)propanamide, N-[(1R)-2-(4-{3-[3-fluoro-4-(5-phenyl-1,2,4-oxadiazol-3-yl)phenoxy]propy}-1-piperazinyl)-1-methyl-2-oxoethyl]-3-methylbutanamide, (2R)-1-[4-(3-{4-[5-(cyclopentylmethyl)-1,2,4-oxadiazol-3-yl]-3-fluorophenoxy}propyl)-1-piperazinyl]-1-oxo-2-propanamine, (2R)-1-[4-(3-{4-[5-(cyclopentylmethyl)-1,2,4-oxadiazol-3-yl]-3-fluorophenoxy}propyl)-1,4-diazepan-1-yl]-1-oxo-2-propanamine, N-(1R)-2-[4-(3-{4-[5-(cyclopentylmethyl)-1,2,4-oxadiazol-3-yl]-3-fluorophenoxy)propyl)-1-piperazinyl]-1-methyl-2 -oxoethyl}propanamide, N-{(1R)-2-{4-(3-{4-[5-(cyclopentylmethyl)-1,2,4-oxadiazol-3-yl]-3-fluorophenoxy}propyl)-1-piperazinyl]-1-methyl-2-oxoethyl}-3,3-dimethylbutanamide, N-{(1R)-2-[4-(3-{4-[5-(cyclopentylmethyl)-1,2,4-oxadiazol-3-yl]-3-fluorophenoxy}propyl)-1-piperazinyl]-1-methyl-2-oxoethyl]-3-(4-morpholinyl)propanamide, N-{(1R)-2-[4-(3-{4-[5-(cyclopentylmethyl)-1,2,4-oxadiazol-3-yl]-3-fluorophenoxy}propyl)-1-piperazinyl]-1-methyl-2-oxoethyl}-4-methylbenzamide, N-{(1R)-2-[4-(3-{4-[5-(cyclopentylmethyl)-1,2,4-oxadiazol-3-yl]-3-fluorophenoxy}propyl)-1-piperazinyl]-1-methyl-2-oxoethyl}-4-fluorobenzamide, N-{(1R)-2-[4-(3-{4-[5-(cyclopentylmethyl)-1,2,4-oxadiazol-3-yl]-3-fluorophenoxy}propyl)-1-piperazinyl]-1-methyl-2-oxoethyl}-4-methoxybenzamide, 3,4-dichloro-N-{(1R)-2-[4-(3-{4-[5-(cyclopentylmethyl)-1,2,4-oxadiazol-3-yl]-3-fluorophenoxy}propyl)-1-piperazinyl]-1-methyl-2-oxoethyl}benzamide, N-}(1R)-2-[4-(3-{4-[5-(cyclopentylmethyl)-1,2,4-oxadiazol-3-yl]-3-fluorophenoxy}propyl)-1-piperazinyl]-1-methyl-2-oxoethyl}-4-(dimethylamino)benzamide, N-{(1R)-2-[4-(3-{4-[5-(cyclopentylmethyl)-1,2,4-oxadiazol-3-yl]-3-fluorophenoxy}propyl)-1-piperazinyl]-1-methyl-2-oxoethyl}nicotinamide, 2-chloro-N-{(1R)-2-[4-(3-{4-[5-(cyclopentylmethyl)-1,2,4-oxadiazol-3-yl]-3-fluorophenoxy}propyl)-1-piperazinyl]-1-methyl-2-oxoethyl}benzamide, N-{(1R)-2-[4-(3-{4-[5-(cyclopentylmethyl)-1,2,4-oxadiazol-3-yl]-3-fluorophenoxy}propyl)-1-piperazinyl]-1-methyl-2-oxoethyl}-1,3-benzodioxole-5-carboxamide, N-{(1R)-2-[4-(3-{4-[5-(cyclopentylmethyl)-1,2,4-oxadiazol-3-yl]-3-fluorophenoxy}propyl)-1-piperazinyl]-1-methyl-2-oxoethyl}-4-isopropoxybenzamide, N-{(1R)-2-[4-(3-{4-[5-(cyclopentylmethyl)-1,2,4-oxadiazol-3-yl]-3-fluorophenoxy}propyl)-1-piperazinyl]-1-methyl-2-oxoethyl}-3-fluoro-4-methoxybenzamide, 4-[({(1R)-2-[4-(3-{4-[5-(cyclopentylmethyl)-1,2,4-oxadiazol-3-yl]-3-fluorophenoxy}propyl)-1-piperazinyl]-1-methyl-2-oxoethyl}amino)carbonyl]benzoic acid, N-((1R)-2-[4-(3-{3-fluoro-4-[5-(3-methylphenyl)-1,2,4-oxadiazol-3-yl]phenoxy}propyl)-1-piperazinyl]-1-methyl-2-oxoethyl}-2-thiophenecarboxamide, N-{(1R)-2-[4-(3-{4-[5-(3-cyanophenyl)-1,2,4-oxadiazol-3-yl]-3-fluorophenoxy}propyl)-1-piperazinyl]-1-methyl-2-oxoethyl}-2-thiophenecarboxamide, N-{(1R)-2-[4-(3-{4-[5-(3,5-dichlorophenyl)-1,2,4-oxadiazol-3-yl]-3-fluorophenoxy}propyl)-1-piperazinyl]-1-methyl-2-oxoethyl}-2-thiophenecarboxamide, N-((1R)-2-{4-[3-(3-fluoro-4-{5-[3-oxo-3-(1-pyrrolidinyl)propyl]-1,2,4-oxadiazol-3-yl}phenoxy)propyl]-1-piperazinyl}-1-methyl-2-oxoethyl)-2-thiophenecarboxamide, ethyl 3-{2-fluoro-4-[3-(4-((2R)-2-[(2-thienylcarbonyl)amino]propanoyl}-piperazinyl)propoxy]phenyl)-1,2,4-oxadiazole-5-carboxylate, N-[(1R)-2-(4-{3-[4-(cyclopropylcarbonyl)phenoxy]propyl)-1-piperazinyl)-1-methyl-2-oxoethyl]-2-methylbenzamide, N-[(1R)-2-(4-{3-[4-(cyclopropylcarbonyl)phenoxy]propyl)-1-piperazinyl)-1-methyl-2-oxoethyl]-3-methoxybenzamide, 4-bromo-N-[(1R)-2-(4-{3-[4-(cyclopropylcarbonyl)phenoxy]propyl)-1-piperazinyl)-1-methyl-2-oxoethyl]benzamide, N-[(1R)-2-(4-{3-[4-(cyclopropylcarbonyl)phenoxy]propyl}-1-piperazinyl)-1-methyl-2-oxoethyl]-4-phenoxybenzamide, N-[(1R)-2-(4-{3-[4-(cyclopropylcarbonyl)phenoxy]propyl}-1-piperazinyl)-1-methyl-2-oxoethyl]-3,5-dimethylbenzamide, N-[(1R)-2-(4-{3-[4-(cyclopropylcarbonyl)phenoxy]propyl}-1-piperazinyl)-1-methyl-2-oxoethyl]-2,5-dimethoxybenzamide, and N-{(1R)-2-[4-(3-{3-fluoro-4-[5-(4-methoxyphenyl)-1,2,4-oxadiazol-3-yl]phenoxy}propyl)-1-piperazinyl]-1-methyl-2-oxoethyl}-2-thiophenecarboxamide.

20. A composition comprising a compound of claim 1, or a pharmaceutically acceptable salt thereof, and a pharmaceutically acceptable carrier.

21. A method for antagonizing the $H_3$ receptor comprising administering a pharmaceutically acceptable amount of a compound of claim 1, or a pharmaceutically acceptable salt thereof, wherein $L^1$, $L^2$, n, $Q^1$, $Q^2$, $R^1$, $R^2$, $R^3$, $R^4$, $R^6$, $R^7$ and $R^8$ are defined above.

* * * * *

UNITED STATES PATENT AND TRADEMARK OFFICE
CERTIFICATE OF CORRECTION

PATENT NO.  : 6,559,140 B2
DATED       : May 6, 2003
INVENTOR(S) : Youssef L. Bennani et al.

It is certified that error appears in the above-identified patent and that said Letters Patent is hereby corrected as shown below:

<u>Column 111,</u>
Line 64, replace "claim 1" with -- claim 15 --.

<u>Column 112,</u>
Line 65, replace "(4-aeetylphenoxy)" with -- (4-acetylphenoxy) --.
Line 66, replace "-2oxoethyl)" with -- 2-oxoethyl) --.

<u>Column 113,</u>
Line 29, replace "pheny l)-1-" with -- phenyl)-1- --.
Line 34, replace "(-1 -hexanone" with -- -1-hexanone --.
Line 57, replace "((1 R)-3-" with -- ((1R)-3- --.

<u>Column 114,</u>
Line 21, replace "(1 R,2S)" with -- (1R,2R) --.
Line 25, replace "-3 -(" with -- -3-( --.
Line 27, replace "butyl (1 R,2S)" with -- butyl (1R,2S) --.
Line 30, replace "(1 R)-5-" with -- (1R)-5- --.
Line 50, replace "(1 R)-2-" with -- (1R)-2- --.
Line 55, replace "(1 S)-2-(4-(2-((4-cyano(" with -- (1S)-2-(4-(2-((4'-cyano( --.
Line 58, replace "4-(2-" with -- 4'-(2- --.
Line 63, replace "oxoethylearbamate" with -- oxoethylcarbamate --.

<u>Column 115,</u>
Lines 5 and 21, replace "((4-cyano" with -- ((4'-cyano --.
Line 15, replace "(1,1-biphenyl)" with -- (1,1'-biphenyl) --.
Line 16, replace "(1 R)" with -- (1R) --.
Line 19, replace "4-(3-(4-" with -- 4'-(3-(4- --.
Lines 39, 43 and 62, replace "((1 R)" with -- ((1R) --.
Line 54, replace "((3 S)" with -- ((3S) --.
Line 65, replace "N-{3-(4-[3-[3-fluoro" with -- N-[3-(4-{3-[3-fluoro --.

<u>Column 116,</u>
Line 15, replace "propyl-1-piperazinyl)" with -- propyl}-1-piperazinyl) --.
Line 32, replace "(4- =3-[3-fluoro" with -- (4-={3-[3-fluoro --.
Line 45, replace "N-(1R)" with -- N-{(1R) --.
Line 46, replace "fluorophenoxy)propyl" with -- fluorophenoxy}propyl --.
Line 48, replace "-2-{4-(3-{4-" with -- -2-[4-(3-{4- --.

UNITED STATES PATENT AND TRADEMARK OFFICE
CERTIFICATE OF CORRECTION

PATENT NO.    : 6,559,140 B2
DATED         : May 6, 2003
INVENTOR(S)   : Youssef L. Bennani et al.

It is certified that error appears in the above-identified patent and that said Letters Patent is hereby corrected as shown below:

<u>Column 117,</u>
Line 5, replace "N-}(1R)" with -- N-{(1R) --.

Signed and Sealed this

Ninth Day of September, 2003

JAMES E. ROGAN
*Director of the United States Patent and Trademark Office*